US008324262B2

(12) United States Patent
Yuan et al.

(10) Patent No.: US 8,324,262 B2
(45) Date of Patent: Dec. 4, 2012

(54) TRICYCLIC NECROSTATIN COMPOUNDS

(75) Inventors: Junying Yuan, Waban, MA (US); Alexei Degterev, Brookline, MA (US); Junichi Hitomi, Brookline, MA (US); Gregory D. Cuny, Somerville, MA (US); Prakash Jagtap, North Andover, MA (US)

(73) Assignees: The Brigham and Women's Hospital, Inc., Boston, MA (US); President and Fellows of Harvard College, Cambridge, MA (US)

( * ) Notice: Subject to any disclaimer, the term of this patent is extended or adjusted under 35 U.S.C. 154(b) by 671 days.

(21) Appl. No.: 12/086,792

(22) PCT Filed: Dec. 20, 2006

(86) PCT No.: PCT/US2006/048583
§ 371 (c)(1),
(2), (4) Date: Jun. 22, 2009

(87) PCT Pub. No.: WO2007/075772
PCT Pub. Date: Jul. 5, 2007

(65) Prior Publication Data
US 2010/0190836 A1 Jul. 29, 2010

Related U.S. Application Data

(60) Provisional application No. 60/751,913, filed on Dec. 20, 2005, provisional application No. 60/843,304, filed on Sep. 8, 2006.

(51) Int. Cl.
*A61K 31/416* (2006.01)
*A61K 31/4162* (2006.01)
*C07D 231/54* (2006.01)
*C07D 491/048* (2006.01)

(52) U.S. Cl. ............ 514/403; 548/359.1; 514/656; 514/680

(58) Field of Classification Search .......... 514/403, 514/646, 656, 680; 548/359.1
See application file for complete search history.

(56) References Cited

U.S. PATENT DOCUMENTS

| | | | |
|---|---|---|---|
| 6,706,766 B2 | 3/2004 | Yuan et al. | |
| 6,756,394 B1 * | 6/2004 | Yuan et al. | 514/389 |
| 6,887,993 B1 | 5/2005 | Tian et al. | |
| 7,144,905 B2 | 12/2006 | Yuan et al. | |
| 7,253,201 B2 | 8/2007 | Yuan et al. | |
| 7,390,836 B2 | 6/2008 | Yuan et al. | |
| 7,491,743 B2 | 2/2009 | Cuny et al. | |
| 2010/0087453 A1 | 4/2010 | Yuan et al. | |
| 2010/0317701 A1 | 12/2010 | Cuny et al. | |
| 2011/0144169 A1 | 6/2011 | Cuny et al. | |

FOREIGN PATENT DOCUMENTS

| | | |
|---|---|---|
| EP | 1270567 | 1/2003 |
| WO | WO 01/28493 | 4/2001 |
| WO | WO 2006/086358 | 8/2006 |

OTHER PUBLICATIONS

U.S. Appl. No. 13/141,545, filed Jun. 22, 2011, Yuan et al.
Fateen et al., "Synthesis of Δ2-Pyrazolines and 1-Naphthols," *Egypt J. Chem.* 15(4) 329-336 (1972).
Hammam et al., "Synthesis of Novel Tricyclic Heterocyclic Compounds as Potential Anticancer Agents Using Chromanone and Thiochromanone as Synthons," *Indian Journal of Chemistry.* 42B: 1985-1993 (2003).
Peesapati et al., "Nitrogen Heterocyclic Systems: Synthesis of 3,3a-trans and cis-2-acetyl/phenyl-3-arylhexahydobenzo[6,7]cyclohepta[1,2-c]pyrazoles," *J. Chem. Research.* S: 372-374 (2001).
Sangwan, "Use of Characteristic $^1$H N.M.R. Chemical Shifts to Differentiate Diastereoisomeric [1]Benzopyrano-[4,3-c]pyrazoles, Pyrazolo[4,3-c]quinlines, and Related Compounds," *J. Chem. Research.* 5: 22-23 (1987).
Sinha et al., "Synthesis of 3, 3a-trans/cis-2-Phenyl/Acetyl-3-Aryl-Tetrahydroindeno/napntho [1, 2-c]- and Hexahydrobenzo [6,7]cyclohepta[1,2-c]pyrazoles as Antiimplantation Agents," *Indian Journal of Chemistry.* 30B: 684-692 (1991).
Teng et al.,"Structure-Activity Relationship Study of Novel Necroptosis Inhibitors," *Bioorg Med Chem Lett.* 15:5039-5044 (2005).
Chinese Patent Office Action (Application No. 200680053077) dated Feb. 1, 2011.
European Patent Office Communication (European Application No. 06847822.1) dated May 5, 2011.
European Search Report (PCT/US2006/048583) dated Aug. 16, 2010.
International Search Report (PCT/US06/048583), dated Dec. 8, 2008.
International Preliminary Report on Patentability (PCT/US06/048583), dated Jan. 13, 2009.
Written Opinion of the International Search Authority (PCT/US06/048583), dated Nov. 21, 2008.
Office Action pertaining to U.S. Appl. No. 09/688,015, mailed May 30, 2001.
Office Action pertaining to U.S. Appl. No. 09/688,015, mailed Mar. 7, 2002.
Office Action pertaining to U.S. Appl. No. 09/688,015, mailed Nov. 5, 2002.
Office Action pertaining to U.S. Appl. No. 10/880,377, mailed Mar. 17, 2006.
Office Action pertaining to U.S. Appl. No. 10/880,377, mailed Jul. 20, 2006.
Australian Patent Office Communication dated Sep. 5, 2011, in Australian Patent Application No. 2006331754.
Chinese Patent Office Communication, dated Nov. 14, 2011, in Chinese Patent Application No. 200680053077.9.
Japanese Patent Office Communication dated Aug. 20, 2012, in Japanese Patent Application No. 2008-547482.

* cited by examiner

*Primary Examiner* — Sreeni Padmanabhan
*Assistant Examiner* — Sahar Javanmard
(74) *Attorney, Agent, or Firm* — Clark & Elbing LLP; Kristina Bieker-Brady

(57) ABSTRACT

The present invention features compounds, pharmaceutical compositions, and methods for treating trauma, ischemia, stroke, degenerative diseases associated with cellular necrosis, and other conditions. Screening assays for identifying compounds useful for treating these conditions are also described.

6 Claims, 35 Drawing Sheets

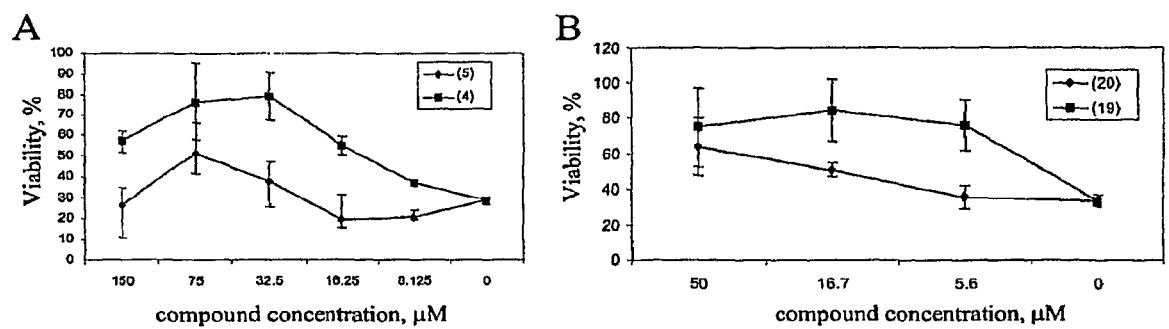
Figures 34A-B

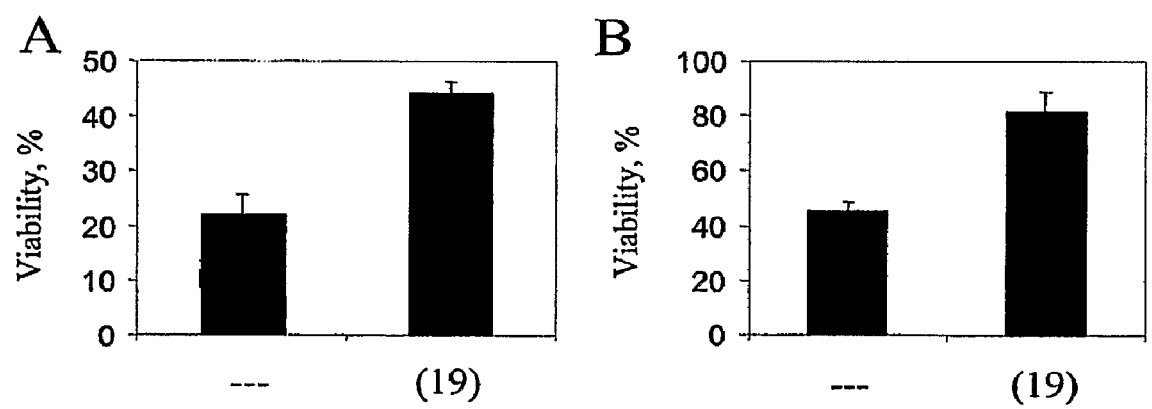
Figures 35A-B

TRICYCLIC NECROSTATIN COMPOUNDS

CROSS-REFERENCE TO RELATED APPLICATIONS

This application is the U.S. National Stage of International Application No. PCT/US2006/048583, filed Dec. 20, 2006, which in turn, claims the benefit of U.S. Provisional Application No. 60/751,913, filed Dec. 20, 2005, and U.S. Provisional Application No. 60/843,304, filed Sep. 8, 2006, each of which is hereby incorporated by reference.

STATEMENT AS TO FEDERALLY SPONSORED RESEARCH

The present research was supported by grants from the National Institutes of Health (grant numbers GM64703, AG012859, and NS37141-08). The U.S. government has certain rights to this invention.

BACKGROUND OF THE INVENTION

In many diseases, cell death is mediated through apoptotic and/or necrotic pathways. While much is known about the mechanisms of action that control apoptosis, control of necrosis is not as well understood. Understanding the mechanisms regulating both necrosis and apoptosis in cells is essential to being able to treat conditions, such as neurodegenerative diseases, stroke, coronary heart disease, kidney disease, and liver disease. A thorough understanding of necrotic and apoptotic cell death pathways is also crucial to treating AIDS and the conditions associated with AIDS, such as retinal necrosis.

Research has shown that caspases play a central role in the induction of apoptosis. Peptide based inhibitors of caspases, such as zVAD-fmk are useful in preventing activation of the apoptotic cell death pathway in cells stimulated to undergo apoptosis by compounds such as TNFα. However, cells treated with zVAD-fmk and these cell death stimuli still die through a caspase-independent form of necrosis.

The discovery of compounds that prevent caspase-independent cell death (e.g., necrosis or necroptosis) would provide useful therapeutic agents for treating conditions in which necrosis occurs, and for preventing the onset of necrosis or necroptosis. These compounds and methods would be particularly useful for treating neurodegenerative diseases, ischemic brain and heart injuries, and head traumas.

SUMMARY OF THE INVENTION

The present invention features compounds, pharmaceutical compositions, kits, and methods for treating a range of conditions, e.g., those in which cell or tissue necrosis is a causative factor or result, those in which loss of proliferative capacity is a causative factor or a result, those in which cytokines of the TNFα family are a causative factor or a result, and those in which RIP1 protein is a contributing factor. The compounds of the present invention can be used, for example, as therapeutics to decrease necrosis in a desired cell, to increase cell proliferation, or to stimulate immune response. The compounds of the present invention can also be used, for example, to treat any of the conditions listed in Table 1. Exemplary conditions are neurodegenerative diseases of the central or peripheral nervous system; the result of retinal neuronal cell death; the result of cell death of cardiac muscle; the result of cell death of cells of the immune system; stroke; liver disease; pancreatic disease; the result of cell death associated with renal failure; heart, mesenteric, retinal, hepatic or brain ischemic injury; ischemic injury during organ storage; head trauma; septic shock; coronary heart disease; cardiomyopathy; bone avascular necrosis; sickle cell disease; muscle wasting; gastrointestinal disease; tuberculosis; diabetes; alteration of blood vessels; muscular dystrophy; graft-versus-host disease; viral infection; Crohn's disease; ulcerative colitis; asthma; any condition in which cell or tissue necrosis is a causative factor or result; any condition in which alteration in cell proliferation, differentiation or intracellular signaling is a causative factor; and any condition in which RIP1 protein is a contributing factor. The invention further features screening assays capable of identifying inhibitors of RIP1, a molecular target of compounds described herein. The additional inhibitors thus identified can be used in methods of disease treatment.

Accordingly, in a first aspect, the invention features a method of treating a subject with a disease or condition listed in Table 1 by administering to the subject an effective amount of a Nec-1e compound, a Nec-2b compound, or a Nec-3b compound. In some instances, the Nec-1e compound is a substantially pure A isomer or B isomer.

The invention also features a method of treating a subject with a disease or condition listed in Table 1 by administering to the subject an effective amount of a Nec-3 compound, wherein said Nec-3 compound is a substantially pure (3R, 3aR)-rel isomer or a substantially pure (3R, 3aS)-rel isomer. In some instances, the Nec-3 compound is a substantially pure (3R, 3aR)-enantiomer, a substantially pure (3R, 3aS)-enantiomer, a substantially pure (3S, 3aR)-enantiomer, or a substantially pure (3S, 3aS)-enantiomer. In some instances, the Nec-3 compound is selected from compounds (1) to (217). For example, the Nec-3 compound may be selected from compounds (141), (161), (166), (167), (169), (171), (178), and (182) of Table 7; compounds (185), (188), (190), (192), and (194) of Table 8; and compounds (147), (148), (150), (151), (154), (158); and (159) of Table 9.

The invention further features a method of treating a subject with a disease or condition listed in Table 2 by administering to the subject an effective amount of a Nec compound. In some instances, the Nec compound is a Nec-1 compound of formula (I):

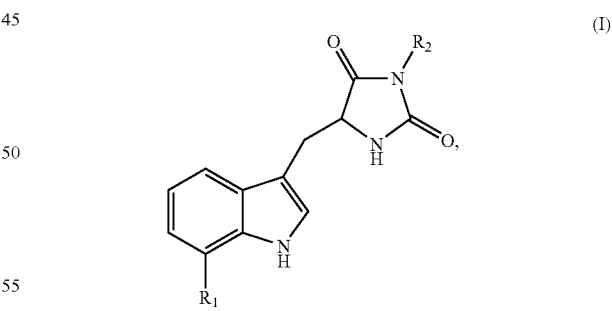

wherein
$R_1$ represents methyl, methoxyl, Cl, Br, or F; and $R_2$ represents alkyl of one to four carbon atoms. In some instances, $R_1$ represents Cl and $R_2$ represents methyl or ethyl. The Nec-1 compound can be a substantially pure A isomer or B isomer.

The invention additionally features a method of treating a subject with a disease or condition listed in Table 3 by administering to the subject an effective amount of a Nec-1c compound.

The invention further features a method of treating a subject with a disease or condition listed in Table 4 by administering to the subject an effective amount of a Nec-1d compound.

In general, the invention features a method of treating a subject with a disease or condition listed in Table 1 by administering to the Subject an effective amount of a Nec compound.

The invention also features a method of treating a subject with a disease or condition listed in Table 1 by administering to the subject an effective amount of geldanamycin. Alternatively, the subject can be treated by administering an effective amount of any RIP 1 inhibitor or HSP90 inhibitor.

The invention further features Nec compounds, pharmaceutical compositions containing Nec compounds together with a pharmaceutically acceptable excipient, and kits that include these compounds or compositions together with instructions for their use. In some instances, the invention features Nec-1e compounds; substantially pure A isomers and B isomers of Nec-1e compounds; Nec-2b compounds; Nec-3b compounds; and substantially pure (3R, 3aR)-rel isomers and (3R, 3aS)-rel isomers of Nec-3 compounds, e.g., selected from compounds (1) to (217) (e.g., compounds (141), (161), (166), (167), (169), (171), (178), and (182) of Table 7; compounds (185), (188), (190), (192), and (194) of Table 8; and compounds (147), (148), (150), (151), (154), (158), and (159) of Table 9). In some instances, the Nec-3 compounds featured herein may be substantially pure (3R, 3aR)-enantiomers, (3R, 3aS)-enantiomers, (3S, 3aR)-enantiomers, or (3S, 3aS)-enantiomers of Nec-3 compounds.

The invention further features a Nec-1 compound of formula (I):

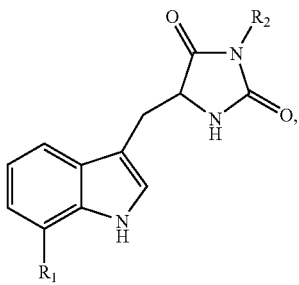

(I)

wherein $R_1$ represents methyl, methoxyl, Cl, Br, or F; and $R_2$ represents alkyl of one to four carbon atoms.

In another instance, the invention features a Nec-1 compound of formula (II):

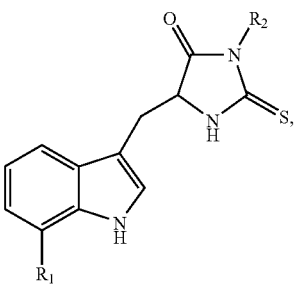

(II)

wherein $R_1$ represents methoxyl, Cl, Br, or F; and $R_2$ represents alkyl of one to four carbon atoms.

In still another instance, the invention features a Nec-1 compound of formula (III):

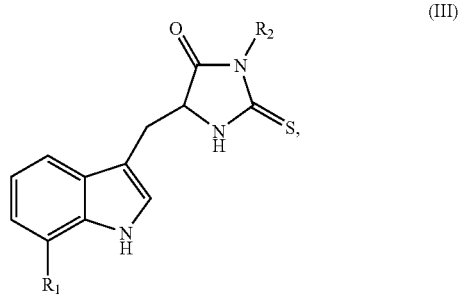

(III)

wherein $R_1$ represents methyl; and $R_2$ represents hydrogen or alkyl of one to four carbon atoms.

The invention further features a Nec-1 compound of formula (XVI):

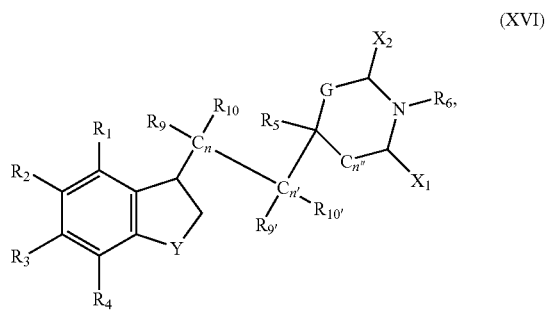

(XVI)

wherein
each of $X_1$ and $X_2$, independently, represents =S, =O, =N, H, $R_{11}$, $SR_{11}$, $NR_{11}$, or $OR_{11}$; Y represents S, NH or $NR_8$; G represents $CH_2$, O, $SR_S$, or $NR_7$; each of $R_1$, $R_2$, and $R_3$, independently, represents H, OH, $OR_8$, F, Cl, Br, I, $N(R_8)_2$, COOH, $CO_2R_8$, $NO_2$, $NHC(O)R_8$, $C_{1-7}$ alkyl, $C_{2-7}$ alkenyl, $C_{2-7}$ alkynyl, $C_{6-12}$ aryl, acyl, acetyl, acylamino, $C_{2-9}$ heteroaryl; $R_4$ represents H, OH, $OR_8$, F, Cl, Br, I, $N(R_8)_2$, COOH, $CO_2R_8$, $NO_2$, $NHC(O)R_8$, acyl, acetyl, acylamino, $C_{1-7}$ alkyl, $C_{2-7}$ alkenyl, $C_{2-7}$ alkynyl, $C_{6-12}$ aryl, $C_{2-9}$ heteroaryl, amine, or piperizine; each of $R_5$, $R_6$, and $R_7$, independently, represents H, OH, $OR_8$, F, Cl, Br, I, $N(R_8)_2$, acyl, acetyl, acylamino, $NO_2$, $C_{1-7}$ alkyl, $C_{2-7}$ alkenyl, or $C_{2-7}$ alkenyl; $R_8$ represents H, OH, $NO_2$, F, Cl, Br, I, $C_{1-7}$ alkyl, $C_{6-12}$ aryl, arylalkyl, $C_{2-7}$ alkenyl, $C_{2-7}$ alkynyl, $C_{2-9}$ heteroaryl, acetyl, methoxyl, amino, acylamino, acyl, or halogen; each of $R_9$, $R_{10}$, $R_{9'}$, $R_{10'}$, independently, represent H, OH, F, Cl, Br, I, $C_{1-7}$ alkyl, $C_{2-7}$ alkenyl, $C_{2-7}$ alkynyl, or a three to six membered cycloalkyl that includes $C_n$, and/or $C_{n'}$, or $R_9$ and/or $R_{10}$ can be absent; $R_{11}$ represents H, OH, $NO_2$, F, Cl, Br, I, acetyl, methoxyl, amino, acylamino, $C_{1-7}$ alkyl, $C_{2-7}$ alkenyl, $C_{2-7}$ alkynyl, or acyl; each of n and n' is an integer from zero to five, inclusive; n" is 0 or 1; and each of bonds (a), (b), and (c) is, independently, a single bond or a double bond, provided that bond (a) and bond (b) are not both double bonds, wherein when $X_1$ is =O, OH, or H, $X_2$ is not =S or $SR_{12}$, where $R_{12}$ is H or alkyl, and wherein $X_1$ and $X_2$ are not both =O. In some instances, each of G and Y represents NH; each of $R_1$, $R_2$, $R_3$, $R_5$, $R_9$, and $R_{10}$ represents H; n is 1; each of n' and n" is 0; (a) is a double bond, and each of (b) and (c) are double bonds. In some instances, $R_4$ represents methyl, methoxyl, Cl, Br, or F; and $R_6$ represents alkyl of one to four carbon atoms. In some instances, $X_1$ is $=$O or $X_2$ is $=$O. Any of the Nec-1 compounds featured herein may be substantially pure A isomers or B isomers.

The invention further features a Nec-2 compound of formula (IV):

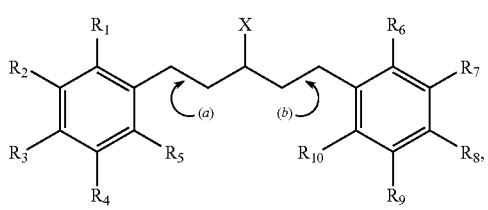

(IV)

wherein each of $R_1$, $R_2$, $R_3$, $R_4$, $R_5$, $R_6$, $R_7$, $R_8$, $R_9$, and $R_{10}$, independently, represents hydrogen, acyl, acetyl, linear and branching alkyl, halogen, amino, methoxyl, nitro, or C(O)$R_{12}$, C(S)$R_{12}$, C(O)O$R_{12}$, C(O)N$R_{12}R_{13}$, C(S)N$R_{12}R_{13}$, or S(O)$R_{12}$, wherein each of $R_{12}$ and $R_{13}$, independently, represents hydrogen, an optionally substituted $C_{1-12}$ alkyl, an optionally substituted $C_6$ or $C_{10}$ aryl, an optionally substituted $C_{2-9}$ heteroaryl, an optionally substituted $C_{7-16}$ aralkyl, or an optionally substituted $C_{2-15}$ heteroaralkyl; the bond indicated by (a) can be a single or double bond; the bond indicated by (b) can be a single or double bond; and X is hydrogen, acyl, acetyl, alkyl, halogen, amino, acylamino, nitro, $=$S, S$R_{11}$, $=$N, N$R_{11}$, $=$O, or O$R_{11}$, wherein $R_{11}$ is hydrogen, acyl, acetyl, alkyl, or acylamino; wherein when each of $R_1$, $R_4$, $R_5$, $R_6$, $R_9$ and $R_{10}$ is hydrogen and each of $R_2$, $R_3$, $R_7$, and $R_8$ is methoxyl, X is not $=$O, hydrogen, or hydroxyl.

The invention further features a Nec-3 compound of formula (V):

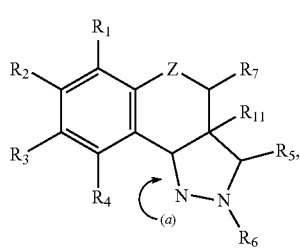

(V)

wherein

Z is a bond, $CH_2$, $CH_2CH_2$, O, S, S(O), S(O$_2$), or N$R_8$; wherein $R_8$ is an optionally substituted $C_{1-6}$ alkyl, an optionally substituted $C_{7-16}$ aralkyl, or an optionally substituted $C_{2-15}$ heteroaralkyl;

the bond indicated by (a) can be a single or double bond;

each of $R_1$, $R_2$, $R_3$, and $R_4$, independently, represents hydrogen, alkanoyl of one to six carbon atoms; alkyl of one to six carbon atoms; alkoxy of one to six carbon atoms; alkoxyalkyl, wherein the alkyl and alkylene groups are independently of one to six carbon atoms; alkylsulfinyl of one to six carbon atoms; alkylsulfinylalkyl, wherein the alkyl and alkylene groups are independently of from one to six carbon atoms; alkylsulfonyl of one to six carbon atoms; alkylsulfonylalkyl, wherein the alkyl and alkylene groups are independently of one to six carbon atoms; $C_{7-16}$ aralkyl; amino; aminoalkyl of one to six carbon atoms; $C_6$ or $C_{10}$ aryl; $C_7$ or $C_{11}$ aryloyl; azido; azidoalkyl of one to six carbon atoms; carboxaldehyde; (carboxaldehyde)alkyl, wherein the alkylene group is of one to six carbon atoms; cycloalkyl of three to eight carbon atoms; cycloalkylalkyl, wherein the cycloalkyl group is of three to eight carbon atoms and the alkylene group is of one to ten carbon atoms; halo; haloalkyl of one to six carbon atoms; $C_{2-9}$ heterocyclyl; $C_{2-9}$ (heterocyclyl)oxy; $C_{3-10}$ (heterocyclyl)oyl; hydroxyl; hydroxyalkyl of one to six carbon atoms; nitro; nitroalkyl of one to six carbon atoms; N-protected amino; N-protected aminoalkyl, wherein the alkylene group is of one to six carbon atoms; thioalkoxy of one to six carbon atoms; thioalkoxyalkyl, wherein the alkyl and alkylene groups are independently of from one to six carbon atoms; $-(CH_2)_qCO_2R_A$, wherein q is zero to four and $R_A$ is selected from the group consisting of (a) $C_{1-6}$ alkyl, (b) $C_6$ or $C_{10}$ aryl and (c) arylalkyl, wherein the alkylene group is of one to six carbon atoms; $-(CH_2)_qCONR_BR_C$, wherein $R_B$ and $R_C$ are independently selected from the group consisting of (a) hydrogen, (b) $C_{1-6}$ alkyl, (c) $C_6$ or $C_{10}$ aryl and (d) arylalkyl, wherein the alkylene group is of one to six carbon atoms; $-(CH_2)_qSO_2R_D$, wherein $R_D$ is selected from the group consisting of (a) $C_{1-6}$ alkyl, (b) $C_6$ or $C_{10}$ aryl and (c) arylalkyl, wherein the alkylene group is of one to six carbon atoms; $-(CH_2)_qSO_2NR_ER_F$, wherein $R_E$ and $R_F$ are independently selected from the group consisting of (a) hydrogen, (b) alkyl, (c) $C_6$ or $C_{10}$ aryl and (d) arylalkyl, wherein the alkylene group is of one to six carbon atoms; $-(CH_2)_qNR_GR_H$, wherein $R_G$ and $R_H$ are independently selected from the group consisting of (a) hydrogen; (b) an N-protecting group; (c) alkyl of one to six carbon atoms; (d) alkenyl of two to six carbon atoms; (e) alkynyl of two to six carbon atoms; (f) $C_6$ or $C_{10}$ aryl; (g) arylalkyl, wherein the alkylene group is of one to six carbon atoms; (h) cycloalkyl of three to eight carbon atoms and (i) cycloalkylalkyl, wherein the cycloalkyl group is of three to eight carbon atoms, and the alkylene group is of one to ten carbon atoms, with the proviso that no two groups are bound to the nitrogen atom through a carbonyl group or a sulfonyl group; $C_{1-6}$ perfluoroalkyl; $C_{1-6}$ perfluoroalkoxy; $C_6$ or $C_{10}$ aryloxy; $C_{3-8}$ cycloalkoxy; $C_{9-14}$ cycloalkylalkoxy; or $C_{7-16}$ arylalkoxy;

$R_5$ is an optionally substituted $C_6$ or $C_{10}$ aryl or an optionally substituted $C_{2-9}$ heteroaryl;

$R_6$ is C(O)$R_9$, C(S)$R_9$, C(O)O$R_9$, C(O)N$R_9R_{10}$, C(S)N$R_9R_{10}$, C(NH)$R_9$, or S(O$_2$)$R_9$, wherein each of $R_9$ and $R_{10}$, independently, represents H, an optionally substituted $C_{1-12}$ alkyl, an optionally substituted $C_{1-7}$ heteroalkyl, an optionally substituted $C_6$ or $c_{10}$ aryl, an optionally substituted $C_{2-9}$ heteroaryl, an optionally substituted $C_{7-16}$ aralkyl, or an optionally substituted $C_{2-15}$ heteroaralkyl;

$R_7$ is hydrogen, $C_{1-6}$ alkyl, an optionally substituted $C_6$ or $C_{10}$ aryl, an optionally substituted $C_{7-16}$ aralkyl, an optionally substituted $C_{2-9}$ heteroaryl, or an optionally substituted $C_{2-15}$ heteroaralkyl; and $R_{11}$ is H, an optionally substituted $C_{1-12}$ alkyl, or an optionally substituted $C_{1-7}$ heteroalkyl, wherein when each of $R_1$, $R_2$, $R_4$, and $R_7$ is selected from the group consisting of hydrogen, amino, halide, and hydroxyl and Z is $CH_2$, $R_3$ is not hydroxyl or methoxyl.

The invention additionally features a Nec-3 compound of formula (VI):

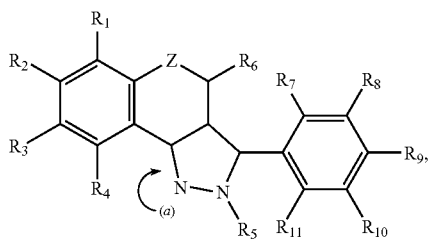

(VI)

wherein

Z is a bond, $CH_2$, $CH_2CH_2$, O, S, S(O), S(O$_2$), or $NR_{12}$; wherein $R_{12}$ is an optionally substituted $C_{1-6}$ alkyl, an optionally substituted $C_{7-16}$ aralkyl, or an optionally substituted $C_{2-15}$ heteroaralkyl;

the bond indicated by (a) can be a single or double bond;

each of $R_1$, $R_2$, $R_3$, $R_4$, $R_7$, $R_8$, $R_9$, $R_{10}$, and $R_{11}$, independently, represents hydrogen, alkanoyl of one to six carbon atoms; alkyl of one to six carbon atoms; alkoxy of one to six carbon atoms; alkoxyalkyl, wherein the alkyl and alkylene groups are independently of one to six carbon atoms; alkylsulfinyl of one to six carbon atoms; alkylsulfinylalkyl, wherein the alkyl and alkylene groups are independently of from one to six carbon atoms; alkylsulfonyl of one to six carbon atoms; alkylsulfonylalkyl, wherein the alkyl and alkylene groups are independently of one to six carbon atoms; $C_{7-16}$ aralkyl; amino; aminoalkyl of one to six carbon atoms; $C_6$ or $C_{10}$ aryl; $C_7$ or $C_{11}$ aryloyl; azido; azidoalkyl of one to six carbon atoms; carboxaldehyde; (carboxaldehyde)alkyl, wherein the alkylene group is of one to six carbon atoms; cycloalkyl of three to eight carbon atoms; cycloalkylalkyl, wherein the cycloalkyl group is of three to eight carbon atoms and the alkylene group is of one to ten carbon atoms; halo; haloalkyl of one to six carbon atoms; $C_{2-9}$ heterocyclyl; $C_{2-9}$ (heterocyclyl)oxy; $C_{3-10}$ (heterocyclyl)oyl; hydroxyl; hydroxyalkyl of one to six carbon atoms; nitro; nitroalkyl of one to six carbon atoms; N-protected amino; N-protected aminoacyl, wherein the alkylene group is of one to six carbon atoms; thioalkoxy of one to six carbon atoms; thioalkoxyalkyl, wherein the alkyl and alkylene groups are independently of from one to six carbon atoms; —(CH$_2$)$_q$CO$_2$R$_A$, wherein q is zero to four and $R_A$ is selected from the group consisting of (a) $C_{1-6}$ alkyl, (b) $C_6$ or $C_{10}$ aryl and (c) arylalkyl, wherein the alkylene group is of one to six carbon atoms; —(CH$_2$)$_q$CONR$_B$R$_C$, wherein $R_B$ and $R_C$ are independently selected from the group consisting of (a) hydrogen, (b) $C_{1-6}$ alkyl, (c) $C_6$ or $C_{10}$ aryl and (d) arylalkyl, wherein the alkylene group is of one to six carbon atoms; —(CH$_2$)$_q$SO$_2$R$_D$, wherein $R_D$ is selected from the group consisting of (a) $C_{1-6}$ alkyl, (b) $C_6$ or $C_{10}$ aryl and (c) arylalkyl, wherein the alkylene group is of one to six carbon atoms; —(CH$_2$)$_q$SO$_2$NR$_E$R$_F$, wherein $R_E$ and $R_F$ are independently selected from the group consisting of (a) hydrogen, (b) alkyl, (c) $C_6$ or $C_{10}$ aryl and (d) arylalkyl, wherein the alkylene group is of one to six carbon atoms; —(CH$_2$)$_q$NR$_G$R$_H$, wherein $R_G$ and $R_H$ are independently selected from the group consisting of (a) hydrogen; (b) an N-protecting group; (c) alkyl of one to six carbon atoms; (d) alkenyl of two to six carbon atoms; (e) alkynyl of two to six carbon atoms; (f) $C_6$ or $C_{10}$ aryl; (g) arylalkyl, wherein the alkylene group is of one to six carbon atoms; (h) cycloalkyl of three to eight carbon atoms and (i) cycloalkylalkyl, wherein the cycloalkyl group is of three to eight carbon atoms, and the alkylene group is of one to ten carbon atoms, with the proviso that no two groups are bound to the nitrogen atom through a carbonyl group or a sulfonyl group; $C_{1-6}$ perfluoroalkyl; $C_{1-6}$ perfluoroalkoxy; $C_6$ or $C_{10}$ aryloxy; $C_{3-8}$ cycloalkoxy; $C_{9-14}$ cycloalkylalkoxy; or $C_{7-16}$ arylalkoxy;

$R_5$ is C(O)R$_{13}$, C(S)R$_{13}$, C(O)OR$_{13}$, C(O)NR$_{13}$R$_{14}$, C(S)NR$_{13}$R$_{14}$, C(NH)R$_{13}$, or S(O$_2$)R$_{13}$, wherein each of $R_{13}$ and $R_{14}$, independently, represents hydrogen, an optionally substituted $C_{1-12}$ alkyl, an optionally substituted $C_{1-7}$ heteroalkyl, an optionally substituted $C_6$ or $C_{10}$ aryl, an optionally substituted $C_{2-9}$ heteroaryl, an optionally substituted $C_{7-16}$ aralkyl, or an optionally substituted $C_{2-15}$ heteroaralkyl; and $R_6$ is hydrogen, $C_{1-6}$ alkyl, an optionally substituted $C_6$ or $C_{10}$ aryl, an optionally substituted $C_{7-16}$ aralkyl, an optionally substituted $C_{2-9}$ heteroaryl, or an optionally substituted $C_{2-15}$ heteroaralkyl, wherein when each of $R_1$, $R_2$, $R_4$, and $R_6$ through $R_{11}$ is selected from the group consisting of hydrogen, amino, halide, and hydroxyl and Z is $CH_2$, $R_3$ is not hydroxyl or methoxyl. In some instances, the bond indicated by (a) is a double bond, and each of $R_1$, $R_2$, $R_4$, $R_6$, $R_7$, $R_8$, $R_{10}$, and $R_{11}$, independently, represents hydrogen. In some instances, each of $R_3$ and $R_9$, independently, represents alkyl of one to six carbon atoms; alkoxy of one to six carbon atoms; halo; or amino.

The invention additionally features a pharmaceutical composition that includes: (i) any of the Nec compounds described herein, e.g., Nec-1e, Nec-2b, or Nec-3b compounds; and (ii) a pharmaceutically acceptable excipient.

The invention further features a kit that includes: (i) any of the Nec compounds described herein, e.g., Nec-1e, Nec-2b, or Nec-3b compounds; and (ii) instructions for administering the compound to a subject with a disease or condition listed in Table 1.

The invention additionally features a method of identifying a candidate compound as a compound that selectively inhibits RIP1, including the following steps: a) incubating a mixture including a RIP1 polypeptide and the candidate compound under conditions such that, in the absence of the compound, the RIP1 polypeptide is capable of undergoing phosphorylation at a reference level; b) detecting the level of RIP1 phosphorylation; c) determining the ratio of the level of RIP1 phosphorylation to the reference level; d) incubating a second mixture including a RIP2 or RIP3 polypeptide and the compound under conditions such that, in the absence of the compound, the RIP2 polypeptide is capable of undergoing phosphorylation at a second reference level; e) detecting the level of RIP2 or RIP3 phosphorylation; and f) determining the ratio of the level of RIP2 or RIP3 phosphorylation to the second reference level. In this method, if the ratio determined in step c) is less than the ratio determined in step f), the compound is found to inhibit RIP1 selectively.

The invention further features a method of identifying a candidate compound as a compound that selectively inhibits RIP1, including the following steps: a) contacting a RIP1 polypeptide and the candidate compound; b) detecting binding of the compound to the RIP1 polypeptide; c) contacting a RIP2 or RIP3 polypeptide and the compound; and d) detecting binding of the compound to the RIP2 or RIP3 polypeptide. In this method, a compound that binds the RIP1 polypeptide and not the RIP2 or RIP3 polypeptide is found to inhibit RIP1 selectively.

Definitions

As used throughout this specification and the appended claims, the following terms have the meanings specified:

By "Nec-1a compound" is meant a compound of formula (VII):

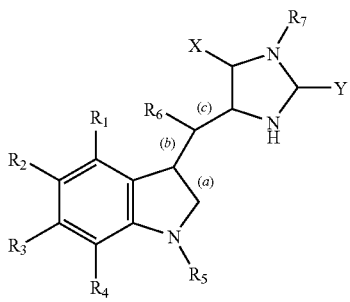

(VII)

wherein each of $R_1$, $R_2$, $R_3$, and $R_4$ is independently selected from the group consisting of hydrogen, carboxy, methyl, hydroxyl, methoxyl, amino, and nitro; $R_5$ is selected from the group consisting of hydrogen, $C_{1-6}$ alkyl, and acyl; $R_6$ is selected from the group consisting of $C_{1-6}$ alkyl, acyl, halogen, hydrogen, or hydroxyl; $R_7$ is selected from the group consisting of methyl, hydroxyl, carboxyl, and $C_{1-6}$ alkyl groups; X is selected from the group consisting of =O, —OH, and —H; Y is selected from the group consisting of =S and —$SR_8$, where $R_8$ is either hydrogen or a $C_{1-6}$ alkyl group; and each of the bonds (a), (b), and (c) independently is either a double or single bond, provided, however, that bond (a) and bond (b) are not both double bonds.

By "Nec-1b compound" is meant a compound of one of formulas (VIII)-(XV).

Compounds of formula (VIII) have the structure:

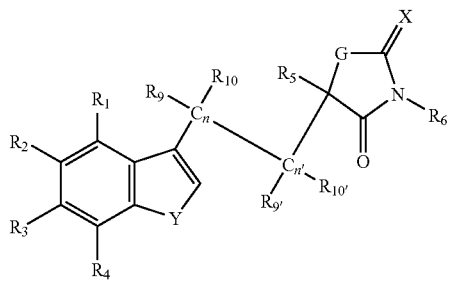

(VIII)

wherein X represents O; Y represents S; G represents O or $NR_7$; each of $R_1$, $R_2$, and $R_3$, independently, represents H, OH, $OR_8$, F, Cl, Br, I, $N(R_8)_2$, COOH, $CO_2R_8$, $NO_2$, NHC(O)$R_8$, lower alkyl, substituted lower alkyl, aryl, substituted aryl, heteroaryl, or substituted heteroaryl; $R_4$ represents H, OH, $OR_8$, F, Cl, Br, I, $N(R_8)_2$, COOH, $CO_2R_8$, $NO_2$, NHC(O)$R_8$, methyl, methoxyl, lower alkyl, substituted lower alkyl, aryl, substituted aryl, heteroaryl, or substituted heteroaryl, amine, or piperizine; each of $R_5$, $R_6$, and $R_7$, independently, represents H or lower alkyl; $R_8$ represents lower alkyl, substituted lower alkyl, aryl, substituted aryl, arylalkyl, alkenyl, alkynyl, heteroaryl, or substituted heteroaryl; each of $R_9$, $R_{10}$, $R_{9'}$, $R_{10'}$, independently, represents H, F, Cl, Br, I, lower alkyl, substituted lower alkyl, or a three to six membered cycloalkyl or substituted cycloalkyl that includes $C_n$ and/or $C_{n'}$; n and n' equals an integer from zero to five.

Compounds of formula (IX) have the structure:

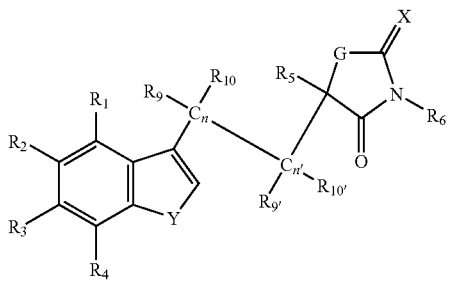

(IX)

wherein X represents O; Y represents $NR_8$; G represents O or $NR_7$; each of $R_1$, $R_2$, and $R_3$, independently, represents H, OH, $OR_8$, F, Cl, Br, I, $N(R_8)_2$, COOH, $CO_2R_8$, $NO_2$, NHC(O)$R_8$, lower alkyl, substituted lower alkyl, aryl, substituted aryl, heteroaryl, or substituted heteroaryl; $R_4$ represents H, OH, $OR_8$, F, Cl, Br, I, $N(R_8)_2$, COOH, $CO_2R_8$, $NO_2$, NHC(O)$R_8$, methyl, methoxyl, lower alkyl, substituted lower alkyl, aryl, substituted aryl, heteroaryl, or substituted heteroaryl, amine, or piperizine; each of $R_5$, $R_6$, and $R_7$, independently, represents H or lower alkyl; $R_8$ represents lower alkyl, substituted lower alkyl, aryl, substituted aryl, arylalkyl, alkenyl, alkynyl, heteroaryl, or substituted heteroaryl; each of $R_9$, $R_{10}$, $R_{9'}$, $R_{10'}$, independently, represents H, F, Cl, Br, lower alkyl, substituted lower alkyl, or a three to six membered cycloalkyl or substituted cycloalkyl that includes $C_n$ and/or $C_{n'}$; n and n' equals an integer from zero to five.

Compounds of formula (X) have the structure:

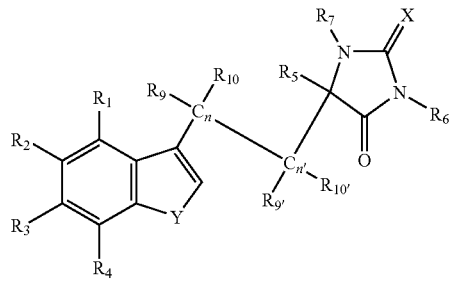

(X)

wherein X represents O; Y represents NH; each of $R_1$, $R_2$, and $R_3$, independently, represents H, $OR_8$, F, Cl, Br, I, $N(R_8)_2$, $CO_2R_8$, $NO_2$, NHC(O)$R_8$, lower alkyl, substituted lower alkyl, aryl, substituted aryl, heteroaryl, or substituted heteroaryl; $R_4$ represents H, $OR_8$, F, Cl, Br, I, $N(R_8)_2$, $CO_2R_8$, $NO_2$, NHC(O)$R_8$, methyl, methoxyl, lower alkyl, substituted lower alkyl, aryl, substituted aryl, heteroaryl, or substituted heteroaryl, amine, or piperizine; each of $R_5$, $R_4$ and $R_7$, independently, represents H or lower alkyl, except $R_6$ can not be methyl, ethyl, propyl, isopropyl or t-butyl when $R_1$, $R_2$, $R_3$, $R_4$, $R_5$ and $R_7$ are H; $R_8$ represents H, lower alkyl, substituted lower alkyl, aryl, substituted aryl, arylalkyl, alkenyl, alkynyl, heteroaryl, or substituted heteroaryl; each of $R_9$, $R_{10}$, $R_{9'}$, $R_{10'}$, independently, represents H, F, Cl, Br, I, lower alkyl, substituted lower alkyl, or a three to six membered cycloalkyl or substituted cycloalkyl that includes $C_n$ and/or $C_{n'}$; n and n' equals an integer from zero to five.

Compounds of formula (XI) have the structure:

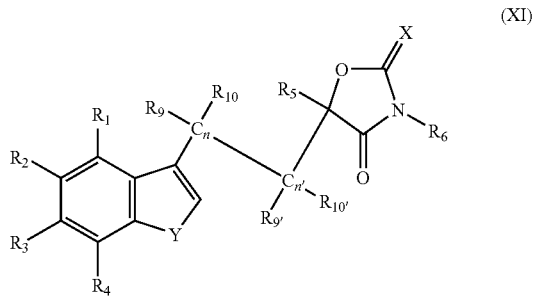

(XI)

wherein X represents O; Y represents NH; each of $R_1$, $R_2$, and $R_3$, independently, represents H, OH, $OR_8$, F, Cl, Br, I, $N(R_8)_2$, COOH, $CO_2R_8$, $NO_2$, $NHC(O)R_8$, lower alkyl, substituted lower alkyl, aryl, substituted aryl, heteroaryl, or substituted heteroaryl; $R_4$ represents H, OH, $OR_8$, F, Cl, Br, I, $N(R_8)_2$, COOH, $CO_2R_8$, $NO_2$, $NHC(O)R_8$, methyl, methoxyl, lower alkyl, substituted lower alkyl, aryl, substituted aryl, heteroaryl, or substituted heteroaryl, amine, or piperizine; each of $R_5$, $R_6$, and $R_7$, independently, represents H or lower alkyl; $R_8$ represents lower alkyl, substituted lower alkyl, aryl, substituted aryl, arylalkyl, alkenyl, alkynyl, heteroaryl, or substituted heteroaryl; each of $R_9$, $R_{10}$, $R_{9'}$, $R_{10'}$, independently, represents H, F, Cl, Br, I, lower alkyl, substituted lower alkyl, or a three to six membered cycloalkyl or substituted cycloalkyl that includes $C_n$ and/or $C_{n'}$; n and n' equals an integer from zero to five.

Compounds of formula (XII) have the structure:

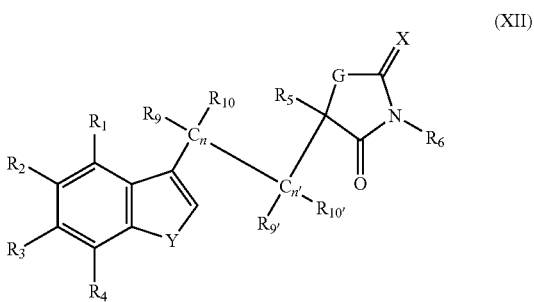

(XII)

wherein X represents S; Y represents S; G represents O or $NR_7$; each of $R_1$, $R_{2\ and\ R3}$, independently, represents H, OH, $OR_8$, F, Cl, Br, I, $N(R_4)_2$, COOH, $CO_2R_8$, $NO_2$, $NHC(O)R_8$, lower alkyl, substituted lower alkyl, aryl, substituted aryl, heteroaryl; or substituted heteroaryl; $R_4$ represents H, OH, $OR_8$, F, Cl, Br, $N(R_8)_2$, COOH, $CO_2R_8$, $NO_2$, $NHC(O)R_8$, methyl, methoxyl, lower alkyl, substituted lower alkyl, aryl, substituted aryl, heteroaryl, or substituted heteroaryl, amine, or piperizine; each of $R_5$, $R_6$, and $R_7$, independently, represents H or lower alkyl; $R_8$ represents lower alkyl, substituted lower alkyl, aryl, substituted aryl, arylalkyl, alkenyl, alkynyl, heteroaryl, or substituted heteroaryl; each of $R_9$, $R_{10}$, $R_{9'}$, $R_{10'}$, independently, represents H, F, Cl, Br, I, lower alkyl, substituted lower alkyl, or a three to six membered cycloalkyl or substituted cycloalkyl that includes $C_n$ and/or $C_{n'}$; n and n' equals an integer from zero to five.

Compounds of formula (XIII) have the structure:

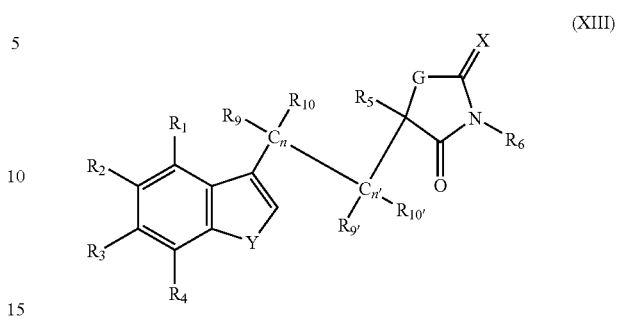

(XIII)

wherein X represents S; Y represents $NR_8$; G represents O or $NR_7$; each of $R_1$, $R_2$, and $R_3$, independently, represents H, OH, $OR_8$, F, Cl, Br, I, $N(R_8)_2$, COOH, $CO_2R_8$, $NO_2$, $NHC(O)R_8$, lower alkyl, substituted lower alkyl, aryl, substituted aryl, heteroaryl, or substituted heteroaryl; $R_4$ represents H, OH, $OR_8$, F, Cl, Br, I, $N(R_8)_2$, COOH, $CO_2R_8$, $NO_2$, $NHC(O)R_8$, methyl, methoxyl, lower alkyl, substituted lower alkyl, aryl, substituted aryl, heteroaryl, or substituted heteroaryl, amine, or piperizine; each of $R_5$, $R_6$, and $R_7$, independently, represents H or lower alkyl; $R_8$ represents lower alkyl, substituted lower alkyl, aryl, substituted aryl, arylalkyl, alkenyl, alkynyl, heteroaryl, or substituted heteroaryl; each of $R_9$, $R_{10}$, $R_{9'}$, $R_{10'}$, independently, represents H, F, Cl, Br, I, lower alkyl, substituted lower alkyl, or a three to six membered cycloalkyl or substituted cycloalkyl that includes $C_n$ and/or $C_{n'}$; n and n' equals an integer from zero to five.

Compounds of formula (XIV) have the structure:

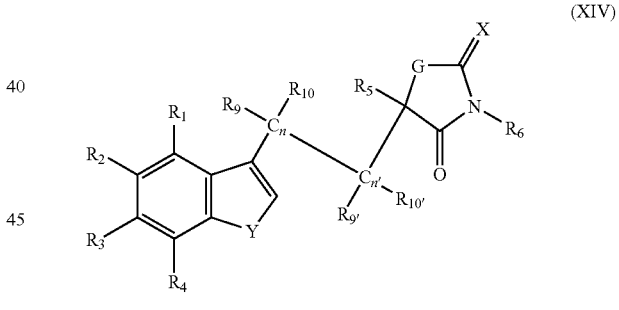

(XIV)

wherein X represents S; Y represents NH; G represents O or $NR_7$; each of $R_1$, $R_2$, and $R_3$, independently, represents H, $OR_8$, F, Cl, Br, I, $N(R_8)_2$, $CO_2R_8$, $NO_2$, $NHC(O)R_8$, lower alkyl, substituted lower alkyl, aryl, substituted aryl, heteroaryl, or substituted heteroaryl; $R_4$ represents H, $OR_8$, F, Cl, Br, I, $N(R_8)_2$, $CO_2R_8$, $NO_2$, $NHC(O)R_8$, aryl, substituted aryl, heteroaryl, or substituted heteroaryl, amine, piperizine, lower alkyl and substituted lower alkyl except for methyl and methoxyl; each of $R_5$, $R_6$ and $R_7$, independently, represents H or lower alkyl, except $R_6$ can not be methyl when $R_1$, $R_2$, $R_3$, $R_4$, $R_5$ and $R_7$ are H; $R_8$ represents H, lower alkyl, substituted lower alkyl, aryl, substituted aryl, arylalkyl, alkenyl, alkynyl, heteroaryl, or substituted heteroaryl; each of $R_9$, $R_{10}$, $R_{9'}$, $R_{10'}$, independently, represents H, F, Cl, Br, I, lower alkyl, substituted lower alkyl, or a three to six membered cycloalkyl or substituted cycloalkyl that includes $C_n$ and/or $C_{n'}$; n and n equals an integer from zero to five.

Compounds of formula (XV) have the structure:

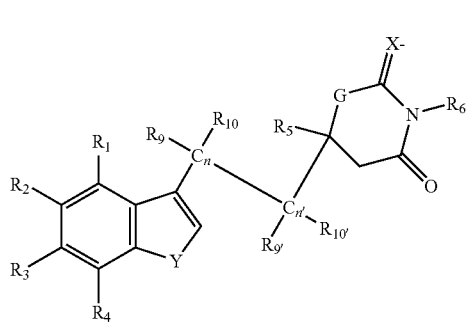

(XV)

wherein X represents S or O; Y represents S, NH or $NR_8$; G represents O or $NR_7$; each of $R_1$, $R_2$, and $R_3$, independently, represents H, $OR_8$, F, Cl, Br, I, $N(R_8)_2$, $CO_2R_8$, $NO_2$, NHC(O)$R_8$, lower alkyl, substituted lower alkyl, aryl, substituted aryl, heteroaryl, or substituted heteroaryl; $R_4$ represents H, $OR_8$, F, Cl, Br, I, $N(R_8)_2$, $CO_2R_8$, $NO_2$, NHC(O)$R_8$, aryl, substituted aryl, heteroaryl, or substituted heteroaryl, amine, piperizine, lower alkyl and substituted lower alkyl; each of $R_5$, $R_6$ and $R_7$, independently, represents H or lower alkyl; $R_8$ represents H, lower alkyl, substituted lower alkyl, aryl, substituted aryl, arylalkyl, alkenyl, alkynyl, heteroaryl, or substituted heteroaryl; each of $R_9$, $R_{10}$, $R_{9'}$, and $R_{10'}$, independently, represents H, F, Cl, Br, I, lower alkyl, substituted lower alkyl, or a three to six membered cycloalkyl or substituted cycloalkyl that includes $C_n$ and/or $C_{n'}$; n and n' equals an integer from zero to five.

By "Nec-1c compound" is meant a Nec-1b compound that is not also a Nec-1a compound.

By "Nec-1d compound" is meant a Nec-1a compound that is not also a Nec-1b compound.

By "Nec-1 compound" is meant a Nec-1a compound, a Nec-1b compound, or a compound of formula (XVI).

Compounds of formula (XVI) have the structure:

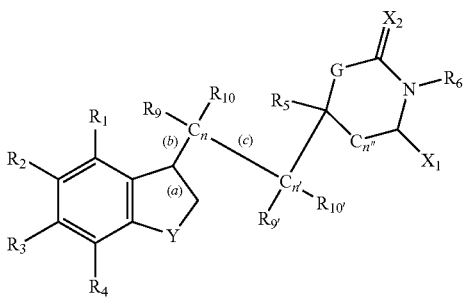

(XVI)

wherein each of $X_1$ and $X_2$, independently, represents =S, =O, =N, H, $R_{11}$, $SR_{11}$, $NR_{11}$, or $OR_{11}$; Y represents S, NH or $NR_8$; G represents $CH_2$, O, $SR_7$, or $NR_7$; each of $R_1$, $R_2$, and $R_3$, independently, represent H, OH, $OR_8$, F, Cl, Br, I, $N(R_8)_2$, COOH, $CO_2R_8$, $NO_2$, NHC(O)$R_8$, $C_{1-7}$ alkyl, $C_{2-7}$ alkenyl, $C_{2-7}$ alkynyl, $C_{6-12}$ aryl, acyl, acetyl, acylamino, $C_{2-9}$ heteroaryl; $R_4$ represents H, OH, $OR_8$, F, Cl, Br, I, $N(R_8)_2$, COOH, $CO_2R_8$, $NO_2$, NHC(O)$R_8$, acyl, acetyl, acylamino, $C_{1-7}$alkyl, $C_{2-7}$ alkenyl, $C_{2-7}$ alkynyl, $C_{6-12}$ aryl, $C_{2-9}$ heteroaryl, amine, or piperizine; each of $R_5$, $R_6$, and $R_7$, independently, represents H, OH, $OR_8$, F, Cl, Br, I, $N(R_8)_2$, acyl, acetyl, acylamino, $NO_2$, $C_{1-7}$ alkyl, $C_{2-7}$ alkenyl, or $C_{2-7}$ alkenyl; $R_8$ represents H, OH, $NO_2$, F, Cl, Br, I, $C_{1-7}$ alkyl, $C_{6-12}$ aryl, arylalkyl, $C_{2-7}$ alkenyl, $C_{2-7}$ alkynyl, $C_{2-9}$ heteroaryl, acetyl, methoxyl, amino, acylamino, acyl, or halogen; each of $R_9$, $R_{10}$, $R_{9'}$, $R_{10'}$, independently, represent H, OH, F, Cl, Br, I, $C_{1-7}$ alkyl, $C_{2-7}$ alkenyl, $C_{2-7}$ alkynyl, or a three to six membered cycloalkyl that includes $C_n$ and/or $C_{n'}$, or $R_9$ and/or $R_{10}$ can be absent; $R_{11}$ represents H, OH, $NO_2$, F, Cl, Br, I, acetyl, methoxyl, amino, acylamino, $C_{1-7}$ alkyl, $C_{2-7}$ alkenyl, $C_{2-7}$ alkynyl, or acyl; each of n and n' is an integer from zero to five, inclusive; n" is 0 or 1; and each of bonds (a), (b), and (c) is, independently, a single bond or a double bond, provided that bond (a) and bond (b) are not both double bonds. Exemplary acyl groups are:

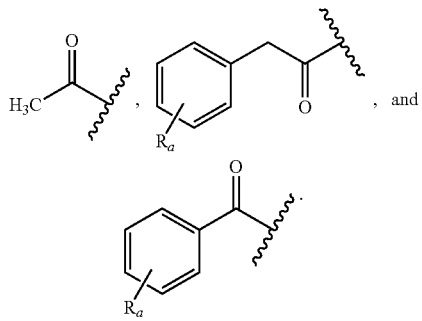

In one embodiment, each of $R_1$, $R_2$, $R_3$, $R_4$, $R_5$, $R_9$, and $R_{10}$ is hydrogen; $R_6$ is a methyl group; n is 1; n' and n" are each 0; $X_1$ is =O; $X_2$ is =S; Y and G are each —NH—; bond (a) is a double bond; and bonds (b) and (c) are each single bonds.

In other embodiments, each of $R_1$, $R_2$, $R_3$, $R_5$, $R_9$, and $R_{10}$ is hydrogen; $R_4$, is methyl or halogen; $R_6$ is a methyl group; n is 1; n' and n" are each 0; $X_1$ is =O; $X_2$ is =S; Y and G are each —NH—; bond (a) is a double bond; and bonds (b) and (c) are each single bonds.

In other embodiments, each of $R_1$, $R_2$, $R_3$, $R_5$, $R_9$, and $R_{10}$ is hydrogen; $R_4$, is hydrogen, methyl, or halogen; $R_6$ is a methyl group or hydrogen; n is 1; n' and n" are each 0; $X_1$ is =O; $X_2$ is =O; Y and G are each —NH—; bond (a) is a double bond; and bonds (b) and (c) are each single bonds.

By "Nec-1e compound" is meant a Nec-1 compound that is neither a Nec-1a compound nor a Nec-1b compound.

By "Nec-2a compound" is meant a compound of formula (XVII) or (XVIII).

Compounds of formula (XVII) have the structure:

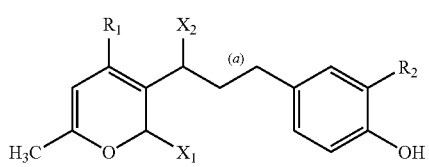

(XVII)

wherein each of $X_1$ and $X_2$ is independently selected from the group consisting of =O, —OH, and —H; $R_1$ is selected from the group consisting of hydrogen and hydroxyl; $R_2$ is selected from the group consisting of hydrogen, sulfate, nitro, and halide; and the bond (a) is either a single or double bond.

Compounds of formula (XVIII) have the structure:

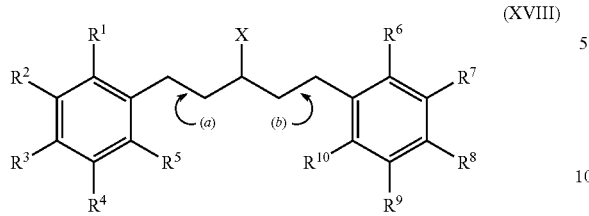

(XVIII)

wherein each R is independently selected from the group consisting of H or CH₃; the bond (a) is either a single or double bond; the bond (b) is either a single or double bond; and X is selected from the group consisting of =O, —OH, and —H.

By "Nec-2 compound" is meant a Nec-2a compound or a compound of formula (XIX).

Compounds of formula (XIX) have the structure:

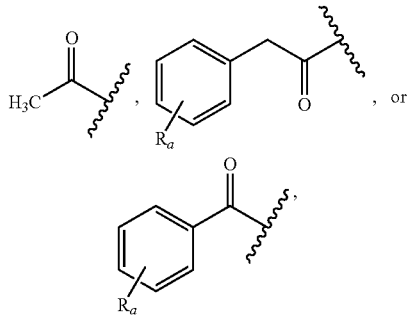

(XIX)

wherein each of $R_1$, $R_2$, $R_3$, $R_4$, and $R_5$, independently, represents H, OH, SO₂, NO₂, F, Cl, Br, I, acyl, acetyl, alkyl, methoxyl, amino, acylamino,

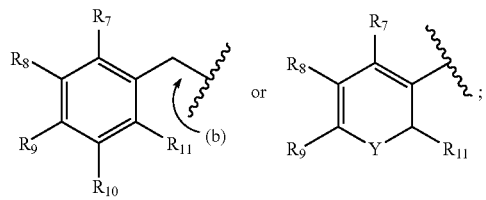

wherein $R_a$ is a $C_{6-42}$ aryl substituent; the bond (a) is either a single or double bond; X represents =O, OH, or H; $R_6$ is:

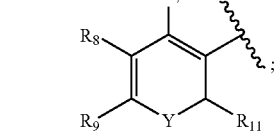

the bond (b) is either a single or double bond, with the proviso that bond (b) is a single bond when n=0; Y is O or S; each of $R_7$, $R_8$, $R_9$, and $R_{10}$, independently, represents H, OH, SO₂, NO₂, F, Cl, Br, I, acyl, acetyl, alkyl, methoxyl, amino, acylamino,

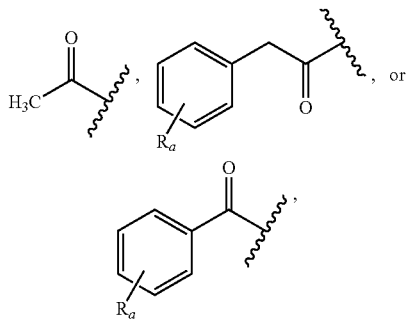

wherein $R_a$ is an $C_{6-12}$ aryl substituent; and $R_{11}$ represents =O, OH, or H.

In one embodiment, $R_6$ is:

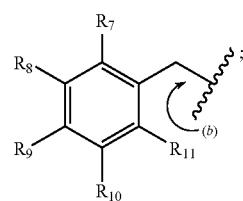

each of $R_1$, $R_4$, $R_5$, $R_7$, $R_{10}$, and $R_{11}$ is hydrogen; each of $R_2$, $R_3$, $R_8$, and $R_9$ is —CH₃; X is =O; and bonds (a) and (b) are each double bonds.

In another embodiment $R_6$ is:

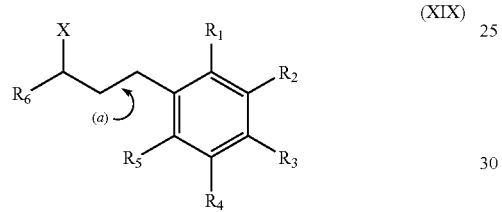

each of $R_{11}$ and X is =O; $R_7$ and $R_3$ are each a hydroxyl group; $R_2$ is a nitro group; $R_9$ is a methyl group; each of $R_1$, $R_4$, $R_5$, and $R_s$ is hydrogen; and the bond (a) is a double bond.

In other embodiments, when the Nec-2 compound has the formula:

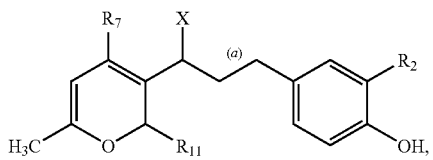

if $R_{11}$ is =O, then X is not =O; or $R_7$ is not a hydroxyl group; or $R_2$ is a not a nitro group; or the bond (a) is not a double bond. If X is =O, then $R_{11}$ is not =O; or $R_7$ is not a hydroxyl group; or $R_2$ is not a nitro group; or the bond (a) is not a double bond. If $R_7$ is a hydroxyl group, then $R_{11}$ and X are not both =O; or $R_2$ is a not a nitro group; or the bond (a) is not a double bond. If $R_2$ is a nitro group, then $R_{11}$ and X are not both =O;

or $R_7$ is not a hydroxyl group; or the bond (a) is not a double bond. If the bond (a) is a double bond, then $R_{11}$ and X are not both =O; or $R_7$ is not a hydroxyl group; or $R_2$ is a not a nitro group; or the bond (a) is not a double bond.

By "Nec-2b compound" is meant a Nec-2 compound that is not also a Nec-2a compound.

By "Nec-3a compound" is meant a compound of formula (XX):

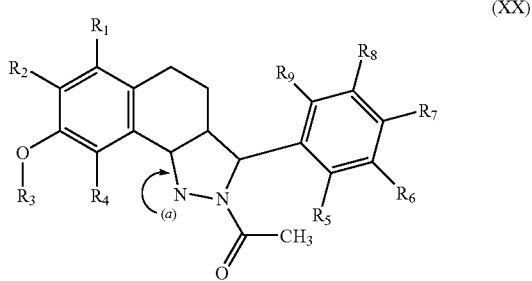

wherein each of $R_1$, $R_2$, $R_4$ $R_5$, $R_6$, $R_7$, $R_8$, and $R_9$ is independently selected from the group consisting of hydrogen, amino, halide, and hydroxyl; $R_3$ is selected from the group consisting of hydrogen and methyl; and the bond (a) is either a single or double bond.

By "Nec-3 compound" is meant a Nec-3a compound, a compound of formula (XXI), or any of compounds (1) to (217).

Compounds of formula (XXI) have the structure:

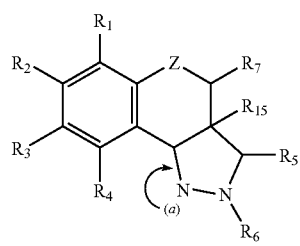

wherein Z is a bond, $CH_2$, $CH_2CH_2$, O, S, S(O), $S(O_2)$, or $NR_8$; where $R_8$ is alkyl, an aralkyl, or heteroaralkyl;

the bond indicated by (a) can be a single or double bond;

each of $R_1$, $R_2$, $R_3$, and $R_4$ independently, represents H; alkanoyl of one to six carbon atoms; alkyl of one to six carbon atoms; alkoxy of one to six carbon atoms; alkoxyalkyl, wherein the alkyl and alkylene groups are independently of one to six carbon atoms; alkylsulfinyl of one to six carbon atoms; alkylsulfinylalkyl, wherein the alkyl and alkylene groups are independently of one to six carbon atoms; alkylsulfonyl of one to six carbon atoms; alkylsulfonylalkyl, wherein the alkyl and alkylene groups are independently of one to six carbon atoms; amino; aminoacyl of one to six carbon atoms; $C_{6-12}$ aryl; $C_{7-16}$ arylalkyl, wherein the alkylene group is of one to six carbon atoms; $C_7$ or $C_{11}$ aryloyl; azido; azidoalkyl of one to six carbon atoms; carboxaldehyde; (carboxaldehyde)alkyl, wherein the alkylene group is of one to six carbon atoms; cycloalkyl of three to eight carbon atoms; cycloalkylalkyl, wherein the cycloalkyl group is of three to eight carbon atoms and the alkylene group is of one to ten carbon atoms; halo; haloalkyl of one to six carbon atoms; $C_{2-9}$ heterocyclyl; $C_{2-9}$(heterocyclyl)oxy; $C_{3-10}$(heterocyclyl)oyl; hydroxy; hydroxyalkyl of one to six carbon atoms; nitro; nitroalkyl of one to six carbon atoms; N-protected amino; N-protected aminoalkyl, wherein the alkylene group is of one to six carbon atoms; thioalkoxy of one to six carbon atoms; thioalkoxyalkyl, wherein the alkyl and alkylene groups are independently of one to six carbon atoms; —$(CH_2)_qCO_2R_A$, wherein q is zero to four and $R_A$ is selected from the group consisting of (a) $C_{1-6}$alkyl, (b) $C_{6-12}$ aryl and (c) arylalkyl, wherein the alkylene group is of one to six carbon atoms;

—$(CH_2)_qCONR_BR_C$, wherein $R_B$ and $R_C$ are independently selected from the group consisting of (a) hydrogen, (b) $C_{1-6}$ alkyl, (c) $C_{6-12}$ aryl and (d) arylalkyl, wherein the alkylene group is of one to six carbon atoms; —$(CH_2)_qSO_2R_D$, wherein $R_D$ is selected from the group consisting of (a) $C_{1-6}$ alkyl, (b) $C_{6-12}$ aryl and (c) arylalkyl, wherein the alkylene group is of one to six carbon atoms; —$(CH_2)_qSO_2NR_ER_F$, wherein $R_E$ and $R_F$ are independently selected from the group consisting of (a) hydrogen, (b) alkyl, (c) $C_{6-12}$ aryl and (d) arylalkyl, wherein the alkylene group is of one to six carbon atoms; —$(CH_2)_qNR_GR_H$, wherein $R_G$ and $R_H$ are independently selected from the group consisting of (a) hydrogen; (b) an N-protecting group; (c) alkyl of one to six carbon atoms; (d) alkenyl of two to six carbon atoms; (e) alkynyl of two to six carbon atoms; (f) $C_{6-12}$ aryl; (g) arylalkyl, wherein the alkylene group is of one to six carbon atoms; (h) cycloalkyl of three to eight carbon atoms and (i) cycloalkylalkyl, wherein the cycloalkyl group is of three to eight carbon atoms, and the alkylene group is of one to ten carbon atoms, with the proviso that no two groups are bound to the nitrogen atom through a carbonyl group or a sulfonyl group; $C_{1-6}$ perfluoroalkyl; $C_{1-6}$ perfluoroalkoxy; $C_6$ or $C_{10}$ aryloxy; $C_{3-8}$ cycloalkoxy; $C_{9-14}$ cycloalkylalkoxy; or $C_{7-16}$ arylalkoxy;

$R_5$ is an optionally substituted $C_6$ or $C_{10}$ aryl or an optionally substituted $C_{2-9}$ heteroaryl;

$R_6$ is $C(O)R_9$, $C(S)R_9$, $C(O)OR_9$, $C(O)NR_9R_{10}$, $C(S)NR_9R_{10}$, $C(NH)R_9$, or $S(O_2)R_9$, where each of $R_9$ and $R_{10}$, independently, represents H, an optionally substituted $C_{1-12}$ alkyl, an optionally substituted $C_{1-7}$ heteroalkyl, an optionally substituted $C_6$ or $C_{10}$ aryl, an optionally substituted $C_{2-9}$ heteroaryl, an optionally substituted $C_{7-16}$ aralkyl, or an optionally substituted $C_{2-15}$ heteroaralkyl;

$R_7$ is H, $C_{1-6}$ alkyl, an optionally substituted $C_6$ or $C_{10}$ aryl, an optionally substituted $C_{7-16}$ aralkyl, an optionally substituted $C_{2-9}$ heteroaryl, or an optionally substituted $C_{2-15}$ heteroaralkyl; and $R_{15}$ is H, an optionally substituted $C_{1-12}$ alkyl, or an optionally substituted $C_{1-7}$ heteroalkyl.

In one embodiment, the bond indicated by (a) is a single bond. In a desirable embodiment, the bond indicated by (a) is a double bond.

In another embodiment, Z is a bond, $CH_2CH_2$, O, S, S(O), $S(O_2)$, or $NR_8$; where $R_8$ is as defined previously herein.

In another embodiment, $R_5$ is an optionally substituted $C_{10}$ aryl or an optionally substituted $C_{2-9}$ heteroaryl group.

In another embodiment, $R_6$ is $C(O)R_9$, where $R_9$ is an optionally substituted $C_{2-12}$ alkyl group. Desirable examples are those in which $R_9$ is a $C_{2-12}$alkyl group substituted with a moiety that increases water solubility such as, for example, a morpholino group, a morpholino amide or morpholinoalkyl ester moiety (e.g. $R_9$ is —$(CH_2)_n$-morpholino, —$(CH_2)_n$CO-morpholino-, or —$(CH_2)_nCO_2(CH_2)_2$-morpholino); a piperazinyl group, a piperazinyl amide, or a piperazinylalkyl ester moiety (e.g. $R_9$ is —$(CH_2)_n$-piperizinyl, is —$(CH_2)_n$—$N_4$-alkylpiperizinyl, —$(CH_2)_n$CO—$N_4$-alkylpiperizinyl-, —$(CH_2)_nCO_2(CH_2)_2$-piperizinyl, or —$(CH_2)_nCO_2(CH_2)_2$—$N_4$-alkylpiperizinyl), where n is an integer of from 1 to 6;

hydroxyl groups (e.g. from 1 to 4 hydroxyl substituents), $C_{2-7}$ acyloxy groups, $C_{2-7}$ carboxylic acid esters, a primary amine, a secondary amine, or a tertiary amine. Also desirable are those alkyl substituents that include a recognition moiety, such as, for example, a biotin moiety, such as, for example —$(CH_2)_n$NH-biotinyl.

In another embodiment, $R_6$ is $C(O)R_9$, $C(S)R_9$, $C(O)OR_9$, $C(O)NR_9R_{10}$, $C(S)NR_9R_{10}$, or $S(O_2)R_9$, where $R_9$ is an optionally substituted $C_6$ or $C_{10}$ aryl, an optionally substituted $C_{2-9}$ heteroaryl, an optionally substituted $C_{7-16}$ aralkyl, or an optionally substituted $C_{2-15}$ heteroaralkyl; and $R_{10}$ is H, an optionally substituted $C_{1-12}$ alkyl, an optionally substituted $C_6$ or $C_{10}$ aryl, an optionally substituted $C_{2-9}$ heteroaryl, an optionally substituted $C_{7-16}$ aralkyl, or an optionally substituted $C_{2-15}$ heteroaralkyl.

In another embodiment, $R_6$ is $C(S)R_9$, $C(O)OR_9$, $C(O)NR_9R_{10}$, $C(S)NR_9R_{10}$, or $S(O_2)R_9$, where $R_9$ and $R_{10}$ are as defined above.

In another embodiment, Z is $CH_2$; each of $R_1$ and $R_4$ is H; $R_2$ is H, $C_{1-6}$ alkoxy, $C_{1-6}$ thioalkoxy, halo, or together with $R_3$ forms a dioxomethylene or a dioxoethylene group; $R_3$ is H, $C_{1-6}$ alkoxy, $C_{1-6}$ thioalkoxy, halo, or together with $R_2$ forms a dioxomethylene or a dioxoethylene group; and $R_5$ is

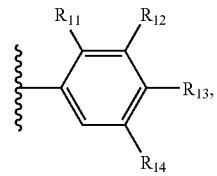

where each of $R_{11}$, $R_{12}$, and $R_{13}$, independently, represents H, $C_{1-6}$ alkoxy, or $C_{1-6}$ thioalkoxy, where $R_{11}$ and $R_{12}$ or $R_{12}$ and $R_{13}$ can together form a dioxomethylene or a dioxoethylene group, and $R_{14}$ is H.

In a desirable example, Z is $CH_2$; the bond indicated by (a) is a double bond each of $R_1$, $R_2$, and $R_4$ is hydrogen; $R_3$ is methoxy; $R_5$ is a 4-methoxyphenyl ring; $R_6$ is a methyl group; and $R_7$ is H.

In yet another embodiment, Z is $CH_2$; the bond indicated by (a) is a double bond; each of R, $R_2$, and It, is independently selected from the group consisting of: hydrogen, amino, halide, and hydroxyl; $R_3$ is hydrogen or methoxy; $R_5$ is a phenyl ring whose substituents at the 2-, 3-, 4-, 5-, and 6-positions are independently selected from the group consisting of: hydrogen, amino, halide, and hydroxyl; $R_7$ is H; and $R_9$ is methyl.

In a desirable example, each of $R_1$, $R_2$, and $R_4$ is hydrogen; $R_3$ is methoxy; $R_5$ is a 4-fluorophenyl ring; $R_6$ is a methyl group; $R_7$ is H; Z is $CH_2$; and the bond indicated by (a) is a double bond.

By "Nec-3b compound" is meant a Nec-3 compound that is not also a Nec-3a compound.

"Nec compound," "necrostatin compound," and "necrostatin" are used interchangeably herein and refer to a Nec-1 compound, a Nec-2 compound, or a Nec-3 compound.

By "decreasing necrosis" is meant reducing the number of cells which undergo necrosis relative to a control cell receiving a cell death stimulus, such as, for example, by contacting the cell with TNFα or DMSO, without a candidate small molecule inhibitor. Preferably necrosis is decreased 10% relative to a control. More preferably necrosis is decreased 50% relative to a control. Most preferably necrosis is decreased 90% relative to a control. Preferably a decrease in necrosis is tested by determining the ATP level in a cell which has received a candidate compound, such as a compound from a chemical library, and comparing it to the ATP level in a control cell. Necrosis is decreased in a cell treated with a candidate compound in which the ATP level does not decrease as much as it does in the control cell.

By "candidate compound" is meant a chemical, be it naturally-occurring or artificially-derived, that is surveyed for its ability to modulate the level of necrosis by employing one of the assay methods described herein. Candidate compounds may include, for example, peptides, polypeptides, synthesized organic molecules, naturally occurring organic molecules, nucleic acid molecules, and components thereof.

By "cell death" is meant the death of a cell by either apoptosis or necrosis.

As used herein, by "necrosis" is meant caspase-independent cell death characterized by cellular ATP depletion. Preferably the cell is depleted of ATP 10% relative to a control cell, receiving vehicle only (for example, DMSO). More preferably, the cell is depleted of ATP 50% relative to a control cell. Most preferably, the cell is depleted of ATP 90% relative to a control cell. Preferably, necrosis is tested by determining the ATP level in a cell which has received a compound, for example, zVAD-fmk, DMSO, or TNFα, and comparing it to the ATP level in a cell receiving vehicle only. Necrosis occurs in a cell treated with a candidate compound in which the ATP level decreases relative to the control cell.

Necrosis may be liquefactive, may affect adipose or hepatic tissue, and may be caseous or fibrinoid. A cell may undergo necrosis in response to ischemic cell injury or viral infection.

By "caspase-independent cell death" is meant cell death that occurs when apoptosis is prevented. Apoptosis may be prevented by contacting a cell with a caspase inhibitor such as zVAD-fmk at a concentration sufficient enough that the cell survives when stimulated to undergo apoptosis, for example, by treatment with an apoptosis-promoting drug or ionizing radiation.

By "apoptosis" is meant cell death characterized by any of the following properties: nuclear condensation, DNA fragmentation, membrane blebbing, or cell shrinkage.

By "modulation of intracellular signaling pathways mediated by TNFα" is meant a change in the communication between components of a cell in response to contacting the cell with TNFα. The change may be in the way or duration in which proteins within the cell interact, or the way or duration in which proteins are altered, such as by phosphorylation or dephosphorylation, or in the way or duration in which proteins interact with DNA.

By "modulation of intracellular signaling pathways mediated by DMSO" is meant a change in the communication between components of a cell in response to contacting the cell with DMSO. The change may be in the way or duration in which proteins within the cell interact, or the way or duration in which proteins are altered, such as by phosphorylation or dephosphorylation, or in the way or duration in which proteins interact with DNA.

By "treating" is meant administering a pharmaceutical composition for prophylactic and/or therapeutic purposes. To "prevent disease" refers to prophylactic treatment of a subject who is not yet ill, but who is susceptible to, or otherwise at risk of, a particular disease. To "treat disease" or use for "therapeutic treatment" refers to administering treatment to a subject already suffering from a disease to improve or stabilize the subject's condition. Thus, in the claims and embodiments, treating is the administration to a subject either for therapeutic or prophylactic purposes.

By "condition" is meant a state of being or feeling. Conditions include, but are not limited to, those listed in Table 1.

As used herein, the terms "an amount effective" and "effective amount" refer to the amount of a compound of the invention required for treating a condition, e.g., a condition of Table 1. Exemplary conditions are neurodegenerative diseases of the central or peripheral nervous system; the result of retinal neuronal cell death; the result of cell death of cardiac muscle; the result of cell death of cells of the immune system; stroke; liver disease; pancreatic disease; the result of cell death associated with renal failure; heart, mesenteric, retinal, hepatic or brain ischemic injury; ischemic injury during organ storage; head trauma; septic shock; coronary heart disease; cardiomyopathy; bone avascular necrosis; sickle cell disease; muscle wasting, gastrointestinal disease; tuberculosis; diabetes; alteration of blood vessels; muscular dystrophy; graft-versus-host disease; viral infection; Crohn's disease; ulcerative colitis; asthma; any condition in which cell or tissue necrosis is a causative factor or result; any condition in which alteration in cell proliferation, differentiation or intracellular signaling is a causative factor; and any condition in which RIP1 protein is a contributing factor. The effective amount used to practice the invention for therapeutic or prophylactic treatment of such conditions varies depending upon the manner of administration, the age, body weight, and general health of the subject. Ultimately, the attending physician or veterinarian will decide the appropriate amount and dosage regimen. Such amount is referred to as an "effective" amount.

By "neurodegenerative disease" is meant a disease characterized by neuronal cell death. Examples of neurodegenerative diseases include, but are not limited to, Alzheimer's disease, amyotropic lateral sclerosis, cerebral ischemia, Creutzfeldt-Jakob disease, Fahr disease, Huntington's disease and related polyglutamine expansion diseases, Lewy body disease, Menke's disease, multiple sclerosis, stroke, and Wilson's disease.

By "neuron" is meant a cell of ectodermal embryonic origin derived from any part of the nervous system of an animal. Neurons express well-characterized neuron-specific markers which include neurofilament proteins, MAP2, and class III β-tubulin. Included as neurons are, for example, hippocampal, cortical, midbrain dopaminergic, motor, sensory, sympathetic, septal cholinergic, and cerebellar neurons.

By a "dosage sufficient to decrease necrosis" is meant an amount of a chemical compound or small molecule which when administered to a subject will decrease necrosis. Preferably necrosis is decreased in the subject 10% relative to an untreated subject. More preferably necrosis is decreased in the subject 50% relative to an untreated subject. Most preferably necrosis is decreased in the subject 90% relative to an untreated subject.

By "measuring necrosis" is meant determining if a cell is dying through necrosis, in the presence of a compound, compared to a cell which is not in the presence of the compound (control cell). Necrosis can be measured by determining cellular ATP levels, wherein a cell that is undergoing necrosis has a decreased level of cellular ATP compared to a control cell. Necrosis may also be measured by staining with a vital dye, for example, trypan blue, wherein a cell which is necrosing will be stained with the vital dye, and a cell which is not necrosing will not be stained with the dye.

By "pharmaceutical composition" is meant a composition containing a compound of the invention, formulated with a pharmaceutically acceptable excipient, and manufactured or sold with the approval of a governmental regulatory agency as part of a therapeutic regimen for the treatment of disease in a mammal. Excipients consisting of ethanol or DMSO are specifically excluded. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or any other formulation described herein.

The term "pharmaceutically acceptable salt," as used herein, represents those salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, S. M Berge et al. describe pharmaceutically acceptable salts in detail in J. Pharmaceutical Sciences, 1977, 66:1-19. The salts can be prepared in situ during the final isolation and purification of the compounds of the invention or separately by reacting the free base group with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts and the like. Representative alkali or alkaline earth metal salts include sodium, lithium, potassium, calcium, magnesium and the like, as well as nontoxic ammonium, quaternary ammonium, and amine cations, including, but not limited to ammonium, tetramethylanunonium, tetraethylammonium, methylamine, dimethylamine, trimethylamine, triethylamine, ethylamine and the like.

The term "pharmaceutically acceptable ester," as used herein, represents esters which hydrolyie in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl group preferably has not more than 6 carbon atoms. Examples of particular esters includes formates, acetates, propionates, butyates, acrylates and ethylsuccinates.

The term "pharmaceutically acceptable prodrugs" as used herein, represents those prodrugs of the compounds of the present invention which are, within the scope of sound medical judgment, suitable for use in contact with the tissues of humans and animals with undue toxicity, irritation, allergic response, and the like, commensurate with a reasonable benefit/risk ratio, and effective for their intended use, as well as the zwitterionic forms, where possible, of the compounds of the invention.

The term "prodrug," as used herein, represents compounds which are rapidly transformed in vivo to the parent compound of the above formula, for example, by hydrolysis in blood. A thorough discussion is provided in T. Higuchi and V. Stella, Pro-drugs as Novel Delivery Systems, Vol. 14 of the A.C.S. Symposium Series, Edward B. Roche, ed., Bioreversible Carriers in Drug Design, American Pharmaceutical Association and Pergamon Press, 1987, and Judkins, et al. Synthetic Communications, 26(23), 4351-4367 (1996), each of which is incorporated herein by reference.

Asymmetric or chiral centers may exist in the compounds of the present invention. The present invention contemplates the various stereoisomers and mixtures thereof. Individual stereoisomers of compounds or the present invention are prepared synthetically from commercially available starting materials which contain asymmetric or chiral centers or by preparation of mixtures of enantiomeric compounds followed by resolution well-known to those of ordinary skill in the art. These methods of resolution are exemplified by (1) attachment of a racemic mixture of enantiomers, designated (+/−), to a chiral auxiliary, separation of the resulting diastereomers by recrystallization or chromatography and liberation of the optically pure product from the auxiliary or (2) direct separation of the mixture of optical enantiomers on chiral chromatographic columns. Enantiomers are designated herein by the symbols "R" or "S," depending on the configuration of substituents around the chiral carbon atom.

Geometric isomers may also exist in the compounds of the present invention. The present invention contemplates the various geometric isomers and mixtures thereof resulting from the arrangement of substituents around a carbon-carbon double bond and designates such isomers as of the Z or E configuration, wherein the term "Z" represents substituents on the same side of the carbon-carbon double bond and the term "E" represents substituents on opposite sides of the carbon-carbon double bond.

Compounds useful in the invention include those described herein in any of their pharmaceutically acceptable forms, including isomers such as diastereomers and enantiomers, salts, e.g., acid or base addition salts, esters, amides, thioesters, solvates, and polymorphs thereof, as well as racemic mixtures and pure isomers of the compounds described herein.

As used herein, "A isomer" refers to a Nec-1 compound (e.g., a Nec-1a compound, a Nec-1b compound, a Nec-1c compound, a Nec-1d compound, or a Nec-1e compound) in which the stereochemistry at position * is as shown in Formula XXXIX:

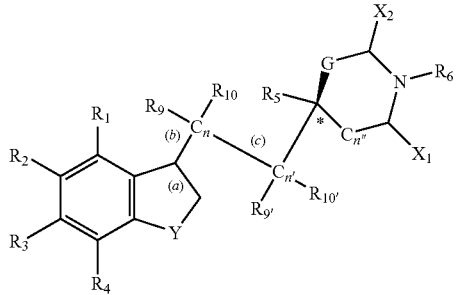

(XXXIX)

By way of example, R-7-Cl—O-Nec-1 is an A isomer, as shown below (note that the hydantoin moiety is flipped in the below representation):

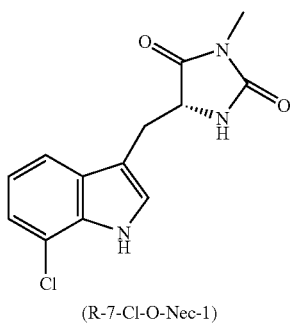

(R-7-Cl-O-Nec-1)

"Substantially pure A isomer" refers to a composition in which the ratio of A isomer to B isomer is at least 10, 20, 30, 100, 200, or even 400.

As used herein, "B isomer" refers to a Nec-1 compound (e.g., a Nec-1a compound, a Nec-1b compound, a Nec-1c compound, a Nec-1d compound, or a Nec-1e compound) in which the stereochemistry at position * is as shown in Formula XXXX:

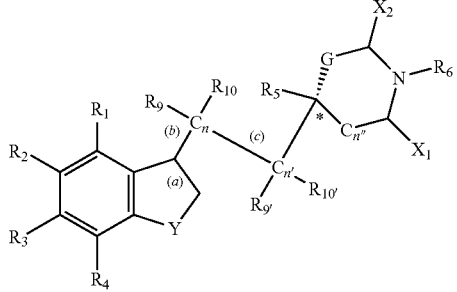

(XXXX)

"Substantially pure B isomer" refers to a composition in which the ratio of B isomer to A isomer is at least 10, 20, 30, 100, 200, or even 400.

By "(3R, 3aR)-rel isomer" (a.k.a. C3/C3a cis isomer) is meant a Nec-3 compound (e.g., a Nec-3a compound or Nec-3b compound) in which the lowest priority substituents (e.g., hydrogens) at positions C3 and C3a, as shown in Formula XXII, are syn with respect to each other. "Substantially pure (3R, 3aR)-rel isomer" refers to a composition in which the ratio of (3R, 3aR)-rel isomer to (3R, 3aS)-rel isomer is at least 10, 20, 30, 100, 200, or even 400.

By "(3R, 3aS)-rel isomer" (a.k.a. C3/C3a trans isomer) is meant a Nec-3 compound (e.g., a Nec-3a compound or Nec-3b compound) in which the lowest priority substituents (e.g., hydrogens) at positions C3 and C3a, as shown in Formula XXII, are anti with respect to each other. "Substantially pure (3R, 3aS)-rel isomer" refers to a composition in which the ratio of (3R, 3aS)-rel isomer to (3R, 3aR)-rel isomer is at least 10, 20, 30, 100, 200, or even 400.

"(3R, 3aR)-enantiomer" refers to a Nec-3 compound (e.g., a Nec-3a compound or Nec-3b compound) in which the absolute stereochemistry at position C3, as shown in Formula XXII, is R, and the absolute stereochemistry at position C3a, as shown in Formula XXII, R, as determined by the Cahn-Ingold-Prelog priority rules. "Substantially pure (3R, 3aR)-enantiomer" refers to a composition in which the ratio of (3R, 3aR)-enantiomer to (3S, 3aS)-enantiomer is at least 10, 20, 30, 100, 200, or even 400.

"(3R, 3aS)-enantiomer" refers to a Nec-3 compound (e.g., a Nec-3a compound or Nec-3b compound) in which the absolute stereochemistry at position C3, as shown in Formula XXII, is R, and the absolute stereochemistry at position C3a, as shown in Formula XXII, is, S, as determined by the Calm-Ingold-Prelog priority rules. "Substantially pure (3R, 3aS)-enantiomer" refers to a composition in which the ratio of (3R, 3aS)-enantiomer to (3S, 3aR)-enantiomer is at least 10, 20, 30, 100, 200, or even 400.

"(3S, 3aR)-enantiomer" refers to a Nec-3 compound (e.g., a Nec-3a compound or Nec-3b compound) in which the absolute stereochemistry at position C3, as shown in Formula XXII, is S, and the absolute stereochemistry at position C3a, as shown in Formula XXII, is, R, as determined by the Cahn-Ingold-Prelog priority rules. "Substantially pure (3S, 3aR)-enantiomer" refers to a composition in which the ratio of (3S, 3aR)-enantiomer to (3R., 3aS)-enantiomer is at least 10, 20, 30, 100, 200, or even 400.

"(3S, 3aS)-enantiomer" refers to a Nec-3 compound (e.g., a Nec-3a compound or Nec-3b compound) in which the absolute stereochemistry at position C3; as shown in Formula XXII, is S, and the absolute stereochemistry at position C3a, as shown in Formula XXII, is, S, as determined by the Cahn-Ingold-Prelog priority rules. "Substantially pure (3S, 3aS)-enantiomer" refers to a composition in which the ratio of (3S, 3aS)-enantiomer to (3R, 3aR)-enantiomer is at least 10, 20, 30, 100, 200, or even 400.

By "ischemia" is meant a cardiovascular disorder characterized by a low oxygen state usually due to the obstruction of the arterial blood supply or inadequate blood flow leading to hypoxia in the tissue.

By "myocardial infarction" is meant a cardiovascular disorder characterized by localized necrosis resulting from obstruction of the blood supply.

By "stroke" is meant a cardiovascular disorder caused by a blood clot or bleeding in the brain, most commonly caused by an interruption in the flow of blood in the brain as from clot blocking a blood vessel. In certain embodiments of the invention, the term "stroke" refers to ischemic stroke or hemorrhagic stroke.

By "trauma" is meant any physical damage to the body caused by violence, accident, fracture, etc.

Definitions Specific to Nec-1b Compounds

The following definitions apply specifically to Nec-1b compounds.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 12 or fewer carbon atoms in its backbone (e.g., $C_1$-$C_{12}$ for straight chain, $C_3$-$C_{12}$ for branched chain), and more preferably 6 or fewer, and even more preferably 4 or fewer. Likewise, preferred cycloalkyls have from 3-10 carbon atoms in their ring structure, and more preferably have 5, 6 or 7 carbons in the ring structure. A $C_{1-7}$ heteroalkyl, for example, includes from 1 to 6 carbon atoms in addition to one or more heteroatoms. Other numbers of atoms and other types of atoms may be indicated in a similar manner.

Unless the number of carbons is otherwise specified, "lower alkyl" as used herein means an alkyl group, as defined above, but having from one to ten carbons, more preferably from one to six carbon atoms in its backbone structure, and even more preferably from one to four carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The terms "halogen" and "halo" are used interchangeably herein and designate —F, —Cl, —Br or —I; the term "sulfhydryl" means —SH; and the term "hydroxyl" means —OH.

The term "methyl" refers to the monovalent radical —$CH_3$, and the term "methoxyl" refers to the monovalent radical —$CH_2OH$.

The term "aralkyl" or "arylalkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein-at least one of the rings is aromatic, e.g., the other cyclic rings can be cycloalkyls, cycloalkenyls, cycloalkynyls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" or "heteroaryl" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, heterocyclyl, aromatic or heteroaromatic moiety, —$CF_3$, —CN, or the like.

As used herein, the definition of each expression, e.g., alkyl, m, n, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, heterocyclyl, aromatic or heteroaromatic moiety, —CF$_3$, —CN, or the like. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention. In certain embodiments, the present invention relates to a compound represented by any of the structures outlined herein, wherein the compound is a single stereoisomer.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed With an appropriate optically-active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g., functioning as inhibitors of cellular necrosis), wherein one or more simple variations of substituents are made which do not adversely affect the efficacy of the compound. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants, which are in themselves known, but are not mentioned here.

For purposes of this invention, the chemical elements are identified in accordance with the Periodic Table of the Elements, CAS version, Handbook of Chemistry and Physics, 67th Ed., 1986-87, inside cover.

Definitions Specific to Non-Nec-1b Compounds

The following definitions apply to all compounds disclosed herein with the exception of Nec-1b compounds, for which alternative definitions are provided above.

In the generic descriptions of non-Nec-1b compounds of this invention, the number of atoms of a particular type in a substituent group is generally given as a range, e.g., an alkyl group containing from 1 to 7 carbon atoms or $C_{1-7}$ alkyl. Reference to such a range is intended to include specific references to groups having each of the integer number of atoms within the specified range. For example, an alkyl group from 1 to 7 carbon atoms includes each of $C_1$, $C_2$, $C_3$, $C_4$, $C_5$, $C_6$, and $C_7$. A $C_{1-7}$ heteroalkyl, for example, includes from 1 to 6 carbon atoms in addition to one or more heteroatoms. Other numbers of atoms and other types of atoms may be indicated in a similar manner As used herein, the terms "alkyl" and the prefix "alk-" are inclusive of both straight chain and branched chain groups and of cyclic groups, i.e., cycloalkyl. If not specified, alkyl means $C_{1-7}$ alkyl. Cyclic groups can be monocyclic or polycyclic and preferably have from 3 to 6 ring carbon atoms, inclusive. Exemplary cyclic groups include cyclopropyl, cyclobutyl, cyclopentyl, and cyclohexyl groups. The $C_{1-7}$ alkyl group may be substituted or unsubstituted. $C_{1-7}$ alkyls include, without limitation, methyl; ethyl; n-propyl; isopropyl; cyclopropyl; cyclopropylmethyl; cyclopropylethyl; n-butyl; iso-butyl; sec-butyl; tert-butyl; cyclobutyl; cyclobutylmethyl; cyclobutylethyl; n-pentyl; cyclopentyl; cyclopentylmethyl; cyclopentylethyl; 1-methylbutyl; 2-methylbutyl; 3-methylbutyl; 2,2-dimethylpropyl; 1-ethylpropyl; 1,1-dimethylpropyl; 1,2-dimethylpropyl; 1-methylpentyl; 2-methylpentyl; 3-methylpentyl; 4-methylpentyl; 1,1-dimethylbutyl; 1,2-dimethylbutyl; 1,3-dimethylbutyl; 2,2-dimethylbutyl; 2,3-dimethylbutyl; 3,3-dimethylbutyl; 1-ethylbutyl; 2-ethylbutyl; 1,1,2-trimethylpropyl; 1,2,2-trimethylpropyl; 1-ethyl-1-methylpropyl; 1-ethyl-2-methylpropyl; and cyclohexyl.

By "$C_{2-7}$ alkenyl" is meant a branched or unbranched hydrocarbon group containing one or more double bonds and having from 2 to 7 carbon atoms. A $C_{2-7}$ alkenyl may optionally include monocyclic or polycyclic rings, in which each ring desirably has from three to six members. The $C_{2-7}$ alkenyl group may be substituted or unsubstituted. $C_{2-7}$ alkenyls include, without limitation, vinyl; allyl; 2-cyclopropyl-1-ethenyl; 1-propenyl; 1-butenyl; 2-butenyl; 3-butenyl; 2-methyl-1-propenyl; 2-methyl-2-propenyl; 1-pentenyl; 2-pentenyl; 3-pentenyl; 4-pentenyl; 3-methyl-1-butenyl; 3-methyl-2-butenyl; 3-methyl-3-butenyl; 2-methyl-1-butenyl; 2-methyl-2-butenyl; 2-methyl-3-butenyl; 2-ethyl-2-propenyl; 1-methyl-1-butenyl; 1-methyl-2-butenyl; 1-methyl-3-butenyl; 2-methyl-2-pentenyl; 3-methyl-2-pentenyl; 4-methyl-2-pentenyl; 2-methyl-3-pentenyl; 3-methyl-3-pentenyl; 4-methyl-3-pentenyl; 2-methyl-4-pentenyl; 3-methyl-4-pentenyl; 1,2-dimethyl-l-propenyl; 1,2-dimethyl-1-butenyl; 1,3-dimethyl-1-butenyl; 1,2-dimethyl-2-butenyl; 1,1-dimethyl-2-butenyl; 2,3-dimethyl-2-butenyl; 2,3-dimethyl-3-butenyl; 1,3-dimethyl-3-butenyl; 1,1-dimethyl-3-butenyl and 2,2-dimethyl-3-butenyl.

By "$C_{2-7}$ alkynyl" is meant a branched or unbranched hydrocarbon group containing one or more triple bonds and having from 2 to 7 carbon atoms. A $C_{2-7}$ alkynyl may optionally include monocyclic, bicyclic, or tricyclic rings, in which each ring desirably has five or six members. The $C_{2-7}$ alkynyl group may be substituted or unsubstituted. $C_{2-7}$ alkynyls include, without limitation, ethynyl, 1-propynyl, 2-propynyl, 1-butynyl, 2-butynyl, 3-butynyl, 1-pentynyl, 2-pentynyl, 3-pentynyl, 4-pentynyl, 5-hexene-1-ynyl, 2-hexynyl, 3-hexynyl, 4-hexynyl, 5-hexynyl; 1-methyl-2-propynyl; 1-methyl-2-butynyl; 1-methyl-3-butynyl; 2-methyl-3-butynyl; 1,2-dimethyl-3-butynyl; 2,2-dimethyl-3-butynyl; 1-methyl-2-pentynyl; 2-methyl-3-pentynyl; 1-methyl-4-pentynyl; 2-methyl-4-pentynyl; and 3-methyl-4-pentynyl.

By "$C_{2-9}$ heterocyclyl" or "$C_{2-9}$ heteroaryl" is meant a stable 5- to 7-membered monocyclic or 7- to 14-membered bicyclic heterocyclic ring which is saturated partially unsaturated or unsaturated (aromatic), and which consists of 2 to 9 carbon atoms and 1, 2, 3 or 4 heteroatoms independently selected from the group consisting of N, O, and S and including any bicyclic group in which any of the above-defined heterocyclic rings is fused to a benzene ring. The heterocyclyl group may be substituted or unsubstituted. The nitrogen and sulfur heteroatoms may optionally be oxidized. The heterocyclic ring may be covalently attached via any heteroatom or carbon atom which results in a stable structure, e.g., an imidazolinyl ring may be linked at either of the ring-carbon atom positions or at the nitrogen atom. A nitrogen atom in the heterocycle may optionally be quaternized. Preferably when the total number of S and O atoms in:the heterocycle exceeds 1, then these heteroatoms are not adjacent to one another. Heterocycles include, without limitation, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cimiolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred 5 to 10 membered heterocycles include, but are not limited to, pyridinyl, pyrimidinyl, triazinyl, furanyl, thienyl, thiazolyl, pyrrolyl, pyrazolyl, imidazolyl, oxazolyl, isoxazolyl, tetrazolyl, benzofuranyl, benzothiofuranyl, indolyl, benzimidazolyl, 1H-indazolyl, oxazolidinyl, isoxazolidinyl, benzotriazolyl, benzisoxazolyl, oxindolyl, betizoxazolinyl, quinolinyl, and isoquinolinyl. Preferred 5 to 6 membered heterocycles include, without limitation, pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl.

By "$C_{6-12}$ aryl" is meant an aromatic group having a ring system comprised of carbon atoms with conjugated π electrons (e.g., phenyl). The aryl group has from 6 to 12 carbon atoms. Aryl groups may optionally include monocyclic, bicyclic, or tricyclic rings, in which each ring desirably has five or six members. The aryl group may be substituted or unsubstituted.

By "$C_{7-14}$ alkaryl" is meant an alkyl substituted by an aryl group (e.g., benzyl, phenethyl, or 3,4-dichlorophenethyl) having from 7 to 14 carbon atoms.

By "$C_{3-10}$ alkheterocyclyl" is meant an alkyl substituted heterocyclic group having from 7 to 14 carbon atoms in addition to one or more heteroatoms (e.g., 3-furanylmethyl, 2-furanylmethyl, 3-tetrahydrofuranylmethyl, or 2-tetrahydrofuranylmethyl).

By "$C_{1-7}$ heteroalkyl" is meant a branched or unbranched alkyl, alkenyl, or alkynyl group having from 1 to 7 carbon atoms in addition to 1, 2, 3 or 4 heteroatoms independently selected from the group consisting of N, O, S, and P. Heteroalkyls include, without limitation, tertiary amines, secondary amines, ethers, thioethers, amides, thioamides, carbamates, thiocarbamates, hydrazones, imines, phosphodiesters, phosphoramidates, sulfonamides, and disulfides. A heteroalkyl may optionally include monocyclic, bicyclic, or tricyclic rings, in which each ring desirably has three to six members. The heteroalkyl group may be substituted or unsubstituted.

By "acyl" is meant a chemical moiety with the formula R—C(O)—, wherein R is selected from $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, or $C_{1-7}$ heteroalkyl.

For any of the above definitions, exemplary substituents include alkoxy; aryloxy; sulfhydryl; alkylthio; arylthio; halide; hydroxyl; fluoroalkyl; perfluoroalkyl; hydroxyalkyl; alkylsulfinyl; alkylsulfonyl; azido; nitro; oxo; acyl derivatives of hydroxyalkyl; —$CO_2R_A$; —$C(O)NR_BR_C$; —$SO_2R_D$; —$SO_2NR_ER_F$; and —$NR_GR_H$; where each of $R_A$, $R_B$, $R_C$, $R_D$, $R_E$, $R_F$, $R_G$, and $R_H$ is, independently, selected from H, $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, $C_{1-7}$ heteroalkyl, and acyl.

By "halide" is meant bromine, chlorine, iodine, or fluorine.

By "fluoroalkyl" is meant an alkyl group that is substituted with a fluorine.

By "perfluoroalkyl" is meant an alkyl group consisting of only carbon and fluorine atoms.

By "hydroxyalkyl" is meant a chemical moiety with the formula —(R)—OH, wherein R is selected from $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, or $C_{1-7}$ heteroalkyl.

By "alkoxy" is meant a chemical substituent of the formula —OR, wherein R is selected from $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, or $C_{1-7}$ heteroalkyl.

By "aryloxy" is meant a chemical substituent of the formula —OR, wherein R is a $C_{6-12}$ aryl group.

By "alkylthio" is meant a chemical substituent of the formula —SR, wherein R is selected from $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, or $C_{1-7}$ heteroalkyl.

By "arylthio" is meant a chemical substituent of the formula —SR, wherein R is a $C_{6-12}$ aryl group.

By "saccharide" is meant an aldose or a ketose, either as a monosaccharide or part of a disaccharide or polysaccharide. Saccharides include glycose, glycosamine, aldohexoses, ketohexoses, aldopentose, ketopentose, disaccharides, polysaccharides of 3-20 saccharide units, and deoxy and halide (e.g., fluorinated), amine, alkanoate, sulfate, and/or phosphate derivatives thereof. Suitable monosaccharides include, but are not limited to, any of several simple open or closed chain sugars (in the L or D configuration), typically having 5 or 6 carbons (a pentose monosaccharide or a hexose monosaccharide), as well as 7 carbons (heptose monosaccharide). Included are sugar derivatives in which the ring oxygen atom has been replaced by carbon, nitrogen or sulfur, amino sugars in which a hydroxyl substituent on the simple sugar is replaced with an amino group or sugars having a double bond between two adjacent carbon atoms. Saccharides which can be used in the compounds and methods of the invention include, without limitation, rhamnose, glucose, digitoxose, digitalose, digginose, sarmentose, vallarose, fructose, glucosamine, 5-thio-D-glucose, nojirimycin, deoxynojirimycin, 1,5-anhydro-D-sorbitol, 2,5-anhydro-D-mannitol, 2-deoxy-D-galactose, 2-deoxy-D-glucose, 3-deoxy-D-glucose, allose, arabinose, arabinitol, fucitol, fucose, galactitol, glucitol, iditol, lyxose, mannitol, levo-rhananitol, 2-deoxy-D-ribose, ribose, ribitol, ribulose, rhamnose, xylose, xylulose, allose, altrose, galactose, gulose, idose, levulose, mannose, psicose, sorbose, tagatose, talose, galactal, glucal, fucal, rhanmal, arabinal, xylal, valienamine, validamine, valiolamine, valiol, valiolon, valienol, valienone, glucuronic acid, galacturonic acid, N-acetylneuraminic acid, gluconic acid D-lactone, galactonic acid γ-lactone, galactonic acid δ-lactone, mannonic acid γ-lactone, D-altro-heptulose, D-manno-heptulose, D-glycero-D-manno-heptose, D-glycero-D-gluco-heptose, D-allo-heptulose, D-altro-3-heptulose, D-glycero-D-manno-heptitol, and D-glycero-D-altro-heptit-ol, among others). Desirably, the saccharide used in the compounds of the invention is of the formula:

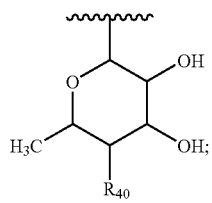

wherein, $R_{40}$ is F, Cl, $CF_3$, OH, $NH_2$, $NHR_{40A}$, $NR_{40B}R_{40C}$, $NHC(O)R_{40D}$; $NHC(S)R_{40E}$, $NHC(O)OR_{40F}$, $NHC(S)OR_{40G}$, $NHC(O)NHR_{40H}$, $NHC(S)NHR_{40I}$, $NHC(O)SR_{40J}$, $NHC(S)SR_{40K}$, or $NHS(O)_2R_{40L}$, and where each of $R_{40A}$, $R_{40B}$, $R_{40C}$, $R_{40D}$, $R_{40E}$, $R_{40F}$, $R_{40G}$, $R_{40H}$, $R_{40I}$, $R_{40J}$, $R_{40K}$, and $R_{40L}$, independently, represents $C_{1-7}$ alkyl, $C_{2-7}$ alkenyl, $C_{2-7}$ alkenyl, $C_{2-6}$ heterocyclyl, $C_{6-12}$ aryl, $C_{7-14}$ alkaryl, $C_{3-10}$ alkheterocyclyl, or $C_{1-7}$ heteroalkyl.

Other features and advantages of the invention will be apparent from the following detailed description and from the claims.

BRIEF DESCRIPTION OF THE DRAWINGS

In FIG. 5A, JK cells were treated with 5 ng/ml of FasL, 1 μg/ml CHX and 100 μM zVAD.fmk and indicated concentrations (in μM) of PARP inhibitors. Cell viability was determined using ATP assay. Values represent the percentages of live cells normalized to the compound treated cells lacking FasL. In FIG. 5B, FADD deficient JK cells were treated with indicated amounts of MNNG (in mM) and 30 μM Nec-1 or 100 μM DPQ for 5 hours. Viability was determined using an TP assay. Values represent the percentages of live cells normalized to the compound treated cells lacking FasL.

FIG. 9A shows a dose-dependent reduction in infarct volume upon pre- or post-occlusion delivery of 7-Cl-Nec-1 in MCAO model. Pre-occlusion delivery was performed by icy injection of 4 μL of 4 mM 7-Cl-Nec-1 5 minutes prior to the onset of two-hour MCAO occlusion and immediately following the cessation of the occlusion at the time of the reperfusion (2 μL per each injection). Post-occlusion delivery was done at the time of reperfusion after two hours of MCAO as well as two hours after the onset of reperfusion (2 μL per each injection). Alternatively, 20 μL of the compound solution was continuously infused icy using a peristaltic pump (infusion) at the time of reperfusion after two hours of occlusion. After the occlusion, animals were allowed to recover for 24 hours, sacrificed, brains removed, fixed, sectioned and infarct volume was determined based on the 2,3,5-triphenyltetrazolium chloride viability staining of the sections. Animal behavior was also scored (see insert). At least six animals were analyzed in each treatment group. **–P<0.05 versus vehicle. Error bars reflect error of the mean values. In FIG. 9B, animal behavior was assessed by an investigator unaware of the treatment group prior to sacrificing animals and scored from 3 (worst) to 0 (no defects). Four to five animals were analyzed in each treatment group. Injections were performed post-occlusion.

In FIG. 10A, the therapeutic window of LDN-53064 (7-Cl-Nec-1) was determined by injecting compounds either 5 minutes pre- and two hours post-occlusion as well as six hours post-occlusion. FIG. 10B shows the additive effect of LDN53064 with zVAD.fmk on infarct size after focal ischemia. Isoflurane-anesthetized SV-129 mice were subjected to two hours transient middle cerebral artery (MCA) occlusion by the intraluminal filament techniques. The mixture solution of LDN53064 (4 mM) and zVAD.fmk (160 ng) (n=16), or zVAD.fmk alone (n=16), or the equivalent amount (4 µl) of vehicle (n=8) was injected, i.c.v, at two or six hours after ischemia. Twenty-four hours following MCA occlusions, infarct size was determined with brain sections TTC staining. FIG. 10C shows intraventricularly delivered zVAD-.fmk with or without 7-Cl-Nec-1 at two hours and five minutes prior to occlusion followed by two hours MCAO. Brains were harvested three hours after reperfusion, lysed, and proteins from the infarcted (+) or control (−) hemispheres from the same animal were subjected to Western blotting using anti-active caspase-3 or anti-tubulin antibodies.

In FIG. 11A, L929 cells or FADD deficient Jurkat cells were treated with 100 µM zVAD.fmk or 10 ng/ml human TNFα in the presence or absence of 30 µM Nec-1. Equal amounts of cellular proteins were subjected to SDS-PAGE and western blotting with anti-LC3 and tubulin antibodies. Arrows point to the LC3II. FIG. 11B shows delayed elevation in the levels of LC3II following transient focal ischemia. Isoflurane-anesthetized SV-129 mice were subjected to two hours transient middle cerebral artery (MCA) occlusion by the intraluminal filament techniques. Ischemic and contralateral areas of the brain were collected at indicated times following MCA, lysed in RIPA buffer and equal amount of total protein were subjected to western blotting using anti-LC3 and tubulin antibodies. FIG. 11C is similar to FIG. 11B, except that mice were injected with 2 µL, of 4 mM 7-Cl-Nec-1 icv at four and six hours, and brains were collected at eight hours after occlusion.

FIG. 12A shows that Nec-1i, an inactive derivative of Nec-1 that lacks the methyl group in the hydantoin moiety, does not inhibit CICD in vitro. FADD-deficient Jurkat cells were treated with 10 ng/ml human TNFα and indicated concentrations of Nec-1 or Nec-1i for 30 hours. Cell viability was determined using an ATP assay. Numbers represent viability normalized to that of the corresponding compound/DMSO-treated cells in the absence of TNFα. FIG. 12B shows that Nec-1i lacks neuroprotective activity in vivo. Mice were injected with 4 µL of 4 mM 7-Cl-Nec-1 and 7-Cl-Nec-1i five minutes prior and immediately following MCAO (2 µL each injection). After the occlusion, animals were allowed to recover for 24 hours, sacrificed, brains removed, fixed, sectioned, and infarct volume was determined based on the 2,3, 5-triphenyltetrazolium triphenyltetrazolium chloride viability staining of the sections. At least five animals were analyzed in each treatment group. **–P<0.05 versus vehicle.

FIG. 12C shows that 7-Cl—O-Nec-1 displays activity comparable to that of 7-Cl-Nec-1 in vivo. Mice were injected with 4 µL of 4 mM 7-Cl-Nec-1 or 7-Cl—O-Nec-1 icy at four and six hours post-occlusion (2 µL each injection). Infarct volume was determined as in FIG. 12A. At least ten animals were analyzed in each treatment group. **–P<0.05 versus vehicle.

In FIG. 14A, mature primary cortical-glia mixed cultures were subjected to OGD for 90 minutes in the presence of glutamate antagonists: 10 µM CNQX/1 µM MX801, 30 µM Nec-1 or TH-Trp (Nec1i) as indicated. Cells were allowed to recover in the presence of the compounds (except for the CNQX/MK801) for 24 hours, and specific neuronal viability was determined using MAP2 cytoblot. Values represent the percentages of live cells normalized to the compound treated cells, which were maintained in glucose-containing, non-deoxygenated media. –P<0.02. In FIG. 14B, mature primary cortical-glia mixed cultures were subjected for OGD for 90 minutes in the presence of 30 µM Nec-1 and 100 µM zVAD.fmk. Cells were allowed to recover in the presence of the compounds for 24 hours, and specific neuronal viability was determined using MAP2 cytoblot. Values represent the percentages of live cells normalized to the compound treated cells, which were maintained in glucose-containing, non-deoxygenated media. –P<0.04.

In FIG. 18A, $CD8^+$ cells were stimulated with 1 µg/ml αCD3 and 100 U/ml mouse IL-2 in the presence of 100 µM zVAD-.fmk with or without 30 µM Nec-1 for 96 hours. Numbers of cells were determined using FACS analyses. Cell numbers are normalized to the number of cells in unstimulated control, which was set as 100%. In FIG. 18B, splenocytes isolated from OT-I mice were stimulated with 10 μM OVA257-264 peptide (Bachem) in the presence of 100 μM zVAD.fmk with or without 30 μM Nec-1 for 72 hours. Cells were stained with αCD8+-FITC antibody (Pharmingen) and CD8+ cell numbers were determined by FACS. Cell numbers are normalized to the number of cells in unstimulated control, which was set as 100%. Percentages of dead cells (line) was determined by co-staining cells with propidium iodide.

In FIG. 19A, purified CD8+ cells were stimulated with with 1 μg/ml αCD3 and 100 U/ml mouse IL-2 in the presence of 100 μM zVAD.fmk with or without 30 μM Nec-1 for 48 hours, after which [³H]-thymidine was added into the media for an additional 24 hours, followed by analysis in a scintillation counter. Values represent fold increase over unstimulated control. In FIG. 19B, purified CD8+ cells were stimulated with with 1 μg/ml αCD3 and 100 U/ml mouse IL-2 in the presence of 100 μM zVAD.fmk with or without 30 μM Nec-1 for 72 hours, after which cells were fixed, stained with propidium iodide, cellular DNA contents were determined by FACS, and the amounts of cells in different stages of the cell cycle (indicated) were determined using ModFit software package (Verity Software House).

FIG. 23A shows that Nec-1 inhibits the autophosphorylation of RIP1. RIP kinase assay was performed essentially as described. Briefly, RIP has been immunoprecipitated (EP) from lysates of WT and RIP-deficient Jurkat cells using agarose-conjugated anti-RIP antibody (Santa Cruz Biotech) and incubated with radioactive μ-P³²-ATP in the presence of the indicated amounts (in μM) of Nec-1 or Nec-1i for 30 min at 30 C. Samples were subjected to SDS-PAGE and ~70 kDa RIP band was visualized by autoradiography. FIG. 23B shows that Nec-1 inhibits the autophosphorylation of transfected RIP1 in vitro. 293T cells were transfected with pRIP 1-FLAG or empty control vector and immunoprecipitations were carried out using anti-M2 FLAG beads (Sigma): The in vitro kinase assay was carried out as in FIG. 23A. FIG. 23C shows that autophosphorylation of RIP1 requires its kinase activity. Expression constructs of flag-tagged WT or a kinase-dead point mutant of RIP1 (K45R) (RIP KD) were transfected into 293T cells, immunoprecipitation was carried out as in FIG. 23B, and the kinase assay was carried out as in FIG. 23A.

FIG. 25A shows the structure of Nec-1. FIG. 25B shows inhibition of cell death of U937 cells treated with TNFα and zVAD.fmk for 72 hours by Nec-1. Cell viability in this and subsequent panels was determined by ATP-based viability assay. Numbers represent percentages of the live cells normalized to those in the untreated control wells. Throughout, error bars represent standard deviations. FIG. 25C shows a dose-response curve (in μM) of Nec-1 and inactive derivative Nec-1i cytoprotection in Jurkat cells treated with FasL-CHX-zVAD.fmk for 30 hours. Numbers represent viability normalized to that of the corresponding compound-treated cells in the absence of FasL. FIG. 25D shows the inhibition of cell death in Jurkat cells stably expressing dimerizable FADD (Jurkat-FF) by Nec-1 after treatment with dimerizer AP20187 and zVAD.fmk for 48 hours. Numbers represent viability normalized to that of the corresponding compound-treated cells in the absence of dimerizer. In addition, control Jurkat cells were also treated with AP20187 in the presence or absence of zVAD.fmk without Nec-1. FIG. 25E, FIG. 25F, and FIG. 25H show inhibition of cell death in BALB/c 3T3 (E), SV40-transformed MEF (F), and L929 (H) cells by Nec-1. Cells were treated with TNFα (E, F, H), zVAD.fmk (E, F), or CHX (F) for 16 (F) or 24 (E, H) hours. Numbers represent viability normalized to that of the compound-treated cells in the absence of TNFα. FIG. 25G shows the dose response of Nec-1 and Nec-1i cytoprotection of FADD-deficient Jurkat cells treated with TNFα for 30 hours (see C for conditions).

FIG. 26A and FIG. 26B show the inhibition of plasma membrane integrity loss and mitochondrial dysfunction by Nec-1. Wild-type (A) and FADD-deficient (B) Jurkat cells were treated with FasL-CHX-zVAD-.fmk (A) or with TNFα (B) for the indicated amounts of time. Where indicated, the cells were also treated with Nec-1 for 24 hours. Cells were stained with DiOC₆ or with annexin V and PI, and percentages of cells with low PI and high annexin V, high PI and high annexin V, high PI and low annexin V, and low DiOC₆ (low mitochondrial membrane potential) are shown. Throughout, error bars represent standard deviations. FIG. 26C shows a demonstration of Nec-1 suppression of necroptosis from Sytox assay. Jurkat-FF cells were treated with AP20187-zVAD.fmk and Nec-1 for 48 hours. Values represent the percentages of live cells normalized to the compound-treated cells lacking dimerizer. Alternatively, BALB/c 3T3 cells were treated with TNFα-zVAD.fmk and 40 μM Nec-1 for 24 hours, or Jurkat cells were treated with FasL-CHX-zVAD.fmk and Nec-1 for 48 hours. FIG. 26D and FIG. 26E show bright-field microscopy of the cytoprotective effect of Nec-1 in (D) Jurkat cells treated with FasL-CHX-zVAD.fmk or (E) L929 cells treated with TNFα for 36 hours. Bright-field images were acquired at 40× magnification. FIG. 26F shows electron microscopy of the effect of Nec-1 in apoptotic or necroptotic Jurkat cells treated with FasL and CHX for 16 hours or TNFα for 6 hours, respectively. Representative EM images are shown. Arrows indicate dead cells. Con indicates vehicle-only control.

FIG. 27A shows the lack of cytoprotection by Nec-1 in apoptotic Jurkat cells treated with FasL-CHX for 24 hours. A time course of cellular changes in the samples not treated with Nec-1 is also shown. Cells were stained with $DiOC_6$ or annexin V and EGFP-PI as described in FIG. 26A and FIG. 26B. FIG. 27B and FIG. 27C show the selective inhibition of necroptosis but not apoptosis by Nec-1 in U937 (B) and BALB/c 3T3 (C) cells treated with TNFα and CHX (B only) without (apoptosis) or with (necroptosis) zVAD.fmk for 48 hours (B) or 24 hours (C). Cell viability was determined by an ATP assay. Numbers represent viability normalized to that of the compound-treated cells in the absence of TNFα. Error bars indicate standard deviations. FIG. 27D shows structures of the selected Nec-1 derivatives.

FIG. 28A shows that necroptosis is distinguishable from oxidative stress-induced cell death. U937 cells were treated with 40 ng/ml human TNFα and zVAD.fmk for 72 hours or 250 μM of menadione for 24 hours in the presence of various antioxidants and 100 μM Nec-1. In this and subsequent panels, cell viability was determined via ATP assay. Numbers represent viability normalized to that of the DMSO-treated cells in the absence of TNFα and menadione. Throughout, error bars represent standard deviations. FIG. 28B shows electron microscopic detection of autophagosomes in FADD-deficient Jurkat cells treated with TNFα with or without 10 mM 3MA for 12 hours. Representative images are shown. FIG. 28C shows induction of LC3-II during necroptosis in L929 and FADD-deficient Jurkat cells treated with TNFα and Nec-1 for 8 and 24 hours, respectively. Protein lysates were subjected to western blotting with antibodies to LC3 and to tubulin. The ratio of LC3-II to tubulin signals was calculated ("Ratio") and normalized to the value in the control sample. FIG. 28D shows the induction of LC3-II during necroptosis in BALB/c 3T3 cells treated with TNFα-zVAD.fmk or FasL-zVAD.fmk and Nec-1 for 24 hours. Alternatively, cells were treated with 2 μM rapamycin. FIG. 28E, FIG. 28F, and FIG. 28G show that there is no inhibition'of necroptosis by suppression of autophagy in BALB/c 3T3 (E), FADD-deficient Jurkat (E), Atg5$^{-/-}$ MEFs (F), and beclin-1 RNAi-expressing BALB/c3T3 (G) cells. Cells were treated with TNFα-zVAD.fmk and 3MA or Nec-1 for 24 or 30 (Jurkat cells) hours. Numbers represent viability normalized to that of the compound-treated cells in the absence of TNFα. In FIG. 28H, expression of beclin-1 ("Bec") and tubulin ("Tub") in the stable populations of cells in FIG. 28G was analyzed by western blotting. Asterisk shows nonspecific band detected by antibody to beclin.

FIG. 30A shows a reduction in infarct volume by administration of Nec-1 but not of Nec-1i. The experiment was performed as described herein; n≧5 for each treatment group. Throughout, error bars represent the standard error of the mean. In all panels, **P<0.05 as compared to vehicle. FIG. 30B shows a dose-dependent reduction in infarct volume and improvement in neurological scores upon pre- or postocclusion (Methods) delivery of 7-Cl-Nec-1. Stock concentrations of the injected compounds are shown.; n26 for each treatment group. In the inset, animal behavior was assessed by an investigator unaware of the treatment group before animals were killed and scored from 3 (worst) to 0 (no defects); n=4-5 in each treatment group. FIG. 30C shows that 7-Cl-Nec-1 does not inhibit caspase-3 activation during brain ischemia. The zVAD.fmk or 7-Cl-Nec-1 were delivered under preocclusion delivery conditions. Brains were harvested three hours after reperfusion and proteins from the infracted (+) or control (−) hemispheres from the same animal were subjected to western blotting using antibodies to active caspase-3 or to tubulin. The ratio of caspase-3 to tubulin signals was calculated and normalized to the values in the corresponding control hemispheres. FIG. 30D shows that 7-Cl—O-Nec-1 has activity comparable to that of 7-Cl-Nec-1in vivo. Mice were injected with 7-Cl-Nec-1 or 7-Cl—O-Nec-1 at four and six hours postocclusion; n≧10 in each treatment group. In FIG. 30E, the therapeutic time window of 7-Cl-Nec-1 in MCAO model is established by injecting compound either five minutes before or immediately after a two-hour MCAO at two, four, or six hours postocclusion; n≧10 in each treatment group. FIG. 30F shows the lack of neuroprotection by zVAD.fmk upon administration six hours postocclusion: The delivery of compounds was performed at two hours, four hours, or six hours after the onset occlusion; n≧8 in each treatment group. P values are shown. FIG. 30G shows the delayed induction of LC3-1I during brain ischemia in vivo. Brains were harvested at indicated time points after occlusion and subjected to western blotting with antibodies to LC3 and to tubulin. LC3-II/tubulin ratio is shown. FIG. 30H shows the inhibition of late induction of LC3-II by delayed administration of 7-Cl-Nec-1 at four and six hours after occlusion. Brains were collected eight hours after occlusion and analyzed as in FIG. 30G.

FIG. 31A shows that Nec-1 specifically prevents necroptosis-associated changes in cell size and shape in FADD-deficient Jurkat cells treated with TNFα for 24 hours. Results of the forward and side scatter FACS analysis are shown. In addition, percentage of PI negative viable cells (±SD value) was determined in each sample. FIG. 31B shows that Nec-1 prevents the loss of proliferative capacity in necroptotic FADD-deficient Jurkat cells treated as in FIG. 31A for the indicated periods of time. Numbers of PI negative viable cells (±SD value) in each sample are shown. FIG. 31C shows that necroptosis and Nec-1 cytoprotection is not associated with significant changes in cell cycle. FADD-deficient Jurkat cells were treated as described in FIG. 31A and cell cycle profiles were analyzed by PI DNA content FACS analysis. Percentages (±SD value) of cells at different stages of cell cycle, determined using ModFit software, are summarized in the table. FIG. 31D shows that Nec-1(1) does not induce non-specific cytotoxicity in FADD-deficient Jurkat cells. FADD-deficient Jurkat cells were treated with indicated concentrations (on log scale, in μM) of Nec-1 and Nec-1i for 24 hours. Cell viability was determined using ATP assay. Numbers represent viability normalized to that of the corresponding DMSO-treated cells. Error bars indicate standard deviation values. FIG. 31E shows that Nec-1 does not significantly affect the morphology of FADD-deficient Jurkat cells treated with the compound for six hours. Cells were fixed, embedded and analyzed using electron microscopy. Representative images are shown. FIG. 31F shows that Nec-1 prevents partial increase in reactive oxygen species (ROS) in necroptotic FADD-deficient Jurkat cells treated as in FIG. 31A. Cells were stained with dyhydroethydium (Molecular Probes) and analyzed by FACS. Percentages (±SD value) of cells with increased ROS levels are shown. FIG. 31G shows that Nec-1 does not significantly affect gene expression in Jurkat cells. Cells were treated with Nec-1 for 16 hours and mRNA from control (Cy5) and Nec-1 (Cy3) samples was subjected to Agilent DNA chip analysis. Red dots are internal reference controls.

FIG. 34A is a graph showing the results of treating Jurkat T cells with Fas ligand (5 ng/ml), cyclohexamide (1 μg/ml) and zVAD (100 μM) in the presence of the indicated amounts of anti-necrotic compounds (4) and (5). Viability was determined 36 hours later using an ATP assay. The viability values are relative to the samples lacking Fas ligand, which were used as 100% viability controls. FIG. 34B is a graph as in FIG. 34A, in which the anti-necrotic compounds are (19) and (20).

FIG. 35A is a graph showing the results of treating SH-SY5Y cells with 1 mM MPP+ in the presence of zVAD (100 μM) and compound (19) (30 μM) for 72 hours. Cell viability was determined using an ATP assay. FIG. 35B is a graph as in FIG. 35A, in which cells were treated in the presence of 100 μM amyloid-beta 25-35 protein rather than MPP+.

DETAILED DESCRIPTION OF THE INVENTION

Figure 1:
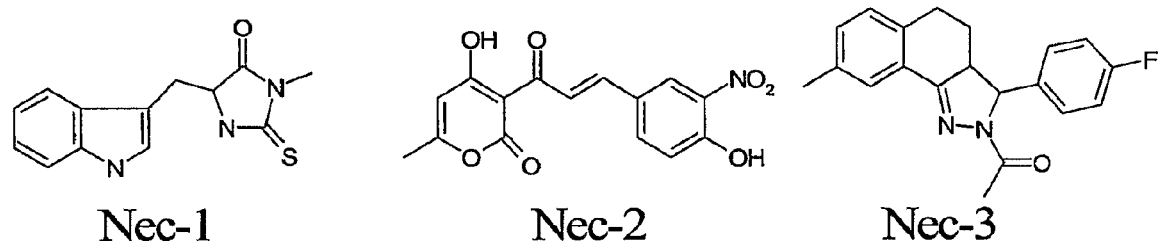
FIG. 1 is a set of structures of three exemplary necrostatins, Nec-1, Nec-2, and Nec-3.

Described herein are compounds, pharmaceutical compositions, kits, screening assays, and methods for treating a range of conditions. While this application focuses on conditions in which cell or tissue necrosis is a causative factor or result, any condition listed in Table 1 may be treated using the methods of the invention. Techniques for making and using the invention are now described in detail.

Compounds

Nec-1 compounds, Nec-2 compounds, and Nec-3 compounds, defined above, are useful in the compositions, kits, and methods of the invention. Compounds of the invention can be synthesized according to methods known in the art. Methods of synthesis for exemplary Nec-1, Nec-2, and Nec-3 compounds are described, for example, in U.S. Patent Application Publication No. 2005/0119260; U.S. Pat. No. 6,756, 394; Teng et al., Bioorg. Med. Chem. Lett. 15:5039-5044, 2005; and Degterev et al., Nat. Chem. Bio. 1:112-119, 2005, each of which is hereby incorporated by reference; and in the examples below.

Each Nec compound that fits one of the definitions above is considered to be described distinctly and individually herein.

Any of the compounds or pharmaceutical compositions of the invention can be used together with a set of instructions, i.e., to form a kit.

Structural Derivatives of Chemical Compounds that Decrease Necrosis

The small molecules identified to decrease necrosis may be structurally modified and subsequently used to decrease necrosis, or to treat a subject with a condition in which necrosis occurs. For example, the small molecules may be modified by any of the following processes: reduction of aliphatic double bonds; reduction of aliphatic ketones; substitution of nitro groups with protons, halides, or sulfates; reduction of C=O double bonds in flavone rings; elimination of oxygens attached to flavone rings; substitution of methoxyl groups with hydroxyl groups; attachment of hydroxyl and amino groups to benzyl rings; reduction of C=N double bonds; elimination of a fluoride or its substitution with a hydroxyl or other halide group; substitution of a hydrogen with an alkyl group; introduction of hydroxyl, methoxyl, amino, and nitro groups into the benzyl ring; reduction of the double bond in the position 2 of the indol; introduction of double bonds in the linker between indol and hydantoin moieties; reduction or alkylation of the thiourea moiety; reduction, alkylation, or acylation of the indol amino group; substitution of the hydantoin 3-methyl group with linear and branching alkyl groups of varying length, and with hydroxyl, methyl, or carboxyl functionalities; and reduction of the hydantoin ketone moiety.

The chemical compounds that decrease necrosis may be modified by one of the above processes or various combinations of the above processes. The methods used to generate structural derivatives of the small molecules that decrease necrosis are readily known to those skilled in the fields of organic and medicinal chemistry.

Therapy

Therapy according to the invention may be performed alone or in conjunction with another therapy, and may be provided at home, the doctor's office, a clinic, a hospital's outpatient department, or a hospital. Any of the conditions listed in Table 1, alone or present in combination, can be treated using the compounds and methods of the invention. Treatment generally begins at a hospital so that the doctor can observe the therapy's effects closely and make any adjustments that are needed. The duration of the therapy depends on the age and condition of the patient, as well as how the patient responds to the treatment. Additionally, a person having a greater risk of developing a condition listed in Table 1 may receive prophylactic treatment to inhibit or delay symptoms of the disease.

TABLE 1 abscess
a condition comprising cell death associated with renal failure
a condition comprising cell death of cardiac muscle
a condition comprising cell death of cells of the immune system
a condition comprising retinal neuronal cell death
activation-induced cell death
acute neurodegeneration
acute, latent, or persistent viral infection
acute neurological disease TABLE 1-continued adenovirus infection
ague
AIDS and associated conditions
alteration of blood vessels
Alzheimer's disease
amyotrophic lateral sclerosis
anemia
ankylosis
anoxia
anthrax lethal toxin induced septic shock
apnea
arthritis
aspergillosis
asphyxiation
asthma
ataxia
atrophy
avascular necrosis
avascular necrosis of the bone
backache
Becker's muscular dystrophy
blastomycosis
bleeding
blennorhea
bone avascular necrosis
cachexia
cancer
candidiasis (allergic, cutaneous, mucocutaneous, or systemic)
cardiac infarction
cardiomyopathy
caries
cell death induced by LPS
cerebral ischemia
chemical imbalance
chromoblastomycosis
chronic neurodegenerative diseases
chronic obstructive pulmonary disease
coccidioidomycosis
colic
condition leading to cell or tissue death
congestive heart failure
constipation
convulsion
coughing
coronary heart disease
Creutzfeldt-Jakob disease
Crohn's disease
cryptococcosis
cyanosis
cytomegalovirus infection
degenerative disease
delayed ischemic brain injury
dementia
diabetes
diarrhea
dizziness
dropsy
dry gangrene
Duchenne muscular dystrophy
dysentery
dyspepsia
dyspnea
edema
emaciation
Epstein-Barr virus infection
facioscapulohumeral muscular dystrophy
Fahr disease
fainting
fatigue
fever
fibrillation
fungal eye, hair, nail, or skin infection
gangrene
gas gangrene
gastrointestinal disease
genetic disease
graft-versus-host disease
head trauma
hemorrhagic stroke
hepatitis virus infection
Hepatitis B
Hepatitis C
herpes simplex virus infection
high blood pressure
histoplasmosis
HIV-associated dementia
HIV-infection and associated conditions
human herpesvirus infection
human papillomavirus infection
human T-Cell leukemia virus infection
Huntington's disease
hydrops
hypertension
hypotension
icterus
immunodeficiency
indigestion
infection
infectious encephalopathy
insomnia
interruption of blood supply
ischemia
ischemic brain disease or injury
ischemic disease or injury
ischemic heart disease or injury
ischemic injury due to organ storage
ischemic kidney disease or injury
ischemic liver disease or injury
ischemic mesenteric injury
ischemic necrosis
ischemic neuronal injury
ischemic retinal injury
ischemic stroke
itching
jaundice
kidney disease
lack of nutrient or oxygen supply
Landouzy-Dejerine muscular dystrophy
Lewy body disease
limb-girdle muscular dystrophy
liver cirrhosis
liver disease
liver fibrosis
lobomycosis
low blood pressure
lumbago
lupus
marasmus
measles virus infection
meningitis
Menkes disease
moist gangrene
multifactorial disease (e.g., HIV infection with opportunistic fungal infection)
multiple sclerosis
muscle wasting
muscular dystrophy
mycetoma
mycotic keratitis
myocardial infarction
myotonia congenita
myotonic dystrophy
necroptosis
necrosis
necrotic ulceration
necrotizing myopathy of intensive care
neurodegenerative disease
neurological disease
noma
oculomycosis (endogenous or extension)
onychomycosis
opportunistic infection
otomycosis
pain
pancreatic disease
pancreatitis (chronic, acute, sterile acute necrotizing, and infected acute necrotizing)
papovavirus (JC or BK) infection
paracoccidioidomycosis
paralysis TABLE 1-continued Parkinson's disease
parvovirus infection
penicilliosis
phaeohyphomycosis
physical trauma
piedra
pityriasis versicolor
poisoning
polyglutamine expansion disease
Pompe's disease
primary systemic infection
pruritus
radiation illness
rash
retinal necrosis
rheum
rhinosporidioisis
sclerosis
seizure
sepsis
septic shock
shock
sickle cell disease
skin eruption
sore
spasm
sphacelation
sphacelus
sporotrichosis
Steinert's disease
stroke
superficial infection
systemic infection
tabes
tachycardia
Thomsen's disease
tinea barbae
tinea capitis
tinea corporis
tinea cruris
tinea favosa
tinea nigra
tinea unguium
tooth decay
trauma
traumatic brain injury
tuberculosis
tumor
ulcerative colitis
upset stomach
Varicella-Zoster virus infection
vertigo
viral infection
vomiting
wasting
Wilson's disease
zygomycosis Exemplary subsets of the conditions listed in Table 1 are shown in Tables 2, 3, and 4.

TABLE 2 a condition comprising retinal neuronal cell death
activation-induced cell death
acute, latent, or persistent viral infection
Becker's muscular dystrophy
cardiomyopathy
chronic obstructive pulmonary disease
congestive heart failure
Crohn's disease
delayed ischemic brain injury
Diabetes
Duchenne muscular dystrophy
facioscapulohumeral muscular dystrophy
graft-versus-host disease
ischemic injury due to organ storage
ischemic mesenteric injury TABLE 2-continued ischemic neuronal injury
ischemic retinal injury
Landouzy-Dejerine muscular dystrophy
limb-girdle muscular dystrophy
liver cirrhosis
liver fibrosis
lupus
muscle wasting
muscular dystrophy
myotonia congenita
myotonic dystrophy
necroptosis
necrotizing myopathy of intensive care
pancreatitis (chronic, acute, sterile acute necrotizing, and infected acute necrotizing)
Pompe's disease
sickle cell disease
Steinert's disease
Thomsen's disease
traumatic brain injury
ulcerative colitis

TABLE 3 a condition comprising retinal neuronal cell death
activation-induced cell death
acute, latent, or persistent viral infection
AIDS
alteration of blood vessels
Becker's muscular dystrophy
cardiomyopathy
chronic obstructive pulmonary disease
congestive heart failure
coronary heart disease
Creutzfeldt-Jakob disease
Crohn's disease
delayed ischemic brain injury
diabetes
Duchenne muscular dystrophy
facioscapulohumeral muscular dystrophy
Fahr disease
gastrointestinal disease
graft-versus-host disease
head trauma
ischemic injury due to organ storage
ischemic mesenteric injury
ischemic neuronal injury
ischemic retinal injury
Landouzy-Dejerine muscular dystrophy
Lewy body disease
limb-girdle muscular dystrophy
liver cirrhosis
liver fibrosis
lupus
Menkes disease
multiple sclerosis
muscle wasting
muscular dystrophy
myotonia congenita
myotonic dystrophy
necroptosis
necrotic ulceration
necrotizing myopathy of intensive care
pancreatic disease
pancreatitis (chronic, acute, sterile acute necrotizing, and infected acute necrotizing)
polyglutamine expansion disease
Pompe's disease
retinal necrosis
sickle cell disease
Steinert's disease
Thomsen's disease
traumatic brain injury
tuberculosis
ulcerative colitis
Wilson's disease

TABLE 4 abscess
a condition comprising cell death associated with renal failure
a condition comprising cell death of cardiac muscle
a condition comprising cell death of cells of the immune system
a condition comprising retinal neuronal cell death
activation-induced cell death
acute neurodegeneration
acute, latent, or persistent viral infection
acute neurological disease
adenovirus infection
ague
anemia
ankylosis
anoxia
anthrax lethal toxin induced septic shock
apnea
arthritis
aspergillosis
asphyxiation
asthma
ataxia
atrophy
avascular necrosis
avascular necrosis of the bone
backache
Becker's muscular dystrophy
blastomycosis
bleeding
blennorhea
bone avascular necrosis
cachexia
cancer
candidiasis (allergic, cutaneous, mucocutaneous, or systemic)
cardiac infarction
cardiomyopathy
caries
cell death induced by LPS
chemical imbalance
chromoblastomycosis
chronic neurodegenerative diseases
chronic obstructive pulmonary disease
coccidioidomycosis
colic
condition leading to cell or tissue death
congestive heart failure
constipation
convulsion
coughing
Crohn's disease
cryptococcosis
cyanosis
cytomegalovirus infection
delayed ischemic brain injury
dementia
diabetes
diarrhea
dizziness
dropsy
dry gangrene
Duchenne muscular dystrophy
dysentery
dyspepsia
dyspnea
edema
emaciation
Epstein-Barr virus infection
facioscapulohumeral muscular dystrophy
fainting
fatigue
fever
fibrillation
fungal eye, hair, nail, or skin infection
gangrene
gas gangrene
genetic disease
graft-versus-host disease
hemorrhagic stroke
hepatitis virus infection
Hepatitis B
Hepatitis C

TABLE 4-continued herpes simplex virus infection
high blood pressure
histoplasmosis
HIV-associated dementia
human herpesvirus infection
human papillomavirus infection
human T-Cell leukemia virus infection
hydrops
hypertension
hypotension
icterus
immunodeficiency
indigestion
infection
infectious encephalopathy
insomnia
interruption of blood supply
ischemia
ischemic injury due to organ storage
ischemic kidney disease or injury
ischemic liver disease or injury
ischemic mesenteric injury
ischemic necrosis
ischemic neuronal injury
ischemic retinal injury
ischemic stroke
itching
jaundice
lack of nutrient or oxygen supply
Landouzy-Dejerine muscular dystrophy
limb-girdle muscular dystrophy
liver cirrhosis
liver fibrosis
lobomycosis
low blood pressure
lumbago
lupus
marasmus
measles virus infection
meningitis
moist gangrene
multifactorial disease (e.g., HIV infection with opportunistic fungal infection)
muscle wasting
muscular dystrophy
mycetoma
mycotic keratitis
myocardial infarction
myotonia congenita
myotonic dystrophy
necroptosis
necrotizing myopathy of intensive care
neurological disease
noma
oculomycosis (endogenous or extension)
onychomycosis
opportunistic infection
otomycosis
pain
pancreatitis (chronic, acute, sterile acute necrotizing, and infected acute necrotizing)
papovavirus (JC or BK) infection
paracoccidioidomycosis
paralysis
Parkinson's disease
parvovirus infection
penicilliosis
phaeohyphomycosis
physical trauma
piedra
pityriasis versicolor
poisoning
Pompe's disease
primary systemic infection
pruritus
radiation illness
rash
rheum
rhinosporidioisis
sclerosis

TABLE 4-continued seizure
sepsis
shock
sickle cell disease
skin eruption
sore
spasm
sphacelation
sphacelus
sporotrichosis
Steinert's disease
superficial infection
systemic infection
tabes
tachycardia
Thomsen's disease
tinea barbae
tinea capitis
tinea corporis
tinea cruris
tinea favosa
tinea nigra
tinea unguium
tooth decay
trauma
traumatic brain injury
tumor
ulcerative colitis
upset stomach
Varicella-Zoster virus infection
vertigo
vomiting
wasting
zygomycosis While any of the Nec compounds described herein can be used to treat any of the conditions listed in the above tables, it is desirable that the conditions in Table 1 be treated with Nec-1e compounds, Nec-2b compounds, or Nec-3b compounds; the conditions in Table 2 be treated with any of the Nec compounds; the conditions in Table 3 be treated with Nec-1c compounds; and the conditions in Table 4 be treated with Nec-1d compounds.

In some embodiments, the compounds and methods of the invention can be used to treat any of the following: a neurodegenerative disease of the central or peripheral nervous system, the result of retinal neuronal cell death, the result of cell death of cardiac muscle, the result of cell death of cells of the immune system; stroke, liver disease, pancreatic disease, the result of cell death associated with renal failure; heart, mesenteric, retinal, hepatic or brain ischemic injury, ischemic injury during organ storage, head trauma, septic shock, coronary heart disease, cardiomyopathy, bone avascular necrosis, sickle cell disease, muscle wasting, gastrointestinal disease, tuberculosis, diabetes, alteration of blood vessels, muscular dystrophy, graft-versus-host disease, viral infection, Crohn's disease, ulcerative colitis, asthma, and any condition in which alteration in cell proliferation, differentiation or intracellular signaling is a causative factor.

Exemplary neurodegenerative conditions are Alzheimer's disease, Huntington's disease, Parkinson's disease, amyotrophic lateral sclerosis, HIV-associated dementia, cerebral ischemia, amyotropic lateral sclerosis, multiple sclerosis, Lewy body disease, Menke's disease, Wilson's disease, Creutzfeldt-Jakob disease, and Fahr disease.

Exemplary muscular dystrophies or related diseases are Becker's muscular dystrophy, Duchenne muscular dystrophy, myotonic dystrophy, limb-girdle muscular dystrophy, Landouzy-Dejerine muscular dystrophy, facioscapulohumeral muscular dystrophy (Steinert's disease), myotonia congenita, Thomsen's disease, and Pompe's disease.

Muscle wasting can be associated with cancer, AIDS, congestive heart failure, and chronic obstructive pulmonary disease, as well as include necrotizing myopathy of intensive care Conditions in which alteration in cell proliferation, differentiation or intracellular signaling is a causative factor include cancer and infection, e.g., by viruses (e.g., acute, latent and persistent), bacteria, fungi, or other microbes.

Exemplary viruses are human immunodeficiency virus (HIV), Epstein-Barr virus (EBV), cytomegalovirus (CMV), human herpesviruses (HHV), herpes simplex viruses (HSV), human T-Cell leukemia viruses (HTLV), Varicella-Zoster virus (VZV), measles virus, papoviruses (JC and BK), hepatitis viruses, adenovirus, panioviruses, and human papillomaviruses.

Compounds and methods of the invention can additionally be used to boost the immune system, whether or not the patient being treated has an immunocompromising condition. For example, a Nec compound can be used in a method to strengthen the immune system during immunization, e.g., by functioning as an adjuvant, or by being combined with an adjuvant.

Administration of pharmaceutical compositions and formulations Pharmaceutical compositions and formulations can be prepared utilizing the Nec-1 compounds, Nec-2 compounds, or Nec-3 compounds of the invention. Pharmaceutical compositions of the invention are prepared in a manner known to those skilled in the art, for example, by means of conventional dissolving, lyophilising, mixing, granulating or confectioning processes. Methods well known in the art for making formulations are found, for example, in Remington: The Science and Practice of Pharmacy, 20th ed., ed. A. R. Gennaro, 2000, Lippincott Williams & Wilkins, Philadelphia, and Encyclopedia of Pharmaceutical Technology, eds. J. Swarbrick and J. C. Boylan, 1988-1999, Marcel Dekker, New York.

A compound identified as capable of treating any of the conditions of Table 1, using any of the methods described herein, may be administered to patients or animals with a pharmaceutically-acceptable diluent, carrier, or excipient, in unit dosage forth. The chemical compounds for use in such therapies may be produced and isolated by any standard technique known to those in the field of medicinal chemistry. Exemplary compounds suitable for treatment in the methods of the invention are Neo-1 compounds, Nec-2 compounds, and Nec-3 compounds. Conventional pharmaceutical practice may be employed to provide suitable formulations or compositions to administer the identified compound to patients suffering from a disease in which necrosis occurs. Administration may begin before the patient is symptomatic.

Any appropriate route of administration may be employed. For example, the therapy may be administered either directly to the site of a predicted cell death event (for example, by injection) or systemically (for example, by any conventional administration technique). Administration of the compound may also be parenteral, intravenous, intraarterial, subcutaneous, intramuscular, intracranial, intraorbital, ophthalmalic, intraventricular, intracapsular, intraspinal, intracisternal, intraperitoneal, intranasal, aerosol, by suppositories, or oral administration. Therapeutic formulations may be in the form of liquid solutions or suspensions; for oral administration, formulations may be in the form of tablets or capsules; and for intranasal formulations, in the form of powders, nasal drops, or aerosols. The dosage of the therapeutic compounds in a pharmaceutically-acceptable formulation depends on a number of factors, including the size and health of the individual patient The dosage to deliver may be determined by one skilled in the art.

Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for compounds that decreases necrosis include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

The compounds, compositions, and methods of the present invention may be used to treat a number of diseases, as described herein. For example, the methods described herein allow for a decrease in cell death occurring through a necrosis pathway. The invention also provides compounds and methods for treating diseases in which necrosis occurs. These compounds and methods can be used to treat conditions such as a neurodegenerative disease, stroke, liver disease, pancreatic disease, ischemic heart or brain injury or other ischemic injuries, head trauma, septic shock, coronary heart disease, gastrointestinal disease, tuberculosis, alteration of blood vessels, viral infection, such as HIV, or conditions associated with a viral infection such as AIDS.

Examples of uses of any pharmaceutical composition of the present invention include treating or ameliorating cell death in the central or peripheral nervous system, retinal neurons, cardiac muscle or immune system cells of an animal; treating or preventing polycystic kidney disease, renal amyloidosis, acute renal failure, cyclosporine A induced murin tubular epithelial cell death, HIV-induced nephropathy or anemia/erythropoiesis in an animal; protecting a mammalian organ or tissue from cell death due to deprivation of normal blood supply; reducing or preventing cell death in a donor organ or tissue after it has been transplanted into a host due to the effects of host immune cells; reducing or preventing the death of mammalian sperm or eggs used in in vitro fertilization procedures; extending the lifespan of a mammalian cell line; treating or ameliorating hair loss or premature graying of the hair in a mammal; treating or ameliorating skin damage of a mammal due to exposure to high levels of radiation, heat or chemicals; treating or ameliorating sepsis in an animal; treating or ameliorating hepatitis in an animal; treating or ameliorating hereditary tyrosinemia type 1 in an animal; treating or ameliorating chronic alcohol ingestion induced buccal mucosa cell death in an animal; treating or ameliorating radiation or ultraviolet-irradiation induced cell death in an animal; treating or ameliorating organ cell death after burn injury; treating or ameliorating small bowel tissue injury after intestinal ischemia-reperfusion; and treating, ameliorating or preventing oral mucositis, gastrointestinal mucositis, bladder mucositis, proctitis, bone marrow cell death, skin cell death or hair loss resulting from chemotherapy or radiation therapy of cancer in an animal.

If desired, treatment with a compound identified according to the methods described above, may be combined with more traditional therapies for a disease characterized by cell death, such as tacrine hydrochloride for the treatment of Alzheimer's disease, or interferon α-1a for the treatment of multiple sclerosis.

Dosage

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient that is effective to achieve the desired therapeutic response for a particular patient composition, and mode of administration, without being toxic to the patient.

The selected dosage level will depend upon a variety of factors including the activity of the particular compound of the present invention employed, or the ester, salt or amide thereof the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated; and like factors well known in the medical arts. A daily, weekly, or monthly dosage (or other time interval) can be used.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required to achieve the desired therapeutic effect and then gradually increasing the dosage until the desired effect is achieved.

In general, a suitable daily dose of a compound of the invention will be that amount of the compound that is the lowest dose effective to produce a therapeutic effect. Such an effective dose will generally depend upon the factors described above. Generally doses of the compounds of this invention for a patient, when used for the indicated effects, will range from about 0.0001 to about 100 mg per kg of body weight per day. Preferably the daily dosage will range from 0.001 to 50 mg of compound per kg of body weight, and even more preferably from 0.01 to 10 mg of compound per kg of body weight.

Combination Therapy

If desired, treatment with Nec compounds can be combined with therapies for the treatment of any of the conditions of Table 1, e.g., conditions involving necrosis or ischemia. Such treatments include surgery, radiotherapy, chemotherapy, or the administration of one or more additional compounds. Exemplary compounds suitable for combination therapy with Nec compounds are described below.

Compounds of the inventions can be administered in combination with compounds that are apoptosis inhibitors, i.e., compounds that inhibit apoptosis, including but not limited to reversible and irreversible caspase inhibitors. An example of an apoptosis inhibitor includes zVAD (N-benzyloxycarbonyl-Val-Ala-Asp-(OMe) fluoromethyl ketone), IETD (N-acetyl-Ile-Glu-Thr-Asp-al) (SEQ ID NO: 1), YVAD (N-benzyloxycarbonyl-Tyr-Val-Ala-Asp-(OMe) fluoromethyl ketone) (SEQ ID NO: 2), DEVD (N-[2-(6-hydroxy-3-oxo-3H-xanthen-9-yl)benzoyl]-L-α-aspartyl-L-α-glutamyl-N-[1S)-1-(carboxymethyl)-3-fluoro-2-oxopropyl]-L-Valinamide) (SEQ ID NO: 3), and LEHD (N-acetyl-Leu-Glu-His-Asp-al) (SEQ ID NO: 4).

In some instances, the compounds of the invention are administered in combination with PARP poly(ADP-ribose)

polymerase inhibitors. Non-limiting examples of PARP inhibitors include 6(5H)-Phenanthridinone, 4-Amino-1,8-naphthalitnide, 1,5-Isoquinolinediol, and 3-Aminobenzamide.

Compounds of the invention can also be administered in combination with Src inhibitors. Src proteins are mammalian cytoplasmic tyrosine kinases that play an extensive role in signal transduction. Examples of Src inhibitors include but are not limited to: PP1(1-(1,1-dimethylethyl)-1-(4-methylphenyl)-1H-pyrazolo[3,4-d]pyrimidin-4-amine), PP2 (3-(4-chlorophenyl)-1-(1,1-dimethylethyl)-1H-pyr-azolo[3,4-d]pyrimidin-4-amine), damnacanthal (3-hydroxy-1-methoxy-2-anthra-quinonecarboxaldehyde), and SU-5565.

The methods of the invention involve, in some aspects, combinations of compounds that are inhibitors of cellular necrosis (e.g., heterocyclic thiohydantoin, hydantoin, oxazolidinone, thioxo-oxazolidinone, pyrimidinone, or oxazinanone compounds, or combinations thereof) with agents for the treatment of cardiovascular disorders. Such agents include anti-inflammatory agents, anti-thrombotic agents, anti-platelet agents, fibrinolytic agents, lipid reducing agents, direct thrombin inhibitors, glycoprotein IIb/IIIa receptor inhibitors, agents that bind to cellular adhesion molecules and inhibit the ability of white blood cells to attach to such molecules (e.g. anti-cellular adhesion molecule antibodies), calcium channel blockers, beta-adrenergic receptor blockers, cyclooxygenase-2 inhibitors, angiotensin system inhibitors, and any combinations thereof. One preferred agent is aspirin.

Anti-inflammatory agents include alclofenac; alclometasone dipropionate; algestone acetonide; alpha amylase; amcinafal; amcinafide; amfenac sodium; amiprilose hydrochloride; anakinra; anirolac; anitrazafen; apazorie; balsalazide disodium; bendazac; benoxaprofen; benzydamine hydrochloride; bromelains; broperamole; budesonide; carprofen; ciclofen; cintazone; cliprofen; clobetasol propionate; clobetasone butyrate; clopirac; cloticasone propionate; cormethasone acetate; cortodoxone; deflazacort; desonide; desoximetasone; dexamethasone dipropionate; diclofenac potassium; diclofenac sodium; diflorasone diacetate; diflurnidone sodium; diflunisal; difluprednate; diftalone; dimethyl sulfoxide; drocinonide; endrysone; enlimomab; enolicam sodium; epirizole; etodolac; etofenamate; felbinac; fenarnole; fenbufen; fenclofenac; fenclorac; fendosal; fenpipalone; fentiazac; flazalone; fluazacort; flufenamic acid; flumizole; flunisolide acetate; flunixin; flunixin meglumine; fluocortin butyl; fluorometholone acetate; fluquazone; flurbiprofen; fluretofen; fluticasone propionate; furaprofen; furobufen; halcinonide; halobetasol propionate; halOpredone acetate; ibufenac; ibuprofen; ibuprofen aluminum; ibuprofen piconol; ilonidap; indomethacin; indomethacin sodium; indoprofen; indoxole; intrazole; isoflupredone acetate; isoxepac; isoxicam; ketoprofen; lofemizole hydrochloride; lomoxicam; loteprednol etabonate; meclofenamate sodium; meclofenamic acid; meclorisohe dibutyrate; mefenamic acid; mesalamine; meseclazone; methylprednisolone suleptanate; morniflumate; nabumetone; naproxen; naproxen sodium; naproxol; nimazone; olsalazine sodium; orgotein; orpanoxin; oxaprozin; oxyphenbutazone; paranyline hydrochloride; pentosan polysulfate sodium; phenbutazone sodium glycerate; pirfenidone; piroxicam; piroxicam cinnamate; piroxicam olamine; pirprofen; prednazate; prifelone; prodolic acid; proquazone; proxazole; proxazole citrate; rimexolone; romazarit; salcolex; salnacedin; salsalate; salycilates; sanguinarium chloride; seclazone; sermetacin; sitdoxicam; sulindac; suprofen; talmetacin; talniflumate; talosalate; tebufelone; tenidap; tenidap sodium; tenoxicam; tesicam; tesimide; tetrydamine; tiopinac; tixocortol pivalate; tolmetin; tolmetin sodium; triclonide; triflumidate; zidometacin; glucocorticoids; and zomepirac sodium.

Anti-thrombotic and fibrinolytic agents include plasminogen (to plasmin via interactions of prekallikrein, kininogens, factors XII, XIIIa, plasminogen proactivator, and tissue plasminogen activator (TPA)) streptokinase; urokinase: anisoylated plasminogen-streptokinase activator complex; prourokinase (pro-UK); rTPA (alteplase or activase); rPro-UK; abbokinase; eminase; sreptase anagrelide hydrochloride; bivalirudin; dalteparin sodium; danaparoid sodium; dazoxiben hydrochloride; efegatran sulfate; enoxaparin sodium; ifetroban; ifetroban sodium; tinzaparin sodium; retaplase; trifenagrel; warfarin; and dextrans.

Anti-platelet agents include clopridogrel; sulfinpyrazone; aspirin; dipyridamole; clofibrate; pyridinol carbamate; PGE; glucagon; antiserotonin drugs; caffeine; theophyllin; pentoxifyllin; ticlopidine; and anagrelide.

Lipid reducing agents include gemfibrozil, cholystyramine, colestipol, nicotinic acid, probucol, lovastatin, fluvastatin, simvastatin, atorvastatin, pravastatin, and cirivastatin.

Direct thrombin inhibitors include hirudin, hirugen, hirulog, agatroban, PPACK, and thrombin aptamers.

Glycoprotein IIb/IIIa receptor inhibitors include both antibodies and non-antibodies, and include but are not limited to ReoPro (abcixamab), lamifiban, and tirofiban.

Calcium channel blockers are a chemically diverse class of compounds having important therapeutic value in the control of a variety of diseases including several cardiovascular disorders, such as hypertension, angina, and cardiac arrhythmias (Fleckenstein, Cir. Res. 52:13-16 (1983); Fleckenstein, Experimental Facts and Therapeutic Prospects, John Wiley, New York (1983); McCall, D., Curr. Pract. Cardiol. 10:1-11 (1985)). Calcium channel blockers are a heterogenous group of drugs that prevent or slow the entry of calcium into cells by regulating cellular calcium channels. (Remington, The Science and Practice of Pharmacy, Nineteenth Edition, Mack Publishing Company, Eaton, Pa., p. 963 (1995)). Most of the currently available calcium channel blockers, and useful according to the present invention, belong to one of three major chemical groups of drugs, the dihydropyridines, such as nifedipine, the phenyl alkyl amines, such as verapamil, and the benzothiazepines, such as diltiazem. Other calcium channel blockers useful according to the invention, include, but are not limited to, amrinone, amlodipine, bencyclane, felodipine, fendiline, flunarizine, isradipine, nicardipine, nimodipine, perhexylene, gallopamil, tiapamil and tiapamil analogues (such as 1993RO-11-2933), phenyloin, barbiturates, and the peptides dynorphin, omega-conotoxin, and omega-agatoxin, and pharmaceutically acceptable salts thereof.

Beta-adrenergic receptor blocking agents are a class of drugs that antagonize the cardiovascular effects of catecholamines in angina pectoris, hypertension, and cardiac arrhythmias Beta-adrenergic receptor blockers include, but are not limited to, atenolol, acebutolol, alprenolol, befunolol, betaxolol, bunitrolol, carteolol, celiprolol, hedroxalol, indenolol, labetalol, levobunolol, mepindolol, methypranol, metindol, metoprolol, metrizoranolol, oxprenolol, pindolol, propranolol, practolol, practolol, sotalolnadolol, tiprenolol, tomalolol, timolol, bupranolol, penbutolol, trimepranol, 2-(3-(1,1-dimethylethyl)-amino-2-hyd-roxypropoxy)-3-pyridenecarbonitril HCl, 1-butylamino-3-(2,5-dichlorophenoxy-)-2-propanol, 1-isopropylamino-3-(4-(2-cyclopropylmethoxyethyl)phenoxy)-2-propanol, 3-isopropylamino-1-(7-methylindan-4-yloxy)-2-butanol, 2-(3-t-butylamino-2-hydroxy-propylthio)-4-(5-carbamoyl-2-thienyl)thiazol,-7-(2-hydroxy-3-t-butylaminpropoxy)phthalide. These compounds can be used as isomeric mixtures, or in their respective levorotating or dextrorotating form.

Cyclooxygenase-2 (COX-2) is an enzyme complex present in most tissues that produces various prostaglandins and thromboxanes from arachidonic acid. A number of selective COX-2 inhibitors are known in the art. These include, but are not limited to, those described in U.S. Pat. Nos. 5,474,995, 5,521,213, 5,536,752, 5,550,142, 5,552,422, 5,604,253, 5,604,260, 5,639,780, 5,677,318, 5,691,374, 5,698,584, 5,710,140, 5,733,909, 5,789,413, 5,817,700, 5,849,943, 5,861,419, 5,922,742, 5,925,631, and 5,643,933. A number of the above-identified COX-2 inhibitors are prodrugs of selective COX-2 inhibitors and exert their action by conversion in vivo to the active and selective COX-2 inhibitors. The active and selective COX-2 inhibitors formed from the above-identified COX-2 inhibitor prodrugs are described in detail in PCT/WO95/00501, PCT/WO95/18799, and U.S. Pat. No. 5,474,995. Given the teachings of U.S. Pat. No. 5,543,297, a person of ordinary skill in the art would be able to determine whether an agent is a selective COX-2 inhibitor or a precursor of a COX-2 inhibitor.

Angiotensin system inhibitors are capable of interfering with the function, synthesis or catabolism of angiotensin II. These agents include, but are not limited to, angiotensin-converting enzyme (ACE) inhibitors, angiotensin II antagonists, angiotensin II receptor antagonists, agents that activate the catabolism of angiotensin II, and agents that prevent the synthesis of angiotensin I from which angiotensin II is ultimately derived. The renin-angiotensin system is involved in the regulation of hemodynamics and water and electrolyte balance. Factors that lower blood volume, renal perfusion pressure, or the concentration of $Na^+$ in plasma tend to activate the system, while factors that increase these parameters tend to suppress its function.

Angiotensin I and angiotensin II are synthesized by the enzymatic renin-angiotensin pathway. The synthetic process is initiated when the enzyme renin acts on angiotensinogen, pseudoglobulin in blood plasma, to produce the decapeptide angiotensin I. Angioterisin I is converted by angiotensin converting enzyme (ACE) to angiotensin II (angiotensin-[1-8] octapeptide). The latter is an active pressor substance which has been implicated as a causative agent in several forms of hypertension in various mammalian species, e.g., humans.

Angiotensin (renin-angiotensin) system inhibitors are compounds that act to interfere with the production of angiotensin II from angiotensinogen or angiotensin I or interfere with the activity of angiotensin II. Such inhibitors are well known to those of ordinary skill in the art and include compounds that act to inhibit the enzymes involved in the ultimate production of angiotensin including renin and ACE. They also include compounds that interfere with the activity of angiotensin II, once produced. Examples of classes of such compounds include antibodies (e.g., to renin), amino acids and analogs thereof (including those conjugated to larger molecules), peptides (including peptide analogs of angiotensin and angiotensin I), pro-renin related analogs, etc. Among the most potent and useful renin-angiotensin system inhibitors are renin inhibitors, ACE inhibitors, and angiotensin II antagonists. In a preferred embodiment of the invention, the renin-angiotensin system inhibitors are renin inhibitors, ACE inhibitors, and angiotensin II antagonists.

Angiotensin II antagonists are compounds which interfere with the activity of angiotensin II by binding to angiotensin II receptois and interfering with its activity. Angiotensin II antagonists are well known and include peptide compounds and non-peptide compounds. Most angiotensin II antagonists are slightly modified congeners in which agonist activity is attenuated by replacement of phenylalanine in position 8 with some other amino acid; stability can be enhanced by other replacements that slow degeneration in vivo. Examples of angiotensin II antagonists include: peptidic compounds (e.g., saralasin, [(San$^1$)(Val$^5$)(Ala$^8$)]angiotensin-(1-8)octapeptide and related analogs); N-substituted imidazole-2-one (U.S. Pat. No. 5,087,634); imidazole acetate derivatives including 2-N-butyl-4-chloro-1-(2-chlorobenzile)imidazole-5-acetic acid (see Long et al., J. Pharmacol. Exp. Ther. 247(1), 1-7 (1988)); 4,5,6,7-tetrahydro-1H-imidazo[4,5-c]pyridine-6-carboxylic acid and analog derivatives (U.S. Pat. No. 4,816,463); N2-tetrazole beta-glucuronide analogs (U.S. Pat. No. 5,085,992); substituted pyrroles, pyrazoles, and tryazoles (U.S. Pat. No. 5,081,127); phenyl and heterocyclic derivatives such as 1,3-imidazoles (U.S. Pat. No. 5,073,566); imidazo-fused 7-member ring heterocycles (U.S. Pat. No. 5,064,825); peptides (e.g., U.S. Pat. No. 4,772,684); antibodies to angiotensin II (e.g., U.S. Pat. No. 4,302,386); and aralkyl imidazole compounds such as biphenyl-methyl substituted imidazoles (e.g., EP Number 253,310, Jan. 20, 1988); ES8891 (N-morpholinoacetyl-(1-naphthyl)-L-alanyl-(4, thiazolyl)-L-alanyl (35,45)-4-amino-3-hydroxy-5-cyclo-hexapentanoyl-N-hexylamide, Sankyo Company, Ltd., Tokyo, Japan); SKF 108566 (E-alpha-2-[2-butyl-1-(carboxy phenyl)methyl]1H-imidazole-5-yl[methylane]-2-thiophenepropanoic acid, Smith Kline Beecham Pharmaceuticals, PA); Losartan (DUP753/MK954, DuPont Merck Pharmaceutical Company); Remikirin (RO42-5892, F. Hoffman LaRoche AG); $A_2$ agonists (Marion Merrill Dow) and certain non-peptide heterocycles (G.D.Searle and Company).

Angiotensin converting enzyme (ACE) is an enzyme which catalyzes the conversion of angiotensin I to angiotensin II. ACE inhibitors include amino acids and derivatives thereof, peptides, including di and tri peptides and antibodies to ACE which intervene in the renin-angiotensin system by inhibiting the activity of ACE thereby reducing or eliminating the formation of pressor substance angiotensin II. ACE inhibitors have been used medically to treat hypertension, congestive heart failure, myocardial infarction and renal disease. Classes of compounds known to be useful as ACE inhibitors include acylmercapto and mercaptoalkanoyl prolines such as captopril (U.S. Pat. No. 4,105,776) and zofenopril (U.S. Pat. No. 4,316,906), carboxyalkyl dipeptides such as enalapril (U.S. Pat. No. 4,374,829), lisinopril (U.S. Pat. No. 4,374,829), quinapril (U.S. Pat. No. 4,344,949), ramipril (U.S. Pat. No. 4,587,258), and perindopril (U.S. Pat. No. 4,508,729), carboxyalkyl dipeptide mimics such as cilazapril (U.S. Pat. No. 4,512,924) and benazapril (U.S. Pat. No. 4,410,520), phosphinylalkanoyl prolines such as fosinopril (U.S. Pat. No. 4,337,201) and trandolopril.

Renin inhibitors are compounds which interfere with the activity of renin. Renin inhibitors include amino acids and derivatives thereof, peptides and derivatives thereof, and antibodies to renin. Examples of renin inhibitors that are the subject of United States patents are as follows: urea derivatives of peptides (U.S. Pat. No. 5,116,835); amino acids connected by nonpeptide bonds (U.S. Pat. No. 5,114,937); di and tri peptide derivatives (U.S. Pat. No. 5,106,835); amino acids and derivatives thereof (U.S. Pat. Nos. 5,104,869 and 5,095,119); diol sulfonamides and sulfinyls (U.S. Pat. No. 5,098,924); modified peptides (U.S. Pat. No. 5,095,006); peptidyl beta-aminoacyl aminodiol carbamates (U.S. Pat. No. 5,089,471); pyrolimidazolones (U.S. Pat. No. 5,075,451); fluorine and chlorine statine or statone containing peptides (U.S. Pat. No. 5,066,643); peptidyl amino diols (U.S. Pat. Nos. 5,063,208 and 4,845,079); N-morpholino derivatives (U.S. Pat. No. 5,055,466); pepstatin derivatives (U.S. Pat. No. 4,980,283);

N-heterocyclic alcohols (U.S. Pat. No. 4,885,292); monoclonal antibodies to renin (U.S. Pat. No. 4,780,401); and a variety of other peptides and analogs thereof (U.S. Pat. Nos. 5,071,837, 5,064,965, 5,063,207, 5,036,054, 5,036,053, 5,034,512, and 4,894,437).

Agents that bind to cellular adhesion molecules and inhibit the ability of white blood cells to attach to such molecules include polypeptide agents. Such polypeptides include polyclonal and monoclonal antibodies, prepared according to conventional methodology. Such antibodies already are known in the art and include anti-ICAM 1 antibodies as well as other such antibodies. Significantly, as is well-known in the art, only a small portion of an antibody molecule, the paratrope, is involved in the binding of antibody to its epitope (see, in general, Clark, W. R. (1986) The Experimental Foundations of Modern Immunology, Wiley & Sons, Inc., New York; Roitt, I. (1991) Essential Immunology, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an $F(ab')_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd Fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (Frs), which maintain the tertiary structure of the paratope (see, in general, Clar, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. Thus, for example, PCT International Publication Number WO 92/04381 teaches the production and use of humanized murine RSV antibodies in which at least a portion of the murine FR regions have been replaced by FR regions of human origin. Such antibodies, including fragments of intact, antibodies with antigen-binding ability, are often referred to as "chimeric" antibodies.

Thus, as will be apparent to one of ordinary skill in the art, the present invention also provides for $F(ab')_2$, Fab, Fv and Fd fragments; chimeric antibodies in which the Fc and/or Fr and/or CDR1 and/or CDR2 and/or light chain CDR3 regions have been replaced by homologous human or non-human sequences; chimeric $F(ab')_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1- and/or CDR2 regions have been replaced by homologous human or nonhuman sequences. The present invention also includes so-called single chain antibodies.

Thus, the invention involves polypeptides of numerous size and type that bind specifically to cellular adhesion molecules. These polypeptides may be derived also from sources other than antibody technology. For example, such polypeptide binding agents can be provided by degenerate peptide libraries which can be readily prepared in solution, in immobilized form or as phage display libraries. Combinatorial libraries also can be synthesized of peptides containing one or more amino acids. Libraries further can be synthesized of peptoids and non-peptide synthetic moieties.

Phage display can be particularly effective in identifying binding peptides useful according to the invention. Briefly, one prepares a phage library (using, e.g., m13, fd, or lambda phage), displaying inserts from 4 to about 80 amino acid residues using conventional procedures. The inserts may represent, for example, a completely degenerate or biased array. One then can select phage-bearing inserts which bind to the cellular adhesion molecule. This process can be repeated through several cycles of reselection of phage that bind to the cellular adhesion molecule. Repeated rounds lead to enrichment of phage bearing particular sequences. DNA sequences analysis can be conducted to identify the sequences of the expressed polypeptides. The minimal linear portion of the sequence that binds to the cellular adhesion molecule can be determined. One can repeat the procedure using a biased library containing inserts containing part of all of the minimal linear portion plus one or more additional degenerate residues upstream or downstream thereof. Yeast two-hybrid screening methods also may be used to identify polypeptides that bind to the cellular adhesion molecules. Thus, cellular adhesion molecules, or a fragment thereof, can be used to screen peptide libraries, including phage display libraries, to identify and select peptide binding partners of the cellular adhesion molecules.

Preventative Therapy

In a patient diagnosed with any of the conditions of Table 1, e.g., heart disease (e.g., coronary heart disease or ischemic heart injury) or degenerative disease (e.g., a neurodegenerative disease, such as Alzheimer's disease or Huntington's disease), any of the above therapies may be administered before the occurrence of the disease phenotype. In particular, compounds shown to decrease necrosis may be administered by any standard dosage and route of administration (as described above).

The methods of the instant invention may be used to decrease necrosis of a cell or to treat disorders described herein in any subject, for example, humans; domestic pets, such as, for example, canines or felines; or livestock.

Geldanamycin

Geldanamycin is an inhibitor of beat shock protein-90 (Hsp90), which is involved in the folding, activation and assembly of a wide range of proteins, including key proteins involved in signal transduction, cell cycle control and transcriptional regulation. The binding of geldanamycin to Hsp90 disrupts Hsp90-protein interactions, preventing the proteins from folding correctly and rendering them susceptible to proteasome-mediated destruction. Among these proteins are many mutated or overexpressed proteins implicated in cancer and other diseases, e.g., p53, Bcr-Abl kinase, Raf-1 kinase, Akt kinase, Npm-Alk kinase p185ErbB2 transmembrane kinase, Cdk4, Cdk6, Wee1, HER2/Neu (ErbB2), and hypoxia inducible factor-1α (HIF-1α) (see, e.g., U.S. Pat. No. 6,887, 993). Geldanamycin is a well-known natural product, obtainable, for example, by culturing the producing organism, *Streptomyces hygroscopicus* var. geldanus NRRL 3602. Geldanamycin derivatives can be made semi-synthetically, by chemical modification of geldanamycin.

Any of the conditions listed in Table 1, e.g., those involving cellular necrosis or ischemia, can be treated using geldanamycin, or a derivative thereof, alone or in combination with one or more Nec compounds. Geldanamycin and derivatives thereof are described, e.g., in U.S. Pat. Nos. 6,887,993, 6,875, 863, 6,872,715, 6,870,049, 6,855,705, 6,852,496, 4,261,989, and 3,987,035.

Screens to Identify Candidate Compounds

Identification of Chemical Compounds that Decrease Cell Necrosis

After a cell receives an initial assault, one or both of the apoptotis or necrosis mechanisms of cell death may be activated. In the present invention, the necrosis pathway was focused upon: Several chemical assaults were used to induce cell death, including exposure to tumor necrosis factor alpha (TNFα) and β-amyloid protein. Various cell types were also used, including human neuroblastoma cells (SH-SY5Y) and human Jurkat T cells. In order to block the apoptosis mechanism, a general caspase inhibitor, Cbz-valine-alanine-aspartyl fluoromethyl ketone (zVAD-fmk, Polverino and Patterson, J. Biol. Chem. 272:7013-7021, 1997), was given. This compound inhibits all caspases and consequently disrupts the apoptosis pathway. Any resulting cell death is assumed to arise from the necrosis mechanism. After administering zVAD-fmk and TNFα to the cells, test compounds were applied to the cells in attempts to rescue them. Therefore, compounds found to restore cell viability using this protocol are inhibitors of the necrosis pathway.

For example, in one approach, zVAD-fmk is added to the culture media of cells at high density (for example, 5×10$^5$ or 7.5×10$^5$ cells/ml), which are capable of undergoing necrosis in response to zVAD-fmk/TNFα. Candidate molecules, for example, chemical compounds from a chemical library, such as, for example, the library of compounds from ChemBridge Research Laboratories, San Diego, Calif.) are added, in varying concentrations to the cells, and the cells are then exposed to TNFα.

The occurrence of necrosis of the treated cells is then measured, for example, by measuring the cellular ATP level of the cells exposed to zVAD-fmk/TNFα (Crouch et al., J. Immunol. Methods 160:81-8, 1993; Storer et al., Mutat. Res. 368:59-101, 1996; and Cree et al., Toxicol. In Vitro 11:553-556, 1997). The level of necrosis in the presence of the candidate molecule is compared to the level of necrosis in the absence of the candidate molecule, all other factors (e.g., cell type and culture conditions) being equal. The importance of zVAD-fmk in the invention is to block cell death that may occur by apoptosis, so that cell death by necrosis can be fully unmasked.

In a second approach, a cell may be exposed to a candidate molecule that decreases necrosis at the same time it is exposed to either zVAD-fmk or TNFα. In a third approach, a cell may be exposed to zVAD-fmk and TNFα first, and then to a candidate compound. The level of necrosis that occurs following each of these approaches is measured as described above.

The effect of candidate molecules on necrosis induced by cell death stimuli, for example, TNFα or DMSO, may also be measured by other methods, for example, vital dye staining, using dyes such as trypan blue or acridine orange/ethidium bromide.

Compounds that decrease necrosis may be purified or substantially purified, or may be one component of a mixture of compounds, such as a pool of chemical compounds. In an assay of a mixture of compounds, the occurrence of necrosis is tested against progressively smaller subsets of the compound pool (e.g., produced by standard purification techniques such as HPLC or FPLC) until a single compound or minimal number of effective compounds is demonstrated to decrease necrosis. A molecule that promotes a decrease in necrosis induced by zVAD-fmk/TNFα is considered particularly useful in the invention; such a molecule may be used, for example, as a therapeutic to decrease necrosis, in a patient with a condition in which necrosis occurs, such as a neurodegenerative disease.

Chemical compounds that are found, by the methods described above, to effectively decrease necrosis induced, for example, by zVAD-fmk/TNFα in an in vitro system may be tested further in animal models. Particularly useful animal models include mouse and rat models of cell death, ischemic brain or heart injury or other ischemic injuries, head trauma, neurodegenerative diseases, coronary heart disease, and septic shock. Examples of such models include SOD or Huntington's disease gene transgenic mice, and other known models, such as those described by Li et al., Hum. Mol. Genet. 8:1227-12236, 1999; Levine et al., Neurosci. Res. 58:515-532, 1999; Vukosavic et al., J. Neurochem. 73:2460-2468, 1999; Gruney, J. Neurol. Sci. 152 suppl. 1:S67-73, 1997; Deshmukh et al., Am. J. Physiol. 273 (4 Pt 1):C1130-1135, 1997; and Isibashi et al., J. Immunol. 163:5666-5677, 1999. Compounds which demonstrate an ability to decrease necrosis in in vivo models may be used as therapeutics to prevent necrosis, as appropriate.

Identification of Chemical Compounds that Decrease zVAD-fmk/DMSO-Induced Cell Necrosis Methods for the identification of chemical compounds that decrease cell necrosis induced, for example, by zVAD-fmk/DMSO at a low cell density (e.g., 1×10$^5$ cells/ml) are achieved essentially as described above, except, the inducer of necrosis is zVAD-fmk/DMSO, rather than zVAD-fmk/TNFα.

RIP1

We have discovered that Nec compounds are capable of inhibiting RIP1 (receptor interacting protein 1) (see, e.g., Example 10). Thus, the invention provides for screening assays to identify candidate compounds in which RIP1 is the target molecule.

RIP1 is a unique death domain-containing kinase that has been shown to interact with Fas and TNFR1. RIP1 contains a N-terminal kinase domain with homology to both Ser/Thr and tyrosine kinases, a C-terminal death domain, and an intermediate domain (IM). Its kinase activity is not required for DR-induced apoptosis nor NFκB activation, which is regulated by the intermediate domain (IM) of RIP. RIP contributes to a wide range of cellular regulatory paradigms, including cytokines, e.g., TNFα and IL-1β, and Toll-like receptor 3 and 4 mediated induction of NFκB.

Figure 22:
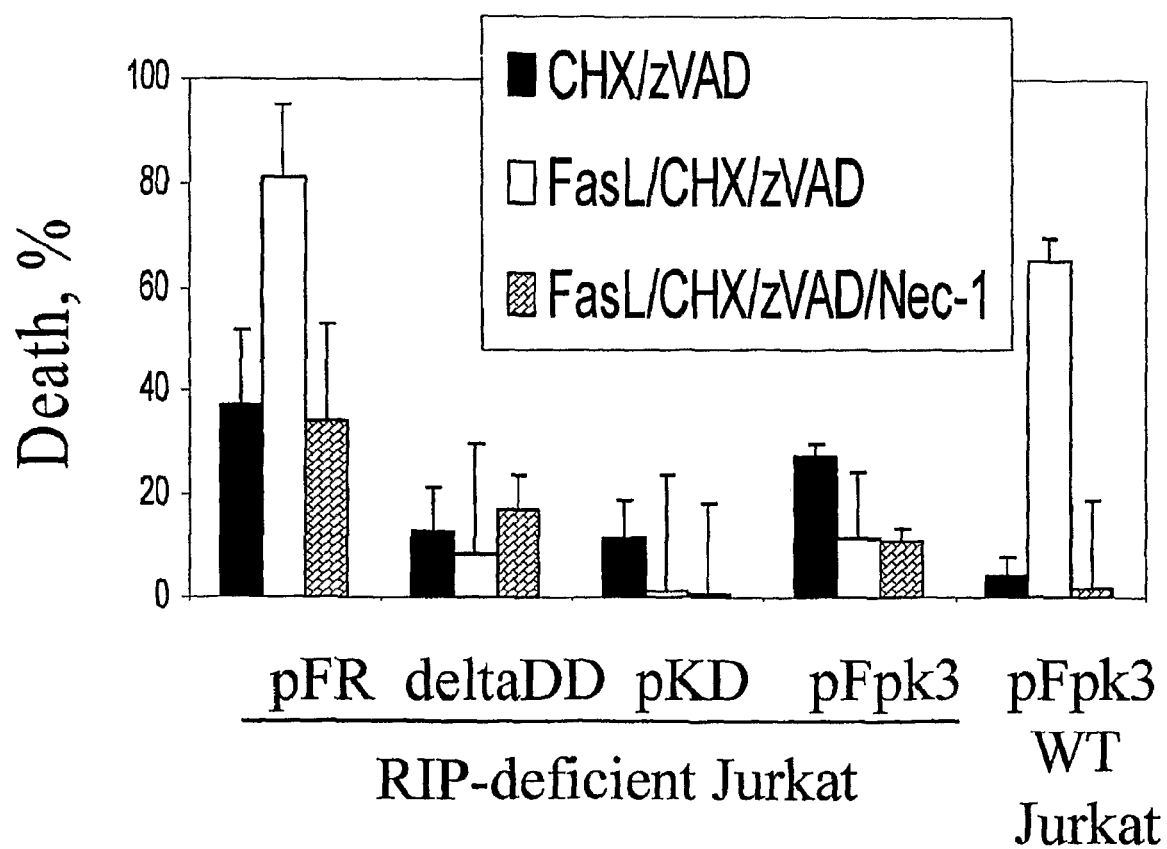
FIG. 22 is a chart showing the requirement for the intact kinase and death domains for the restoration of necroptosis in RIP-deficient Jurkat cells. RIP-deficient Jurkat cells were transiently electroporated with the following constructs: RIP-FKBP12₃-Myc (pFR), RIP (1-580)-FKBP12₃-Myc (delta DD), RIP (1-287)-FKBP12₃-Myc (pKD, kinase domain only) and F1CBP12₃-Myc (pFpk3), encoding different domains of RIP fused to the FKBP12-based dimerization cassette. Alternatively, wild type Jurkat cells were electroporated with pFpk3. In all conditions, pEGFP vector (Clontech) was added to track electroporated cells. Cells were treated with FasL (5 ng/m1), cycloheximide (1 μg/ml), zVAD.fmk (100 μM) and Nec-1 (30 μM) for 48 hours. Cells were stained with propidium iodide, which selectively stains dead cells, and percentages of cells which lost GFP expression and were PI-positive in each sample (death, %) were determined.

Kinase activity of RIP1 is essential for the alternative necrotic cell death pathway mediated by FasL, TNFα and TRAIL, which we subsequently termed necroptosis. We have analyzed the domains of RIP required for the death receptor-induced necroptosis in RIP-deficient clone of Jurkat cells, which are otherwise insensitive to this pathway due to the lack of RIP. As shown in FIG. 22, not only the kinase domain of RIP is required to mediate necroptosis triggered by Fas ligand (FasL)/cyclohexamide and zVAD.fmk, but the death domain of the molecule is also required. In addition, we have found that the activation of RIP1 kinase by dimerization is sufficient to induce necroptosis inhibitable by Nec-1. Thus, the kinase activity of RIP1 represents an essential upstream signaling step in necroptosis.

Based on our discovery, screening assays may be performed in which

RIP1 is utilized as a target, and candidate compounds are assayed for their ability to bind to or otherwise inhibit RIP1. For example, assays that measure inhibition of autophosphorylation of RIP1 can be used. Alternatively, assays that measure binding of a candidate compound to RIP1 are useful in the methods of the invention. Many other variations of binding assays are known in the art and can be employed. RIP1 binding assays are described, e.g., in U.S. Pat. No. 6,211,337, which is hereby incorporated by reference.

To identify compounds that are specific for RIP1, screening assays can be performed using multiple targets. For example, for a given candidate compound, the binding, autophosphorylation, or other measure of target activity may be assayed for both RIP1 and RIP2, or alternatively both RIP1 and RIP3, and the results compared (see, e.g., Example 10). Candidate compounds that exert a greater effect on RIP1 than RIP2, RIP3, or another homologue or other molecule chosen for this purpose, are considered to be specific for RIP1, and may be particularly desirable in the methods of the invention.

Alternate Screening Assays

Any method for measuring protein interactions or inhibition of the activity of a target molecule (e.g., RIP1) may be utilized. Such methods include, but are not limited to fluorescence polarization assays, mass spectrometry (Nelson and Krone, J. Mol. Recognit., 12:77-93, 1999), surface plasmon resonance (Spiga et al., FEBS Lett., 511:33-35, 2002; Rich and Mizka, J. Mol. Recognit., 14:223-228, 2001; Abrantes et al., Anal. Chem., 73:2828-2835, 2001), fluorescence resonance energy transfer (FRET) (Bader et al., J. Biomol. Screen, 6:255-264, 2001; Song et al., Anal. Biochem. 291: 133-41, 2001; Brockhoff et al., Cytometry, 44:338-248, 2001), bioluminescence resonance energy transfer (BRET) (Angers et al., Proc. Natl. Acad. Sci. USA, 97:3684-3689, 2000; Xu et al., Proc. Natl. Acad. Sci. USA, 96:151-156, 1999), fluorescence quenching (Engelborghs, Spectrochim. Acta A. Mol. Biomol. Spectrosc., 57:2255-2270, 1999; Geoghegan et al., Bioconjug. Chem. 11:71-77, 2000), fluorescence activated cell scanning/sorting (Barth et al., J. Mol. Biol., 301:751-757, 2000), ELISA, and radioimmunoassay (RIA).

Candidate Compounds

In general, candidate compounds used in the screening assays of the invention are identified from large libraries of both natural products, synthetic (or semi-synthetic) extracts or chemical libraries, according to methods known in the art.

Additional Methods

Antibodies and Reagents

FasL (used at 10 ng ml$^{-1}$) and zVAD.fmk (used at 100 μM) were from Alexis Biochemicals. Human or mouse (used for MEF cells) TNF (used at 10 ng ml$^{-1}$) was from Cell Sciences. Sytox Green, TO-PRO-3 and DiOC$_6$ were from Molecular Probes. Propidium iodide was from Roche. The dimerizing agents AP1510 and AP20187 (both used at 100 nM) were obtained from Ariad Pharmaceuticals. CHX (used at 1 μg ml$^{-1}$), antioxidants (N-acetyl cysteine (NAC), used at 2.5 mM; superoxide dismutase (SOD), 800 U ml$^{-1}$; catalase (cat.), 1,400 U ml$^{-1}$; vitamin E (vit. E), 5 mM), phalloidin-TRITC and all common chemicals were from Sigma. The following antibodies were used: mouse anti-β-tubulin (Stressgen), rabbit anti-LC3, rabbit anti-beclin-1 (Santa Cruz), rabbit anti-giantin (Covance), mouse anti-KDEL (Stressgen) and mouse anti-cytochrome c (Pharmingen). Secondary horseradish peroxidase (HRP)-conjugated antibodies were from Southern Biotech. Secondary Alexa 488-conjugated antibodies were from Molecular Probes; Cy3-conjugated antibodies were from Jackson ImmunoResearch.

Chemical Screening

We plated U937 cells in 384-well plates at 5,000-10,000 cells per well in 40-μl phenol red-free RPMI 1640 medium containing 100 μM zVAD.fmk and 40 ng ml$^{-1}$ human TNFα using a Multidrop dispenser (Thermo Electron). We added 100 nl of the DiverSetE (5 mg ml$^{-1}$ in DMSO, Chembridge) using a Seiko-based custom-built pin transfer robot (Institute of Chemistry and Cell Biology, Harvard Medical School). After 72 hours, we assessed cell viability using a luminescence-based ATP assay (ATPLite-M, PerkinElmer). We also dispensed cells not treated with TNFα in each plate as a positive control. We purchased Nec-1 and other preliminary positive hits from Chembridge for individual retesting.

Cell Viability Assays

We seeded cells in 96-well plates (white plates for luminescent assays; black plates for fluorescent assays; clear plates for MTT assay) at the density of 5,000-10,000 cells per well for adherent cells or 20,000-50,000 cells per well for suspension cells in 100 μl of the appropriate phenol red-free media. After incubation, we determined cell viability using one of the following methods. For the ATP assay, we used luminescence-based commercial kits (CellTiter-Glo, Promega or ATPLite-M, PerkinElmer) and analyzed luminescence using a Wallac Victor II plate reader (PerkinElmer). For Sytox assay, we incubated cells with 1 μM Sytox Green reagent for thirty minutes at 37° C., and then performed fluorescent reading. Subsequently, we added 5 μl of 20% Triton X-100 solution into each well to produce maximal lysis and incubated cells for one hour at 37° C., then performed the second reading. We calculated the ratio of values (percentage of dead cells in each well) before and after Triton treatment and normalized it to the relevant controls not subjected to cytotoxic stimuli, as indicated in figure legends. For the MTT assay, we used the CellTiter 96 AQ$_{ueous}$ Non-Radioactive Cell Proliferation Assay kit (Promega). For PI exclusion assays, we added 2 μg ml$^{-1}$ PI into the medium and immediately analyzed samples using FACSCalibur (BD Biosciences). For PI-annexin V assay we used the ApoAlert Annexin V-EGFP Apoptosis Kit (Clontech). For DioC6 staining, we incubated cells with 40 nM DiOC$_6$ for thirty minutes at 37° C., washed once and analyzed in FACSCalibur. For ROS analysis, we incubated cells with 5 μM dihydroethidium (Molecular Probes) for thirty minutes at 37° C., washed once and analyzed in FACSCalibur. We acquired bright-field images of the cells using an Axiovert 200 microscope (Zeiss).

Transient Focal Cerebral Ischemia in the Mouse

Animals were maintained in accordance with the "Guide for the Care and Use of Laboratory Animals" (National Research Council, 1996). We anesthetized spontaneously breathing adult male SV-129 mice (19-23 g; Taconic Farms) with 2% isoflurane and maintained them on 0.8-1% isoflurane in 70% N$_2$O and 30% O$_2$ using a Fluotec 3 vaporizer (Colonial Medical). We occluded the left MCA with an intraluminal 8-0 nylon monofilament (Ethicon) coated with a mixture of silicone resin (Xantopren, Bayer Dental) and a hardener (Elastomer Activator, Bayer Dental). The procedure lasted fifteen minutes, and the anesthesia was discontinued. We briefly reanesthetized animals two hours later with isoflurane, and withdrew the filament. Eighteen hours after reperfusion we divided forebrains into five coronal (2-mm) sections using a mouse brain matrix (RBM-2000C; Activational Systems), and stained the sections with 2% 2,3,5-triphenyltetrazolium chloride (Sigma). We quantified infarct areas using an image-analysis system (Bioquant IV, R & M Biometrics) and calculated infarct volume directly by adding the infarct volume in each section.

For drug administration, we dissolved 7-Cl-Nec-1 or other derivatives in 4% methyl-β-cyclodextrin (Sigma) solution in PBS and administered it through intracerebroventricular administration at the time points indicated. Typically, we performed two 2-μl injections of 4 mM stock solution (unless otherwise indicated). For preocclusion delivery, we performed injections five minutes before the onset of 2-h MCAO occlusion and immediately after the cessation of the occlusion, at the time of the reperfusion. For postocclusion delivery, we performed injections at the time of reperfusion after two hours of MCAO as well as two hours after the onset of reperfusion. In the case of infusion, we infused 20 μl of compound over a thirty minute time period. In the case of injection six hours after occlusion, we injected a single 4-μl dose. In the case of zVAD.fmk administration, we added it to the Nec-1 formulation and administered a total dose of 160 ng.

Cell Culture

We prepared mouse embryonic fibroblasts as in Nakagawa et al., Nature 403:98-103, 2000, and immortalized through infection with SV-40-encoding retrovirus. Atg5$^{-/-}$MEF cells have been previously described (see, e.g., Kuma et al., Nature 432:1032-1036, 2004).

DNA Chip Analyses

We double purified mRNA from the cells using Poly(A) Purist kit (Ambion). Agilent DNA chip analysis was performed by Harvard Center for Genomics Research.

Immunofluorescence

We washed Balbc 3T3 cells in PBS, fixed the cells in 4% formaldehyde for fifteen minutes at 25° C., rinsed them twice in PBS, and permeabilized/blocked in 0.4% Triton X-100, 10% normal goat or donkey serum (Jackson Immunoresearch) in PBS for 30 minutes at 25° C. We incubated the samples with the appropriate primary antibodies, diluted according to the manufacturer's instructions in 0.1% Triton, 1% serum in PBS, for sixteen hours at 4° C., followed by three washes with PBS and incubation with fluorophore-conjugated secondary antibodies diluted 1:200 in the same buffer as primary antibodies for thirty minutes at 25° C. Following two washes with PBS, we stained the cells with TO-PRO-3 or phalloidin-TRITC, diluted in PBS according to manufacturer's instructions, for ten minutes at 25° C., washed them once with PBS, and mounted the samples using ProLong Antifade kit (Molecular Probes). We acquired the images using a Nikon spinning disk confocal microscope and analyzed them using Metamorph software (Universal Imaging).

Propidium Iodide DNA Content Analysis

After the appropriate treatment, we washed Jurkat cells once, resuspended them in PBS, and fixed the cells by adding four volumes of ice cold 100% ethanol. Cells remained on ice for one hour, after which we discarded the fixing solution, washed the cells once in PBS, resuspended them in PBS supplemented with 50 μg/ml PI and 5 μg/ml RNAse A (Sigma), and incubated samples in the dark for fifteen minutes at 37° C. followed by analysis in FACSCalibur. We analyzed the data using ModFit software (Verity Software House).

Immunoblotting

We lysed cells in 20 mM HEPES, pH 7.5, 150 mM NaCl, 1% Triton X-100, 10 mM tetrasodium pyrophosphate, 100 mM NaF, 17.5 mM β-glycerophosphate buffer supplemented with Complete Mini Protease Inhibitor tablet (Roche). We determined protein concentrations using Bio-Rad Protein Assay reagent and subjected equal amounts of protein to western blotting using antibodies described in the Figure captions. In case of ischemic brain samples, we dissected out injured regions of the cortexes, lysed them in RIPA buffer (50 mM Tris-HCl, pH 8.0, 150 mM NaCl, 5 mM EDTA, 0.1% SDS, 0.5% sodium deoxycholate, 1% NP-40, supplemented with Complete Mini protease inhibitors) and subjected equal amounts of proteins to western blotting. Results of the western blotting were quantified using Scion Image software (Scion Corporation).

Electroporation of Jurkat Cells pcDNA3-RIP-(1-580)-Fpk3-Myc, pcDNA3-RIP-(1-287)-Fpk3-Myc (pFR-KD) and pcDNA3-RIP-(1-580)-K45M-Fpk3-Myc, encoding RIP protein lacking DD domain, kinase domain of RIP and kinase dead mutant RIP, respectively, fused to three copies of FKBP 12 protein, and a control vector, pcDNA3-Fpk3-Myc (pFpk), were a generous gift of G. Nunez (University of Michigan). We amplified full length RIP using corresponding cDNA and cloned it into pcDNA3-RIP-(1-580)-Fpk3-Myc, replacing truncated RIP, to generate full length RIP-encoding dimerization construct (pFR). We used this construct to generate kinase dead mutant (pFR-K45M) with the help of QuikChange mutagenesis kit (Stratagene).

To generate pFF construct encoding FADD dimerization cassette, consisting of myristoylation signal followed by two copies of the 36v mutant FKBP12 (Fv2E) and coding region of FADD, we PCR-amplified Fv2E and FADD using pC4M-Fv2E plasmid (Ariad Pharmaceuticals) and FADD cDNA, respectively, and cloned these fragments into pcDNA6 vector (Invitrogen).

For electroporation, we resuspended 20×10$^6$ FADD-deficient Jurkat cells in 1 ml hypoosmolar buffer (Eppendorf), supplemented with 1.25% DMSO, mixed cells with 18 μg of the RIP vector/and 2 μg of empty pEGFP vector and performed electroporation using Gene Pulser II (Bio-Rad). We allowed cells to rest for five to ten minutes and then transferred them into 4 ml of RPM11640 media, supplemented with 1.25% DMSO, 1% glutamine, 1% antibiotic-antimycotic mixture (Invitrogen) and 10% heat-inactivated fetal calf serum. Three hours later, we separated live cells using Ficoll-Paque (Pharmacia), washed them once and resuspended them in the media containing dimerizing agent AP1510 (Ariad Pharmaceuticals) and other chemicals as described. After treatment for the indicated period of time, we added 2 μg/ml of PI to each sample, and determined percentages of viable PI-negative GFP-expressing cells. Alternatively, we selected a stable clone of Jurkat cells expressing dimerizable FADD (JK-FF) in blasticidin (Invitrogen).

Generation of Viral RNAi Vectors

We directly ligated oligonucleotides containing RNAi sequences into pSRP vector, which is based on pMSCV-puro (Invitrogen) viral vector and contains an H1 promoter. We used the published sequence of murine beclin-1 (see, e.g., Yu et al., Science 304:1500-2502, 2004). We generated the virus by co-transfection of the pSRP-based vector with the plasmids encoding retroviral Gag/Pol and VSV-G proteins into human HEK 293T cells. We infected Balbc 3T3 cells three times with each virus, followed by selection with puromycin. We used stable populations of cells to analyze target protein expression and cell viability.

EXAMPLES

The following examples are provided to illustrate the invention. These examples should not be construed as limiting.

Example 1

Characterization of Small Molecule Inhibitors of CICD/Necroptosis

Using a known paradigm of death receptor mediated caspase-independent cell death in human U937 cells, we established a high-throughput screen in 384 well format for small molecule inhibitors of caspase-independent cell death (CICD). In this system, U937 cells were induced to undergo CICD in the presence of TNFα and zVAD.fmk, and the rate of cell death was determined by an ATP-Lite-M assay, a commercial luminescence-based assay measuring cellular ATP levels (Packard). U937 cells were chosen because these cells can be induced to undergo CICD very efficiently upon TNFα/zVAD treatment in the absence of additional, stress-inducing sensitizing stimuli, such as CHX, making this system perfectly suited for reliable identification of CICD inhibitors. Furthermore, rapid suspension growth kinetics of U937 cells results in the availability of large quantities of cells, which translates into robust signals ideal for high throughput screening. ATP-Lite-M assay was chosen because among all the different assay systems tested, it gives the most consistent and robust signal, which is also critical for high throughput screening. Exposure of U937 cells to TNFα alone led to partial cell death, whereas co-treatment with TNFα and caspase inhibitor zVAD.fmk produced significant increase in the amount of cell death and ATP loss consistent with the published observations. In addition, in the presence of zVAD-.fmk, the morphology of cell loss changed from apoptosis with cell shrinkage, nuclear fragmentation, membrane blebbing to necrosis, characterized by cell swelling, increase in cytosolic density, and early loss of plasma membrane integrity. Other cell death assays, such as an MTT assay (mitochondrial metabolism) and Sytox assay (permeability of the plasma membrane), were used as alternative means to validate the screen, and consistently produced results similar to those obtained using ATP-Lite-M assay, which confirmed that the ATP-Lite-M assay can be used to accurately measure the extent of CICD. Another commercial ATP assay, Cell-Titer-Glo (Promega), was also used in some subsequent analyses due to its superior sensitivity compared to ATP-Lite-M assay and produced comparable results.

A diverse chemical collection of approximately 15,000 small molecules obtained from both commercial sources as well as from combinatorial chemistry syntheses was screened using the U937 cell death assay, and 3 compounds (necrostatins) with highest activity were selected for further analyses (FIG. 1). These compounds, Nec-1, Nec-2, and Nec-3, are exemplary members of the Nec-1 compound, Nec-2 compound, and Nec-3 compound classes, respectively (defined above).

The EC50's of these Nec compounds in inhibiting CICD vary, but are generally in the sub-/low micromolar range (Table 5). In this table, EC50 values represent the concentration required to rescue 50% of cell death in FADD deficient Jurkat cells treated with TNFα for 36 hours, which induces CICD as determined by ATP assays, with the following exceptions: values for Nec-2 were obtained using Jurkat cells expressing dimerizable FADD treated with dimerizer/zVAD for 36 hours and assayed for ATP levels. LD50 values were calculated based on treatment of corresponding Jurkat cell's with the compounds in the absence of TNFα or dimerizer. None of these compounds caused an increase in ATP levels in control healthy cells.

TABLE 5

|  | Nec-1 | Nec-2 | Nec-3 |
| --- | --- | --- | --- |
| EC50 (µM) | 0.494 | 27.3 | 0.97 |
| LD50 (µM) | 374 | 134 | 143 |

Figure 2:
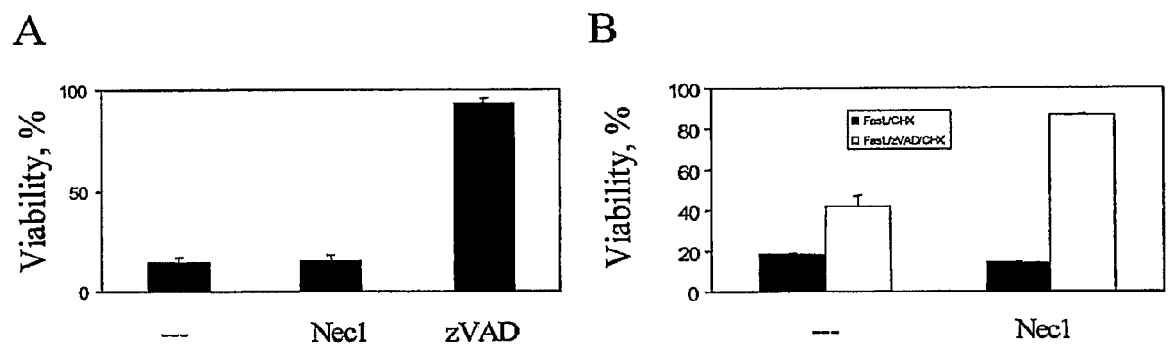
FIG. 2 is a pair of charts showing the selective inhibition of CICD by Nec-1. Jurkat cells were treated with 5 ng/ml of FasL without (A) or with cyclohexamide (CHX) (B) to induce apoptosis, or 5 ng/ml FasL, 1 μg/ml of CHX and 100 μM of zVAD.fmk to induce CICD (13). Nec-1 (30 μM) protected against CICD induced by FasL/CHX/zVAD (B) but not apoptosis induced by FasL or FasL/CHX (A and B). Cell viability was determined after 24 hours of incubation with indicated reagents using CellTiter-Glo ATP assay. The values represent viability relative to the control Jurkat cells without the treatment of FasL, which was set as 100% viability.

The first isolated necrostatin, Nec-1, which showed the highest necrostatic activity, was further characterized in a number of cellular assays. In order to test the selectivity of Nec-1, its inability to block apoptosis was verified. Fas ligand-induced apoptosis of Jurkat cells was protected by pan caspase inhibitor zVAD.fmk, but not by Nec-1 (FIG. 2A). Co-treatment of Jurkat cells with FasL and CHX also induced apoptosis, which could not be inhibited by Nec-1 (FIG. 2B). Co-treatment with CHX made the cells more sensitive to CICD induction by FasL in the presence of zVAD.fmk, and it was efficiently inhibited by Nec-1 (FIG. 2B). Similar protection from DR-induced CICD, but not apoptosis, was also observed in other cell types, such as U937, Balbc3T3, and mouse embryonic fibroblasts (MEF). In addition, other necrostatins were also found to be specific CICD inhibitors. These results indicate that the selected compounds are specific inhibitors of CICD and can be utilized to selectively target necroptotic signaling pathways. The failure of necrostatins to inhibit apoptosis further supports the notion that CICD represents a distinct cellular process, rather than apoptosis lacking certain caspase-dependent features.

In addition to the selective inhibition of necroptotic, but not apoptotic, death, the strict selectivity of effects of Nec-1 was also confirmed by showing a lack of compound effect on multiple aspects of cellular physiology. We found that Nec-1 had no general effect in healthy cells on the ATP levels, mitochondrial membrane potential, plasma membrane integrity, cell shape or size, cell cycle distribution, proliferation, global thRNA expression, the intracellular levels of reactive oxygen species, cell adhesion, actin and microtubule cytoskeleton or the morphology of various cellular compartments, e.g., nuclei, Golgi apparatus, ER and mitochondria.

Nec-1 demonstrated consistent activity against CICD in a variety of cellular systems including CICD of human monocytic U937 and mouse fibroblast Balbc 3T3 induced by TNFα/zVAD.fmk, CICD induced by dimerized exogenous FADD and/or RIP in Jurkat cells in the presence of zVAD-.fmk, CICD induced by FasL/CHX/zVAD.fmk, TNFα-induced CICD in FADD deficient mutant clone of Jurkat cells, and CICD induced by TNFα in mouse fibrosarcoma L929 cells. Inhibition of caspases in these systems has been previously reported to turn apoptosis into necrotic death; the exceptions were L929 and FADD deficient cells, where induction of necrotic death was previously demonstrated to be a primary cell death response in the absence of caspase inhibitors and, consistently, we observed inhibition of death by Nec-1 in the absence of zVAD.fmk. The ability of Nec-1 to inhibit CICD in all of those systems indicates that its effect is not limited to the U937 cells treated with TNFα/z-VAD.fmk, the assay used for the original screen, and that a similar necroptotic pathway is triggered in multiple cell types in response to various DR-related death-inducing stimuli. Furthermore, these data show that CICD is not just a by-product of failed apoptosis, but at least in some cases it is a primary death mechanism activated in the absence of apoptosis.

Figure 3:
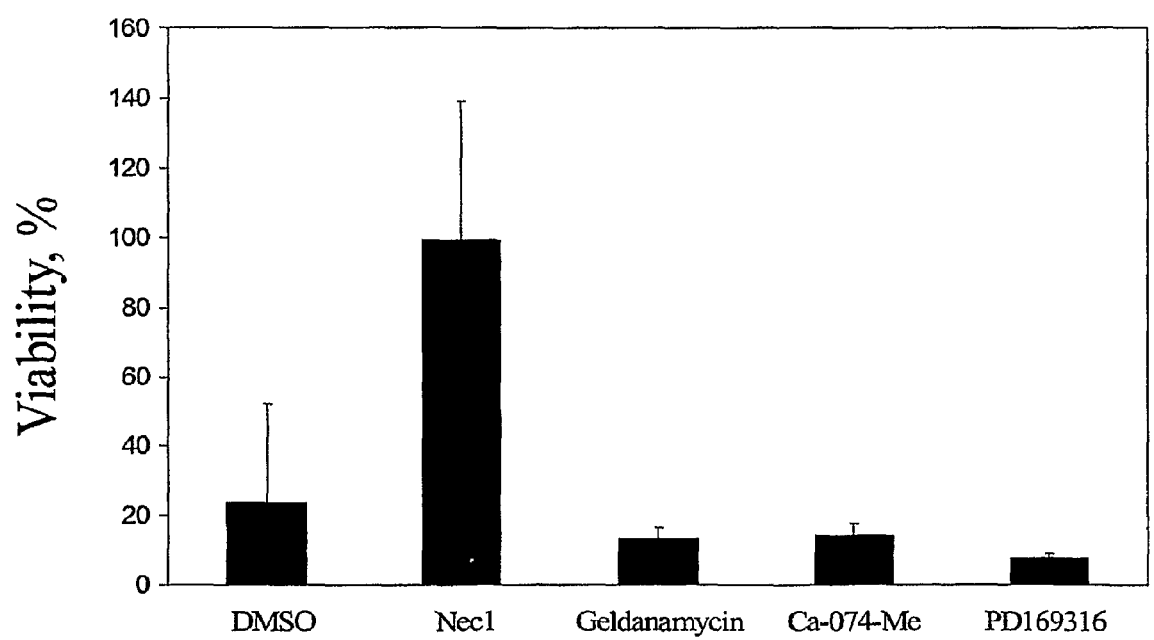
FIG. 3 is a chart showing that Nec-1 protects L929 cells from CICD. L929 cells were treated for 72 hours with 40 ng/ml Of TNFα and one of the indicated reagents: 50 μM Nec-1, 2 μg/ml Hsp-90 inhibitor geldanamycin, 5 μM cathepsin B inhibitor Ca-074-Me and 5 μM p38 inhibitor PD169316. These compounds were selected for their protection from CICD either in Jurkat or Balbc 3T3 cells. Cell viability was determined using ATP-Lite-M ATP assay (Packard). The values represent viability relative to the control lacking TNFα, which was set as 100% viability.

A number of compounds, including antioxidants PDTC and BHA, and hsp90 inhibitor geldanamycin, have been reported to have anti-CICD activities. In addition, we found that cathepsin B inhibitor Ca-074-Me and p38 inhibitors have anti-CICD activities in certain selected cell lines. We compared the activities of these compounds with Nec-1. Interestingly, we found that Nec-1 is the only compound that has anti-CICD activities in all cell based assays. For instance, p38 inhibitor PD169316 inhibits CICD in 3T3 cells and cathepsin B inhibitor Ca-074-Me inhibits CICD in Jurkat and 3T3 cells, but neither these compounds nor geldanamycin work in L929 cells (FIG. 3), unlike Nec-1. These data underscore the unique ability of the high-throughput screening approach to produce universal inhibitors of CICD.

Consistent with this notion, we have determined that necroptotic cell death in Jurkat and Balbc 3T3 cells cannot be blocked by small molecule inhibition of such factors as the mitochondrial permeability transition pore (MPTP), calpains, calcium homeostasis perturbation, HtrA2/Omi, phospholipase A2 and nitric oxide synthase, or the RNAi-mediated downregulation of Apoptosis Inducing Factor (AIF). We also screened a Biomol/ICCB chemical library of 489 compounds with known biological activities and found that no compound could block CICD in all cell types, as Nec-1 does. These results underscore the uniqueness of necrostatins' activity in blocking necroptotic cell death.

Figure 4:
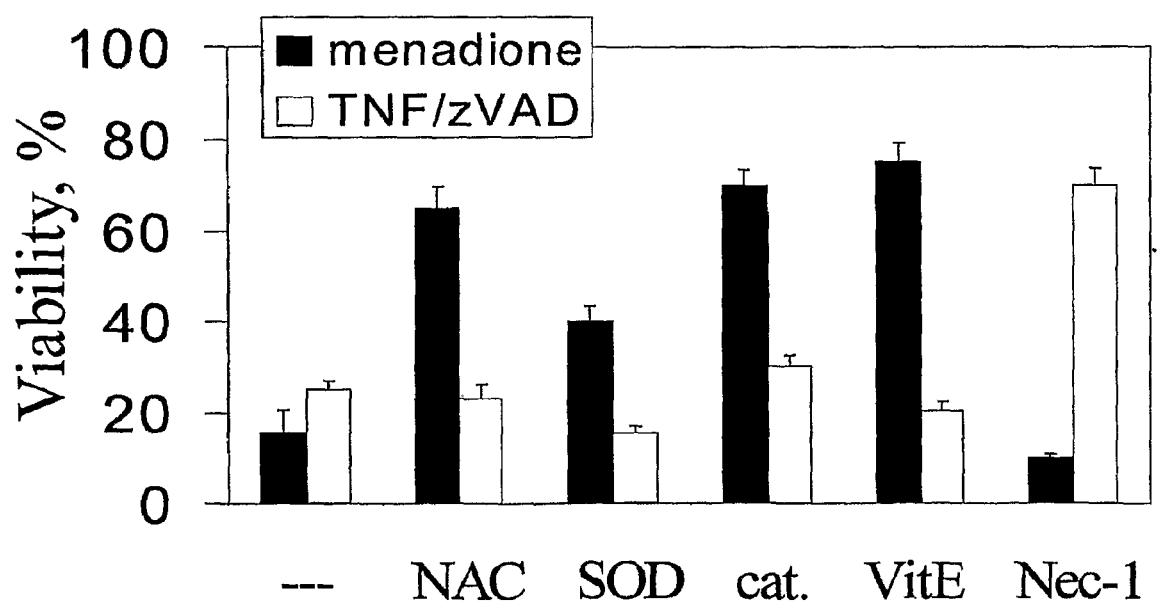
FIG. 4 is a chart showing that Nec-1 is not an antioxidant. U937 cells were seeded into 96 well plates and treated with 40 ng/ml of TNFα, 100 μM zVAD.fmk (TNF+zVAD) for 72 hours or 250 μM of oxidative stress inducing agent menadione for 24 hours and 2.5 mM N-acetyl cysteine (NAC), 800 U/ml of superoxide dismutase (SOD), 1400 U/ml of catalase, 5 mM vitamin E (vit. E), 100 μM of Nec-1. Viability of TNFα/zVAD/DMSO or manadione/DMSO blank treated cells is also shown (-). Viability was determined using ATP-Lite-M assay (Packard). Numbers represent percentages of live cells. The values were normalized relative to the zVAD or DMSO treated controls, which were set as 100% viability.

Since it has been previously suggested that CICD may be inhibitable by anti-oxidants, we examined whether CICD of U937 cells induced by TNFα/z-VAD.fmk can be inhibited by anti-oxidants, and whether Nec-1 can inhibit cell death induced by oxidative stress. U937 cells were treated with TNFα/zVAD.fmk for 72 hours or oxidative stress inducing agent menadione for 24 hours. Nec-1 provided expected protection against TNFα/zVAD.fmk but not menadione induced cell death, whereas anti-oxidant agents N-acetyl-cysteine, superoxide dismutase, catalase, vitamin E provided protection against menadione but not that of TNFα/zVAD induced cell death (FIG. 4). We conclude that although reactive oxygen species (ROS) may be involved in certain types of CICD, ROS is not a key mediator of necroptotic cell death pathway. Furthermore, it makes it extremely unlikely that Nec-1 protects TNFα/zVAD.fmk induced cell death through an anti-oxidant mechanism.

Figure 5:
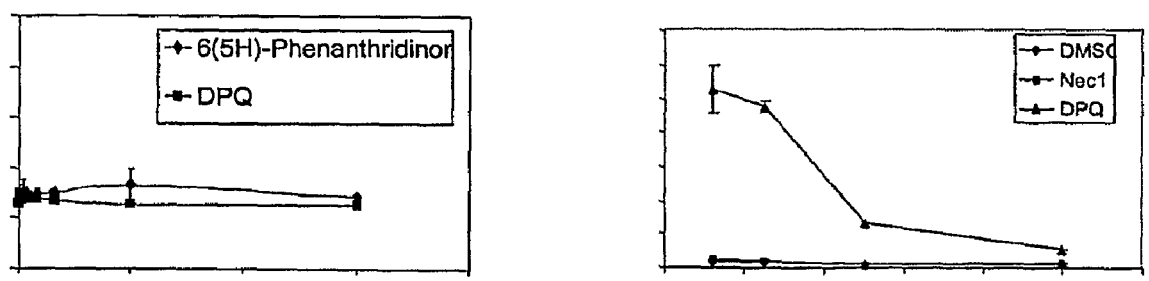
FIG. 5 is a pair of charts showing that the effect of Nec-1 is distinguishable from that of a PARP inhibitor.

PARP-1 is a nuclear protein that responds to DNA damage by catalyzing the conversion of the respiratory coenzyme nicotinamide adenine dinucleotide (NAD$^+$) into protein-bound ADP-ribose polymers, with concomitant release of nicotinamide (D'Amours et al., 1999). In addition to its involvement in DNA damage, PARP-1 has been shown to contribute to the caspase-independent component of the neuronal cell death induced by glutamate excitotoxicity, ischemic injury and MPTP. Therefore, we examined the possibility that Nec-1 may act as a PARP inhibitor. However, since PARP inhibitors, 6(5H)-Phenanthridione or DPQ (3,4-Dihydro-5[4(1-piperindinyl)butoxy]-1(2H)-isoquinoline), failed to inhibit CICD of Jurkat cells (FIG. 5A) as well as in any of the CICD systems described above, including U937 and Balbc 3T3 cells, nor was PAR-polymer production detected in necroptotic cells, we concluded that PARP is unlikely to be a key regulator of CICD. Furthermore, Nec-1 failed to protect cells from DNA alkylating agent 1-methyl-3-nitro-1-nitrosoguanidine (MNNG)-induced death (FIG. 5B), which is mediated through PARP activation.

In addition, Nec-1 and other necrostatins inhibit all manifestations of necroptotic death, including: changes in shape and size (forward/side scatter analyses), ATP loss (ATP assay), mitochondrial dysfunction (MTT assay and DiOC6 staining) and plasma membrane permeabilization (Sytox/PI assays). Furthermore, Nec-1 allowed proliferation of TNFα-treated FADD-deficient cells at a rate indistinguishable from untreated cells. Consistent with these results, morphological analyses using electron microscopy (EM), fluorescent and bright field microscopy demonstrated that Nec-1 inhibited all manifestations of necroptotic cell death.

Example 2

Medicinal Chemistry Study of Necrostatins

Figure 6:
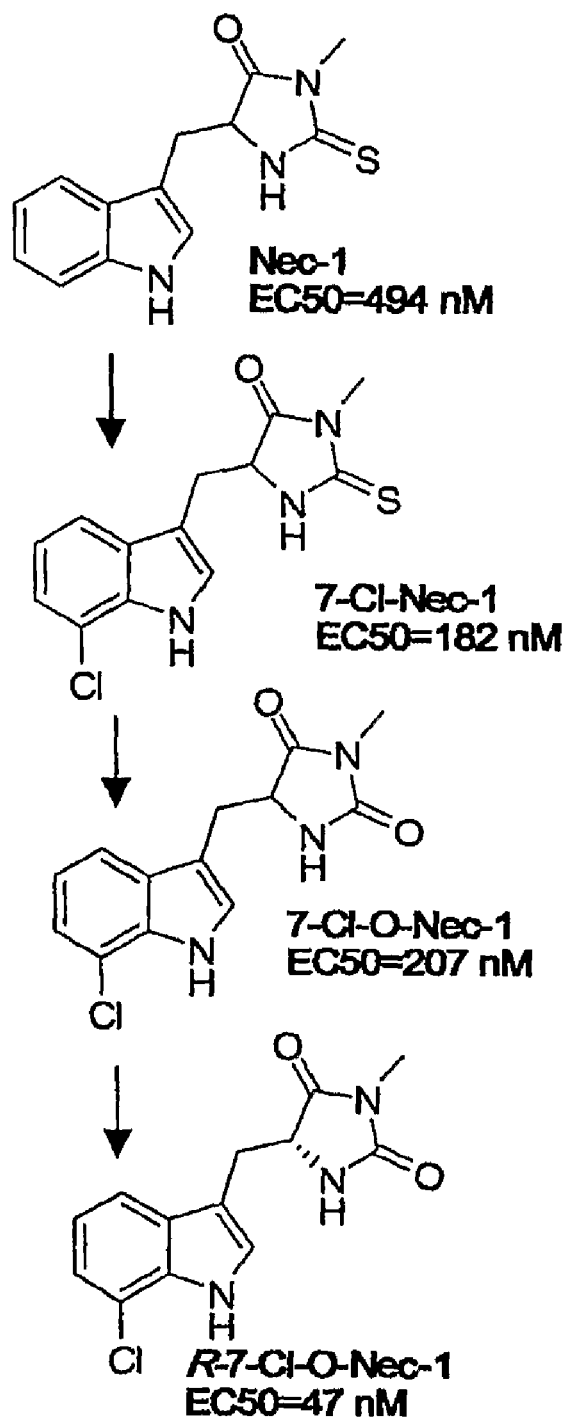
FIG. 6 is a set of structures showing key improvements to the Nec-1 series of compounds.
Figure 7:
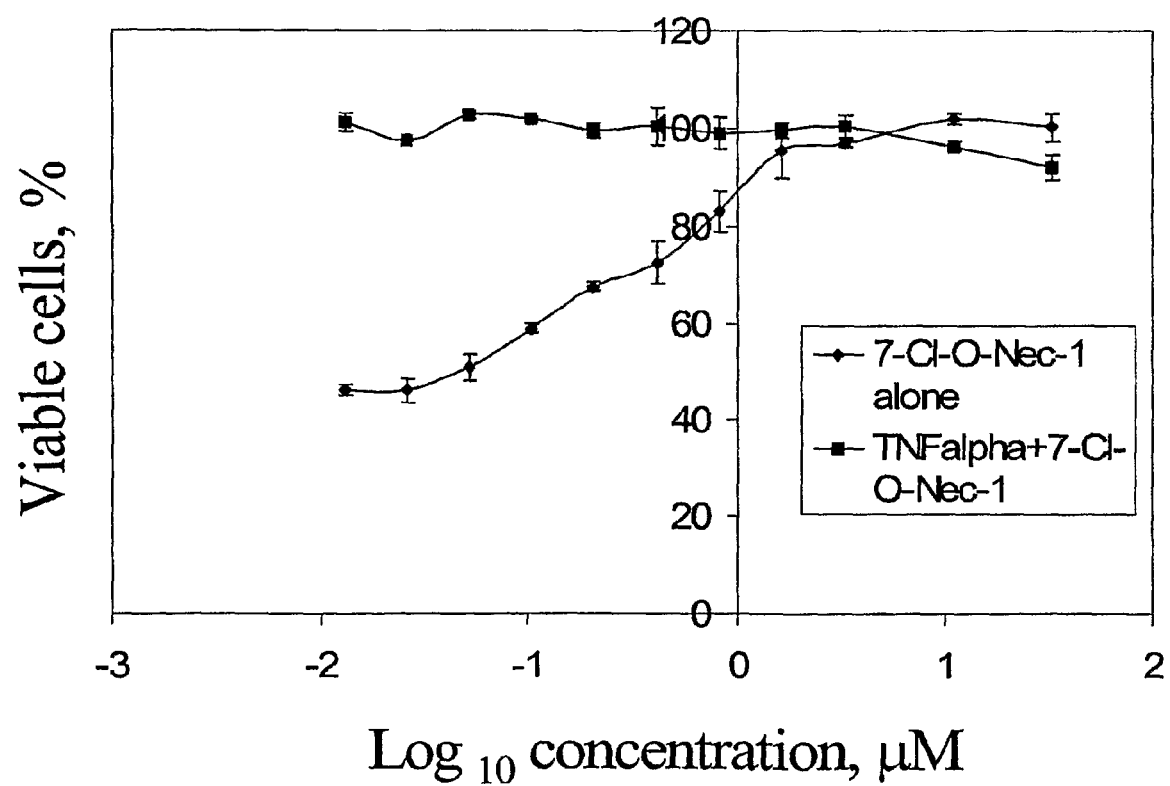
FIG. 7 is a chart showing the dose-dependent response curve of 7-Cl—O-Nec-1. FADD deficient Jurkat cells were treated for 36 hours with 10 ng/ml of human TNFα, which induces CICD. Viability of the cells treated with compound alone or in combination with TNFα was determined using CellTiter-Glo ATP assay. The former values were used to calculate toxicity. The ratio of the ATP content in the wells with the same drug concentration with and without TNFα was used to determine specific protection by the compound.

Systematic modifications of the original high-throughput screening hit, Nec-1 (methylthiohydantoin-tryptophane, MTH-Trp) (EC$_{50}$=494 nM), were performed in order to improve its efficacy, reduce its toxicity and to increase its metabolic stability (FIG. 6). Initially, the thiohydantoin portion of the molecule was not changed. Instead, various modifications to the indole ring were investigated. The indole ring was replaced with a benzothiophene, a benzene ring, and a pyridine. However, all of these changes were detrimental to the molecule's activity. Next, a survey of various substituents on the indole ring was conducted. We discovered that introduction of small electron-neutral (i.e. methyl), electron-donating (i.e. methoxy), or electron-withdrawing (i.e. chloride) groups to the 7-position of the indole ring increased anti-CICD activity. For example, the 7-chloro derivative, 7-Cl-Neo-1, had the highest activity among these derivatives with an EC$_{50}$=182 nM in Jurkat FADD deficient cells treated with TNFα. This molecule was selected for further study in our in vivo ischemic brain injury model. Several positions (including the 2- and 4-positions) of the indole ring were found not to tolerate any substitution, whereas substitution at the 5- and 6-positions was not completely prohibited, but did result in a loss of potency. Likewise, the methylene bridge between the hydantoin ring and the indole also did not tolerate any substitution. Finally, compounds with the indole nitrogen unsubstituted were found to be best. With the indole portion of the molecule optimized, the thiohydantoin portion was then scrutinized. In particular, we examined the conversion of the thiohydantoin to a hydantoin ring, anticipating that the latter would be less toxic and offer greater metabolic stability. The resulting derivative, 7-Cl-O-Nec-1, had equally potent anti-CICD activity, but significantly reduced nonspecific toxicity (LD$_{50}$>1 mM). The substituents on the two nitrogens of the hydantoin ring were also examined. The urea nitrogen was found to only tolerate small non-branched alkyl groups (i.e., Me and Et). The dose-dependent response curve is shown in FIG. 7.

Figure 8:
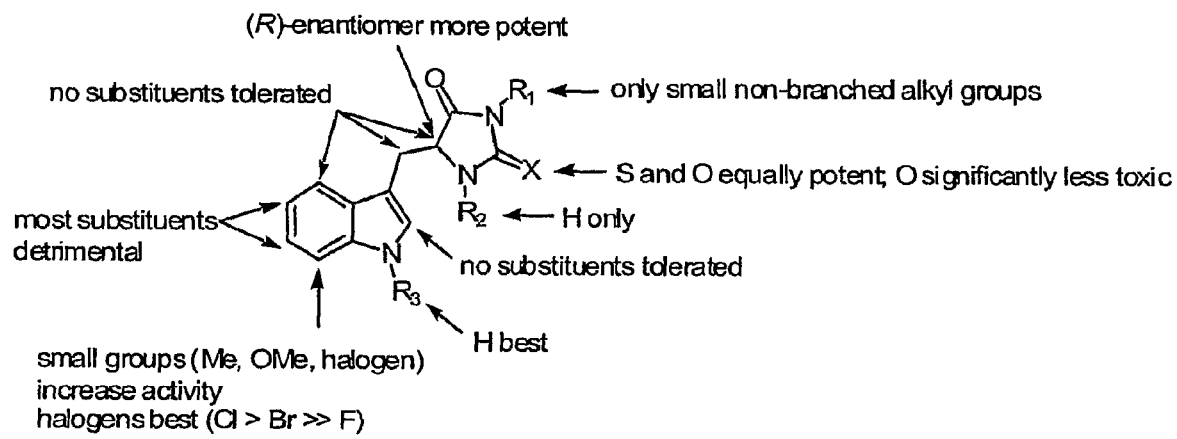
FIG. 8 is a summary of the structure-activity relationship (SAR) for Nec-1.

Neither the amide nitrogen of the hydantoin nor the alpha-carbon to the amide was tolerant of any substitution. Next, the enantiomers of 7-Cl-O-Nec-1 were prepared. The (R)-enantiomer (also referred to as the "A isomer") (EC$_{50}$=47 nM) was found to be about 4 times more potent than the (S)-enantiomer (also referred to as the "B isomer") at inhibiting CICD. A complete summary of the structure-activity-relationship (SAR) of the Nec-1 series for inhibiting CICD is shown in FIG. 8. An understanding of the Nec-1 SAR has resulted in the preparation of derivatives with potent in vitro and in vivo anti-CICD activity, minimum non-specific toxicity and potentially greater metabolic stability.

Example 3

In vivo Efficacy of Nec-1 Derivatives in a Mouse Model of Ischemic Brain Injury

Figure 9:
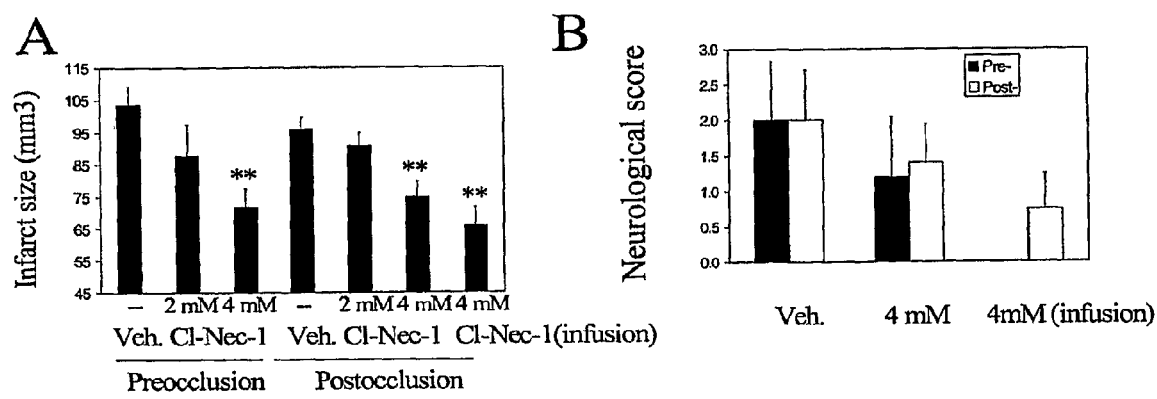
FIG. 9 is a pair of charts showing that 7-Cl-Nec-1 inhibits brain ischemia in vivo.

Studies were performed on the effect of Nec-1 derivatives in the mouse two-hour middle cerebral artery occlusion (MCAO)/reperfusion model of brain ischemia. A significant dose-dependent decrease in infarction volume and behavioral changes (associated with ischemic injury) were detected upon icv injection (FIG. 9).

Figure 10:
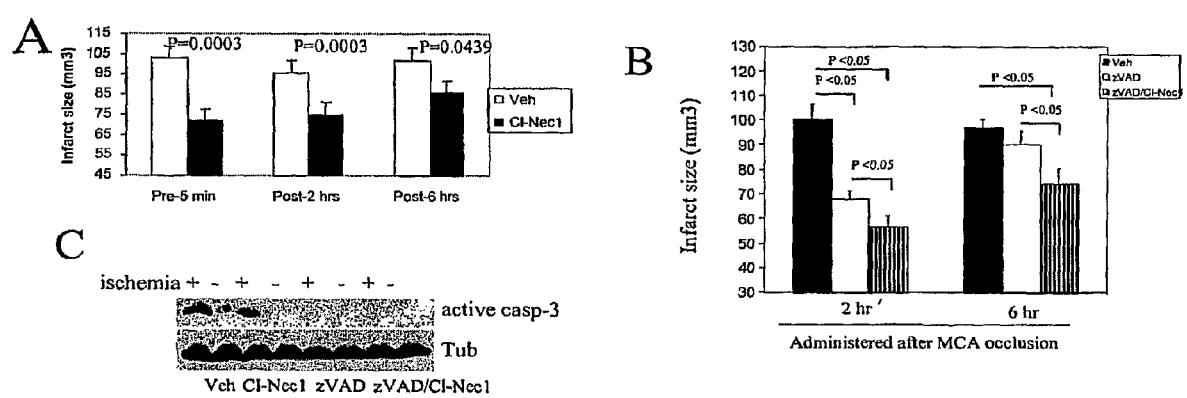
FIG. 10 is a set of charts and a gel showing an extended treatment window of MCAO in vivo and additive effect with zVAD.fmk.

Injection of 7-Cl-Nec-1 up to six hours after the onset of brain ischemic injury still offered protection (FIG. 10A), which exceeds the therapeutic window reported for the majority of the currently pursued drug candidate classes, including inhibitors of excitotoxicity (e.g., MK-801, a glutamate receptor antagonist, stops working if administered after one hour post-occlusion) and apoptosis (zVAD.fmk is effective up to three hours postocclusion) using the two-hour ischemia-reperfusion model following MCA occlusion. Induction of both apoptosis and necrosis during ischemic brain injury predicts that necrostatins should exhibit additive protective effect with that of caspase inhibitors. We examined this possibility by comparing the effect of zVAD.fmk alone or in combination with Nec-1. Nec-1 demonstrated an additive protective effect with the caspase inhibitor when administrated together with zVAD.fmk two hours after the onset of ischemic injury, a time window when caspase inhibitors are still highly effective (FIG. 10B). Interestingly, when administered six hours after the onset of ischemic injury, which is the time point when caspase inhibitors are no longer effective, Nec-1 still demonstrated statistically significant protection (FIG. 10B). Furthermore, the neuroprotective effect of 7-Cl-Nec-1 was not associated with a reduction of caspase-3 activation (FIG. 10C).

These results support the idea that necrostatins: 1) target an independent non-apoptotic pathway of cell death, 2) can provide additional protection over apoptosis inhibitors, and 3) display extended window of opportunity, due to the delayed induction of CICD, making this class of compounds very promising candidates for the treatment of ischemic brain injury. The delayed nature of CICD, detected in our in vivo studies, actually makes CICD potentially a more "druggable" target for anti-stroke treatment than other forms of ischemic cell death with a more rapid onset.

Example 4

Accumulation of LC3II in CICD and in Ischemic Brain Injury

Figure 11:
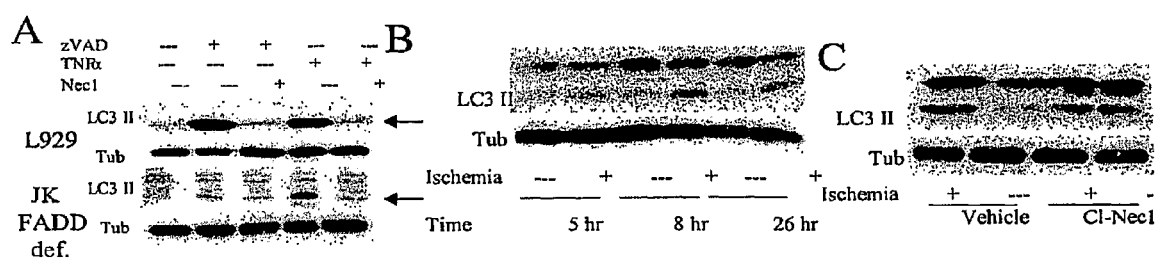
FIG. 11 is a set of gels showing the detection of cleaved LC3 in CICD of cultured cells and in ischemic brain injury.
Figure 12:
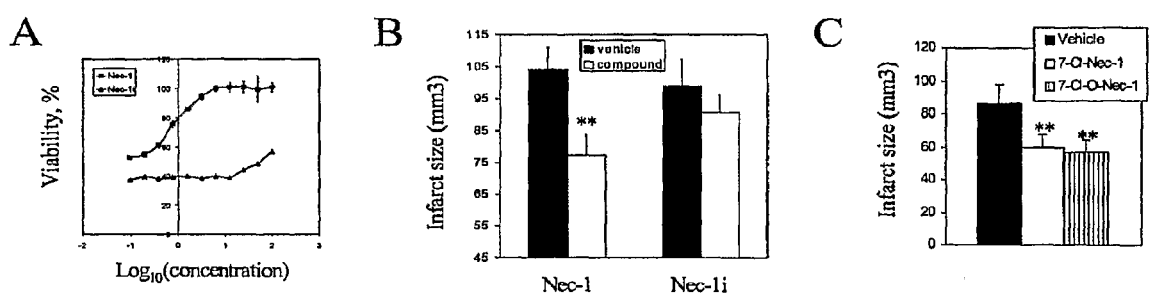
FIG. 12 is a set of charts showing in vivo SAR of Nec-1.

We determined whether autophagy, a protein degradation/catabolic mechanism, is activated during necroptotic cell death, as suggested by a previous report implicating the role of autophagy in zVAD.fmk-induced CICD of L929 cells. We used the accumulation of the phosphatidylethanolamine-conjugated fragment of microtubule-associated protein 1 light chain 3 II (LC3II) as a marker, as it has been shown to be an early and critical step in the formation of autophagy vacuoles. Indeed, the LC3II accumulation was detected in necroptotic Balbc 3T3 cells treated with TNFα/zVAD or FasL/zVAD (FIG. 11A) as well as other cell lines, e.g. JK and U937 cells. Furthermore, the appearance of LC3II was efficiently inhibited by Nec-1, consistent with the role of Nec-1 in inhibiting CICD (FIG. 11A). The accumulation of LC3II was also detected in ischemic brains (FIG. 12B). Interestingly, the increase in the amount of LC3II occurred with delayed kinetics as opposed to markers of apoptosis, e.g., caspase-3 activation occurred early and was detectable one hour after occlusion, whereas the levels of LC3II were only beginning to raise at five hours and peaked around eight hours post MCA occlusion. Furthermore, delayed administration of Nec-1 inhibited LC3II generation, consistent with the delayed activation of CICD during brain ischemia. These results support the notion that CICD is a type of delayed neuronal cell death after ischemic injury and provide a rationale as to why Nec-1 is able to reduce infarct volume when delivered six hours post-injury. Moreover, these results provide necrostatin-independent confirmation of the similarities in the molecular events occurring during ischemic brain damage and in DR-induced CICD in cell culture models.

Example 5

Structure-Function Analyses of Nec-1 Activity In vivo

To confirm the specificity of Nec-1's activity in vivo, we performed SAR analysis for protection against ischemic brain injury in vivo. First, we tested Nec-1i, an inactive derivative of Nec-1 that lacks the methyl group in the hydantoin moiety (FIG. 12A), in the MCAO model. When delivered in two doses prior and immediately following the reperfusion, the condition where Nec-1 provided the greatest protection (FIG. 10), Nec-1i failed to exert a statistically significant effect on infarct volume (FIG. 12B). We also tested 7-Cl-O-Nec-1 in the MCAO model. As shown above, substituting sulfur in the hydantoin moiety of 7-Cl-Nec-1 with oxygen did not result in a change in its anti-CICD activity in vitro (FIG. 12C). Similarly 7-Cl-O-Nec-1 displayed activity indistinguishable from that of 7-Cl-Nec-1 in vivo, even though we compared the two compounds under more stringent conditions (delayed injections at four and six hours) than those used for Nec-1i test (FIG. 12C). Overall, our data demonstrate a strict correlation between the inhibition of CICD in vitro and anti-ischemic activity of 7-Cl-Nec-1 in vivo, providing a strong support for our hypothesis that neuroprotection by Nec-1 is accomplished through the inhibition of CICD.

Example 6

Nec-1 Activity in Immune Cell Regulation

In a number of instances, caspases, and especially caspase-8, has been reported to play either a pro-survival function in the primary immune cells or positively contribute to their activation and differentiation in response to the appropriate antigenic stimulus. In some cases, activation of the nonapoptotic cell death mechanisms has been directly suggested, such as activation-induced cell death (AICD) of T cells and lipopolysaccharide/zVAD.fmk-induced killing of monocytic/macrophage cells. We verified that in these instances cells are undergoing Nec-1 -dependent CICD.

Figure 13:
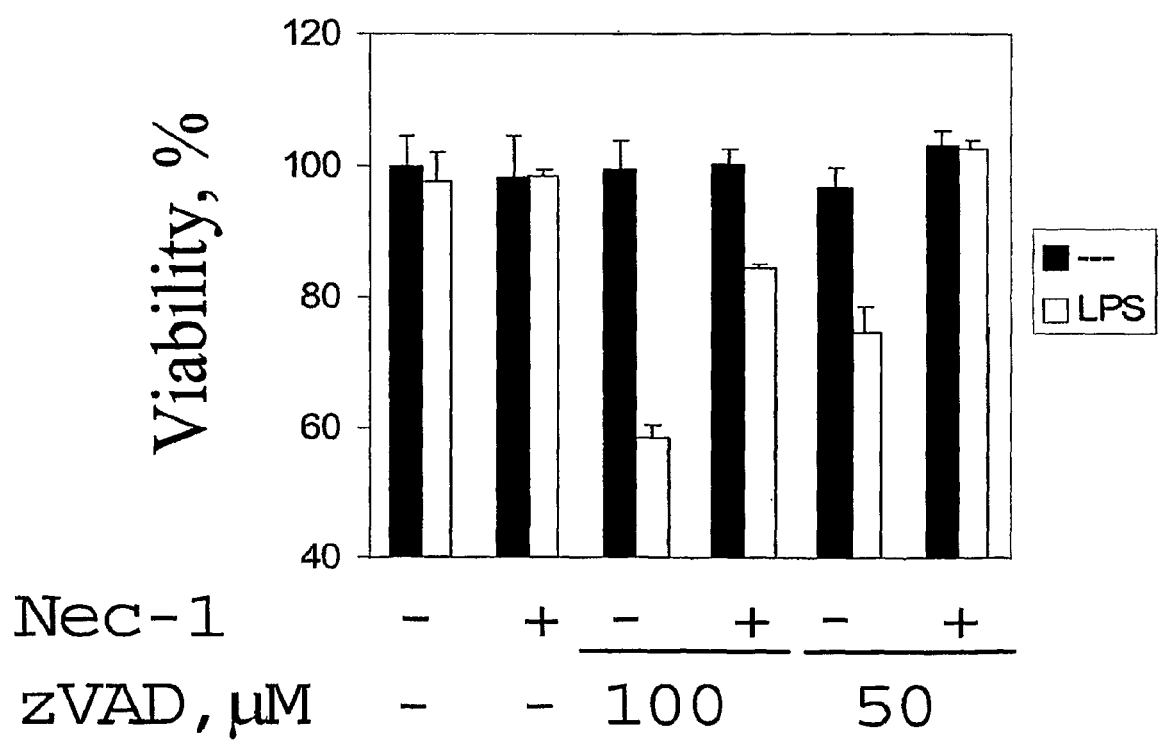
FIG. 13 is a chart showing that Nec-1 protects from CICD induced by LPS in macrophage cells. Mouse RAW264.7 cells were treated with 10 ng/ml LPS, 50 or 100 µM zVAD.fmk and 30 µM Nec-1 or Nec-1 as indicated. Cell viability was determined 24 hours later using an ATP assay. Values represent the percentages of live cells normalized to the control DMSO-treated cells.

The activation of mouse macrophages or macrophage cell lines (RAW264.7) by LPS has been shown to sensitize them to caspase inhibition-induced (zVAD.fmk) death. Treatment with Nec-1 efficiently inhibited LPS-mediated sensitization of RAW264.7 cells to dose-dependent toxicity of zVAD.fmk (FIG. 13).

Example 7

Nec-1 Protects Primary Neurons Against Oxygen-Glucose Deprivation Induced Cell Death In vitro Oxygen-glucose deprivation (OGD) of cultured primary cortical neurons, which mimics some aspects of in vivo ischemic brain injury during stroke, has been shown to induce necrosis, which was not protected by zVAD.fmk. Nec-1 attenuated OGD-induced death of cortical neurons (FIG.

Figure 14:
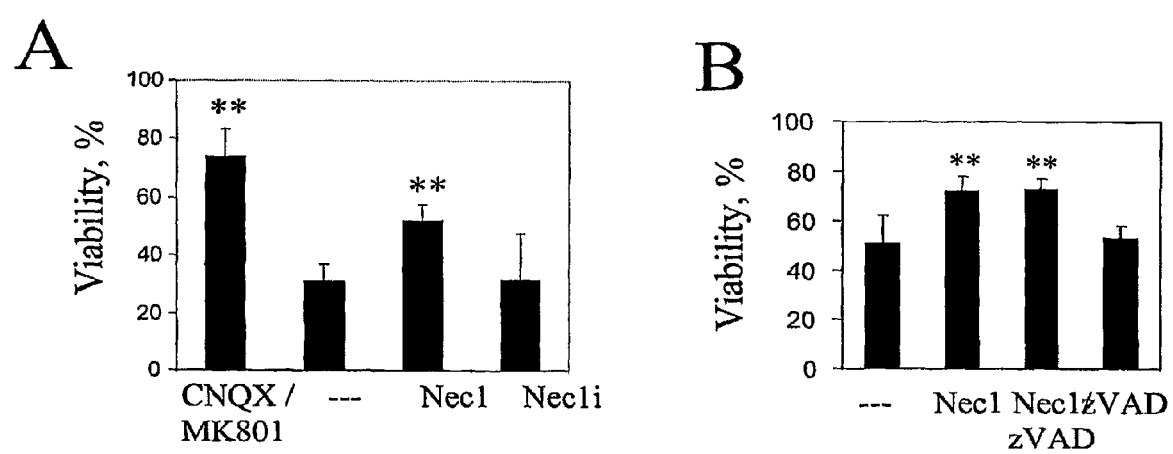
FIG. 14 is a pair of charts showing that Nec-1 protects primary cortical neurons from oxygen-glucose deprivation induced cell death.

14A). Nec1i, an inactive analog of Nec-1 lacking just N-methyl group (R1 in FIG. 8, see activity in FIG. 14A), failed to rescue neuronal cell death (FIG. 14A). Consistent with previously published data, we did not detect any protection by zVAD.fmk in this model, nor did we see any enhancement of Nec-1 protection in the presence of zVAD.fmk (FIG. 14B). Therefore, CICD, but not apoptosis, may represent one of the primary cell death pathways in cortical neurons under OGD conditions, similarly to that of FADD deficient-JK cells treated with TNFα.

Example 8

Neuroprotective Activity of Necrostatins in Other Models of Neurodegeneration

Figure 15:
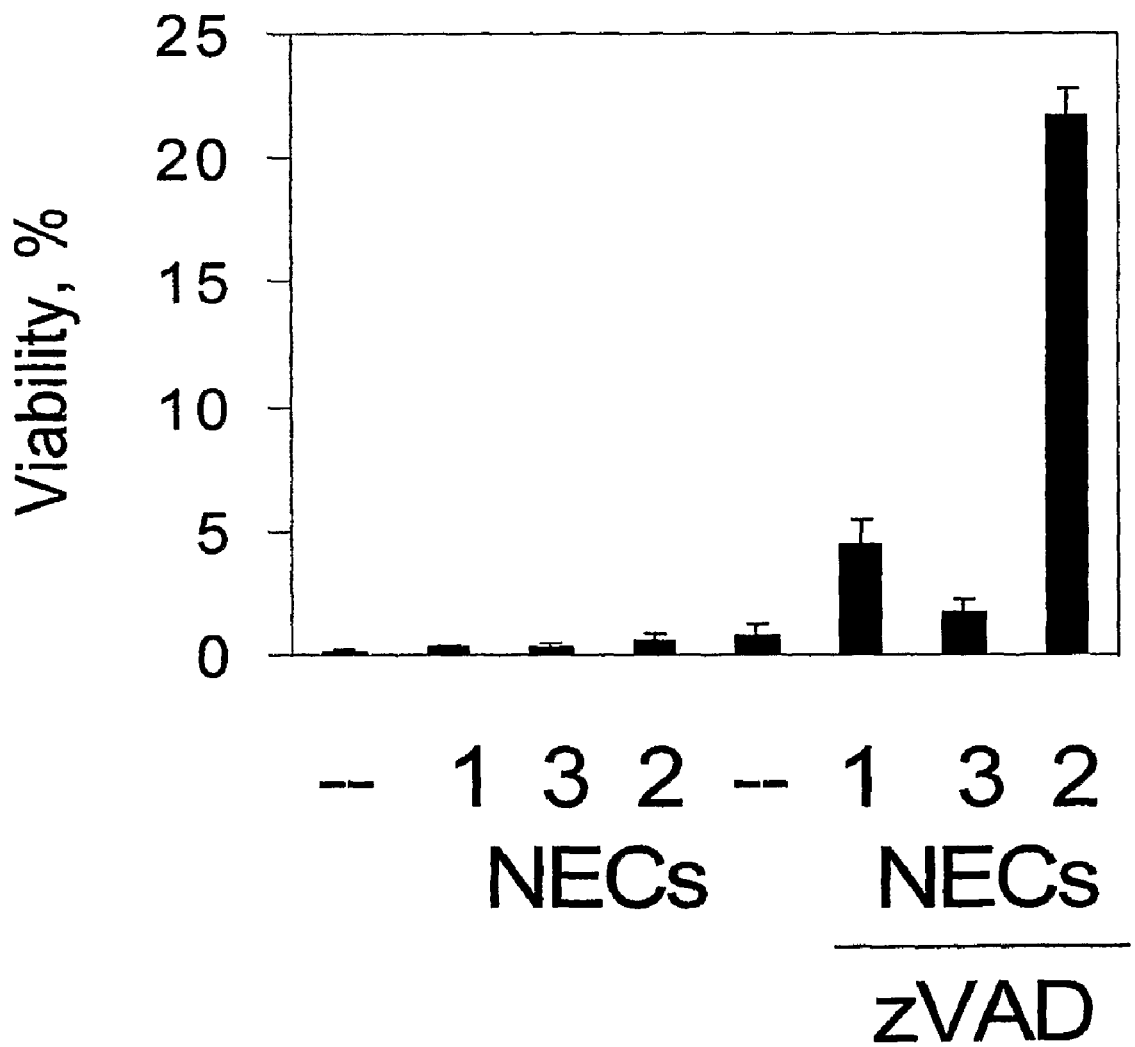
FIG. 15 is a chart showing that necrostatins attenuate $MPP^+$ cytotoxicity in human SH-SY5Y neuroblastoma cells. Cells were treated with 5 mM $MPP^+$ in the presence or absence of 100 µM zVAD.fmk and 30 µM necrostatins for 72 hours, followed by an ATP assay. Values represent cell viability normalized to the corresponding compound treated controls not treated with $MPP^+$.

As described above, nonapoptotic cell death has been prominently implicated in various types of neuronal cell death in addition to ischemic injury. For example, developmental studies suggested activation of the intrinsic necrotic-like program in the motor neurons in caspase-deficient mice, reminiscent of the activation of CICD in our experiments upon caspase inhibition. In case of Parkinson's disease, although apoptosis has been proposed to be the primary mechanism activated by MPTP or its metabolite $MPP^+$, agents causing Parkinson's-like symptoms in animal models, inhibition of caspases has been shown to result in necrosis-like death, indicative of CICD. To this end, we have observed inhibition of $MPP^+$/zVAD-induced death by necrostatins in two different dopaminergic neuron cell lines in vitro (human SH-SY5Y and mouse SN-4741 cells) (FIG. 15). This effect was especially pronounced in case of Nec-2, suggesting that this molecule might be targeting the step especially important for $MPP^+$ toxicity. Notably, an inactive analog of Nec-2, lacking the nitro group, failed to decrease $MPP^+$ cytotoxicity in SN-4741 cells.

Figure 16:
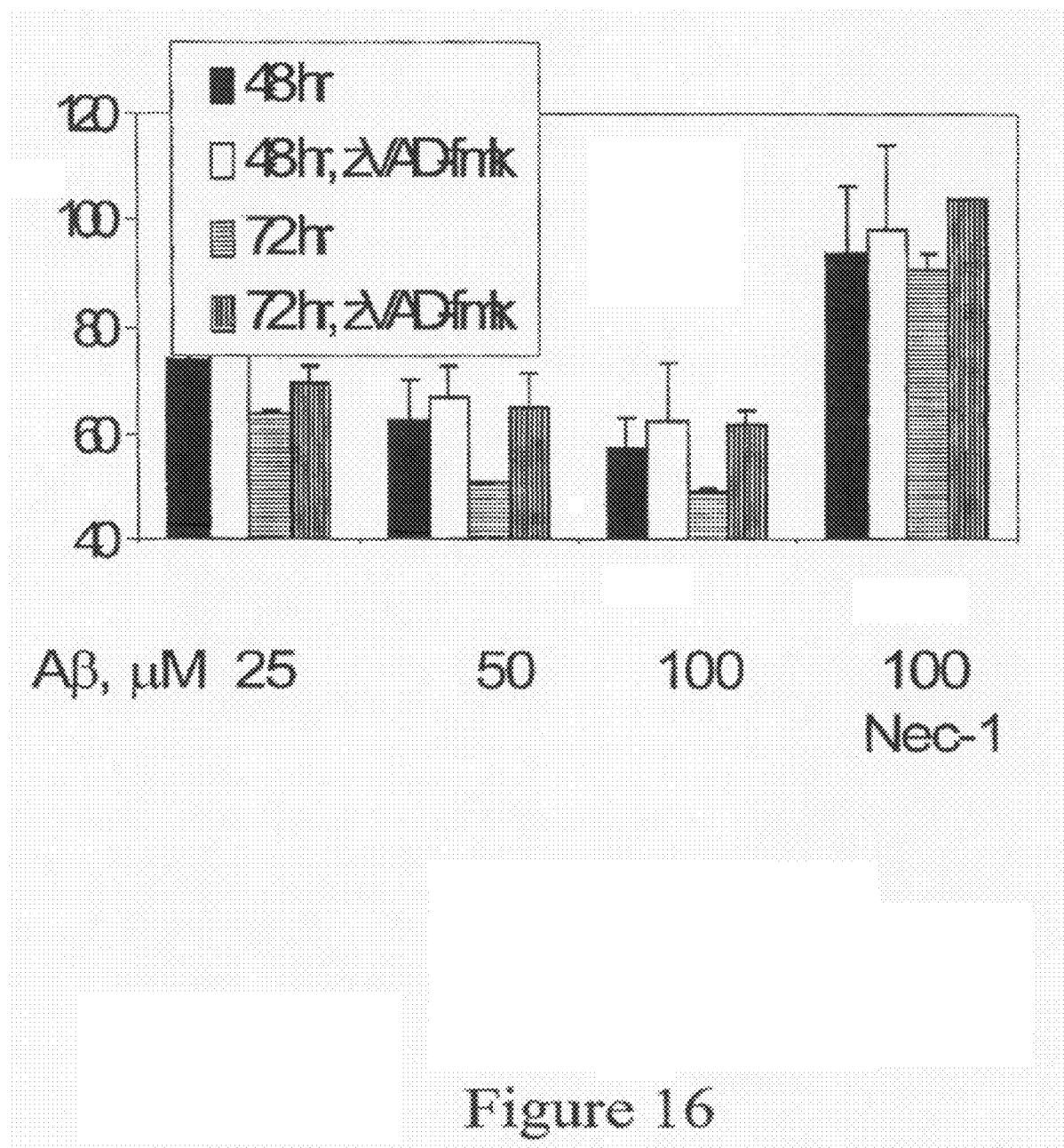
FIG. 16 is a chart showing the protection by Nec-1 from amyloid-beta toxicity. Rat hippocampal neurons (E17) were treated with the indicated concentrations of Aβ25-35 in the presence of zVAD-fmk and Nec-1 for 48 or 72 hours. Viability was determined using an ATP assay. Similar results were also obtained using Aβ1-42.

In addition, we observed attenuation of the aggregated amyloid-beta peptide (Aβ) toxicity in primary rat hippocampal neurons by Nec-1 (FIG. 16). Aggregation of Aβ, produced as a result of abnormal processing of the amyloid precursor protein, is the primary cause of Alzheimer's disease.

Interestingly, similar to the OGD-induced death, neurotoxicity in other paradigms of neurodegeneration was attenuated by Nec-1 even in the absence of caspase inhibitors, potentially indicating that endogenous conditions within neuronal populations might be non-permissive for the execution of apoptosis, making CICD a primary mechanism of pathologic neuronal death.

Example 9

Nec-1 Activity in Immune Cell Regulation

Figure 17:
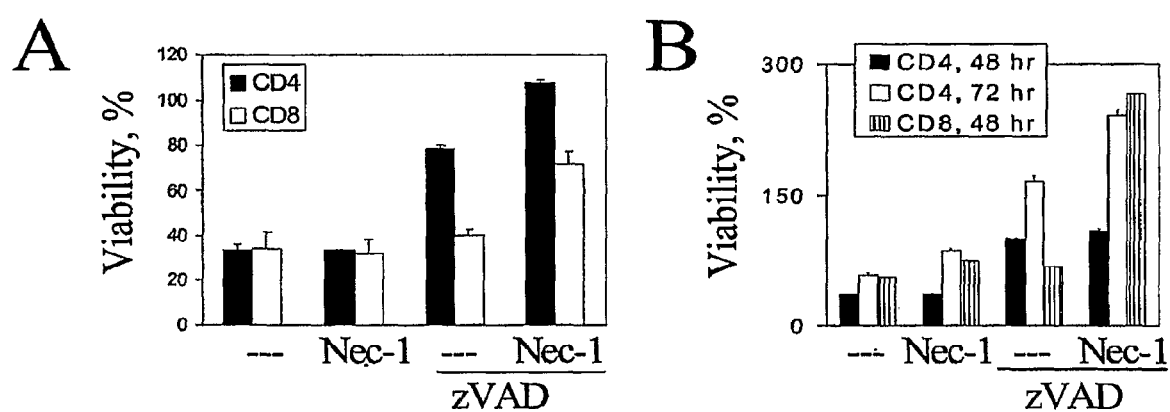
FIG. 17 is a pair of charts showing inhibition of AICD by Nec-1. Primary mouse $CD4^+$ and $CD^+8$ T cells were induced to undergo AICD by first stimulating cells with 1 µg/ml αCD3 and 1 µg/ml αCD28 antibody ($CD4^+$) or 100 U/ml mouse IL-2 for ($CD8^+$) 72 hours antibody, followed by resting in 100 U/ml of mIL-2 for hours and reactivation with αCD3 with ($CD8^+$) or without ($CD4^+$) mIL-2 in the presence of 100 µM zVAD.fmk with or without 30 µM Nec-1 as indicated for 48 hours. Cell viability was assessed using Sytox Green (Molecular Probes) (CD8) or propidium iodide exclusion (CD4) assays in FIG. 17A or ATP assay in FIG. 17B. Numbers represent the percentages of live cells normalized to the corresponding compound treated controls lacking αCD3.

Activation-Induced Cell Death (AICD) of T cells, a process that limits the re-activation of T cells to prevent the development of an autoimmune response, is an example of caspase-independent cell death under normal physiological conditions. Re-activation of mouse $CD4^+$ cells resulted in efficient induction of cell death (FIG. 17). Nec-1 displayed very little effect on the viability of re-activated T cells in the absence of zVAD.fmk, and the addition of zVAD.fmk alone was only partially protective. However, Nec-1 and zVAD.fmk together efficiently abrogated cell death (FIG. 17). Very similar results were obtained in AICD of $CD8^+$ cells, except protection by zVAD.fmk was less pronounced, suggesting more efficient induction/execution of CICD in this subtype of T cells (FIG. 17). There results indicate that apoptosis is the primary mode of AICD, whereas caspase inhibition triggers efficient induction of CICD.

A number of reports have suggested that primary activation and effector function development in primary mouse and human T and B lymphocytes, monocytes and natural killer cells is inhibited by the presence of zVAD.fmk or by the inactivation of caspase-8. Whereas in various sub-classes of human T cells are succeptable to this regulation, mouse $CD8^+$ cytotoxic lymphocytes (CTL), but not helper $CD4^+$ cells appear to depend on caspase activity for primary activation. We have verified whether dependence on caspase activity in this case reflects involvement of Nec-1-controlled signaling steps.

Figure 18:
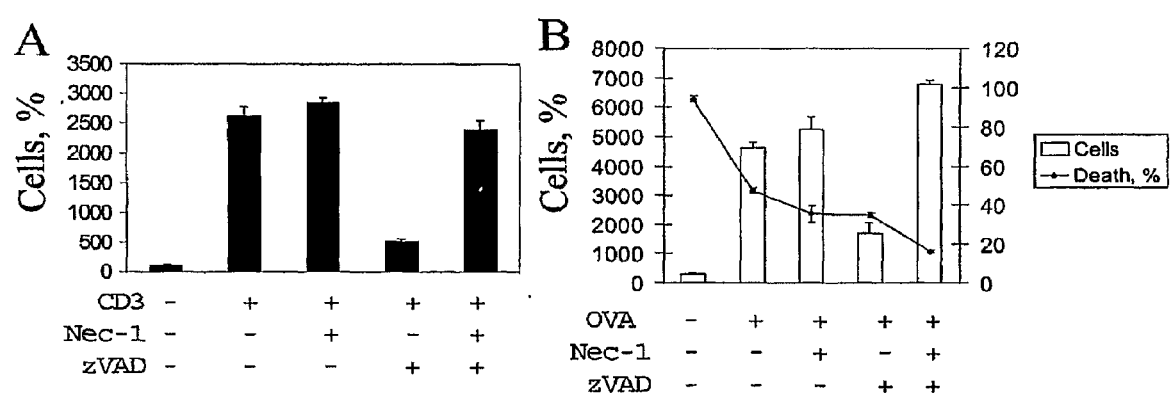
FIG. 18 is a pair of charts showing that Nec-1 restores normal activation of CTLs inhibited by caspase inhibition.

Activation of the primary CTLs by stimulation with αCD3 antibody, assessed through the increase in cell numbers, was suppressed by zVAD. This effect of caspase inhibition was completely suppressed by Nec-1, which allowed accumulation of CTLs in the presence of zVAD.fmk (FIG. 18A). Specificity of this effect is underscored by the lack of Nec-1 effect in the cells not treated with zVAD. The same result was obtained with stimulation of CTL T cell receptors (TCR) specific for a particular antigen, oavlbumin peptide 257-264, isolated from a transgenic TCR OT-I mouse line (FIG. 18B).

Figure 19:
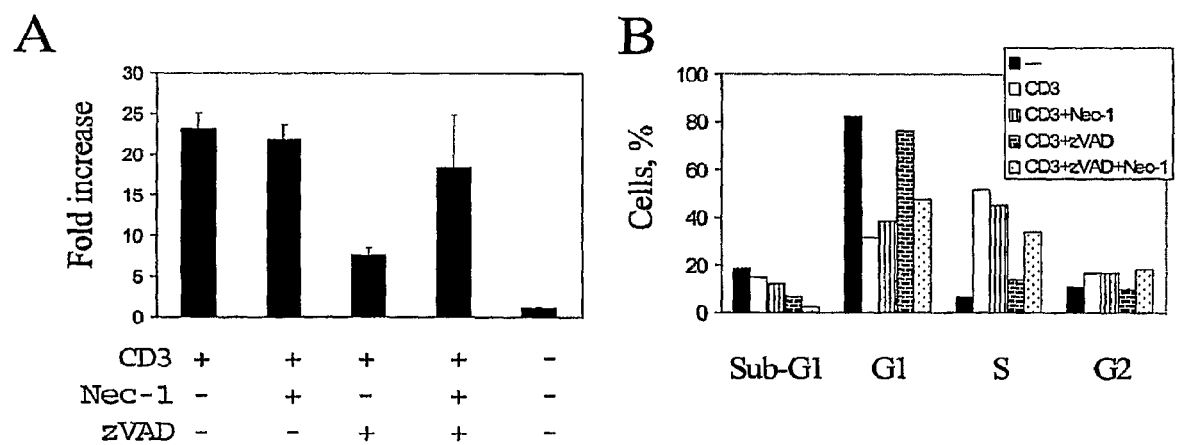
FIG. 19 is a pair of charts showing the restoration of CTL proliferation by Nec-1.

The suppression of CTL activation by zVAD.fmk was not due to the induction of necroptotic cell death by combination of TCR signal and caspase inhibitor, as decrease in cell numbers was not associated with increase in cell death in zVAD-.fmk-treated sample (FIG. 18B). This effect of zVAD fmk was due to the inhibition of cell proliferation assessed by cellular DNA incorporation of [$^3$H]-thymidine and this suppression of cell proliferation was prevented in the presence of Nec-1 (FIG. 19A). Consistent with this observation, zVAD-.fmk prevented G1 to S-phase entry of the CTLs following TCR signal and this effect was attenuated by Nec-1 (FIG. 19B).

Figure 20:
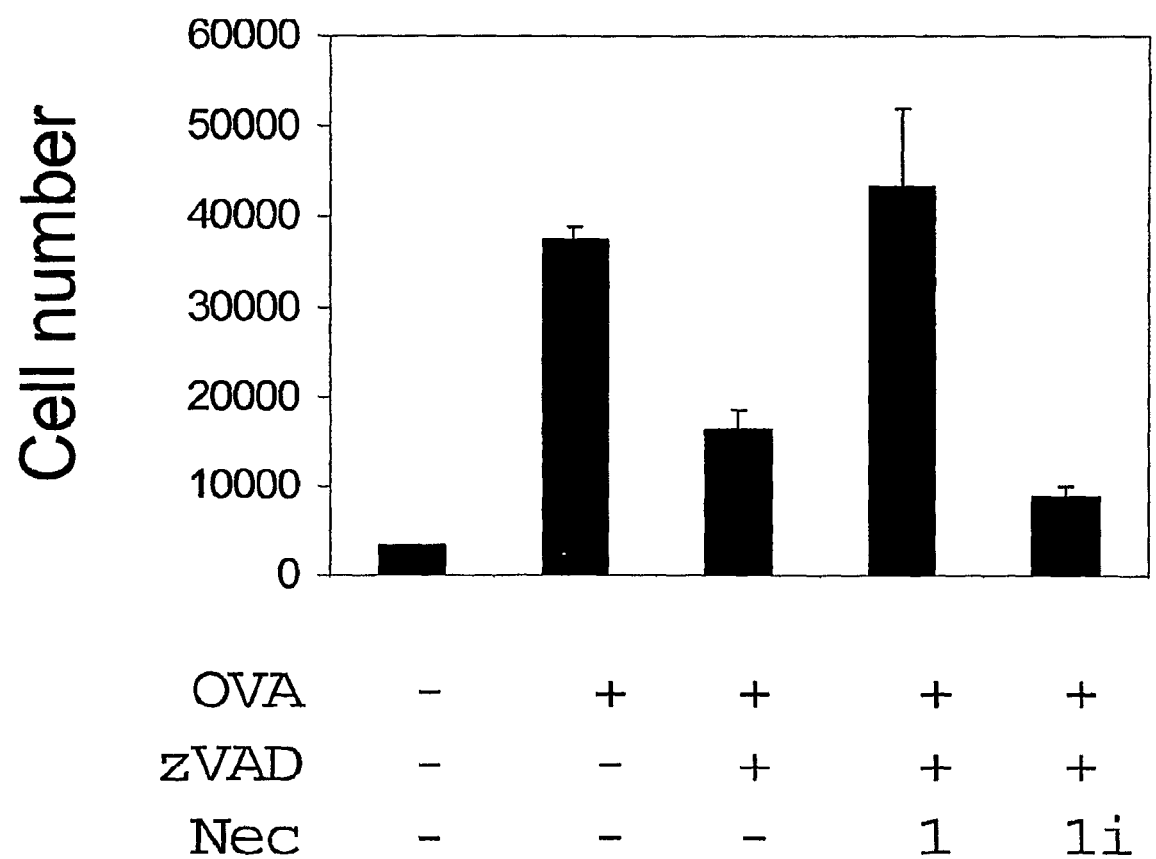
FIG. 20 is a chart showing that Nec-1i does not affect T cell proliferation. Splenocytes isolated from OT-I mice were stimulated with 10 μM OVA257-264 peptide (Sachem) in the presence of 100 μM zVAD.fmk with or without 30 μM Nec-1 or Nec-1i for 72 hours. Cells were stained with αCD8+-FITC antibody (Pharmingen), and CD8+ cell numbers were determined by FACS. Cell numbers are normalized to the number of cells in unstimulated control, which was set as 100%. Percentages of dead cells (line) were determined by co-staining cells with propidium iodide.

The effect of Nec-1 was specific and associated with the similar target as its CICD-suppressing activity as Nec-1i, the inactive derivative of Nec-1, failed to restore T cell proliferation (FIG. 20).

Figure 21:
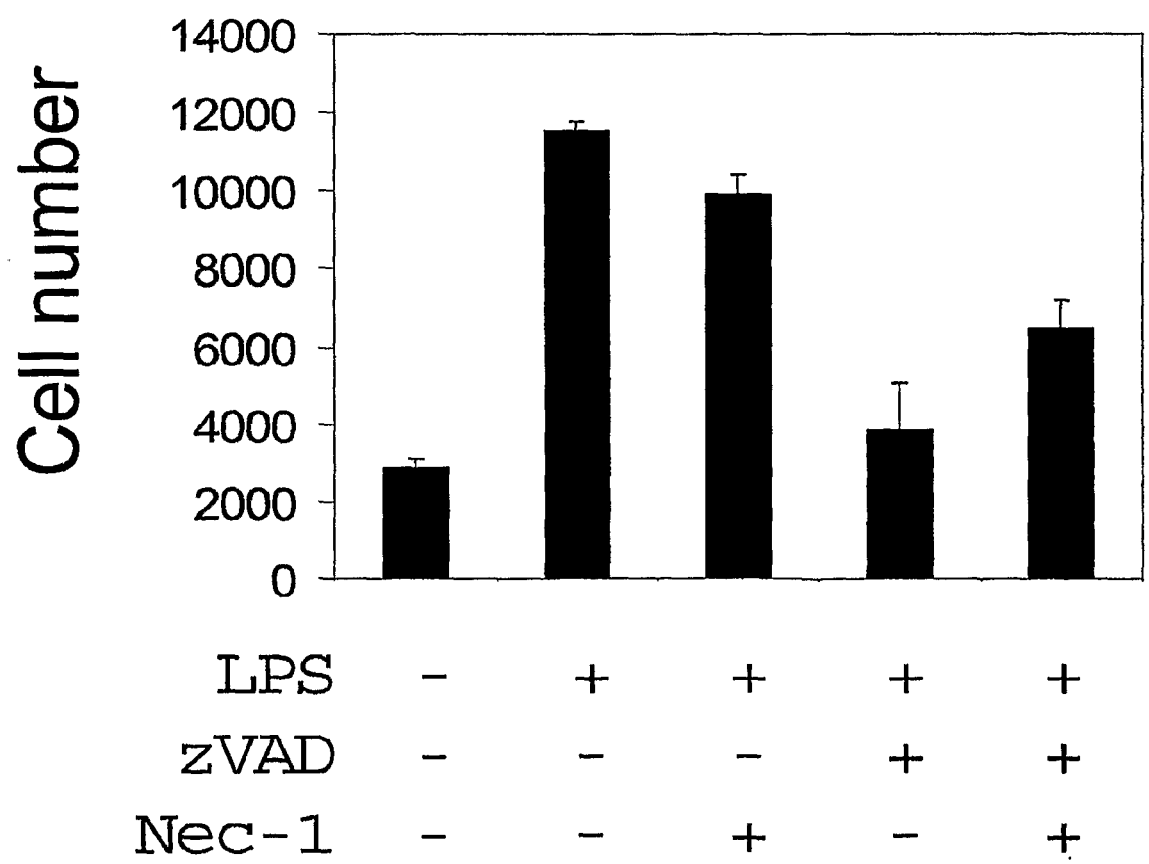
FIG. 21 is a chart showing that Nec-1 promotes B cell activation. Splenocytes were stimulated with 10 μg/m LPS and 25 ng/ml of mouse IL-4 in the presence of 100 μM zVAD.fmk with or without 30 μM Nec-1 or Nec-1i for 72 hours. Cells were stained with αB220-FITC antibody (Pharmingen), and B cell numbers were determined by FACS. Cell numbers are normalized to the number of cells in unstimulated control, which was set as 100%.

Finally, consistent with the deficient B cell activation caused by human caspase-8 mutation, Nec-1 also attenuated suppression of B cell activation by zVAD.fmk (FIG. 21).

Example 10

Molecular Basis for Nec-1 Activity

Figure 23:
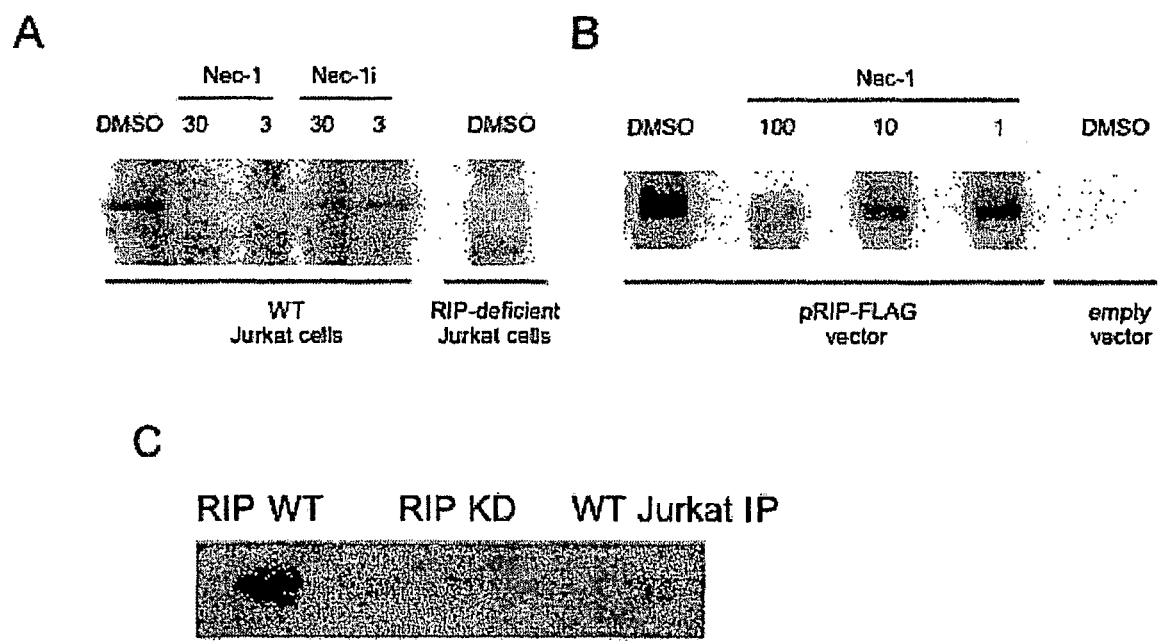
FIG. 23 is a set of gels showing that Nec-1 inhibits the autophosphorylation of RIP in vitro.

Using a commercial antibody for RIP that can efficiently immunoprecipitate endogenous RIP protein (Santa Cruz) and a kinase assay for autophosphorylation of immunoprecipitated RIP1, we demonstrated that immunoprecipitated RIP1 as well as transfected RIP1, IPed using FLAG antibody, undergo autophosphorylation in vitro (FIG. 23). The presence of Nec-1 inhibited the autophosphorylation of RIP1 in vitro; while Nec-1i, the inactive derivative of Nec-1, showed significantly reduced activity in inhibiting RIP1 autophosphorylation (FIG. 23A). The specificity of this in vitro kinase assay is demonstrated by the inability of RIP1 deficient Jurkat cells to undergo such autophosphorylation after immunoprecipitation and in vitro kinase assay (FIG. 23A). Furthermore, the phosphorylation event represents the autocatalytic activity of RIP kinase as only wild type RIP, but not its kinase catalytically inactive K45M mutant, displayed autophosphorylation activity upon overexpression in 293T cells (FIG. 23C). These results indicate that Nec-1 targets the kinase activity of RIP1. Since the kinase activity of RIP1 is essential and specific for this alternative cell death pathway, this result is entirely consistent with the ability of Nec-1 to target necroptosis specifically. Identification of RIP1 kinase activity as a target for Nec-1 also provides a further validation for our cell-based screen to identify specific inhibitors of necroptosis.

Figure 24:
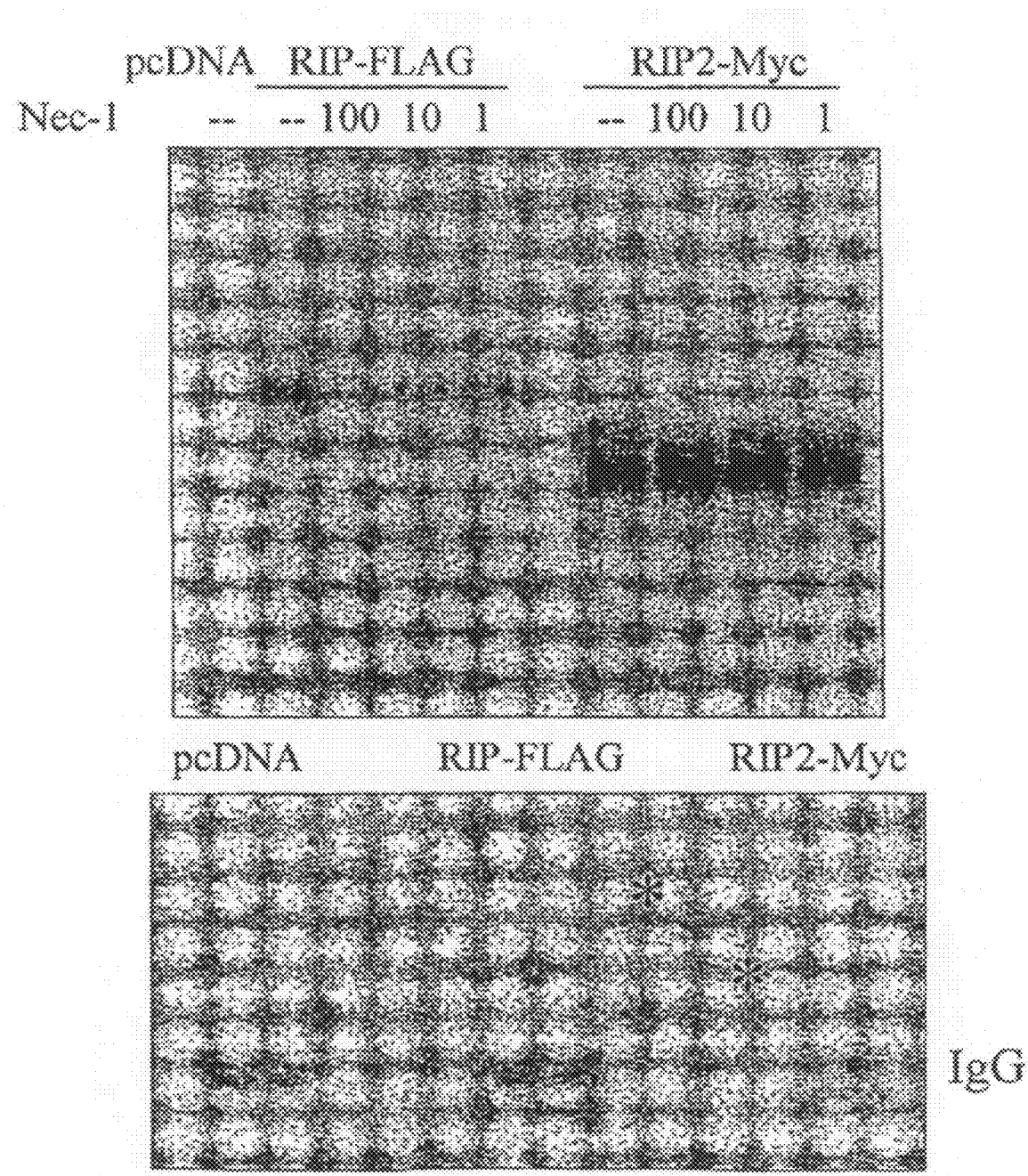
FIG. 24 is a pair of gels showing the lack of a Nec-1 effect on RIP2 autophosphorylation. 293T cells were transfected with RIP-FLAG or RIP2-Myc vectors. Proteins were immunoprecipitated using FLAG or Myc antibodies, respectively, and kinase reactions in the presence of the indicated amounts of Nec-1 (in μM) were performed as described in FIG. 23. In the bottom panel, amounts of proteins comparable to the ones used in kinase reactions were subjected to SDS-PAGE, and protein amounts were visualized by Coomassie Blue staining. Major bands corresponding to phosphorylated. RIP, RIP2, asterisks, and IgG are shown.

As a control for Nec-1 specificity, we compared the inhibition of overexpressed RIP and its'closest homolog RIP2/RICK, which share >30% identity in the kinase domain, by Nec-1 using the same assay as described in FIG. 23B and FIG. 23C. As shown in FIG. 24, Nec-1 had no effect on RIP2 autophosphorylation, despite both proteins being expressed at the comparable levels (see bottom panel). This result, along with the lack of a Nec-1i effect in the case of RIP, confirms the specificity of Nec-1 inhibition of RIP kinase activity.

Interestingly, recent analyses of caspase-inhibition dependent suppression of B and T cell proliferation suggested that it is caused by the loss of NFκB activation. Therefore, our data suggesting restoration of B and T cell activation by Nec-1 under caspase-inhibited conditions directly implicate Nec-1 in paradigms of cellular regulation involving NFκB activation. These include, in addition to immune regulation, such pathologies as muscular dystrophy and others described herein, as well as innate immune responses mediated by RIP and diseases involving TNFα and IL-1β.

Example 11

Further Characterization of Necrostatin-1

Necrotic cell death is common in a wide variety of pathological conditions, including stroke. Very little attempt, however, has been made to develop therapeutics to specifically target necrosis because of the conventional notion that, unlike apoptosis, necrotic cell death is a nonregulated response to overwhelming stress. The demonstration of a common necrotic cell-death pathway activated by a classical DR signal in the absence of any cellular damage directly challenges this notion and suggests that a portion of necrotic cell death in vivo might in fact be regulated by cellular machinery. This, in turn, may provide an unprecedented opportunity to selectively target pathological necrotic cell death.

In this and the next several examples, we used small molecules to define the nonapoptotic pathway mediated by death-domain receptors in the absence of caspase signaling. We identified necrostatin-1 (Nec-1), a specific and potent small-molecule inhibitor of cell death caused by DR stimulation in the presence of caspase inhibition in multiple cell types. These results provide the first direct evidence that DR signaling triggers a common alternative nonapoptotic cell-death pathway, which we term necroptosis. Using Nec-1, we demonstrated that necroptosis is a delayed component of ischemic neuronal injury and may therefore represent a promising therapeutic target for the treatment of stroke.

Because chemical inhibitors of caspases have been instrumental in the characterization of apoptosis in mammalian systems, we expected that specific necroptotic inhibitors would be equally useful for demonstrating the existence of a common, alternative cell-death pathway in multiple cell types, for providing specific tools to distinguish necroptosis from other cell-death processes, and as potential lead molecules targeting the nonapoptotic component of pathologic cell death for therapeutic benefit. We screened a chemical library of ~15,000 compounds for chemical inhibitors of the necrotic death of human monocytic U937 cells induced by TNFα and zVAD.fmk, which we used as an operational definition of necroptosis. This screen resulted in the selection of Nec-1, which efficiently blocked necroptotic death in U937 cells in a concentration-dependent fashion (FIG. 25A and FIG. 25B).

Next, we used Nec-1 as a tool to examine whether the DR-induced nonapoptotic cell death observed in disparate cell types is mediated by a common mechanism. Nec-1 inhibited all published examples of necrotic cell death induced by DR activation in the presence of caspase inhibitors, including the necrotic death of (i) Jurkat cells induced by FasL, cycloheximide (CHX) and zVAD.fmk (FasL-CHX-zVAD.fmk, FIG. 25C), (ii) Jurkat cells stably expressing FADD fused to the FKBP12-based dimerization domain (JK-FF) in the presence of chemical dimerizer AP20187 and zVAD.fmk (FIG. 25D), (iii) BALB/c 3T3 cells treated with TNFα and zVAD.fmk (TNFα-zVAD.fmk) or FasL and zVAD.fmk (FasL-zVAD.fmk, FIG. 25E), and (iv) MEF (FIG. 25F), HT29, and IEC-18 and HL-60 cells treated with TNFα-zVAD.fmk.

Figure 25:
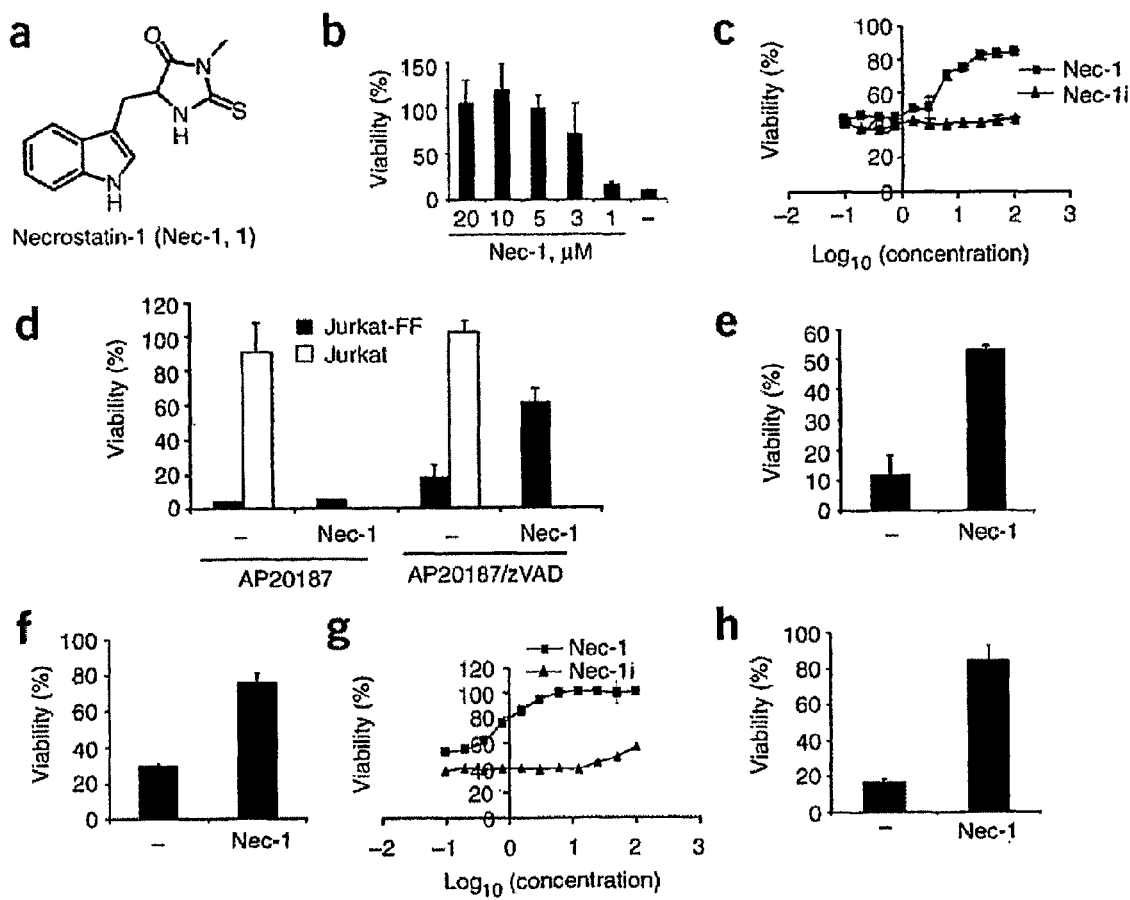
FIG. 25 shows the identification of Nec-1 as a necroptosis inhibitor.
Figure 26:
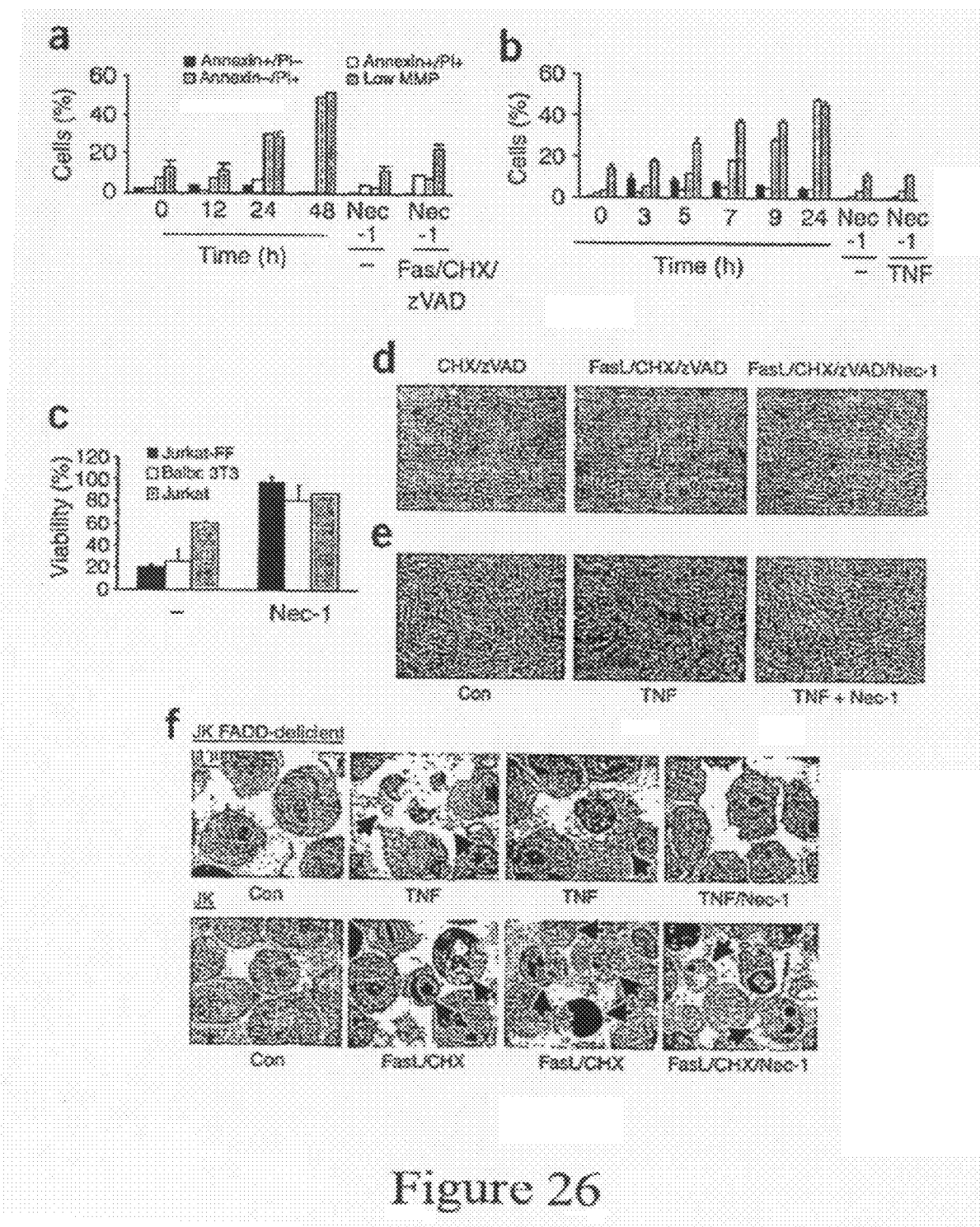
FIG. 26 shows the efficient inhibition of all manifestations of necroptosis by Nec-1.
Figure 27:
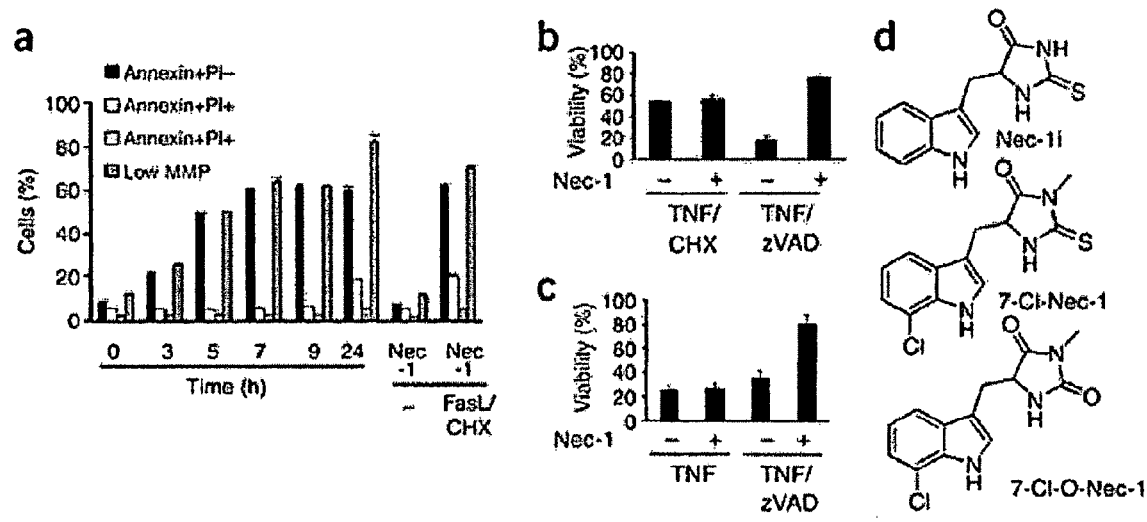
FIG. 27 shows the specificity of Nec-1.
Figure 28:
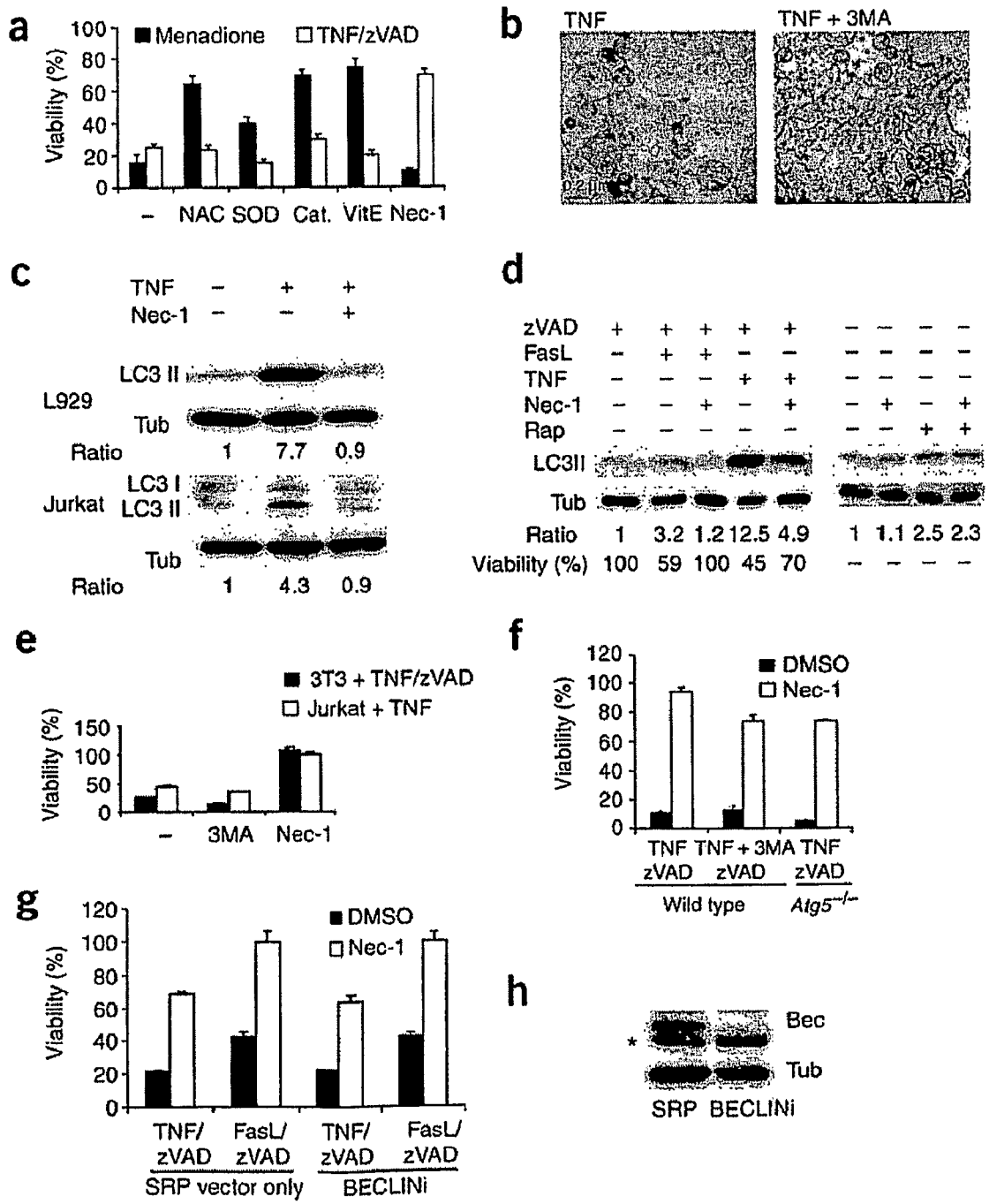
FIG. 28 shows the roles of oxidative stress and autophagy in necroptosis.
Figure 29:
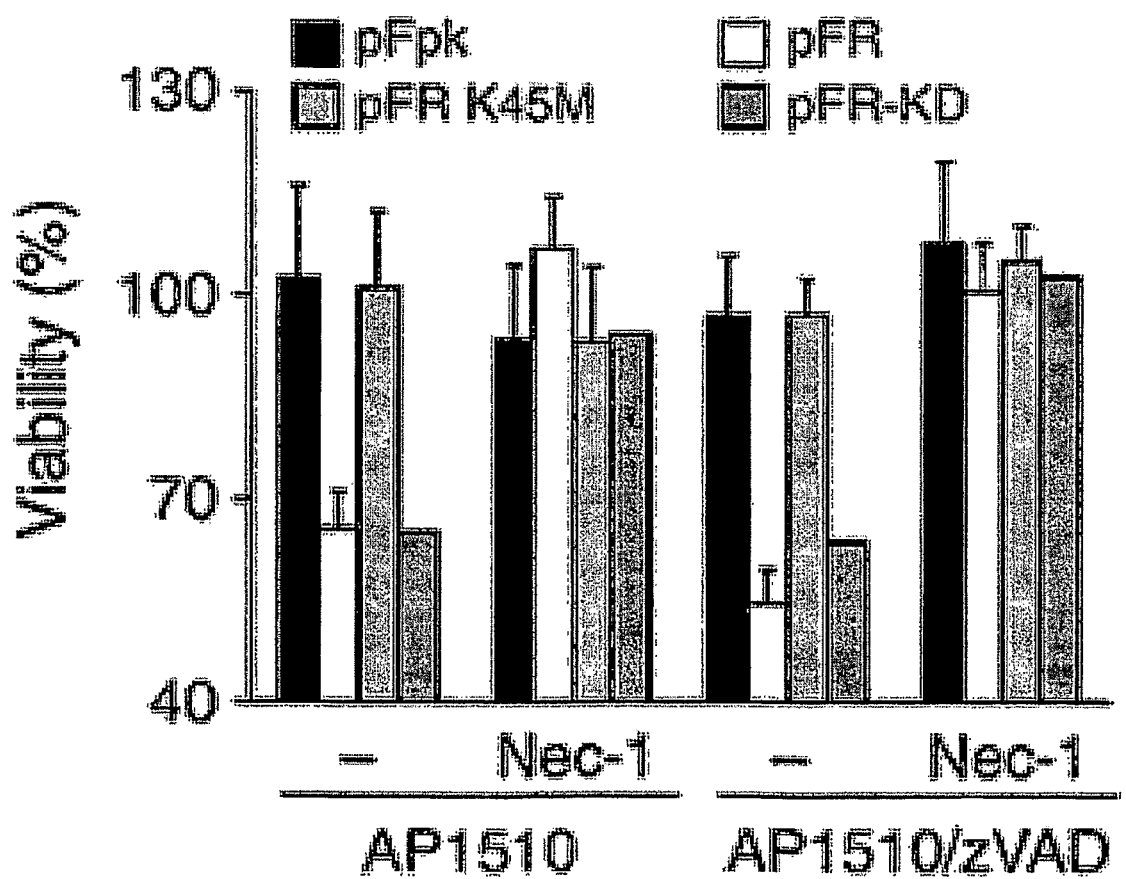
FIG. 29 is a chart showing that Nec-1 inhibits RIP kinase-induced necroptosis. FADD-deficient Jurkat cells were transiently electroporated with pEGFP and vectors encoding the FKBP12-based dimerization domain alone (pFpk) or fused to RIP (pFR), a kinase-inactive K45M mutant of RIP (pFR K45M), and kinase domain of RIP (pFR-KD) and treated 6 hours later with dimerizer AP1510 without or with zVAD-.fmk and Nec-1 for 48 hours. Percentage of PI-negative, GFP-positive cells ("Viability, %") was determined by FACS. Numbers represent viability normalized to that of the compound-treated cells in the absence of dimerizer. Error bars represent standard deviations.
Figure 30:
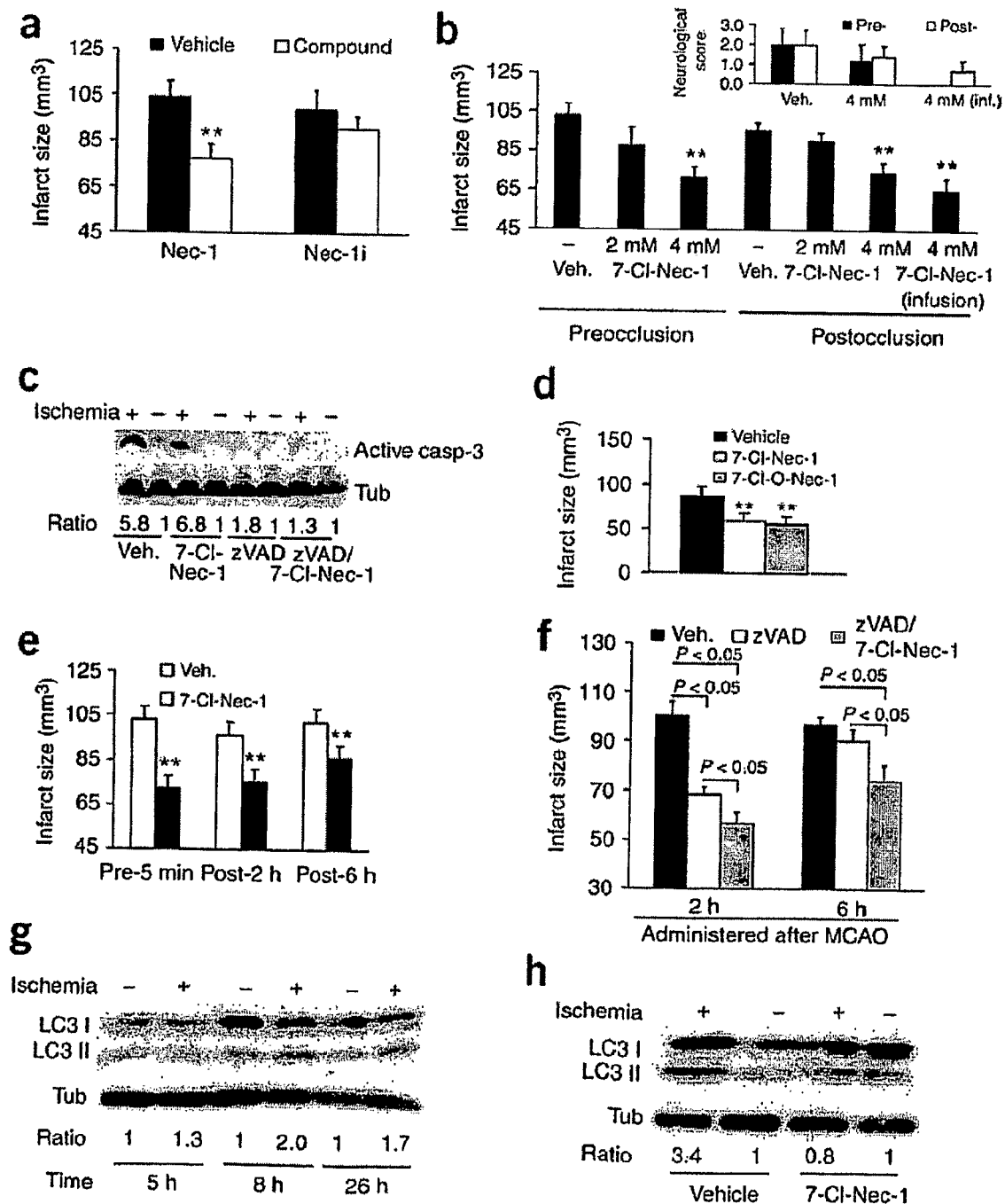
FIG. 30 shows the inhibition of in vivo ischemic injury by Nec-1.

Although Nec-1 was selected in a screen with zVAD.fmk, its action is not dependent upon pharmacological inhibition of caspases. Consistent with the direct activation of necroptosis, Nec-1 prevented the death of TNFα-treated FADD-deficient Jurkat cells, which are unable to activate caspases in response to DR signaling, even in the absence of zVAD.fmk (FIG. 25G). Similarly, Nec-1 efficiently inhibited the TNFα-induced necrotic death of L929 cells, which does not require exogenous caspase inhibitors (FIG. 25H). Overall, the ability of Nec-1 to inhibit cell death in all of these systems provides the first direct demonstration of the existence of a common necroptotic pathway mediated by DR signaling. Because the induction of necroptosis in FADD-deficient Jurkat cells does not rely on the presence of other chemicals (CHX, zVAD.fmk), we used this system to determine the effective concentration for half-maximum response ($EC_{50}$) for Nec-1 of 494±125 nM (FIG. 25G). Efficient protection from necroptosis by Nec-1 was confirmed by several different assays, including forward- and side-scatter analyses of cell size (FIG. 31), ATP level (FIG. 25), mitochondrial dysfunction (FIG. 26A and FIG. 26B), plasma membrane permeabilization (FIG. 26A-FIG. 26C), and cell proliferation (FIG. 20-31). Consistent with these results, morphological analyses based on electron, fluorescent and bright-field microscopy demonstrated that Nec-1 inhibited all manifestations of necroptotic cell death (FIG. 26D-FIG. 26F, FIG. 31, and FIG. 32). These results establish Nec-1 as a potent and efficient inhibitor of necroptosis.

Example 12

Specificity of Nec-1

To establish the specificity of Nec-1, we compared its effects on DR-induced apoptosis as compared to necroptosis, which can be readily distinguished by morphological criteria and selective dye staining. Nec-1 had no effect on FasL-CHX-induced accumulation of annexin V-positive and propidium iodide (PI)-negative cells, a result indicative of apoptosis (FIG. 27A). Conversely, Nec-1 efficiently inhibited the simultaneous loss of mitochondrial membrane potential and plasma membrane integrity in FADD-deficient Jurkat cells treated with TNFα. (FIG. 26A) or wild-type Jurkat cells treated with FasL-CHX-zVAD.fmk (FIG. 26B). The onset of apoptosis was notably faster than that of necroptosis in response to the similar stimuli (FasL-CHX and FasL-CHX-zVAD.fmk, respectively; see FIG. 26B and FIG. 27A), which might suggest that apoptosis usually masks or preempts necroptosis in this cell type because of its faster kinetics.

Consistent with this observation, Nec-1 had no effect on apoptotic morphology (cytoplasm condensation, chromatin marginalization, nuclear fragmentation and plasma membrane blebbing) in FasL-CHX-treated apoptotic Jurkat cells (FIG. 26F), whereas it completely inhibited the appearance of necrotic morphology (nuclear condensation, organelle swelling, early loss of plasma membrane integrity and the appearance of translucent cytosol; see FIG. 26D and FIG. 26F) in TNFα-treated, FADD-deficient Jurkat cells. Selective protection from necroptosis induced by DR signaling was also observed in other cell-death assays (FIG. 25D, FIG. 27B, and FIG. 27C). These results establish the selectivity of Nec-1 in inhibiting necroptosis and point to the divergent regulation of these two types of cell death. Consistent with this model, overexpression of Bcl-$x_L$, in Jurkat cells, which potently suppressed apoptosis, did not inhibit necroptosis.

Figure 31:
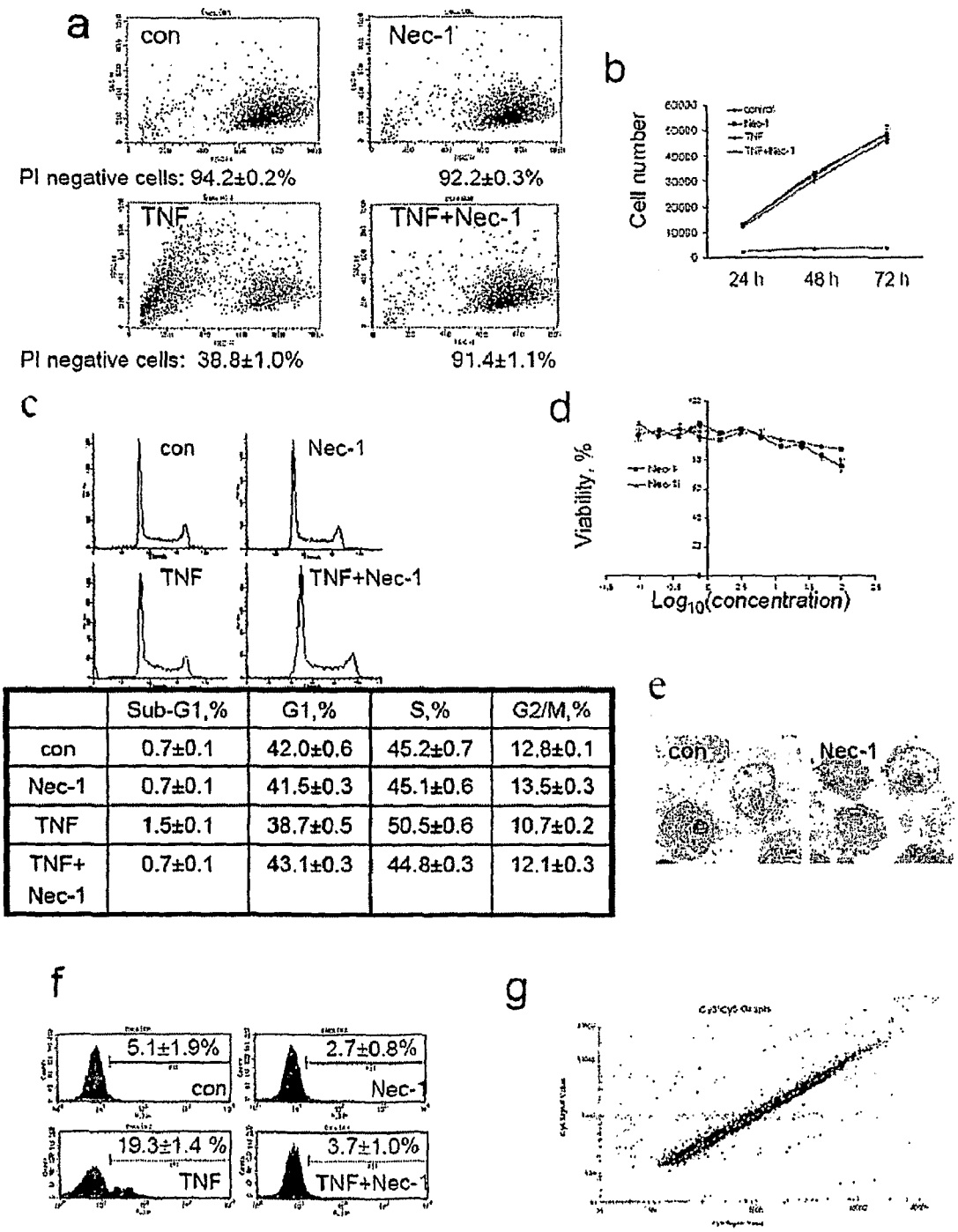
FIG. 31 shows that Nec-1 specifically and efficiently inhibits necroptosis.
Figure 32:
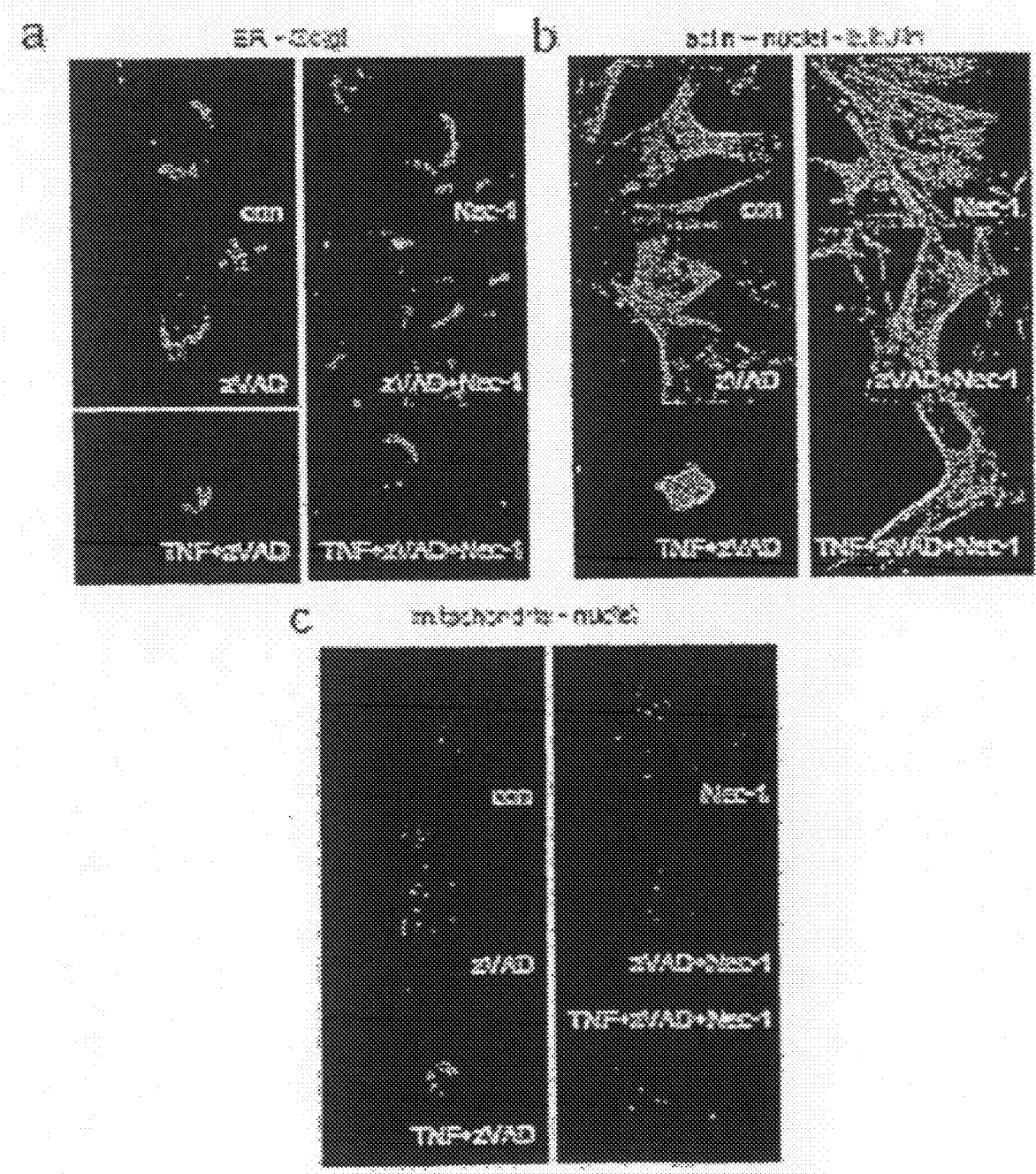
FIG. 32 shows that Nec-1 inhibits multiple necroptosis-associated morphological changes. Balbc 3T3 cells treated with TNFα, zVAD.fmk and Nec-1 for 24 hours. Cells were fixed and stained with anti-giantin (Golgi, green)/anti-KDEL (ER, red) antibodies (FIG. 32A), anti-β-tubulin (tubulin, green)/TO-PRO-3 dye (nuclei, blue)/phalloidin-TRITC (actin, red) (FIG. 32B) and anti-cytochrome c (mitochondria, red)/TO-PRO-3 (nuclei, blue) (FIG. 32C).

To further establish the specificity of Nec-1, we analyzed its possible effect on other cell physiological parameters. We found that Nec-1 had no general effect in healthy cells on ATP levels, mitochondrial membrane potential, plasma membrane integrity, cell shape or size, cell cycle distribution, proliferation, global mRNA expression as reflected in Agilent mRNA chip analysis, the intracellular levels of reactive oxygen species (ROS), cell adhesion, actin and microtubule cytoskeletons, or the morphology of various cellular compartments, for example, nuclei, Golgi apparatus, endoplasmic reticulum and mitochondria (FIG. 31 and FIG. 32). These observations suggest that Nec-1 is specific for necroptosis. To further characterize the specificity of Nec-1, we performed extensive structure-activity relationship analyses and found that most of the 93 chemical modifications of Nec-1 that we tested resulted in either substantial or complete loss of activity. For example, elimination of the methyl group in the hydantoin moiety (Nec-1i; FIG. 27D) completely abolished antinecroptotic activity (FIG. 25C and FIG. 25G). Of all Nec-1 modifications tested, only two types of changes preserved its antinecroptotic activity. First, the addition of a chlorine to the phenyl ring of Nec-1 (7-Cl-Nec-1; FIG. 27D) resulted in an approximately 2.7-fold increase in activity ($EC_{50}$=182±24 nM). Second, changing the sulfur in the hydantoin moiety, which is a potential metabolic liability, to oxygen did not affect the antinecroptotic activity of Nec-1 (7-Cl-O-Nec-1; FIG. 27D; EC50=206±33 nM). Such stringent structural requirements point to the highly specific mode of necrostatin cytoprotection.

Finally, we compared the activity of Nec-1 to that of other small-molecule regulators of cellular signaling. Our analyses revealed that necroptotic cell death in Jurkat and BALB/c 3T3 cells cannot be blocked by small-molecule inhibition of such factors as the mitochondrial permeability transition pore, calpains, calcium homeostasis perturbation, poly(ADP-ribose) polymerase (PARP), HtrA2/Omi, phospholipase A2 and nitric oxide synthase, or the RNAi-mediated downregulation of apoptosis-inducing factor. Furthermore, we screened a chemical library of 489 compounds with known biological activities (BIOMOL ICCB Known Bioactives library; http://iccb.med.harvard.edu) and found that no compound could block necroptosis in all cell types, as does Nec-1. These results underscore the unique nature of necroptosis regulation and Nec-1 activity.

Oxidative stress has been suggested as having a role in DR-induced caspase-independent cell death in some cell types, including U937 and L929. However, we found that only a small fraction of TNFα-treated necroptotic FADD-deficient Jurkat cells showed an increase in ROS (~30% of dying cells; see FIG. 31), whereas necroptosis triggered by FADD dimerization was not accompanied by oxidative stress, as previously reported. Consistent with this observation, necroptosis in Jurkat cells was not inhibited by the antioxidant BHA, nor did any chemical from a panel of general antioxidants protect U937 cells from necroptosis (FIG. 28A), despite the reported protection by BHA in this cell type. Conversely, Nec-1 did not block the "classic" oxidative stress-induced necrosis caused by menadione (FIG. 28A). From these results, we concluded that oxidative stress, although important in some systems, does not play a universal role in necroptotic signaling and that Nec-1 does not act as antioxidant in inhibiting necroptosis.

Example 13

Activation of Autophagy by Necroptotic Signaling

Autophagy, a large-scale protein degradation and catabolic mechanism, has been implicated in caspase-independent cell death, although its functional role remains a subject of debate. The EM analysis of necroptotic Jurkat cells demonstrated the presence of double membrane-enclosed vesicles filled with electron-dense material (FIG. 28B), which are indicative of autophagy. We therefore further investigated the role of autophagy in necroptosis. We used the appearance of the phosphatidylethanolamine (PE)-conjugated form of microtubule-associated protein 1 light chain 3 (LC3-II) as a marker of autophagy, as it has been shown to play an early and critical role in the formation of the autophagosomes. Indeed, autophagy, as indicated by the increase in the levels of LC3-II, was induced in a number of necroptotic systems, including FADD-deficient Jurkat cells and L929 cells treated with TNFα (FIG. 28C), BALB/c 3T3 cells treated with TNFα-zVAD.fmk or FasL-zVAD.fmk (FIG. 28D), and U937 cells treated with TNFzVAD.fmk. Whereas the production of LC3-II results from a multistep process, including the cleavage of the LC3 to the LC3-I form followed by its conjugation to PE, we did not detect the intermediate LC3-I species in every cell type examined; this suggests that it may be rapidly processed into LC3-II in some contexts. However, necroptosis proceeded normally in the presence of 3-methyladenine (3MA), an inhibitor of autophagy (FIG. 28E), in autophagy-deficient Atg5$^{-/-}$ MEF cells (FIG. 28F) and in cells where the critical autophagic factor beclin-1 was knocked down by RNAi (FIG. 28G and FIG. 28H). These results establish autophagy as a common downstream consequence of necroptosis, rather than a contributing factor to necroptotic cell death. On the other hand, although inhibition of autophagy had no effect on the final demise of Jurkat cells, it resulted in the marked accumulation of electron-dense cytoplasmic material (FIG. 28B), indicating a failure to remove cellular debris. Notably, whereas the treatment with Nec-1 efficiently blocked the necroptotic LC3-II induction as well as the formation of autophagic vesicles (FIG. 26F, FIG. 28C, and FIG. 28D), it had no effect on the LC3-II induction caused by rapamycin, a classical inducer of autophagy (FIG. 28D), a result indicating that Nec-1 inhibits a necroptotic signaling step upstream of autophagy but does not inhibit autophagy per se.

Example 14

Inhibition of RIP-Induced Necroptosis by Necrostatin

Previous analyses have suggested that the kinase activity of the DR-interacting protein RIP serves as a bifurcation point separating necroptosis from other DR-dependent pathways. Indeed, dimerized full-length RIP or its kinase domain alone is sufficient to induce kinise-dependent necroptotic cell death, which was inhibited by Nec-1 (FIG. 29); this result confirmed that Nec-1 specifically affects the necroptotic branch of DR signaling. Taken together, our results demonstrate that Nec-1 targets a critical common necroptotic step downstream of DRs but upstream of a number of execution events, including mitochondrial dysfunction, loss of plasma membrane integrity and autophagic clearance of cellular debris.

Example 15

Necroptosis Contributes to Ischemic Neuronal Injury

The stringent specificity of Nec-1 in inhibiting necroptosis prompted us to use it to explore the previously unknown role of necroptosis in vivo. Neuronal cell death caused by ischemic injury is known to contain a substantial nonapoptotic component, and the involvement of DRs in the ischemic brain injury has been suggested. Therefore, we hypothesized that ischemic brain injury may create conditions that are nonoptimal for apoptosis but suitable for necroptosis.

To examine the involvement of necroptosis in ischemic brain injury, we determined the effect of Nec-1 on ischemic damage resulting from middle cerebral artery occlusion (MCAO) in mice. Intracerebroventricular administration of Nec-1 significantly (P<0.05) reduced the infarct volume after MCAO, which suggested that necroptosis could be involved in this form of pathologic death (FIG. 30A). For more detailed analyses, we switched to 7-Cl-Nec-1, which showed greater activity in vitro. 7-Cl-Nec-1 also provided a significant (P<0.05) and dose-dependent reduction in the infarct volume and a proportionate improvement in the neurological score after MCAO (FIG. 30B).

Figure 33:
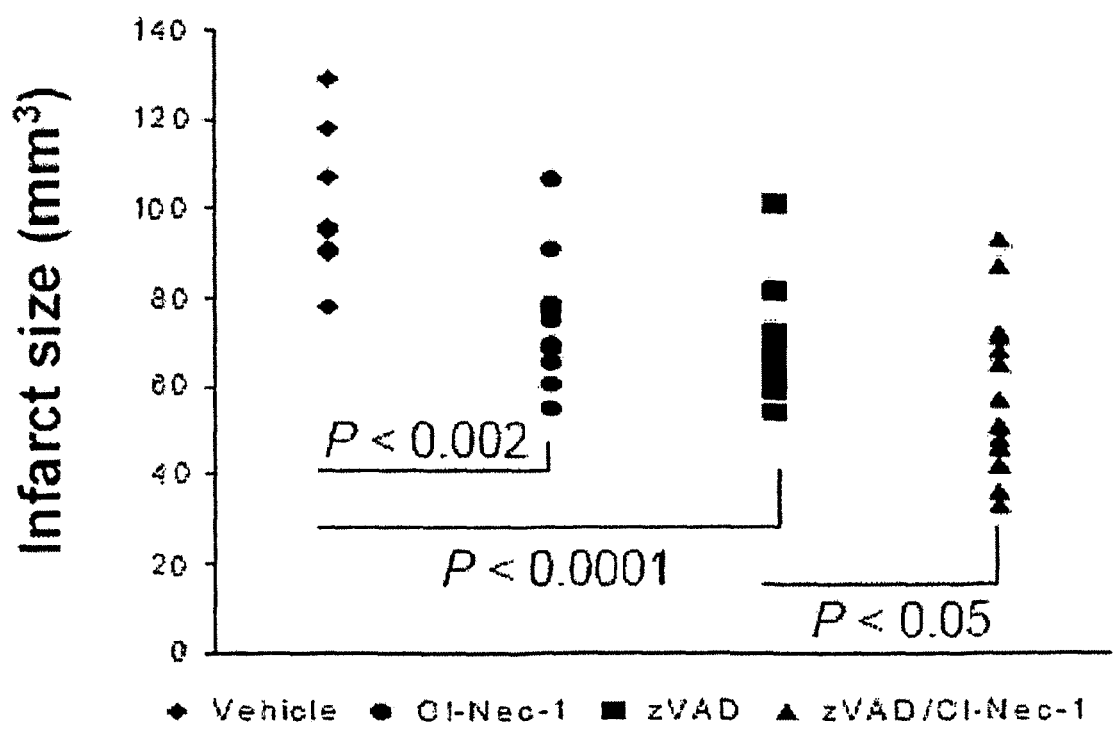
FIG. 33 shows the additive effects of 7-Cl-Nec-1 and zVAD.fmk on inhibition of ischemia-induced neuronal death in vivo. The icy delivery of zVAD.fmk was performed alone or in combination with 7-Cl-Nec-1 at two hours and four hours after the onset of two hours occlusion. Infarct volumes in individual animals are shown. At least eight animals were analyzed in each treatment group. P values are shown.

We next examined the specificity of 7-Cl-Nec-1 activity in vivo. Consistent with the specificity of Nec-1 in blocking necroptosis but not apoptosis in vitro, treatment with 7-Cl-Nec-1 did not block caspase-3 activation during ischemic brain injury, whereas zVAD.fmk did (FIG. 30C). Furthermore, coadministration of zVAD fmk and 7-Cl-Nec-1 resulted in a significant (P<0.05) additive effect (FIG. 33), though extensive optimization would be required to assess the full extent of neuroprotection by the combination treatment. In addition, 7-Cl-Nec-1 did not affect blood oxygen and $CO_2$ levels, body temperature or cerebral blood flow, which indicated that it does not prevent ischemic cell death through a nonspecific effect on general physiology.

To confirm the mode of action of Nec-1 in vivo, we performed a structure-activity relationship analysis of its protection against ischemic brain injury. First, Nec-1i, an inactive derivative of Nec-1 that lacks a single methyl group (FIG. 27D), did not significantly affect infarct volume (FIG. 30A). Second, 7-Cl-O-Nec-1 (FIG. 27D), possessing antinecroptotic activity in vitro similar to that of 7-Cl-Nec-1 (FIG. 27D), showed activity indistinguishable from that of 7-Cl-Nec-1 in vivo (FIG. 30D). These data demonstrate a strict correlation between the inhibition of necroptosis in vitro and the anti-ischemic activity of 7-Cl-Nec-1 in vivo, providing strong support for our hypothesis that neuroprotection by Nec-1 is accomplished through the inhibition of necroptosis.

Notably, the protective effect of 7-Cl-Nec-1 was readily detectable even when the compound was administered six hours after the onset of injury (FIG. 30E), at which point the administration of zVAD.fmk no longer reduces infarct volume (FIG. 30F). We reasoned that this extended time window of neuroprotection by 7-Cl-Nec-1 in vivo might reflect a delayed induction of necroptosis during ischemic brain injury. To verify this hypothesis, we analyzed the induction of $LC_3$-II during MCAO, as our in vitro analyses suggested that this event is associated with necroptosis. We observed that although LC3-II was clearly induced after ischemic brain injury, it did not reach the maximal level until eight hours postocclusion (FIG. 30G). Furthermore, delayed injection of 7-Cl-Nec-1 at four and six hours postocclusion still efficiently blocked the LC3-II increase at the eight-hour time point (FIG. 30H), confirming that the late induction of LC3-II in vivo indeed reflects the delayed activation of necroptosis.

Example 16

Preparation of Nec-1 and its Derivatives

Nec-1 is commercially available from Sigma-Aldrich.

We prepared Nec-1i according to methods known in the art (see, e.g., Suzuki et al., Can. J. Biochem. 55:521-527, 1977). We prepared 7-Cl-Nec-1 according to Scheme 1:

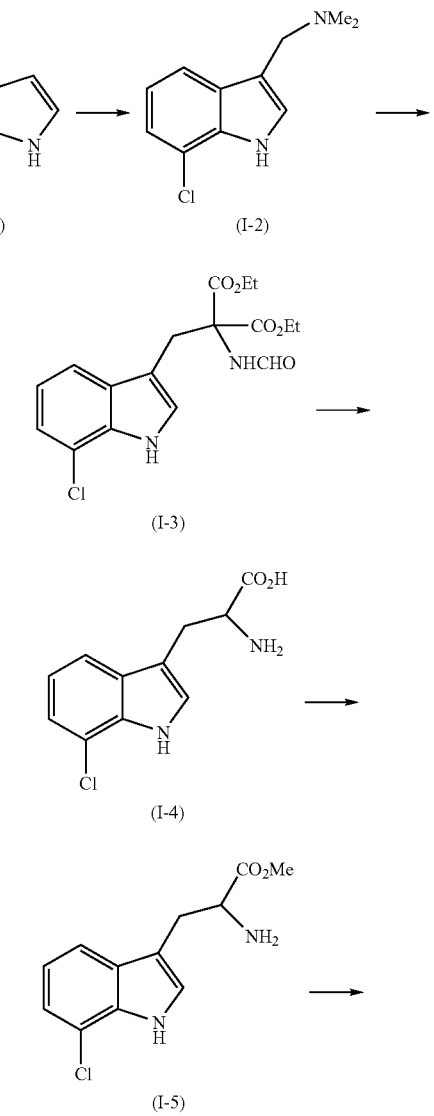

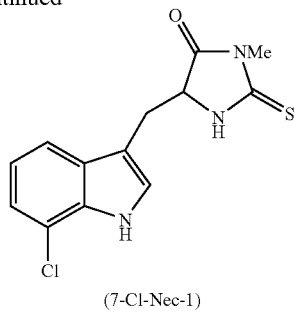

(7-Cl-Nec-1)

We added dimethyl amine (2.05 mL, 16.3 mmol, 40% solution) to a mixture of acetic acid (13.6 mL) and formaldehyde (0.340 mL, 4.5 mmol, 37% solution) under argon. We stirred the reaction mixture for 10 minutes and then treated it with 7-chloroindole (I-1) (604 mg, 4.0 mmol). We stirred the resulting mixture at room temperature for ~16 hours. We first neutralized the reaction mixture with $K_2CO_3$, then basified it with NaOH (2N), and then extracted it in ethyl acetate, washed with water, dried, and concentrated. We recrystallized obtained solid from ethyl acetate and hexane to give (I-2): yield 86%, mp 136° C.-138° C., $^1$H NMR (500 MHz, $CDCl_3$): 2.27(s, 6H), 3.61 (s, 2H), 7.04 (dd, J=8.0 and 8.0 Hz, 1H), 7.15 (d, J=2.5 Hz, 1H), 7.18 (d, J=7.5 Hz, 1H), 7.60 (d, J=7.5 Hz, 1H), 8.53 (s, 1H).

We refluxed a suspension of (I-2) (2.8 mmol), 2-formylamino-malonic acid diethyl ester (3.1 mmol), and NaOH (30 mg) in toluene (20 mL) under argon for three days. We concentrated the reaction mixture and purified it by column chromatography on silica gel using 40% ethyl acetate-hexane to give (I-3): yield 65%, mp 170° C.-174° C., $^1$H NMR (500 MHz, $CDCl_3$): 1.28 (t, J=7.5 Hz, 6H), 3.87 (s, 2H), 4.17-4.31 (in, 4H), 6.80 (s, 1H), 7.00 (d, J=2.5 Hz, 1H), 7.02 (dd, J=7.5 and 8.0 Hz, 1H), 7.17 (d, J=7.5 Hz, 1H), 7.40 (d, J=8.0 Hz, 1H), 8.18 (d, J=1.0 Hz, 1H), 8.32 (s, 1H).

We treated a solution of (1-3) in THF with NaOH (300 mg in 10 mL water) at room temperature for 24 hours. We slowly acidified the mixture with acetic acid (5 mL) and then refluxed it for 24 hours. We concentrated the reaction mixture under vacuum, and treated it with diluted HCl (10 mL, 3M) and then again refluxed for ~16 hours. We allowed the reaction to cool to room temperature and adjusted pH to 6.0 with 2M KOH. We filtered the white solid that formed, washed it with water, and dried it under vacuum to give (I-4): yield 83%, mp 236° C.-239° C., $^1$H NMR (500 MHz, DMSO-$d_6$): 2.95-3.00 (dd, J=8.5 and 15 Hz, 1H), 3.24-3.28 (dd, J=4.0 and 15 Hz, 1H), 3.41-3.43 (dd, J=4.0 and 8.5 Hz, 1H), 6.95 (dd, J=7.5 and 7.5 Hz, 1H), 7.10 (d, J=7.5 Hz, 1H), 7.22 (s, 1H), 7.52 (d, J=7.5 Hz, 1H), 11.18 (s, 1H).

We dissolved thionyl chloride (0.09 mL, 1.2 mmol) in 3 mL of anhydrous methanol at 0° C. and then added this solution to a flask containing crude (I-4) (200 mg, 0.5 mmol). After stirring at −5° C. for four hours, we allowed the reaction mixture to warm to room temperature and stirred it overnight before being concentrated. We collected the white solid, washed it with ethyl acetate and dried it in vacuo. We directly used the product (I-5) without further purification.

We added triethyl amine (0.1 mL) to a solution of (I-5) (1.0 mmol) in dichloromethane (10 mL) followed by methyl-isothiocyanate (7.4 mg, 0.1 mmol). We stirred the reaction mixture at room temperature for one hour and then concentrated it. We purified the obtained residue by column chromatography on silica gel using 30% ethyl acetate in hexane to give (7-Cl-Nec-1): mp 249° C.-253° C.; $^1$H NMR ($d_6$-DMSO-$CDCl_3$, 500 MHz) δ 3.02 (s, 3H), 3.18-3.22 (dd, 1H, J1=14.5 Hz, J2=5.5 Hz); 3.30-3.34 (dd, 1H, J1=14.5 Hz, J2=5.5 Hz); 4.35 (dd, 1H, J1=5.5 Hz, J2 =4.5 Hz); 7.00 (t, 1H, J=7.5 Hz); 7.13 (d, 1H, J=7.5 Hz); 7.19 (d, 111, J=2.0 Hz); 7.52 (d, 1H, J=7.5 Hz); 9.92 (s, 1H), 10.45 (s, 1H); $^{13}$C NMR, ($d_6$-DMSO, 100 MHz) δ 25.92, 26.61, 59.45, 108.84, 115.64, 117.56, 119.45, 120.46, 125.44, 129.19, 132.59, 174.43, 182.83; Analysis calculated for $C_{13}H_{12}ClN_3OS$: C, 53.15; H, 4.12; N, 14.30. Found: C, 53.16; H, 4.21; N, 14.01.

The oxygen-containing derivative of (7-Cl-Nec-1), (7-Cl-O-Nec-1), was prepared according to Scheme 2:

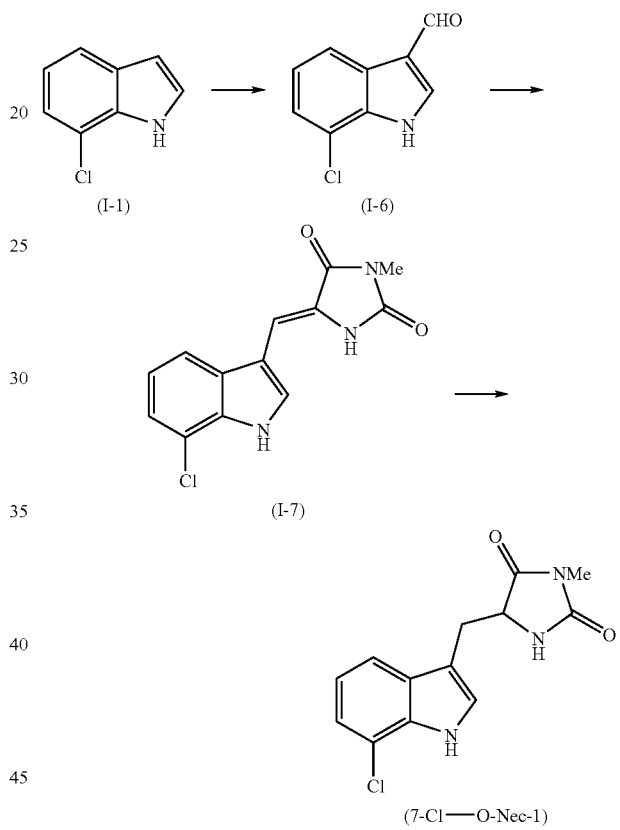

Scheme 2.

We added phosphorus oxychloride (0.66 mL, 7 mmol) dropwise to anhydrous DMF (5 mL) at 0° C. under argon. Next, we added a solution of (I-1) (1 g, 6.6 mmol) in anhydrous DMF (15 mL) dropwise at room temperature and stirred the resulting mixture for two hours. We poured the reaction mixture into ice and saturated $NaHCO_3$ and extracted it with ethyl acetate. We washed the combined organic solutions with saturated NaCl (10mL×3), dried it over anhydrous $MgSO_4$, filtered and concentrated it to give 990 mg of product, (I-6), as a yellow-orange solid (83%). $^1$H NMR (500 MHz, DMSO-$d_6$) δ 12.22 (1H, br s), 9.93 (1H, s), 8.34 (1H, s), 8.07 (1H, d, J=9.0 Hz), 7.57 (1H, d, J=1.5), 7.25 (1H, dd, J=1.8, 7.8 Hz).

We heated a mixture of (I-6) (1 mmol) and 1-methylimidazol-2,5(1;3H)-dione (which we synthesized according to the method used by Janin et al., Eur. J. Org. Chem. 2002: 1763-1769, 2002) (250mg, 2.5 mmol) in piperidine (2 mL) at 110° C. for four hours undet an argon atmosphere. Then, we allowed the reaction mixture to cool in a refrigerator (~5° C.)

with the addition of ether (2 mL). We filtered the precipitate and washed it with ether to give (I-7). $^1$H NMR (500 MHz, DMSO-d$_6$): δ 12.15 (1H, br s), 10.26 (1H, br s), 8.23 (1H, s), 7.79 (1H, d, J=8.0 Hz), 7.27 (1H, d, J=8.0 Hz,), 7.13 (1H, t, J=7.8 Hz), 6.82 (1H, s), 2.97 (3H, s).

We added CoCl$_2$ (1.0 mmol) and NaBH$_4$ (10 mmol) portion wise to a solution of (I-7) (0.5 mmol) in a mixed solvent of anhydrous MeOH/THF (1:1, 40 mL) We stirred the mixture at room temperature overnight and then diluted it with ethyl acetate (100 mL) We washed the mixture sequentially with saturated NaHCO$_3$ (30 mL), 1N HCl (30 mL), saturated NaCl (30 mL) and then dried it over anhydrous MgSO$_4$, filtered and concentrated it. We purified the crude product by column chromatography on silica gel to give (7-Cl-O-Nec-1): mp 173° C.-175° C.; $^1$H NMR (CDCl$_3$, 500 MHz) δ 8.43 (1H, br s), 7.50 (1H, d, J=8.0 Hz), 7.22 (1H, d, J=7.5 Hz), 7.13 (1H, d, J=2.0 Hz), 7.06 (1H, t, J=7.8 Hz), 5.69 (1H, br s), 4.27 (1H, ddd, J=1.0, 3.5, 8.8 Hz,), 3.43 (1H, dd, J=3.5, 14.5 Hz), 3.01 (1H, dd, J=9.3, 14.8 Hz), 2.95 (3H, s); 13C NMR, (CDCl$_3$, 100 MHz) δ 173.4, 157.2, 133.6, 128.4, 123.6, 122.0, 120.8, 117.2, 116.9, 111.0, 58.0, 28.1, 24.5; Elemental analysis calculated for C$_{13}$H$_{21}$ClN$_3$O$_2$: C, 56.22; H, 4.36; N, 15.13. Found: C, 56.19; H, 4.41; N, 15.10.

Example 17

Necrosis in Cells in Response to zVAD-fmk and TNFα

The cell lines U-937 and BALB/c 3T3 were assayed for the occurrence of necrosis in response to the combined treatment of zVAD-fmk, a caspase inhibitor, and TNFα, a cell death stimulator. The cells (5×10$^5$ cells/ml) were exposed to zVAD-fmk (100 μM) and human TNFα (40 ng/ml) for 72 hours. Induction of necrosis was assayed by measuring the cellular ATP levels in response to TNFα (Crouch et al., supra, Storer et al., supra, and Cree et al., supra). Cells which underwent necrosis exhibited decreased cellular ATP levels relative to controls cells which received no treatment, zVAD-fmk (100 μM) alone; or human TNFα (40 ng/ml) alone. It was found that the cells underwent necrosis in response to treatment with zVAD-fmk and TNFα. The cells were also observed morphologically for the occurrence of apoptosis or necrosis, for example, by analyzing the cells for membrane blebbing and nuclear condensation.

Example 18

Identification of Small Molecules that Decrease Necrosis

The U-937 cell line was used to screen a library of 16,000 small molecule chemical compounds for a compound's ability to decrease necrosis induced by exposure of the cell to zVAD-fmk and TNFα. The library of chemical compounds used in this screen was obtained from ChemBridge (ChemBridge Corporation, San Diego Calif.).

In a primary screen, U-937 cells (5×10$^5$ or 7.5×10$^5$ cells/nil) were first exposed to zVAD-fmk (100 μM). Thirty minutes later the same cells were exposed to a chemical compound from the library (5 mg/ml, dissolved in 0.1-0.5 μl of DMSO, giving a final DMSO concentration of 0.3% to 1.5%). After an additional thirty minutes, TNFα (40 ng/ml) was added to the cell culture medium. The cells were then incubated at 37 C for 72 hours, and were then assayed for cellular ATP levels. Compounds which did not prevent a decrease in cellular ATP levels were compounds which did not prevent necrosis in response to treatment of the cell with zVAD-fmk and TNFα. Compounds which maintained cellular ATP levels were compounds which blocked necrosis triggered by zVAD-fmk and TNFα.

As a result of the primary screen, 50 chemical compounds from the library were identified to decrease necrosis induced by zVAD-fmk and TNFα. These compounds were selected for a second round of screening for compounds that decrease necrosis induced by zVAD-fmk and TNFα.

In a secondary screen, the compounds identified from the first screen, above, to decrease necrosis induced by zVAD-fmk and TNFα were assayed for their potency. Serial dilution of each chemical compound was performed and the compounds were administered to U-937 cells, as per the primary screen. The concentrations of each compound were 70 μM, 23 μM, 8 μM, and 2.5 μM. The level of necrosis occurring in response to zVAD-fmk, TNFα, and the various concentrations of chemical compounds was assayed as described above for the primary screen.

As a result of the secondary screen, four chemical compounds from the ChemBridge library, ChemBridge Compound Nos. 115807, 115681, 210227, and 215686, were identified to decrease necrosis in response to exposure of the cell to zVAD-fmk and TNFα. The structures of these compounds are as follows:

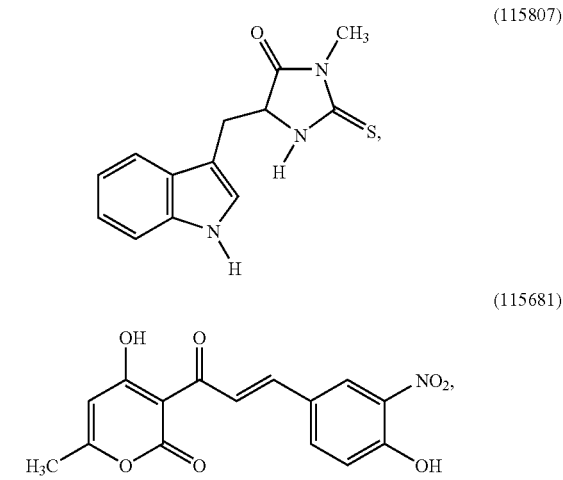

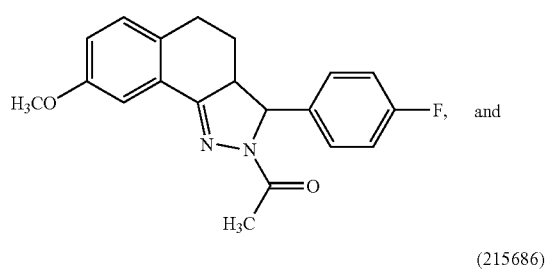

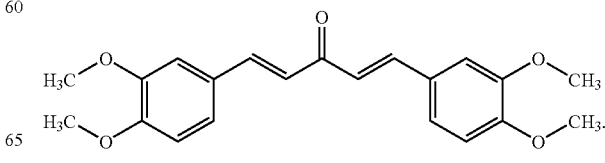

Example 19

Protection of Cells from Necrosis by Exposure to zVAD-fmk and DMSO

Exposure of low density U-937 cells ($1\times10^5$ cells/ml) to zVAD-fmk (100 µM) and DMSO (0.5%) for 72 hours results in cell death by necrosis. The compounds identified to decrease cell necrosis triggered by zVAD-fmk and TNFα, compounds 115807, 115681, 210227, and 215686 from the ChemBridge chemical library, were also evaluated for their ability to decrease cell necrosis induced by zVAD-fmk and DMSO. The cells ($1\times10^5$ cells/ml) were first exposed to zVAD-fmk, and then thirty minutes later to the above-identified small molecules that decrease necrosis. After an additional 30 minutes, the cells were exposed to DMSO. 72 hours after exposure to the compounds, cellular ATP levels were measured, as described above. All four chemical compounds that decreased necrosis induced by zVAD-fmk/TNFα also decreased necrosis induced by zVAD-fmk/DMSO.

Example 20

Preparation of Compounds of Formula (XXII)

One compound identified as an inhibitor of necrosis was ChemBridge compound number 210227 (Nec-3). Analogs of this compound have been previously described (El-Rayyes and Al-Jawhery, J. Heterocyclic Chem. 23:135-140, 1986; Sinha and Rastogi, Indian J. Chem 0.308:684-692, 1991;

Szöllösy et al., J. Chem. Soc., Perkin Trans. 2 1991:489-493) and the reported biological activities for this structure class include weak antiamoebic activity.

In the present invention, novel analogs of ChemBridge compound no. 210227 have been prepared and are represented by formula (XXII). In one example, the starting point for the synthesis of a compound of formula (XXII) begins with a tetralone of formula (XXIII), which can either be obtained from commercial sources or can be prepared by methods known to those skilled in the art (see, for example Zubaidha et al., Tetrahedron 47:5759, 1991; Kumar, Organic Preparations and Procedures International 29:477-79, 1997; and Cui et al., Tetrahedron Lett. 44:4007-4010, 2003).

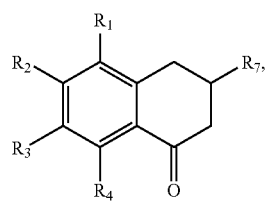

(XXIII)

Compounds of formula (XXIII) can be converted to 2-arylidene- or 2-heteroarylidine-1-tetralones (XXIV) by their condensation with aromatic or heteroaromatic aldehydes $R_5$-CHO, respectively, in an alcoholic solvent in the presence of a catalytic amount of base (such as, for example, sodium hydroxide, potassium hydroxide, or piperidine) or acid (such as, for example, $H_2SO_4$, $H_3PO_4$, or HCl) to produce a compound of formula (XXIV)

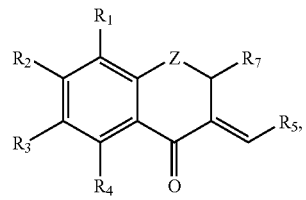

(XXIV)

where Z is $CH_2$ and $R_7$ is H

Compounds of formula (XXIV) can then be reacted with hydrazine and a carboxylic acid, such as, for example, $R_9CO_2H$, where $R_9$ is an optionally substituted $C_{1-12}$ alkyl, an optionally substituted $C_6$ or $C_{10}$ aryl, an optionally substituted $C_{2-9}$ heteroaryl, an optionally substituted $C_{7-16}$ aralkyl, or an optionally substituted $C_{2-15}$ heteroaralkyl, to produce compounds of formula (XXII):

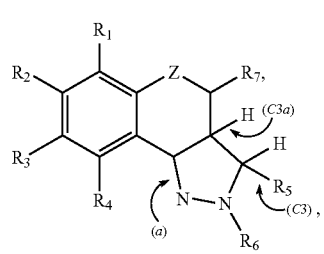

(XXII)

where Z is $CH_2$, $R_7$ is H, $R^6$ is —C(O)$R_9$, where $R_9$ is as previously defined herein, the bond indicated by (a) is a double bond, and $R_1$, $R_2$, $R_3$, $R_4$, and $R_5$ are as defined previously herein. In this reaction, a mixture of cis and trans isomers is usually formed, which can be subsequently separated by chromatographic techniques known in the art.

Alternatively, compounds of formula (XXIV) can be reacted with hydrazine alone, or with hydrazine and a sterically hindered carboxylic acid, such as, for example, trimethylacetic acid, to produce compounds of formula (XXII) where $R_6$ is H. When the reaction with hydrazine is performed in the absence of the carboxylic acid, the trans isomer is predominantly formed (i.e., the hydrogens at C3 and C3a are trans). In the presence of a carboxylic acid, a mixture of cis and trans isomers is usually formed, which can be subsequently separated by chromatographic techniques. The nitrogen atom that bears $R_6$ can then be acylated with an activated carboxylic acid or thiocarboxylic acid, such as, for example, an acyl chloride, to form compounds of formula (XXII) in which $R_6$ is —C(O)$R_9$ or —C(S)$R_9$; reacted with a chloroformate to produce compounds of formula (XXII) in which $R_6$ is —C(O)O$R_9$; reacted with phosgene or thiophosgene, followed by reaction with an amine to produce compounds of formula (XXII) in which $R_6$ is —C(O)N$R_9R_{10}$ or —C(S)N$R_9R_{10}$, respectively; or reacted with a sulfonyl chloride to produce compounds of formula (XXII) in which $R_6$ is —S($O_2$)$R_9$, where $R_9$ and $R_{10}$ are as previously defined herein.

To produce compounds of formula (XXII) in which Z is a bond, an ethylene moiety, an oxygen atom, a sulfur atom, or includes a nitrogen atom; aromatic or heteroaromatic aldehydes $R_5$—CHO can be reacted with 1-indanones of formula (XXV), 1-benzosuberones of formula (XXVI), 4-chromanones of formula (XXVII), 1-thio-4-chromanones of formula (XXVIII), or quinolinones of formula (XXIX), respectively, in an alcoholic solvent using a catalytic amount of base or acid in a manner similar to that previously described herein for the conversion of compounds of formula (XXIII) to compounds of formula (XXIV). The resulting α,β-unsubstituted ketone of formula (XXIV) can then be reacted with hydrazine, followed by reaction with reagents that form $R_6$ substituents, as previously described herein.

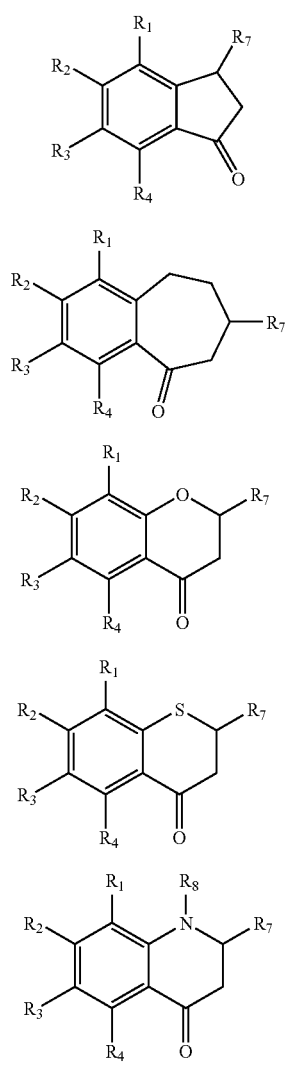

To produce compounds of formula (XXII) in which Z is S(O) or S(O$_2$), compounds of formula (XXVIII) can be treated with an oxidizing agent, such as, for example dimethyldioxirane, and the resulting sulfoxide or sulfone carried forward by treatment with $R_5$—CHO, and then hydrazine and $R_6$—CO$_2$H, as previously described.

Compounds of formula (XXII) where the bond indicated by (a) is a single bond can be obtained by reducing the corresponding compounds of formula (XXII), where the bond indicated by (a) is a double bond, in a catalytic hydrogenation procedure.

Should it be necessary in any of the synthetic steps used to produce compounds of formula (XXII) to protect a reactive functionality from unwanted reaction, any of the substituents $R_1$, $R_2$, $R_3$, $R_4$, $R_5$, or $R_6$ can be protected as described in Greene, "Protective Groups In Organic Synthesis, 3$^{rd}$ Edition" (John Wiley & Sons, New York, 1999), which is incorporated herein by reference.

Examples of compounds of formula (XXII) are presented in Table 6,

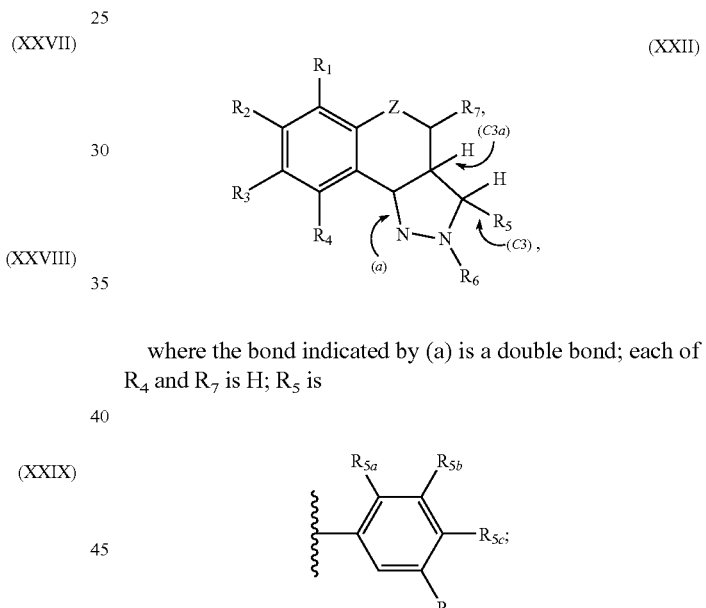

where the bond indicated by (a) is a double bond; each of $R_4$ and $R_7$ is H; $R_5$ is

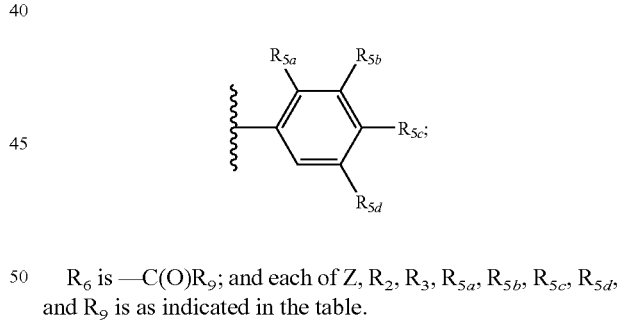

$R_6$ is —C(O)$R_9$; and each of Z, $R_2$, $R_3$, $R_{5a}$, $R_{5b}$, $R_{5c}$, $R_{5d}$, and $R_9$ is as indicated in the table.

TABLE 6

| Cmpd No. | Z | $R_1$ | $R_2$ | $R_3$ | $R_{5a}$ | $R_{5b}$ | $R_{5c}$ | $R_{5d}$ | $R_9$ | C3/C3a* |
|---|---|---|---|---|---|---|---|---|---|---|
| 1 | CH$_2$ | H | H | H | H | H | F | H | CH$_3$ | trans |
| 2 | CH$_2$ | H | H | H | H | H | F | H | CH$_3$ | cis |
| 3 | CH$_2$ | H | H | H | H | F | H | H | CH$_3$ | cis |
| 4 | CH$_2$ | H | H | OCH$_3$ | H | H | F | H | CH$_3$ | cis |
| 5 | CH$_2$ | H | H | OCH$_3$ | H | H | F | H | CH$_3$ | trans |
| 6 | CH$_2$ | H | H | OCH$_3$ | H | H | F | H | H | cis |
| 7 | CH$_2$ | H | H | OCH$_3$ | H | H | F | H | H | trans |
| 8 | CH$_2$ | H | H | OCH$_3$ | H | F | H | F | CH$_3$ | cis |
| 9 | CH$_2$ | H | H | OCH$_3$ | H | F | H | F | CH$_3$ | trans |
| 10 | CH$_2$ | H | H | OCH$_3$ | H | H | OH | H | CH$_3$ | cis |
| 11 | CH$_2$ | H | H | OCH$_3$ | H | H | NH$_2$ | H | CH$_3$ | cis |
| 12 | CH$_2$ | H | H | OH | H | H | OH | H | CH$_3$ | cis |

TABLE 6-continued

| Cmpd No. | Z | $R_1$ | $R_2$ | $R_3$ | $R_{5a}$ | $R_{5b}$ | $R_{5c}$ | $R_{5d}$ | $R_9$ | C3/C3a* |
|---|---|---|---|---|---|---|---|---|---|---|
| 13 | $CH_2$ | H | $OCH_3$ | H | H | H | F | H | $CH_3$ | cis |
| 14 | $CH_2$ | H | $OCH_3$ | H | H | H | F | H | $CH_3$ | trans |
| 15 | $CH_2$ | H | $OCH_3$ | $OCH_3$ | H | H | F | H | $CH_3$ | cis |
| 16 | $CH_2$ | H | $OCH_3$ | $OCH_3$ | H | H | F | H | $CH_3$ | trans |
| 17 | $CH_2$ | H | H | $OCH_3$ | H | $NO_2$ | H | H | $CH_3$ | cis |
| 18 | $CH_2$ | H | H | $OCH_3$ | H | $NO_2$ | H | H | $CH_3$ | trans |
| 19 | $CH_2$ | H | H | $OCH_3$ | H | H | $OCH_3$ | H | $CH_3$ | cis |
| 20 | $CH_2$ | H | H | $OCH_3$ | H | H | $OCH_3$ | H | $CH_3$ | trans |
| 21 | $CH_2$ | H | H | $OCH_3$ | H | H | $CF_3$ | H | $CH_3$ | cis |
| 22 | $CH_2$ | H | H | $OCH_3$ | H | $OCH_3$ | H | H | $CH_3$ | cis |
| 23 | $CH_2$ | H | H | $OCH_3$ | H | H | $NO_2$ | H | $CH_3$ | cis |
| 24 | $CH_2$ | H | H | H | H | H | $OCH_3$ | H | $CH_3$ | cis |
| 25 | $CH_2$ | H | H | $OCH_3$ | H | H | $OCH_3$ | H | H | cis |
| 26 | $CH_2$ | H | H | $OCH_3$ | H | H | $OCH_3$ | H | H | trans |
| 27 | $CH_2$ | H | H | $OCH_3$ | H | H | $OCH_2CH_2OH$ | H | $CH_3$ | cis |
| 28 | $CH_2$ | H | H | $OCH_3$ | H | H | $OCH_2Ph$ | H | $CH_3$ | cis |
| 29 | $CH_2$ | H | H | $OCH_3$ | H | H | $NO_2$ | H | H | cis |
| 30 | $CH_2$ | H | H | $OCH_3$ | H | H | $NO_2$ | H | H | trans |
| 31 | $CH_2$ | $OCH_3$ | H | H | H | H | $OCH_3$ | H | $CH_3$ | cis |
| 32 | $CH_2$ | H | H | $OCH_3$ | $OCH_3$ | H | $OCH_3$ | H | $CH_3$ | cis |
| 33 | $CH_2$ | H | H | $OCH_3$ | H | $OCH_3$ | $OCH_3$ | H | $CH_3$ | cis |
| 34 | $CH_2$ | H | H | $OCH_3$ | H | $OCH_2O$ | H | H | $CH_3$ | cis |
| 35 | $CH_2$ | H | H | $OCH_3$ | $OCH_2O$ | | H | H | $CH_3$ | cis |
| 36 | $CH_2$ | H | H | $OCH_3$ | H | $OCH_2CH_2O$ | | H | $CH_3$ | cis |
| 37 | $CH_2$ | H | H | $OCH_3$ | $OCH_3$ | H | H | H | $CH_3$ | cis |
| 38 | $CH_2$ | H | H | $OCH_3$ | H | H | $OCH(CH_3)_2$ | H | $CH_3$ | cis |
| 39 | $CH_2$ | H | H | $OCH_3$ | H | H | $OCH_3$ | H | $CH_2CH_3$ | cis |
| 40 | $CH_2$ | H | H | $OCH_3$ | H | $OCH_3$ | H | $OCH_3$ | $CH_3$ | cis |
| 41 | $CH_2$ | H | H | $OCH_3$ | H | $OCH_3$ | H | $OCH_3$ | $CH_3$ | trans |
| 42 | $CH_2$ | H | H | $OCH_3$ | H | H | $OCH_3$ | H | $CH_2Cl$ | cis |
| 43 | $CH_2$ | H | H | $OCH_3$ | H | H | F | H | $CH_2N(CH_3)_2$ | trans |
| 44 | $CH_2$ | H | H | $OCH_3$ | H | H | F | H | $CH_2OAc$ | trans |
| 45 | $CH_2$ | H | H | $OCH_3$ | H | H | F | H | $CH_2OH$ | trans |
| 46 | $CH_2$ | H | H | $OCH_3$ | H | H | $OCH_3$ | H | $CH_2N(CH_3)_2$ | cis |
| 47 | $CH_2$ | H | H | $OCH_3$ | H | H | $OCH_3$ | H | $CH_2OAc$ | cis |
| 48 | $CH_2$ | H | H | $OCH_3$ | H | H | $OCH_3$ | H | $CH_2OH$ | cis |
| 49 | $CH_2$ | H | H | $OCH_3$ | H | H | $NHC(O)CH_2$—OAc | H | $CH_3$ | cis |
| 50 | $CH_2$ | H | H | $OCH_3$ | H | H | OAc | H | $CH_3$ | cis |
| 51 | $CH_2$ | H | H | OAc | H | H | OAc | H | $CH_3$ | cis |
| 52 | a bond | H | H | $OCH_3$ | H | H | F | H | $CH_3$ | |
| 53 | $CH_2CH_2$ | H | H | $OCH_3$ | H | H | F | H | $CH_3$ | |
| 54 | O | H | H | $CH_3$ | H | H | F | H | $CH_3$ | cis |
| 55 | O | H | H | $CH_3$ | H | H | F | H | $CH_3$ | trans |
| 56 | $CH_2$ | H | H | $NO_2$ | H | H | $OCH_3$ | H | $CH_3$ | trans |
| 57 | $CH_2$ | H | H | $NO_2$ | H | H | $OCH_3$ | H | $CH_3$ | cis |
| 58 | $CH_2$ | H | H | F | H | H | $OCH_3$ | H | $CH_3$ | trans |
| 59 | $CH_2$ | H | H | F | H | H | $OCH_3$ | H | $CH_3$ | cis |
| 60 | $CHN_3$ | H | H | $OCH_3$ | H | H | $OCH_3$ | H | $CH_3$ | cis |
| 61 | $CHNH_2$ | H | H | $OCH_3$ | H | H | $OCH_3$ | H | $CH_3$ | cis |
| 62 | $CHN(CH_3)_2$ | H | H | $OCH_3$ | H | H | $OCH_3$ | H | $CH_3$ | cis |
| 63 | O | H | H | $OCH_3$ | H | H | $OCH_3$ | H | $CH_3$ | trans |
| 64 | O | H | H | $OCH_3$ | H | H | $OCH_3$ | H | $CH_3$ | cis |
| 65 | O | H | H | F | H | H | $OCH_3$ | H | $CH_3$ | trans |
| 66 | O | H | H | F | H | H | $OCH_3$ | H | $CH_3$ | cis |
| 67 | S | H | H | $OCH_3$ | H | H | $OCH_3$ | H | $CH_3$ | trans |
| 68 | S | H | H | $OCH_3$ | H | H | $OCH_3$ | H | $CH_3$ | cis |
| 69 | $SO_2$ | H | H | $OCH_3$ | H | H | $OCH_3$ | H | $CH_3$ | trans |
| 70 | $SO_2$ | H | H | $OCH_3$ | H | H | $OCH_3$ | H | $CH_3$ | cis |
| 71 | $CH_2$ | H | H | $OCH_3$ | H | H | $OCH_3$ | H | $CF_3$ | cis |
| 72 | $CH_2$ | H | H | H | H | H | F | H | $CH_3$ | trans |
| 73 | $CH_2$ | H | H | $OCH_3$ | H | H | $NO_2$ | H | $CH_3$ | trans |
| 74 | $CH_2$ | H | H | H | H | H | $OCH_3$ | H | $CH_3$ | trans |
| 75 | $CH_2$ | H | H | $OCH_3$ | H | H | $OCH_2Ph$ | H | $CH_3$ | trans |
| 76 | $CH_2$ | $OCH_3$ | H | H | H | H | $OCH_3$ | H | $CH_3$ | trans |
| 77 | $CH_2$ | H | H | $OCH_3$ | H | $OCH_2O$ | | H | $CH_3$ | trans |
| 78 | $CH_2$ | H | H | $OCH_3$ | H | $OCH_2CH_2O$ | | H | $CH_3$ | trans |
| 79 | $CH_2$ | H | H | $OCH_3$ | H | H | $OCH_3$ | H | $CH_2CH_3$ | trans |
| 80 | $CH_2$ | H | H | $OCH_3$ | H | H | $OCH_3$ | H | $CH_2OAc$ | trans |
| 81 | $CH_2$ | H | H | $OCH_3$ | H | H | $OC(O)CH_3$ | H | $CH_3$ | cis |
| 82 | $CH_2$ | H | H | OCamphanyl | H | H | OCamphanyl | H | $CH_3$ | cis |
| 83 | $CH_2$ | H | H | $OC(O)CH_3$ | H | H | $OC(O)CH_3$ | H | $CH_3$ | cis |
| 84 | $CH_2$ | H | H | $OCH_3$ | H | H | OCamphanyl | H | $CH_3$ | cis |
| 85 | $CH_2$ | H | H | $OCH_3$ | H | H | $OCH_3$ | H | $(CH_2)_3CO_2CH_3$ | cis |
| 86 | $CH_2$ | H | H | $OCH_3$ | H | H | $OCH_3$ | H | $(CH_2)_3CO_2H$ | cis |
| 87 | $CH_2$ | H | H | $OCH_3$ | H | H | $OCH_3$ | H | $(CH_2)_3C(O)$-morpholine | cis |

TABLE 6-continued

| Cmpd No. | Z | $R_1$ | $R_2$ | $R_3$ | $R_{5a}$ | $R_{5b}$ | $R_{5c}$ | $R_{5d}$ | $R_9$ | C3/C3a* |
|---|---|---|---|---|---|---|---|---|---|---|
| 88 | $CH_2$ | H | H | $OCH_3$ | H | H | $OCH_3$ | H | $CH_2NHCH_3$ | cis |
| 89 | $CH_2$ | H | H | $OCH_2Ph$ | H | H | $OCH_3$ | H | $CH_3$ | cis |
| 90 | $CH_2$ | H | H | $O(CH_2)_3$—C(O)-morpholine | H | H | $OCH_3$ | H | $CH_3$ | cis |
| 91 | $CH_2$ | H | H | $O(CH_2)_2$-morpholine | H | H | $OCH_3$ | H | $CH_3$ | cis |
| 92 | $CH_2$ | H | H | $OCH_3$ | H | H | $OCH_3$ | H | $CH_2OCH_3$ | cis |
| 93 | $CH_2$ | H | H | $OCH_3$ | H | H | $OCH_3$ | H | OH | cis |
| 94 | $CH_2$ | H | H | $OCH_3$ | H | H | $OCH_3$ | H | $(CH_2)_8C(O)$-morpholine | cis |
| 95 | $CH_2$ | H | H | $OCH_3$ | H | H | $SCH_3$ | H | $CH_3$ | cis |
| 96 | $CH_2$ | H | H | $OCH_3$ | H | H | $O(CH_2)_2$-morpholine | H | $CH_3$ | cis |
| 97 | $CH_2$ | H | H | $OCH_3$ | H | H | $OCH_3$ | H | $CF_3$ | cis |
| 98 | $CH_2$ | H | H | $OCH_3$ | H | H | $OCH_3$ | H | $C(O)CH_3$ | cis |
| 99 | $CH_2$ | H | H | $OCH_3$ | H | H | $OCH_3$ | H | $(CH_2)_3C(O)$—$NH(CH_2)_3CO_2Et$ | cis |
| 138 | $CH_2$ | H | H | $OCH_3$ | H | H | $OCH_3$ | H | $(CH_2)_3CO_2CH_3$ | trans |

*the indicated relative stereochemistry relates to the hydrogens at C3 and C3a ("cis" = (3R, 3aR)-rel isomer; "trans" = (3R, 3aS)-rel isomer)

Other examples of compounds of formula (XXII) can be selected from the group of compounds consisting of:

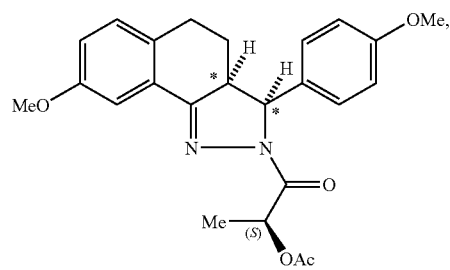

(100)

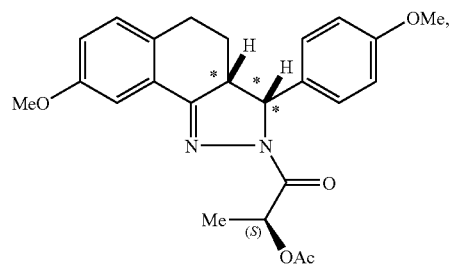

(101)

* relative stereochemistry defined; absolute stereochemistry not defined.

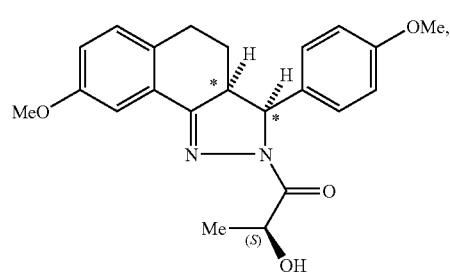

(102)

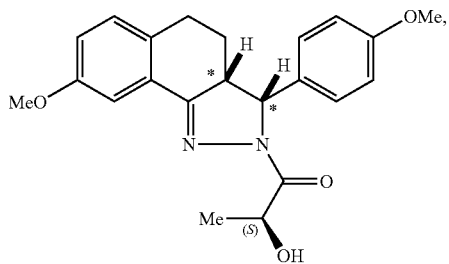

(103)

* relative stereochemistry defined; absolute stereochemistry not defined

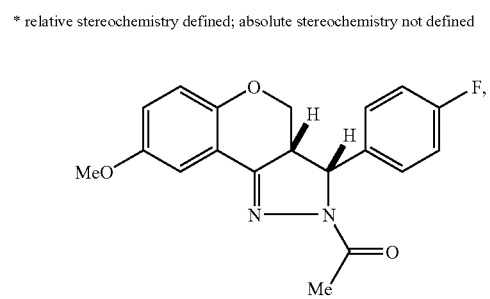

(104)

(105)

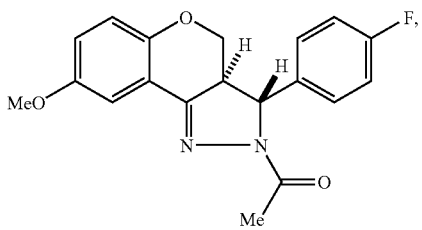

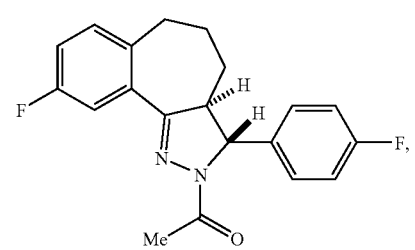

(106)

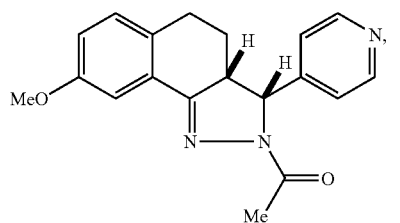
(107)
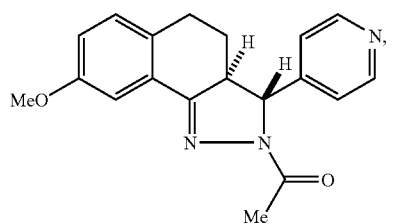
(108)
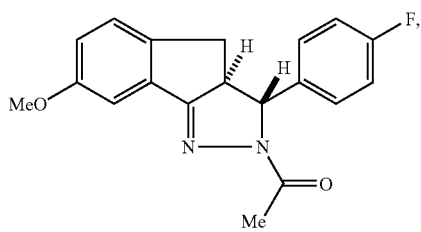
(109)
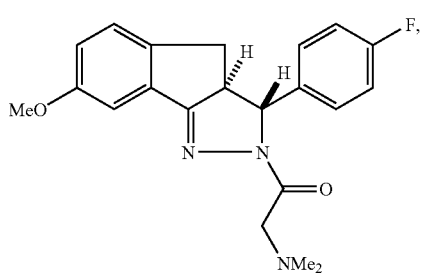
(110)
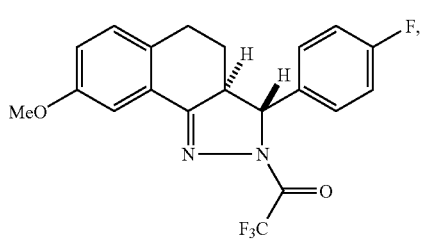
(111)
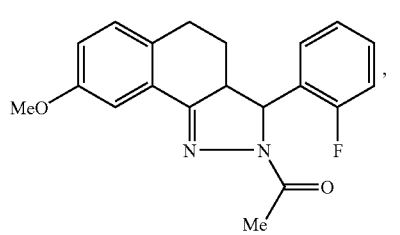
(112)
mixture of cis and trans isomers
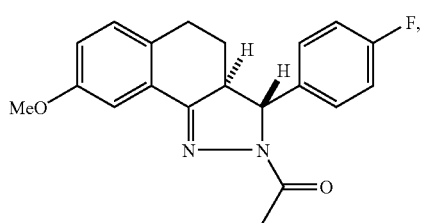
(113)
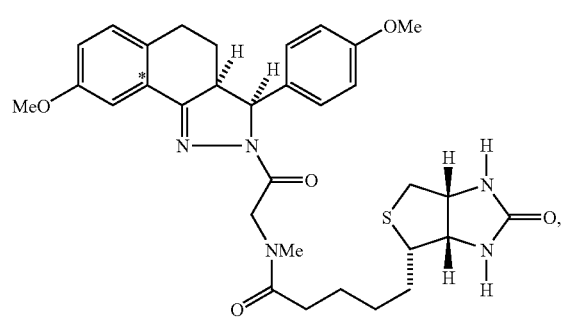
(114)
* relative stereochemistry defined; absolute stereochemistry not defined. All other stereocenters are absolute.
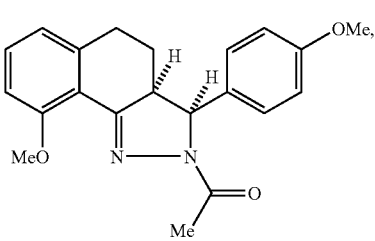
(115)
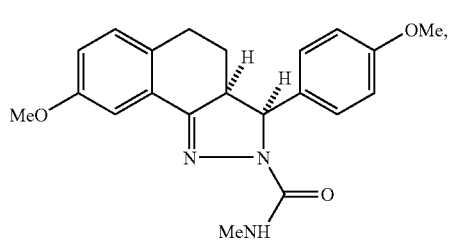
(116)
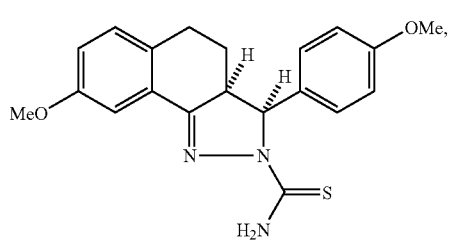
(117)

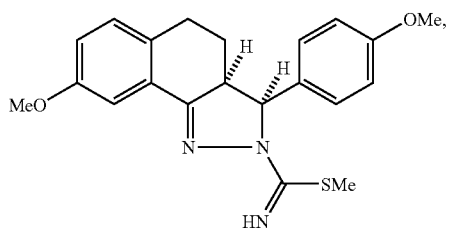
(118)
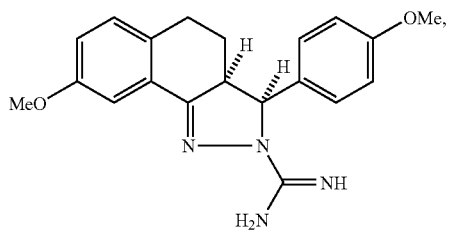
(119)
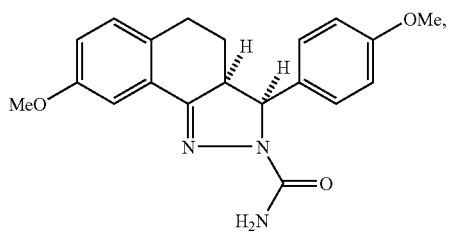
(120)
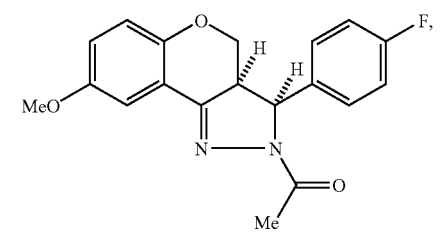
(121)
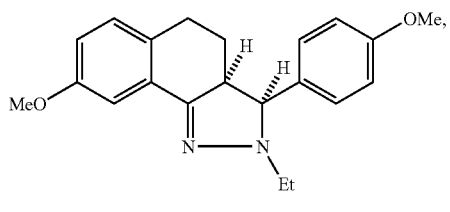
(122)
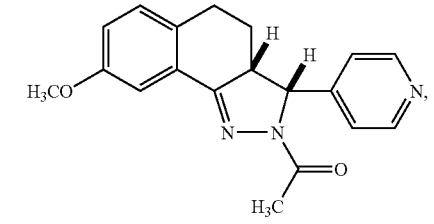
(123)
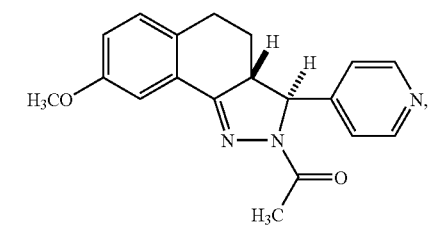
(124)
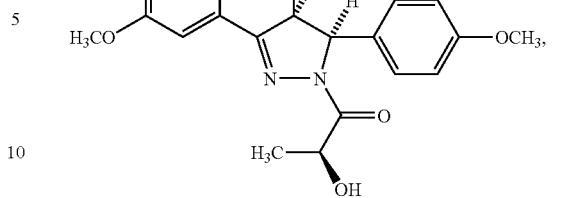
(125)
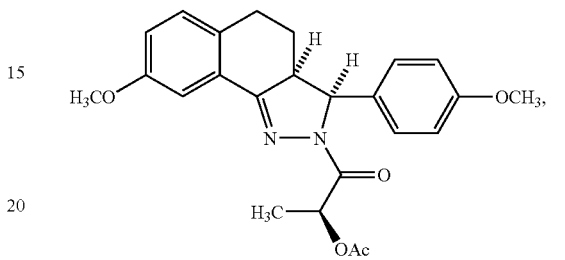
(126)
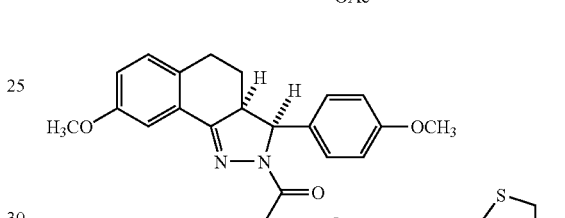
(127)
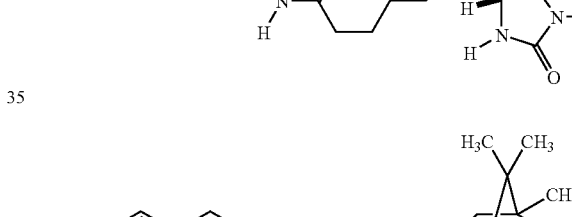
(128)
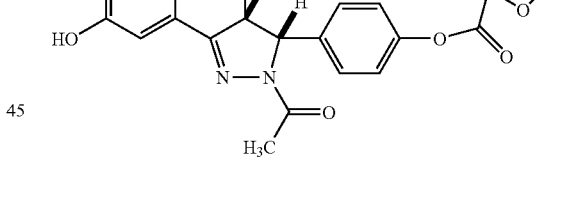
(129)
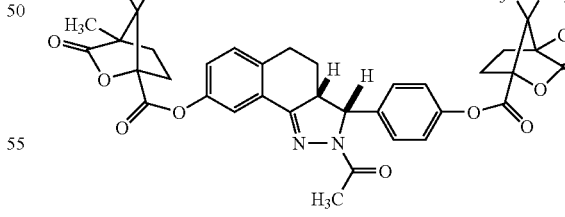
(129)
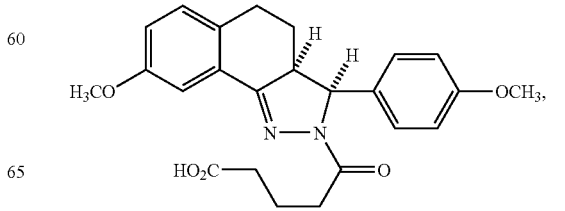
(130)

(131)

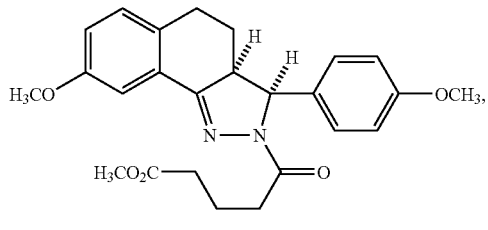

(132)

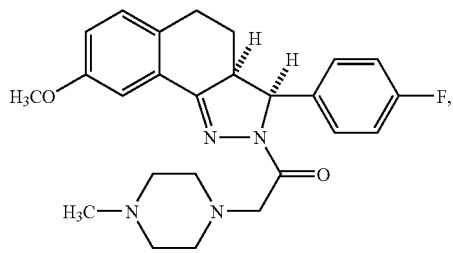

(133)

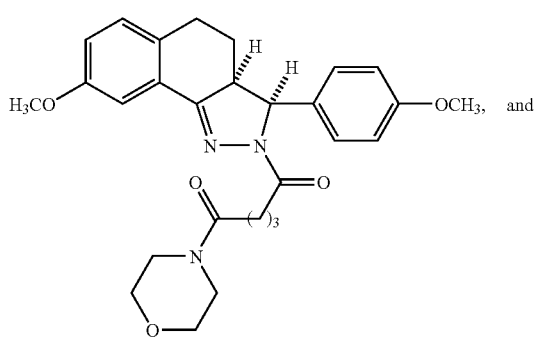

(134)

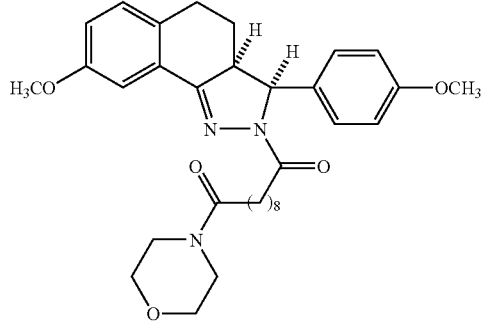

where the relative stereochemistries of the hydrogens at C3 and C3a are as shown and the absolute configuration at these chiral centers allows for both enantiomers.

Example 21

Inhibition of Necrosis by Compounds of Formula (XXII)

Compounds of formula (XXII) were assayed for anti-necrotic activity by the procedure described for the secondary screen in Example 18, with lower concentrations of the test compounds used in the assay and with human Jurkat T cells used instead of U-937 cells. Initially, compound libraries were screened for inhibition of cell death induced by TNFα in the presence of zVAD in human B cell line U-937. One compound identified as an inhibitor of necrosis was (140). The initial test sample was a mixture of diasteromers. Several derivatives of (140) have been reported in the literature (El-Rayyes, N. R.; Al-Jawhery, A. *J. Heterocyclic Chem.* 1986, 23, 135-140; Sinha, A. K.; Rastogi, S. N. *Indian J. Chem.* 1991, 30B, 684-692; Szöllösy, Á; Tóth, G.; Lóránd, T.; Kónya, T.; Aradi, F.; Lévai, A. *J. Chem. Soc. Perkin Trans.* 2 1991, 489-493). The reported biological activities, in the scientific literature, for this structure class include weak anti-amoebic activity.

(140)

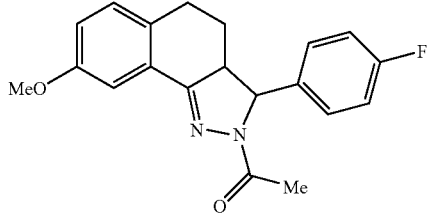

The trans isomer (5) and cis isomer (4) were prepared as outlined in Scheme 3. Initially, 6-methoxytetralone (I-8) was allowed to react with p-fluorobenzaldehyde (I-9) in the presence of base (sodium hydroxide) to give the chalcone (I-10). This material was then treated with hydrazine hydrate in the presence of excess acetic acid to produce the diasteromers (5) and (4). These compounds were readily separated. An alternative synthesis was also used as illustrated in Scheme 4. Treating tetralone (I-8) with 4-methoxybenzaldehyde (I-11) produced chalcone (I-12). Next, the chalcone was allowed to react with hydrazine hydrate in the presence of excess trimethyl acetic acid to produce the diasteromers (I-13) and (I-14), which were separated. In the absence of an organic acid, such as trimethyl acetic acid, only the trans isomer (I-13) was formed. Each diasteromer was then allowed to react with acetic anhydride and a catalytic amount of DMAP (4-dimethylaminopyridine) to yield (20) and (19), respectively.

Scheme 3

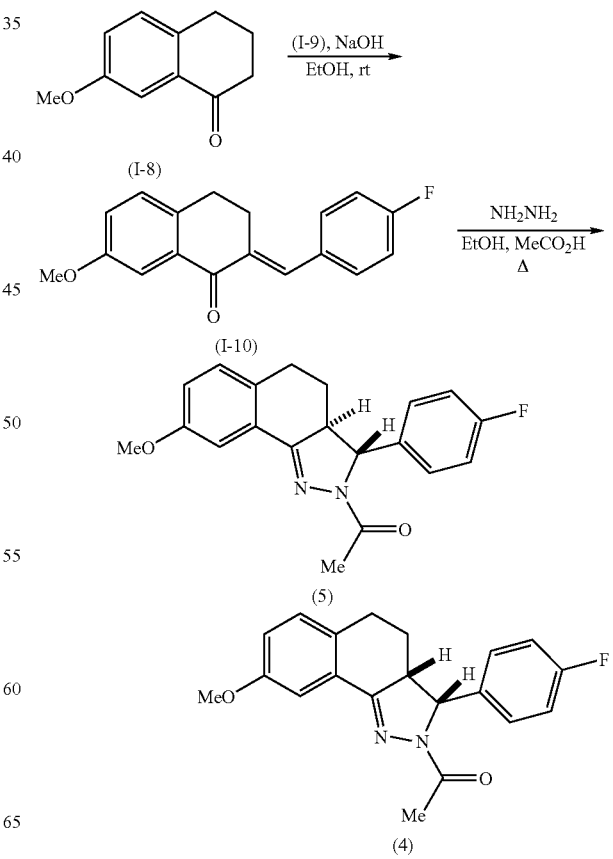

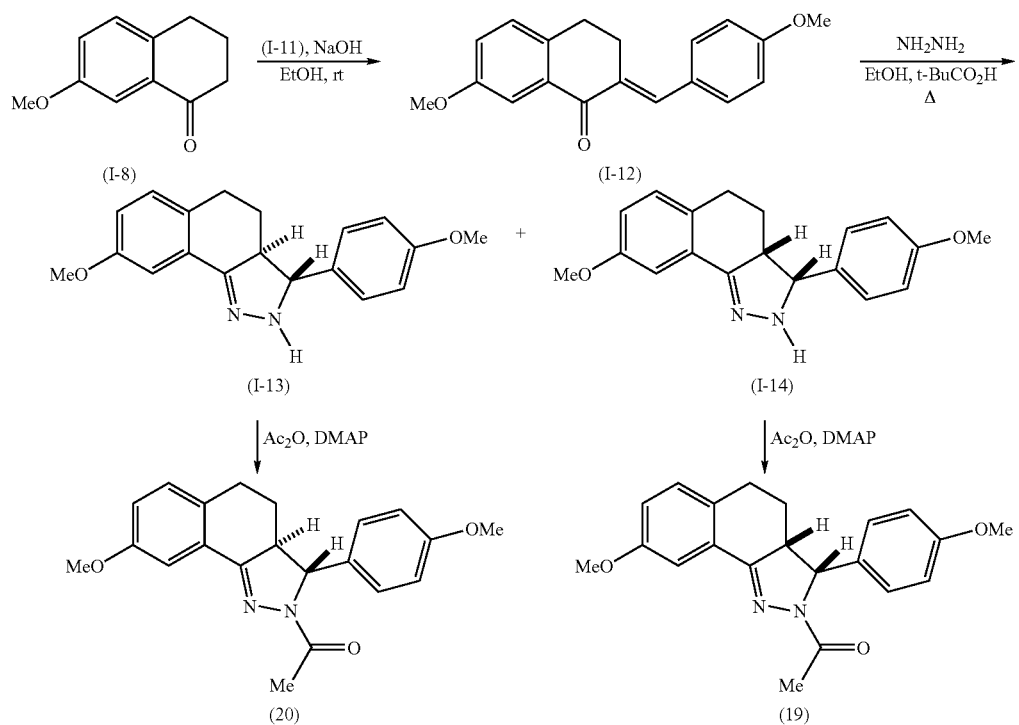

Compounds were also tested in another necrosis assay utilizing human Jurkat T cells, Fas ligand to induce cell death, and zVAD to inhibit the apoptosis pathway. After 36 hours, cell viability was measure by the commercial CellTiter ATP cell viability assay (Promega). In the case of (4)/(5) and (19)/(20), only the cis isomers (4) (FIG. 34A) and (19) (FIG. 34B) were found to efficiently inhibit necrosis and result in high cell viability.

As noted above, a structure-activity-relationship (SAR) study was conducted in order to increase anti-necrosis activity. The compounds prepared and assayed include compounds (1)-(217) (e.g., those compounds listed in Table 6 and those that follow). These compounds were prepared utilizing analogous protocols that were employed for preparing (4), (5), (19), and (20). Compounds (135), (136), and (137) were prepared as shown in Scheme 5.

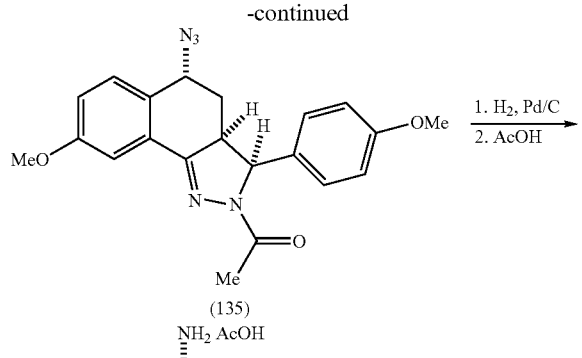

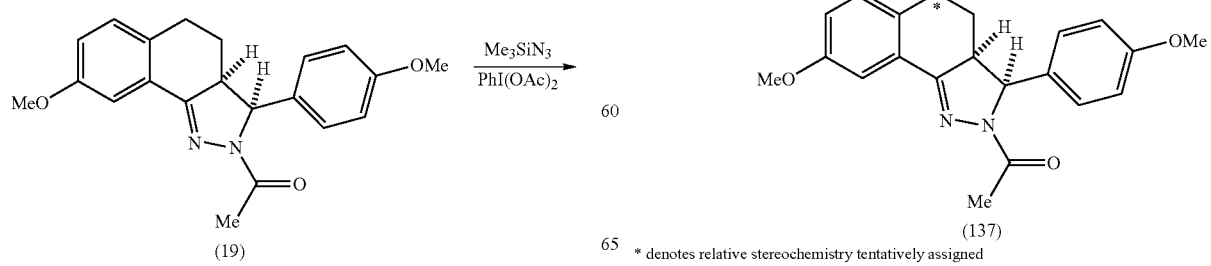

* denotes relative stereochemistry tentatively assigned

To further verify that (19) can protect neuronal cells from necrosis, it was tested using two different neurotoxins in the human neuroblastoma cell line SH-SY5Y in the presence of zVAD. Cell death was induced by β-amyloid, a cellular model of Alzheimer's disease, and methylpyridinium ion (MPP+), a cellular model of Parkinson's disease. In both cases, the compound was effective in reducing toxicity as measured by cellular ATP levels (FIGS. 35A and 35B).

The compounds described herein are inhibitors of cellular necrosis that are effective at maintaining cell viability when the cells are challenged with toxins (e.g., Fas ligand, MPP+ or β-amyloid) and the apoptosis pathway has been interrupted by the addition of zVAD. This protection was found in different cell types, such as human neuronal cells and human T-cells. Compounds described herein may be useful as therapeutic agents (alone or in combination with other compounds) for the treatment of humans afflicted with an acute or chronic neurological disease. In addition, compounds of this invention may be useful for assay development of novel molecular targets integral to induced necrotic cell death.

Preparation and Characterization of Compounds

General Procedure for the synthesis of 2-arylidene-1-tetralones and 2-(arylidene)-choman-4-ones, exemplified for 2-(4-fluorobenzylidene)-7-methoxy-1-tetralone: To a solution of 7-methoxy-1-tetralone (1.760 g, 0.01 mol) and 4-fluorobenzaldehyde (1.240 g, 0.01 mol) in ethanol (20 mL) was added slowly a solution of NaOH (0.012 mol, 8 N) at room temperature. The mixture was stirred for two hours. The solid precipitated was collected by filtration, and then washed sequentially with ethanol, water, and again with ethanol. The solid was dried in vacuo to dive 2-(4-fluorobenzylidene)-7-methoxy-1-tetralone (2.485 g, 88%): mp 129-30° C., $^1$H NMR (500 MHz, CDCl$_3$): 2.88-2.91 (m, 2H), 3.06-3.10 (m, 2H), 3.87 (s, 3H), 7.06-7.13 (m, 3H), 7.17 (d, J=8.4 Hz, 1H), 7.42 (d, J=5.2 Hz, 1H), 7.44 (d, J=5.6 Hz, 1H), 7.61 (d, J=3.2 Hz, 1H), 7.81 (s, 1H). HFABMS m/z 283.1134 (calc for C$_{18}$H$_{16}$FO$_2$, MH$^+$, 283.1134).

General procedure for the preparation of 3,3a-trans and 3,3a-cis N-acetyl-1-[3-(aryl)-3,3a,4,5-tetrahydro-benzo[g]indazoles] and N-acetyl-1-(3-aryl-3a,4-dihydro-3H-chromeno[4,3-c]pyrazoles), exemplified for (4) and (5): A solution of 2-(4-fluorobenzylidene)-7-methoxy-1-tetralone (0.300 g, 0.001 mol), hydrazine hydrate (0.3 mL) in acetic acid (3 mL) was refluxed at 120° C. for 15 h. The reaction mixture was concentrated and then dissolved in ethyl acetate. The organic layer was washed sequentially with water, saturated aqueous NaHCO$_3$, water and brine, dried on anhydrous Na$_2$SO$_4$, filtered and concentrated. The residue obtained was purified by silica gel column using ethyl acetate-hexane (3:7) to give (5) (0.051 g, 21%), and (4) (0.109 g, 45%). Yields are based on the recovery of starting material (95 mg).

(5): mp 165-67° C., $^1$H NMR (400 MHz, CDCl$_3$): 1.94-1.99 (m, 1H), 2.29-231 (m, 1H), 2.32 (s, 3H), 2.40-2.42 (m, 2H), 3.16-3.22 (m, 1H), 3.89 (s, 3H), 4.95 (d, J=9.6 Hz, 1H), 6.93-6.96 (dd, J=2.8 and 8.4 Hz, 1H), 7.04-7.08 (t, J=8.8 Hz, 2H), 7.12 (d, J=8.4 Hz, 1H), 7.28-7.32 (m, 2H), 7.46 (d, J=2.4 Hz, 1H). Anal. Calcd for C$_{20}$H$_{19}$FN$_2$O$_2$: C, 70.99; H, 5.66; N, 8.28. Found: C, 70.75; H, 5.63; N, 8.17.

(4): mp 182-85° C., $^1$H NMR (400 MHz, CDCl$_3$): 1.02-1.06 (m, 1H), 1.75-1.78 (m, 1H), 2.48 (s, 3H), 2.81-2.87 (m, 2H), 3.54-3.57 (m, 1H), 3.90 (s, 3H), 5.72 (d, J=12.0 Hz, 1H), 6.93-7.11 (m, 6H), 7.56 (d, J=4.0 Hz, 1H). $^{13}$C NMR (400 MHz, CDCl$_3$): 22.13, 24.50, 28.30, 48.77, 55.73, 62.61, 107.83, 112.70, 115.62, 118.72, 127.99, 128.21, 130.26, 132.25, 132.92, 155.79, 158.35, 161.13, 163.58, 168.72. Anal. Calcd for C$_{20}$H$_{19}$FN$_2$O$_2$: C, 70.99; H, 5.66; N, 8.28. Found: C, 70.72; H, 5.69; N, 8.15.

(14): yield 18%, mp 228-30° C., $^1$H NMR (400 MHz, CDCl$_3$): 1.89-2.00 (m, 1H), 2.24-2.30 (m, 1H), 2.38 (s, 3H), 2.88-2.94 (m, 2H), 3.12-3.19 (m, 1H), 3.83 (s, 3H), 4.89 (d, J=9.6 Hz, 1H), 6.68 (d, J=2.4 Hz, 1H), 6.83-6.85 (dd, J=2.4 and 8.4 Hz, 1H), 7.00-7.06 (m, 2H), 7.26-7.29 (m, 2H), 7.90 (d, J=8.8 Hz, 1H). Anal. Calcd for C$_{20}$H$_{19}$FN$_2$O$_2$: C, 70.99; H, 5.66; N, 8.28. Found: C, 70.76; H, 5.66; N, 8.24.

(13): yield 20%, $^1$H NMR (400 MHz, CDCl$_3$): 1.00-1.07 (m, 1H), 1.74-1.76 (m, 1H), 2.42 (s, 3H), 2.76-2.89 (m, 2H), 3.49-3.56 (m, 1H), 3.81 (s, 3H), 5.67 (d, J=10.8 Hz, 1H), 6.65 (s, 1H), 6.83-6.85 (dd, J=6.0 and 2.4 Hz, 1H), 6.94-7.06 (m, 4H), 7.99 (d, J=9.2 Hz, 1H). Anal. Calcd for C$_{20}$H$_{19}$FN$_2$O$_2$: C, 70.99; H, 5.66; N, 8.28. Found: C, 70.92; H, 5.66; N, 8.28.

(16): yield 28%, mp 231-33° C., $^1$H NMR (400 MHz, CDCl$_3$): 1.92-1.97 (m, 1H), 2.24-2.27 (m, 1H), 2.40 (s, 3H), 2.86-2.90 (m, 2H), 3.11-3.18 (m, 1H), 3.89 (s, 3H), 3.96 (s, 3H), 4.89 (d, J=9.6 Hz, 1H), 6.63 (s, 1H), 7.01-7.06 (dd, J=2.4 and 8.8 Hz, 2H), 7.26-7.29 (m, 2H), 7.38 (s, 1H). HFABMS m/z 369.5 (talc for C$_{21}$H$_{22}$FN$_2$O$_3$, MH$^+$, 369.4095).

(15): yield 33%, mp 189-93° C., $^1$H NMR (400 MHz, CDCl$_3$): 1.01-1.08 (m, 1H), 1.72-1.77 (m, 1H), 1.44 (s, 3H), 2.72-2.93 (m, 2H), 3.48-3.55 (m, 1H), 3.88 (s, 3H), 3.95 (s, 3H), 5.67 (d, J=10.8 Hz, 1H), 6.60 (s, 1H), 6.94-6.99 (dd, J=9.2 and 8.8 Hz, 2H), 7.04-7.07 (m, 2H), 7.47 (s, 1H). Anal. Calcd for C$_{21}$H$_{21}$FN$_2$O$_3$: C, 68.46; H, 5.75; N, 7.60. Found: C, 68.54; H, 5.61; N, 7.74.

(1): yield 15%, mp 168-71° C., $^1$H NMR (400 MHz, CDCl$_3$): 2.00-2.04 (m, 1H), 2.31-2.35 (m, 1H), 2.42 (s, 3H), 2.96-2.99 (m, 2H), 3.19-3.25 (m, 1H), 4.97 (d, J=12.0 Hz, 1H), 7.07 (t, J=8.0 Hz, 2H), 7.22 (d, J=8.0 Hz, 1H), 7.28-7.35 (m, 4H), 7.99 (d, J=8.0 Hz, 1H). Anal. Calcd for C$_{19}$H$_{17}$FN$_2$O: C, 74.01; H, 5.56; N, 9.08. Found: C, 73.88; H, 5.48; N, 9.12.

(2): yield 23%, mp 166-68° C., $^1$H NMR (400 MHz, CDCl$_3$): 1.06-1.11 (m, 1H), 1.77-1.81 (m, 1H), 2.47 (s, 3H), 2.87-2.95 (m, 2H), 3.56-3.63 (m, 1H), 5.72 (d, J=12.0 Hz, 1H), 7.00 (t, J=8.0 Hz, 2H), 7.06-7.10 (m, 2H), 7.19 (d, J=8.0 Hz, 1H), 7.28-7.36 (m, 2H), 8.09 (d, J=8.0 Hz, 1H). Anal. Calcd for C$_{19}$H$_{17}$FN$_2$O: C, 74.01; H, 5.56; N, 9.08. Found: C, 73.79; H, 5.52; N, 9.11.

(3): yield 30%, mp 196-99° C., $^1$H NMR (400 MHz, CDCl$_3$): 1.92-1.99 (m, 1H), 2.27-2.32 (m, 1H), 2.42 (s, 3H), 2.86-2.89 (m, 2H), 3.14-3.20 (m, 1H), 3.87 (s, 3H), 4.93 (d, J=7.2 Hz, 1H), 6.91-7.01 (m, 3H), 7.08-7.10 (m, 2H), 7.29-7.34 (m, 1H), 7.43 (d, J=2.0 Hz, 1H). HFABMS m/z 339.1419 (calc for C$_{20}$H$_{19}$FN$_2$O$_2$, MH$^+$, 339.1509).

(72): yield 39%, mp 176-77° C., $^1$H NMR (400 MHz, CDCl$_3$): 1.00-1.08 (m, 1H), 1.75-1.80 (m, 1H), 2.46 (s, 3H), 2.75-2.83 (m, 2H), 3.52-3.60 (m, 1H), 3.87 (s, 3H), 5.69 (d, J=11.2 Hz, 1H), 7.76-6.79 (dd, J=2.4 and 9.6 Hz, 1H), 6.86-6.95 (m, 3H), 7.06 (d, J=8.8 Hz, 1H), 7.23-7.28 (m, 1H), 7.53 (d, J=3.2 Hz, 1H). $^{13}$C NMR (400 MHz, CDCl$_3$): 22.18, 24.54, 28.97, 46.79, 55.75, 62.97, 107.18, 113.16, 114.65, 118.71, 121.92, 128.05, 130.27, 132.13, 139.57, 155.62, 156.22, 161.60, 164.24, 168.50. Anal. Calcd for C$_{20}$H$_{19}$FN$_2$O$_2$: C, 70.99; H, 5.66; N, 8.28. Found: C, 71.03; H, 5.29; N, 8.31.

(20): yield 25%, mp 146-48° C., $^1$H NMR (400 MHz, CDCl$_3$): 1.89-1.95 (m, 1H), 2.25-2.29 (m, 1H), 2.39 (s, 3H), 2.85-2.87 (m, 2H), 3.16-3.23 (m, 1H), 3.79 (s, 3H), 3.86 (s, 3H), 4.91 (d, J=9.2 Hz, 1H), 6.87-6.93 (m, 3H), 7.09 (d, J=8.4 Hz, 1H), 7.22-7.25 (m, 2H), 7.44 (d, J=2.4 Hz, 1H). Anal. Calcd for C$_{21}$H$_{22}$N$_2$O$_3$: C, 71.98; H, 6.33; N, 7.99. Found: C, 71.68; H, 6.20; N, 7.92.

(19): yield 30%, mp 151-53° C., $^1$H NMR (400 MHz, CDCl$_3$): 1.03-1.11 (m, 1H), 1.72-1.76 (m, 1H), 2.44 (s, 3H), 2.77-2.91 (m, 2H), 3.47-3.55 (m, 1H), 3.75 (s, 3H), 3.87 (s, 3H), 5.66 (d, J=11.2 Hz, 1H), 6.80 (d, J=8.8 Hz, 2H), 6.89-6.92 (dd, J=3.2 and 8.8 Hz, 1H), 6.99 (d, J=8.4 Hz, 2H), 7.06 (d, J=8.4 Hz, 1H), 7.54 (d, J=2.8 Hz, 1H). $^{13}$C NMR (400 MHz, CDCl$_3$): 22.15, 24.42, 28.93, 48.84, 55.42, 55.70, 63.03, 107.76, 112.66, 114.15, 118.56, 127.44, 127.88, 128.39, 129.26, 130.24, 132.32, 155.60, 158.28, 159.14, 168.56. Anal. Calcd for C$_{21}$H$_{22}$N$_2$O$_3$: C, 71.98; H, 6.33; N, 7.99. Found: C, 72.14; H, 6.42; N, 7.78.

(76): yield 27%, mp 175-78° C., $^1$H NMR (500 MHz, CDCl$_3$): 1.85-1.89 (m, 1H), 2.32-2.35 (m, 1H), 2.38 (s, 3H), 2.53-2.60 (m, 1H), 3.09-3.18 (m, 2H), 3.79 (s, 3H), 3.84 (s, 3H), 4.91 (d, J=9.5 Hz, 1H), 6.86-6.89 (m, 3H), 7.23-7.27 (m, 3H), 7.57 (d, J=7.5 Hz, 1H). Anal. Calcd for C$_{21}$H$_{22}$N$_2$O$_3$: C, 71.98; H, 6.33; N, 7.99. Found: C, 71.72; H, 6.35; N, 8.02.

(31): yield 43%, mp 203-207° C., $^1$H NMR (500 MHz, CDCl$_3$): 0.98-1.07 (m, 1H), 1.74-1.79 (m, 1H), 2.43 (s, 3H), 2.45-2.52 (m, 1H), 3.04-3.09 (m, 1H), 3.48-3.54 (m, 1H), 3.76 (s, 3H), 3.82 (s, 3H), 5.68 (d, J=11.0 Hz, 1H), 6.80 (d, J=8.5 Hz, 2H), 6.86 (d, J=8.0 Hz, 1H), 7.00 (d, J=8.5 Hz, 2H), 7.24 (t, J=8.0 Hz, 1H), 7.68 (d, J=8.0 Hz, 1H). Anal. Calcd for C$_{21}$H$_{22}$N$_2$O$_3$: C, 71.98; H, 6.33; N, 7.99. Found: C, 71.98; H, 6.05; N, 8.06.

(115): yield 27%, mp 157-60° C., $^1$H NMR (500 MHz, CDCl$_3$): 1.09-1.18 (m, 1H), 1.67-1.72 (m, 1H), 2.49 (s, 3H), 2.83-2.95 (m, 2H), 3.53-3.59 (m, 1H), 3.78 (s, 3H), 3.98 (s, 3H), 5.57 (d, J=11.0 Hz, 1H), 6.77 (d, J=7.0 Hz, 1H), 6.80 (d, J=9.0 Hz, 2H), 6.84 (d, J=9.0 Hz, 1H), 7.04 (d, J=9.0 Hz, 2H), 7.25 (t, J=9.0 Hz, 1H). Anal. Calcd for C$_{21}$H$_{22}$N$_2$O$_3$: C, 71.98; H, 6.33; N, 7.99. Found: C, 71.25; H, 6.44; N, 7.94.

(74): yield 20%, mp 260-62° C., $^1$H NMR (500 MHz, CDCl$_3$): 1.91-2.00 (m, 1H), 2.27-2.32 (m, 1H), 2.38 (s, 3H), 2.99-2.95 (m, 2H), 3.20-3.25 (m, 1H), 3.78 (s, 3H), 4.91 (d, J=9.5 Hz, 1H), 6.88 (d, J=9.0 Hz, 2H), 7.17 (d, J=2.5 Hz, 1H), 7.23-7.34 (m, 4H), 7.86 (d, J=7.0 Hz, 1H). Anal. Calcd for C$_{20}$H$_{20}$N$_2$O$_2$: C, 74.98; H, 6.29; N, 8.74. Found: C, 74.15; H, 6.18; N, 8.58.

(24): yield 30%, mp 257-60° C., $^1$H NMR (400 MHz, CDCl$_3$): 1.01-1.11 (m, 1H), 1.70-1.75 (m, 1H), 2.40 (s, 3H), 2.76-2.89 (m, 2H), 3.47-3.54 (m, 1H), 3.71 (s, 3H), 5.63 (d, J=11.2 Hz, 1H), 6.76 (d, J=8.4 Hz, 2H), 6.96 (d, J=8.8 Hz, 2H), 7.11 (d, J=6.8 Hz, 1H), 7.23-7.29 (m, 2H), 8.02-8.04 (dd, J=1.6 and 7.6 Hz, 1H). Anal. Calcd for C$_{20}$H$_{20}$N$_2$O$_2$: C, 74.98; H, 6.29; N, 8.74. Found: C, 74.73; H, 6.32; N, 8.75.

(73): yield 20%, mp 170-75° C., $^1$H NMR (400 MHz, CDCl$_3$): 1.90-2.01 (m, 1H), 2.23-2.28 (m, 1H), 2.38 (s, 3H), 2.83-2.87 (m, 2H), 3.10-3.17 (m, 1H), 3.83 (s, 3H), 4.98 (d, J=9.2 Hz, 1H), 6.89-6.91 (dd, J=2.4 and 7.6 Hz, 1H), 7.07 (d, J=8.4 Hz, 1H), 7.40 (d, J=2.4 Hz, 1H), 7.43 (d, J=8.4 Hz, 2H), 8.19 (d, J=8.4 Hz, 2H). HFABMS m/z 366.1462 (calc for C$_{20}$H$_{19}$N$_3$O$_4$, MH$^+$, 366.1454).

(23): yield 29%, mp 219-21° C., $^1$H NMR (400 MHz, CDCl$_3$): 0.91-1.01 (m, 1H), 1.71-1.75 (m, 1H), 2.43 (s, 3H), 2.75-2.82 (m, 2H), 3.57-3.64 (m, 1H), 3.84 (s, 3H), 5.74 (d, J=11.6 Hz, 1H), 6.88-6.91 (dd, J=3.2 and 8.4 Hz, 1H), 7.22 (d, J=9.6 Hz, 2H), 7.48 (d, J=3.2 Hz, 1H), 8.13 (d, J=9.6 Hz, 2H). Anal. Calcd for C$_{20}$H$_{19}$N$_3$O$_4$: C, 65.74; H, 5.24; N, 11.50. Found: C, 65.48; H, 5.09; N, 11.38.

(75): yield 11%, mp 149-51° C., $^1$H NMR (500 MHz, CDCl$_3$): 1.88-1.97 (m, 1H), 2.25-2.29 (m, 1H), 2.39 (s, 3H), 2.86-2.88 (m, 2H), 3.17-3.22 (m, 1H), 3.87 (s, 3H), 4.95 (d, J=9.2 Hz, 1H), 5.07 (s, 2H), 6.90-6.92 (dd, J=3.0 and 9.0 Hz, 1H), 6.96 (d, J=9.0 Hz, 2H), 7.09 (d, J=8.5 Hz, 2H), 7.23 (d, J=8.5 Hz, 2H), 7.25 (s, 1H), 7.30-7.43 (m, 4H). Anal. Calcd for C$_{27}$H$_{26}$N$_2$O$_3$: C, 76.03; H, 6.14; N, 6.57. Found: C, 76.07; H, 5.95; N, 6.60.

(28): yield 41%, mp 156-61° C., $^1$H NMR (400 MHz, CDCl$_3$): 1.01-1.14 (m, 1H), 1.72-1.79 (m, 1H), 2.45 (s, 3H), 2.75-2.83 (m, 2H), 3.87 (s, 3H), 4.99 (s, 2H), 5.67 (d, J=10.8 Hz, 1H), 6.87-6.92 (m, 2H), 6.99 (d, J=8.4 Hz, 2H), 7.06 (d, J=8.8 Hz, 2H), 7.30-7.40 (m, 7H), 7.54 (d, J=3.2 Hz, 1H). Anal. Calcd for C$_{27}$H$_{26}$N$_2$O$_3$: C, 76.03; H, 6.14; N, 6.57. Found: C, 76.01; H, 5.87; N, 6.60.

(77): yield 21%, mp 165-69° C., $^1$H NMR (500 MHz, CDCl$_3$): 1.87-1.94 (m, 1H), 2.25-2.29 (m, 1H), 2.41 (s, 3H), 2.86-2.88 (m, 2H), 3.14-3.19 (m, 1H), 3.84 (s, 3H), 4.87 (d, J=9.4 Hz, 1H), 5.94 (s, 2H), 6.76-6.78 (m, 3H), 6.90-6.93 (dd, J=3.0 and 8.5 Hz, 1H), 7.09 (d, J=9.0 Hz, 1H), 7.42 (d, J=2.5 Hz, 1H). Anal. Calcd for C$_{21}$H$_{20}$N$_2$O$_4$: C, 69.22; H, 5.53; N, 7.69. Found: C, 68.94; H, 5.65; N, 7.60.

(34): yield 41%, mp 206-209° C., $^1$H NMR (500 MHz, CDCl$_3$): 1.08-1.17 (m, 1H), 1.75-1.80 (m, 1H), 2.42 (s, 3H), 2.76-2.84 (m, 2H), 3.47-3.53 (m, 1H), 3.87 (s, 3H), 5.62 (d, J=11.4 Hz, 1H), 5.90 (s, 2H), 6.52 (d, J=1.5 Hz, 1H), 6.57-6.59 (dd, J=1.5 and 8.0 Hz, 1H), 6.72 (d, J=7.5 Hz, 1H), 6.90-6.92 (dd, J=3.0 and 8.5 Hz, 1H), 7.07 (d, J=8.2 Hz, 1H), 7.52 (d, J=2.5 Hz, 1H). Anal. Calcd for C$_{21}$H$_{20}$N$_2$O$_4$: C, 69.22; H, 5.53; N, 7.69. Found: C, 69.00; H, 5.23; N, 7.55.

(78): yield 28%, mp 194-97° C., $^1$H NMR (500 MHz, CDCl$_3$): 1.82-1.94 (m, 1H), 2.25-2.30 (m, 1H), 2.40 (s, 3H), 2.82-2.84 (m, 2H), 3.16-3.20 (M, 1H), 3.86 (s, 3H), 4.27 (s, 4H), 4.82 (d, J=9.0 Hz, 1H), 6.77-6.81 (m, 2H), 6.84 (d, J=8.0 Hz, 1H), 6.90-6.92 (dd, J=3.0 and 9.0 Hz, 1H), 7.08 (d, J=8.5 Hz, 1H), 7.42 (d, J=2.5 Hz, 1H). Anal. Calcd for C$_{22}$H$_{22}$N$_2$O$_4$: C, 69.83; H, 5.86; N, 7.40. Found: C, 68.58; H, 5.75; N, 7.25.

(36): yield 17%, mp 189-93° C., $^1$H NMR (500 MHz, CDCl$_3$): 1.06-1.15 (m, 1H), 1.78-1.80 (m, 1H), 2.41 (s, 3H), 2.75-2.86 (m, 2H), 3.46-3.52 (m, 1H), 3.87 (s, 3H), 4.22 (s, 4H), 5.60 (d, J=11.5 Hz, 1H), 6.55-6.58 (m, 2H), 6.76 (d, J=8.5 Hz, 1H), 6.89-6.91 (dd, J=3.0 and 9.0 Hz, 1H), 7.06 (d, J=8.0 Hz, 1H), 7.52 (d, J=3.0 Hz, 1H). Anal. Calcd for C$_{22}$H$_{22}$N$_2$O$_4$: C, 69.83; H, 5.86; N, 7.40. Found: C, 69.53; H, 5.70; N, 7.27.

(89): yield 36%, mp 155-57° C., $^1$H NMR (500 MHz, CDCl$_3$): 1.03-1.12 (m, 1H), 1.72-1.77 (m, 1H), 2.44 (s, 3H), 2.74-2.86 (m, 2H), 3.48-3.54 (m, 1H), 3.75 (s, 3H), 5.12 (s, 2H), 5.66 (d, J=10.5 Hz, 1H), 6.80 (d, J=8.5 Hz, 2H), 6.96 (d, J=3.0 Hz, 1H), 6.99 (d, J=8.5 Hz, 2H), 7.07 (d, J=8.0 Hz, 2H), 7.33-7.47 (m, 4H), 7.64 (d, J=3.0 Hz, 1H). Anal. Calcd for C$_{27}$H$_{26}$N$_2$O$_3$: C, 76.03; H, 6.14; N, 6.57. Found: C, 76.01; H, 5.87; N, 6.60.

(95): yield 22%, mp 144-47° C., $^1$H NMR (500 MHz, CDCl$_3$): 1.02-1.09 (m, 1H), 1.73-1.76 (m, 1H), 2.43 (s, 3H), 2.45 (s, 3H), 2.74-2.86 (m, 2H), 3.50-3.56 (m, 1H), 3.87 (s, 3H), 5.66 (d, J=10.5 Hz, 1H), 6.90-6.92 (dd, J=3.0 and 8.5 Hz, 1H), 6.99 (d, J=8.5 Hz, 2H), 7.06 (d, J=8.5 Hz, 1H), 7.16 (d, J=8.5 Hz, 2H), 7.53 (d, J=3.0 Hz, 1H). Anal. Calcd for C$_{21}$H$_{22}$N$_2$O$_2$S: C, 68.82; H, 6.05; N, 7.64. Found: C, 68.76; H, 6.00; N, 7.66.

(105): yield 15%, mp 218-20° C., $^1$H NMR (400 MHz, CDCl$_3$): 2.36 (s, 3H), 2.42 (s, 3H), 3.53-3.57 (m, 1H), 4.13-4.19 (m, 1H), 4.60-4.64 (m, 1H), 4.99 (d, J=8 Hz, 1H), 6.85 (d, J=8 Hz, 1H), 7.05-7.09 (m, 2H), 7.16-7.31 (m, 3H), 7.63 (s, 1H). HFABMS m/z 325.1354 (calc for C$_{19}$H$_{17}$FN$_2$O$_2$, MH$^+$, 325.1352).

(104): yield 42%, mp 243-46° C., $^1$H NMR (400 MHz, CDCl$_3$): 2.36 (s, 3H), 2.48 (s, 3H), 3.29 (t, J=12 Hz, 1H), 3.72-3.83 (m, 1H), 4.14-4.18 (m, 1H), 5.77 (d, J=12 Hz, 1H), 6.82 (d, J=8 Hz, 1H), 7.0-7.15 (m, 5H), 7.78 (s, 1H). HFABMS m/z 325.1359 (calc for C$_{19}$H$_{17}$FN$_2$O$_2$, MH$^+$, 325.1352).

(121): yield 32%, mp 245° C. $^1$H NMR (500 MHz, CDCl$_3$): 2.45 (s, 3H), 3.21-3.27 (m, 1H), 3.84 (s, 3H), 3.82-3.87 (m, 1H), 4.10-4.14 (dd, J=10.5 and 12.5 Hz, 1H), 4.55-4.59 (dd, J=6.0 and 10.5 Hz, 1H), 5.75 (d, J=10.5 Hz, 1H), 6.82 (d, J=9.0 Hz, 1H), 6.91-6.94 (dd, J=3.5 and 9.5 Hz, 1H), 6.98-7.01 (dd, J=8.5 and 8.5 Hz, 2H), 7.06-7.08 (m, 2H), 7.33 (d, J=3.5 Hz, 1H). HFABMS m/z 341.1304 (calc for $C_{19}H_{17}FN_2O_3$, MH$^+$, 341.1301).

(91): yield 33%, mp 122-26° C., $^1$H NMR (500 MHz, CDCl$_3$): 1.02-1.11 (m, 1H), 1.72 (m, 1H), 2.44 (s, 3H), 2.60 (t, J=4.5 Hz, 4H), 2.76-2.84 (m, 4H), 3.48-3.54 (m, 1H), 3.74-3.79 (m, 7H), 4.16-4.19 (m, 2H), 5.66 (d, J=10.5 Hz, 1H), 6.80 (d, J=8.5 Hz, 2H), 6.90-6.93 (dd, J=3.0 and 9.0 Hz, 1H), 6.99 (d, H=8.5 Hz, 2H), 7.06 (d, J=9.0 Hz, 1H), 7.55 (d, J=3.0 Hz, 1H). HFABMS m/z 450.2391 (calc for $C_{26}H_{31}N_3O_4$, MH$^+$, 450.2393).

(90): 32% yield, mp 185-87° C., $^1$H NMR (400 MHz, CDCl$_3$): 1.01-1.09 (m, 1H), 1.72-1.77 (m, 1H), 2.15-2.20 (m, 2H), 2.44 (s, 3H), 2.73-2.85 (m, 2H), 3.48-3.53 (m, 3H), 3.63-3.68 (m, 6H), 3.75 (s, 3H), 4.08-4.12 (m, 2H), 5.65 (d, J=10.5 Hz, 1H), 6.80 (d, J=8.5 Hz, 2H), 6.88-6.90 (dd, J=3.0 and 8.5 Hz, 1H), 6.99 (d, J=8.5 Hz, 2H), 7.05 (d, J=8.5 Hz, 1H), 7.53 (d, J=3.0 Hz, 1H). HFABMS m/z 492.2493 (calc for $C_{28}H_{33}N_3O_5$, MH$^+$, 492.2498).

Preparation of (11): A mixture of (23) (0.260 mg, 0.71 mmol), 5% Pd—C (25 mg) in ethanol (10 mL) and methanol (5 mL) was stirred under a hydrogen atmosphere for 2 days. The mixture was filtered, washed sequentially with ethyl acetate and acetic acid. The combined filtrates were concentrated. The solid obtained was recrystallized from ethyl acetate to give (11) (0.205 g, 86%): mp 224-26° C., $^1$H NMR (400 MHz, CDCl$_3$): 0.79-0.83 (m, 1H), 1.47-1.50 (m, 1H), 2.52 (m, 5H), 3.19-3.26 (m, 1H), 3.60 (s, 3H), 5.31 (d, J=10.8 Hz, 1H), 6.33 (d, J=8.0 Hz, 2H), 6.55-6.49 (m, 3H), 6.81 (d, J=8.4 Hz, 1H), 7.26 (m, 1H). HFABMS m/z 336.1717 (calc for $C_{20}H_{21}N_3O_2$, MH$^+$, 336.1712).

Preparation of (10): A mixture of (28) (0.370 mg, 0.86 mmol), 5% Pd—C (10 mg) in ethyl acetate (20 mL) was stirred under a hydrogen atmosphere for 20 h and then filtered though the pad of celite. The celite was then washed sequentially with ethyl acetate and acetic acid. The combined filtrates were concentrated. The solid obtained was recrystallized from ethyl acetate to give (10) (0.185 g, 63%): mp 240-41° C., $^1$H NMR (400 MHz, d$_6$-DMSO-CDCl$_3$): 0.99-1.11 (m, 1H), 1.72-1.76 (m, 1H), 2.43 (s, 3H), 2.67-2.83 (m, 2H), 3.46-3.53 (m, 1H), 3.87 (s, 3H), 5.61 (d, J=10.8 Hz, 1H), 6.74 (d, J=8.4 Hz, 2H), 6.87 (d, J=8.8 Hz, 2H), 6.61 (m, 1H), 7.07 (d, J=8.4 Hz, 1H), 7.43-7.46 (m, 1H), 7.52 (d, J=3.2 Hz, 1H). Anal. Calcd for $C_{20}H_{20}N_2O_3$: C, 71.41; H, 5.99; N, 8.33. Found: C, 71.12; H, 5.94; N, 8.32.

Preparation of (12): To a solution of (10) (0.100 g, 0.28 mmol) under an argon atmosphere in dichloromethane (5 mL) was added BBr$_3$ (1.0 mL, 1.0 M solution in dichloromethane) at −78° C. The reaction mixture was stirred at rt for 1 h and then poured into an ice cold solution of HCl (1.0 N). The mixture was extracted in ethyl acetate. The organic layer was washed with water, dried over anhydrous Na$_2$SO$_4$, filtered and concentrated. The solid obtained was recrystallized from ethyl acetate to give (12): (0.062 g, 67%): mp 164-67° C., $^1$H NMR (400 MHz, DMSO-CDCl$_3$): 0.70-0.90 (m, 1H), 1.41-1.46 (m, 1H), 2.41-2.57 (m, 5H), 3.15-3.22 (m, 1H), 5.29 (d, J=11.2 Hz, 1H), 6.43 (d, J=6.8 Hz, 2H), 6.53-6.57 (m, 3H), 6.68 (d, J=8.4 Hz, 1H), 7.19 (s, 1H). HFABMS m/z 323.1399 (calc for $C_{19}H_{18}N_2O_3$, MH$^+$, 323.1396).

Preparation of (26) and (25): A solution of 2-(4-methoxybenzylidene)-7-methoxy-1-tetralone (2.0 g, 0.0068 mol), hydrazine hydrate (2.0 mL) in formic acid (20 mL) was heated at 120° C. for 2 days. The reaction mixture was concentrated and then extracted with ethyl acetate. The organic layer was washed sequentially with water, saturated aqueous NaHCO$_3$, water and brine, dried over anhydrous Na$_2$SO$_4$, filtered, and then concentrated. The residue was purified by column chromatography on silica gel using ethyl acetate-hexane (3:7) as eluent to give compounds (26) (0.740 g, 32%) and (25) (0.905 g, 40%).

(26): mp 166-68° C., $^1$H NMR (400 MHz, CDCl$_3$): 1.90-1.99 (m, 1H), 2.27-2.31 (m, 1H), 2.86-2.90 (m, 2H), 3.21-3.28 (m, 1H), 3.80 (s, 3H), 3.86 (s, 3H), 4.89 (d, J=9.6 Hz, 1H), 6.90-6.98 (m, 3H), 7.10 (d, J=8.8 Hz, 1H), 7.25-7.27 (m, 2H), 7.43 (d, J=2.4 Hz, 1H), 8.97 (s, 1H). Anal. Calcd for $C_{20}H_{20}N_2O_3$: C, 71.41; H, 5.99; N, 8.33. Found: C, 71.16; H, 6.03; N, 8.26.

(25): mp 155-59° C., $^1$H NMR (400 MHz, CDCl$_3$): 1.01-1.12 (m, 1H), 1.69-1.74 (m, 1H), 2.68-2.85 (m, 2H), 3.49-3.76 (m, 1H), 3.76 (s, 3H), 3.81 (s, 3H), 5.58 (d, J=11.2 Hz, 1H), 6.78-7.04 (m, 6H), 7.48 (d, J=3.2 Hz, 1H), 8.94 (s, 1H). Anal. Calcd for $C_{20}H_{20}N_2O_3$: C, 71.41; H, 5.99; N, 8.33. Found: C, 71.08; H, 5.66; N, 8.28.

Preparation of (79) and (39): A solution of 2-(4 methoxybenzylidene)-7-methoxy-1-tetralone (0.500 g, 1.7 mmol) and hydrazine hydrate (0.5 mL) in propionic acid (5 mL) was refluxed at 140° C. for 2 days. The reaction mixture was concentrated, and the residue dissolved in ethyl acetate (25 mL). The mixture was washed sequentially with water, saturated aqueous NaHCO$_3$ and water, dried over anhydrous Na$_2$SO$_4$, filtered and concentrated. The residue was purified by column chromatography on silica gel using ethyl acetate-hexane (3:7) as eluent to give (79) (0.217 g, 35%) and (39) (0.252 g, 41%).

(79): mp 133-36° C., $^1$H NMR (400 MHz, CDCl$_3$): 1.15 (t, J=7.6 Hz, 3H), 1.85-1.96 (m, 1H), 2.23-2.29 (m, 1H), 2.74-2.87 (m, 4H), 3.15-3.22 (m, 1H), 3.78 (s, 3H), 3.86 (s, 3H), 4.89 (d, J=9.6 Hz, 1H), 6.87-6.92 (m, 3H), 7.08 (d, J=8.4 Hz, 1H), 7.23 (d, J=8.8 Hz, 2H), 7.44 (d, J=2.4 Hz, 1H). Anal. Calcd for $C_{22}H_{24}N_2O_3$: C, 72.50; H, 6.64; N, 7.69. Found: C, 72.33; H, 6.50; N, 7.61.

(39): mp 150-52° C., $^1$H NMR (400 MHz, CDCl$_3$): 1.05-1.10 (m, 1H), 1.21 (t, J=8.0 Hz, 3H), 1.70-1.78 (m, 1H), 2.74-2.88 (m, 4H), 3.47-3.52 (m, 1H), 3.75 (s, 3H), 3.87 (s, 3H), 5.65 (d, J=11.2 Hz, 1H), 6.80 (d, J=8.4 Hz, 2H), 6.89-6.92 (dd, J=3.2 and 8.4 Hz, 1H), 6.98 (d, J=8.8 Hz, 2H), 7.06 (d, J=8.4 Hz, 1H), 7.54 (d, J=3.2 Hz, 1H). Anal. Calcd for $C_{22}H_{24}N_2O_3$: C, 72.50; H, 6.64; N, 7.69. Found: C, 72.29; H, 6.57; N, 7.77.

General procedure for the preparation of 3,3a-trans and 3,3a-cis N-Substituted-1-[3-(aryl)-3,3a,4,5-tetrahydrobenzo[g]indazoles], exemplified for (138) and (85)): A solution of 2-(4-methoxybenzylidene)-1-tetralone (1.0 g, 0.0034 mol), trimethylacetic acid (5.0 g), hydrazine hydrate (1.0 mL) in ethanol (5 mL) was refluxed for 6 hours, and then concentrated. The residue obtained was dissolved in ethyl acetate (200 mL) and then washed with water. The organic layer was slowly poured into a saturated NaHCO$_3$ solution (250 mL). The resulting solution was slowly treated with methyl-5-chloro-5-oxovalerate (1.410 mL, 0.01 mol). The mixture was stirred at room temperature for 30 minutes. The ethyl acetate layer was separated, washed sequentially with water and brine, dried over anhydrous Na$_2$SO$_4$, filtered and concentrated. The residue was purified by column chromatography on silica gel column using ethyl acetate-hexane (3:7) as eluent to give compounds (138) (47%) and (85) (23%).

(138): mp 145-47° C., $^1$H NMR (500 MHz, CDCl$_3$): 1.89-2.04 (m, 3H), 2.24-2.29 (m, 1H), 2.40 (t, J=7.6 Hz, 2H), 2.83-2.88 (m, 4H), 3.16-3.21 (m, 1H), 3.65 (s, 3H), 3.79 (s, 3H), 3.87 (s, 3H), 4.89 (d, J=9.4 Hz, 1H), 6.87-6.92 (m, 3H), 7.09 (d, J=8.5 Hz, 1H), 7.23 (d, J=9.0 Hz, 1H), 7.44 (d, J=2.5 Hz, 1H). HFABMS m/z 437.2079 (calc for C$_{25}$H$_{28}$N$_2$O$_5$, MH$^+$, 437.2076).

(85): mp 159-61° C., $^1$H NMR (500 MHz, CDCl$_3$): 1.08-1.11 (m, 1H), 1.71-1.76 (m, 1H), 2.02-2.09 (m, 2H), 2.44 (t, J=8.0 Hz, 2H), 2.78-2.96 (m, 4H), 3.47-3.53 (m, 1H), 3.66 (s, 3H), 3.75 (s, 3H), 3.88 (s, 3H), 5.64 (d, J=11.0 Hz, 1H), 6.80 (d, J=9.0 Hz, 2H), 6.90-6.92 (dd, J=3.0 and 8.5 Hz, 1H), 6.98 (d, J=8.5 Hz, 2H), 7.06 (d, J=8.0 Hz, 1H), 7.53 (d, J=3.0 Hz, 1H). HFABMS m/z 437.2075 (calc for C$_{25}$H$_{28}$N$_2$O$_5$, MH$^+$, 437.2076).

(80): 11% yield, mp 159-61° C., $^1$H NMR (400 MHz, CDCl$_3$): 1.87-1.98 (m, 1H), 2.13 (s, 3H), 2.26-2.31 (m, 1H), 2.86-2.89 (m, 2H), 3.17-3.24 (m, 1H), 3.78 (s, 3H), 3.86 (s, 2H), 3.46-3.50 (m, 1H), 3.51 (s, 3H), 3.75 (s, 3H), 3.87 (s, 3H), 4.54 (d, J=16.0 Hz, 1H), 4.66 (d, J=16.0 Hz, 1H), 5.68 (d, J=11.0 Hz, 1H), 6.80 (d, J=9.5 Hz, 2H), 6.91-6.93 (dd, J=3.0 and 9.0 Hz, 1H), 6.98 (d, J=9.5 Hz, 2H), 7.07 (d, J=8.0 Hz, 1H), 7.50 (d, J=3.0 Hz, 1H). HFABMS m/z 381.1810 (calc for C$_{22}$H$_{24}$N$_2$O$_4$, MH$^+$, 381.1814).

(97): yield 22%, mp 220-22° C., $^1$H NMR (500 MHz, CDCl$_3$): 1.09-1.18 (m, 1H), 1.75-1.80 (m, 1H), 2.77-2.89 (m, 2H), 3.53-3.59 (m, 1H), 3.76 (s, 3H), 3.87 (s, 3H), 5.68 (d, J=10 Hz, 1H), 6.84 (d, J=8.5 Hz, 2H), 6.94-6.97 (dd, J=3.0 and 8.5 Hz, 1H), 7.01 (d, J=8.5 Hz, 2H), 7.07 (d, J=8.5 Hz, 1H), 7.56 (d, J=3.0 Hz, 1H). HFABMS m/z 405.1432 (calc for C$_{21}$H$_{19}$F$_3$N$_2$O$_3$, MH$^+$, 405.1426).

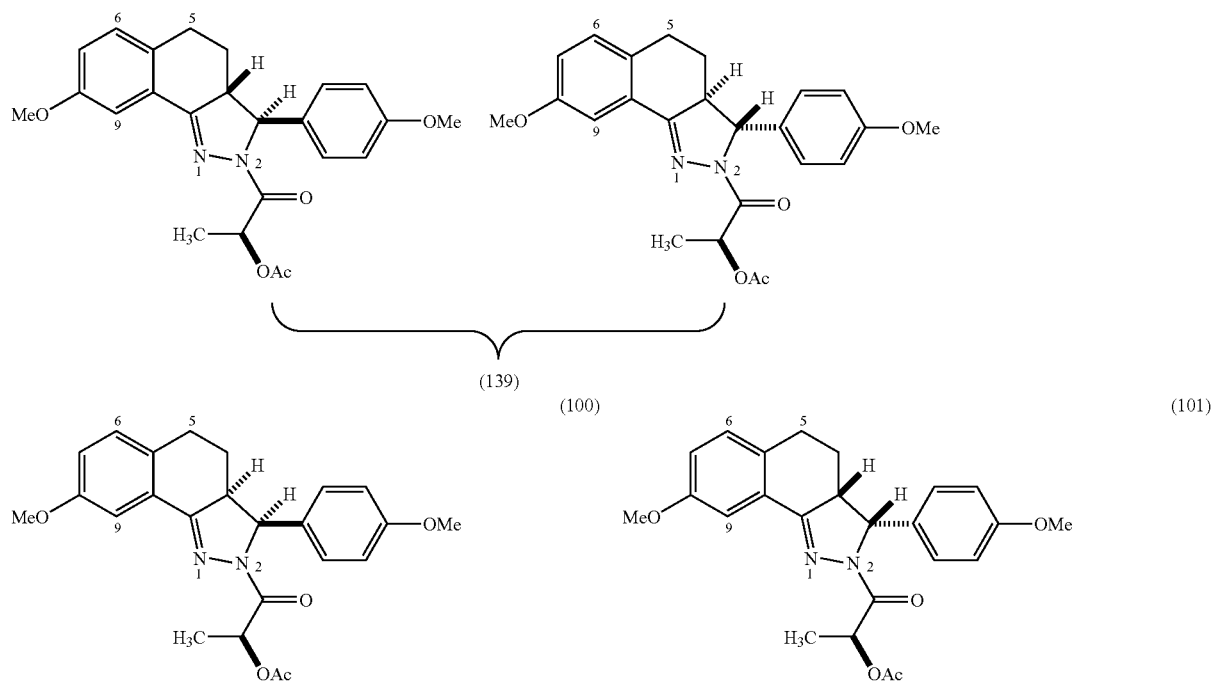

3H), 4.90 (d, J=9.2 Hz, 1H), 5.09 (d, J=15.6 Hz, 1H), 5.22 (d, J=15.6 Hz, 1H), 6.87-6.95 (m, 3H), 7.10 (d, J=8.8 Hz, 1H), 7.24 (d, J=8.8 Hz, 2H), 7.41 (d, J=3.2 Hz, 1H). Anal. Calcd for C$_{23}$H$_{24}$N$_2$O$_5$: C, 67.83; H, 5.90; N, 6.86. Found: C, 67.32; H, 5.88; N, 6.97.

(47): 68% yield, mp 201-204° C., $^1$H NMR (400 MHz, CDCl$_3$): 1.05-1.16 (m, 1H), 1.73-1.77 (m, 1H), 2.16 (s, 3H), 2.72-2.89 (m, 2H), 3.48-3.55 (m, 1H), 3.75 (s, 3H), 3.87 (s, 3H), 5.16-5.25 (m, 2H), 5.64 (d, J=11.2 Hz, 1H), 6.80 (d, J=8.8 Hz, 2H), 6.91-6.94 (dd, J=2.0 and 8.4 Hz, 1H), 6.99 (d, J=8.8 Hz, 2H), 7.07 (d, J=7.49 (d, J=3.2 Hz, 1H). Anal. Calcd for C$_{23}$H$_{24}$N$_2$O$_5$: C, 67.83; H, 5.90; N, 6.86. Found: C, 67.38; H, 5.87; N, 6.91.

(93): mp 47-50° C., thick oil, $^1$H NMR (500 MHz, CDCl$_3$): 1.04-1.09 (m, 1H), 1.27-1.38 (m, 9H), 1.59-1.64 (m, 2H), 1.68-1.76 (m, 2H), 2.29 (t, J=7.5 Hz, 2H), 2.72-2.88 (m, 4H), 3.48-3.64 (m, 1H), 3.65 (s, 3H), 3.75 (s, 3H), 3.87 (s, 3H), 5.64 (d, J=11.0 Hz, 1H), 6.79 (d, J=9.0 Hz, 2H), 6.89-6.91 (dd, J=2.5 and 8.5 Hz, 1H), 6.98 (d, J=9.0 Hz, 2H), 7.06 (d, J=8.5 Hz, 1H), 7.54 (d, J=2.5 Hz, 1H). HFABMS m/z 507.2853 (calc for C$_{30}$H$_{38}$N$_2$O$_5$, MH$^+$, 507.2859).

(20): yield 16%, mp 157-59° C., $^1$H NMR (500 MHz, CDCl$_3$): 1.06-1.12 (m, 1H), 1.75-1.77 (m, 1H), 2.76-2.88 (m, 2H), Preparation of 3,3a-trans and 3,3a-cis 2-Acetoxy-1-[8-methoxy-3-(4-methoxy-phenyl)-3,3a,4,5-tetrahydro-benzo[g]-indazol-2-yl]-propan-1-one ((139), (100), and (101)): A solution of 2-(4-methoxy-benzylidene)-1-tetralone (1.1 g, 0.0037 mol), trimethylacetic acid (6.0 g), hydrazine hydrate (1.1 mL) in ethanol (5 mL) was refluxed for 6 h, and concentrated under vacuum. The residue obtained was dissolved in ethyl acetate (200 mL) and it was slowly poured on saturated NaHCO$_3$ solution (200 mL), and the resulting solution was slowly treated with (S)-acetoxy-propionyl chloride (2.350 mL, 0.018 mol), and stirred at room temperature for 30 minutes. The ethyl acetate layer was separated, washed with water, brine, dried on Na$_2$SO$_4$ and concentrated. The residue purified on the silica gel column using ethyl acetate-hexane (35%). Earlier fractions furnished (139) (0.440 g, 28%), and the later fractions furnished (100) (0.508 g, 32%), and (101) (0.130 mg, 8%).

(139): mp 146-50° C., $^1$H NMR (500 MHz, CDCl$_3$): 1.50 (d, J=7.0 Hz, 3H), 1.58 (d, J=7.0 Hz, 3H), 1.88-1.99 (m, 2H), 2.08 (s, 3H), 2.09 (s, 3H), 2.24-2.32 (m, 2H), 2.82-2.92 (m, 4H), 3.14-3.20 (m, 2H), 3.79 (s, 6H), 3.87 (s, 6H), 4.91-4.98 (m, 2H), 5.86-5.93 (m, 2H), 6.86-6.94 (m, 5H), 7.10 (d, J=8.5

Hz, 2H), 7.19-7.26 (m, 5H), 7.41-7.43 (m, 2H). Anal. Calcd for $C_{24}H_{26}N_2O_5$: C, 68.23; H, 6.20; N, 6.63. Found: C, 67.96; H, 6.20; N, 6.36.

(100): mp 70-76° C. (dec.), $^1$H NMR (500 MHz, CDCl$_3$): 0.97-1.06 (m, 1H), 1.56 (d, J=7.0 Hz, 3H), 1.75-1.79 (m, 1H), 2.10 (s, 3H), 2.73-2.86 (m, 2H), 3.48-3.53 (m, 1H), 3.74 (s, 3H), 3.86 (s, 3H), 5.64 (d, J=11.0 Hz, 1H), 6.03 (dd, J=7.0 and 14.0 Hz, 1H), 6.81 (d, J=9.0 Hz, 2H), 6.90-6.92 (dd, J=3.0 and 9.0 Hz, 1H), 7.02-7.06 (m, 3H), 7.51 (d, J=3.0 Hz, 1H). HFABMS m/z 423.1927 (calc for $C_{24}H_{26}N_2O_5$, MH$^+$, 423.1920).

(101): mp 139-42° C. (dec.), $^1$H NMR (400 MHz, CDCl$_3$): 1.12-1.18 (m, 1H), 1.60 (d, J=6.8 Hz, 3H), 1.70-1.74 (m, 1H), 2.12 (s, 3H), 2.78-2.85 (m, 2H), 3.50-3.57 (m, 1H), 3.75 (s, 3H), 3.85 (s, 3H), 5.65 (d, J=11.2 Hz, 1H), 5.80-5.90 (dd, J=5.6 and 11.6 Hz, 1H), 6.79 (d, J=8.4 Hz, 2H), 6.91-6.97 (m, 3H), 7.07 (d, J=8.0 Hz, 1H), 7.52 (d, J=3.2 Hz, 1H). Anal. Calcd for $C_{24}H_{26}N_2O_5$: C, 68.23; H, 6.20; N, 6.63. Found: C, 67.99; H, 6.32; N, 6.50.

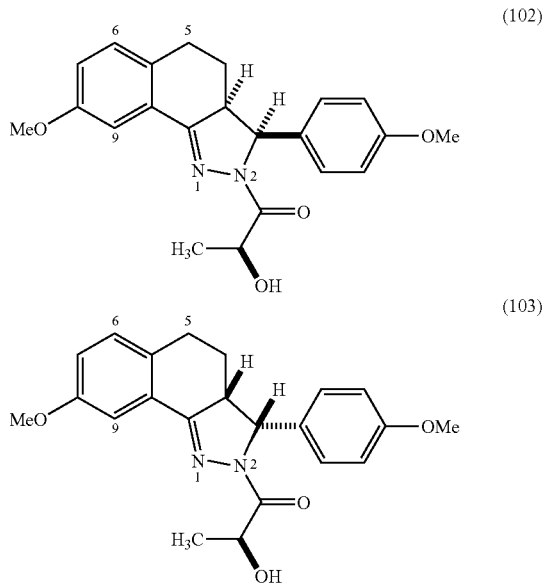

Preparation of (102): To a solution of (103) (0.50 g, 0.11 mmol) in methanol (5 mL), was added NaOH (50%, 1 mL) at room temperature. The reaction mixture was stirred at room temperature for 23 hours. Then it was diluted with ethyl acetate. The organic layer was washed with water, dried over anhydrous Na$_2$SO$_4$, filtered and concentrated. The residue obtained was purified by column chromatography on silica gel using ethyl acetate-hexane (3:7) as eluent to furnish (102) (0.027 g, 60%): mp 207-211° C., $^1$H NMR (400 MHz, CDCl$_3$): 1.06-1.14 (m, 1H), 1.50 (d, J=6.4 Hz, 3H), 1.72-1.80 (m, 1H), 2.76-2.88 (m, 2H), 3.50-3.59=8 (m, 1H), 3.59 (d, J=8.0 Hz, 1H), 3.75 (s, 3H), 3.85 (s, 3H), 4.96-4.04 (m, 1H), 5.63 (d, J=10.4 Hz, 1H), 6.82 (d, J=8.8 Hz, 2H), 6.92-7.00 (m, 3H), 7.08 (d, J=8.4 Hz, 1H), 7.51 (d, J=2.4 Hz, 1H). Anal. Calcd for $C_{22}H_{24}N_2O_4$: C, 69.46; H, 6.36; N, 7.36. Found: C, 69.07; H, 6.25; N, 7.21.

Preparation of (103): To a solution of (101) (0.50 g, 0.11 mmol) in methanol (5 mL), was added NaOH (50%, 1 mL) at room temperature. The reaction mixture was stirred at room temperature for 23 h. Then it was diluted with ethyl acetate. The organic layer was washed with water, dried over anhydrous Na$_2$SO$_4$, filtered and concentrated. The residue obtained was purified column chromatography on silica gel using ethyl acetate-hexane (3:7) as eluent to furnish (103) (0.031 g, 69%): mp 83-88° C., $^1$H NMR (500 MHz, CDCl$_3$): 1.07-1.16 (m, 1H), 1.56 (d, J=7.0 Hz, 3H), 1.73-1.78 (m, 1H), 2.77-2.88 (m, 2H), 3.50-3.56 (m, 1H), 3.76 (s, 3H), 3.88 (s, 3H), 4.88-4.96 (m, 1H), 5.72 (d, J=13.0 Hz, 1H), 6.83 (d, J=8.5 Hz, 1H), 6.93-6.96 (dd, J=3.0 and 9.0 Hz, 1H), 7.00 (d, J=8.5 Hz, 2H), 7.09 (d, J=8.5 Hz, 1H), 7.52 (d, J=3.0 Hz, 1H). Anal. Calcd for $C_{22}H_{24}N_2O_4$: C, 69.46; H, 6.36; N, 7.36. Found: C, 68.74; H, 6.27; N, 7.22.

Preparation of (98): To a solution of (102) (80 mg, 0.21 mmol), N-methylmorpholine-oxide hydrochloride (75 mg, 0.63 mmol) in dichloromethane (5 mL) was added tetrapropylammonium perruthenate (5 mg), and stirred at room temperature for 5 min. Then it was filtered, concentrated and purified on the silica gel column using an eluent 25% ethyl acetate-hexane to give (98) (62 mg, 78%): mp 175-78° C., $^1$H NMR (500 MHz, CDCl$_3$): 1.09-1.13 (m, 1H), 1.74-1.78 (m, 1H), 2.76-2.88 (m, 2H), 3.77 (s, 3H), 3.84 (s, 3H), 5.65 (d, J=10.5 Hz, 1H), 6.85 (d, J=8.5 Hz, 2H), 6.92-6.94 (dd, J=3.0 and 8.5 Hz, 1H), 7.04 (d, J=8.5 Hz, 2H), 7.07 (d, J=8.5 Hz, 1H), 7.44 (d, J=3.0 Hz, 1H). HFABMS m/z 379.1658 (calc for $C_{22}H_{22}N_2O_4$, MH$^+$, 379.1661).

Preparation of (48): To a solution of (47) (0.150 g, 0.36 mmol) in methanol (10 mL) was added NaOH (50%, 2 mL) at room temperature. The reaction mixture was stirred at room temperature for 24 hours before being diluted with ethyl acetate. The organic layer was washed with water, dried over anhydrous Na$_2$SO$_4$, filtered and concentrated. The residue obtained was purified by column chromatography on silica gel column using ethyl acetate-hexane (4:6) as eluent to furnish (48) (0.105 g, 78%): mp 163-64° C., $^1$H NMR (400 MHz, CDCl$_3$): 1.06-1.17 (m, 1H), 1.72-1.78 (m, 1H), 2.76-2.89 (m, 2H), 3.76 (s, 3H), 3.87 (s, 3H), 4.55-7.70 (m, 2H), 5.66 (d, J=10.0 Hz, 1H), 6.82 (d, J=9.2 Hz, 2H), 6.92-6.95 (dd, J=2.4 and 8.8 Hz, 1H), 6.99 (d, J=9.2 Hz, 2H), 7.07 (d, J=8.4 Hz, 1H), 7.50 (d, J=2.4 Hz, 1H). $^{13}$C NMR (400 MHz, CDCl$_3$): 24.38, 28.90, 48.57, 55.46, 55.76, 61.40, 69.61, 108.02, 114.34, 119.12, 127.53, 127.84, 128.47, 13032, 132.61, 157.67, 158:36, 159.42, 168.66. Anal. Calcd for $C_{21}H_{22}N_2O_4$: C, 68.84; H, 6.05; N, 7.65. Found: C, 68.98; H, 6.04; N, 7.58.

General procedure for the preparation of N-alylcarboxylic acids of 3,3a-cis-1-[3-(aryl)-3,3a,4,5-tetrahydro-benzo[g]indazoles], exemplified for (86): To a solution of (85) (0.185 g, 0.42 mmol) in methanol (10 mL) and THF (5 mL) was added NaOH (10 N, 1 mL) at room temperature. The reaction mixture was stirred at room temperature for 3 h before being diluted with ethyl acetate. The organic layer was washed with water, dried over anhydrous Na$_2$SO$_4$, filtered and concentrated. The solid obtained was recrystallized from ethyl acetate-hexane to give (86) (0.154 g, 86%): mp 170-76° C., $^1$H NMR (500 MHz, CDCl$_3$): 1.07-1.10 (m, 1H), 1.70-1.75 (m, 1H), 2.05-2.09 (m, 2H), 2.42-2.48 (m, 2H), 2.76-3.02 (m, 4H), 3.48-3.54 (m, 1H), 3.75 (s, 3H), 3.87 (s, 3H), 5.64 (d, J=13.75 Hz, 1H), 6.80 (d, J=8.5 Hz, 2H), 6.90-6.93 (dd, J=3.0 and 8.5 Hz, 1H), 6.98 (d, J=8.5 Hz, 2H), 7.06 (d, J=8.5 Hz, 1H), 7.52 (d, J=3.0 Hz, 1H). HFABMS m/z 423.1926 (calc for $C_{24}H_{26}N_2O_5$, MH$^+$, 423.1920).

(83): 95% yield, $^1$H NMR (500 MHz, CDCl$_3$): 1.05-1.08 (m, 1H), 1.32-1.38 (m, 8H), 1.59-1.78 (m, 4H), 2.32 (t, J=8.0 Hz, 2H), 2.79-2.89 (m, 4H), 3.46-3.52 (m, 1H), 3.74 (s, 3H), 3.83-3.85 (m, 1H), 3.87 (s, 3H), 5.65 (d, J=11.5 Hz, 1H), 6.79 (d, J=8.5 Hz, 2H), 6.89-6.91 (dd, J=3.0 and 8.5 Hz, 1H), 6.97 (d, J=8.5 Hz, 2H), 7.06 (d, J=8.5 Hz, 1H), 7.54 (d, J=3.0 Hz, 1H), 8.65 (s, 1H), HFABMS m/z 493.2707 (calc for $C_{29}H_{36}N_2O_5$, MH$^+$, 493.2702).

General procedure for the preparation of N-alylcarboxamides of 3,3a-cis-1-[3-(aryl)-3,3a,4,5-tetrahydro-benzo[g]indazoles], exemplified for (87): To a suspension of (86) (0.120 g, 028 mmol), HUBT (0.108 g, 0.28 mmol), 1-[3-(dimethylamino)propyl-3-ethyl-carbodiimide (0.085 g, 0.28 mmol), and N,N-diisopropylethyl amine (0.1 mL, 0.56 mmol) under an argon atmosphere in $CH_2Cl_2$ (10 mL) was added morpholine (0.050 mL, 0.58 mmol) at room temperature. The reaction mixture was stirred at room temperature for 16 hours. The reaction mixture was diluted with dichloromethane (20 mL) and the organic layer was washed sequentially with HCl (1 N), water, brine, dried over anhydrous $Na_2SO_4$, filtered and concentrated. The residue was purified by column chromatography on silica gel using ethyl acetate-hexane (8:2) as eluent to give (87) (0.106 g, 75%): mp 163-66° C., $^1$H NMR (500 MHz, $CDCl_3$): 1.04-1.10 (m, 1H), 1.70-1.78 (m, 1H), 2.01-2.07 (m, 2H), 2.41-2.45 (m, 2H), 2.77-3.00 (m, 6H), 3.44-3.53 (m, 3H), 3.61-3.64 (m, 6H), 3.75 (s, 3H), 3.88 (s, 3H), 5.64 (d, J=13.75 Hz, 1H), 6.80 (d, J=9.0 Hz, 2H), 6.90-6.92 (dd, J=3.0 and 8.5 Hz, 1H), 6.98 (d, J=8.5 Hz, 2H), 7.06 (d, J=8.5 Hz, 1H), 7.52 (d, J=3.0 Hz, 1H). HFABMS m/z 492.2491 (calc for $C_{28}H_{33}N_3O_5$, $MH^+$, 492.2498).

(94): 72% yield, mp 112-16° C., $^1$H NMR (500 MHz, $CDCl_3$): 1.03-1.12 (m, 2H), 1.32-1.40 (m, 8H), 1.60-1.64 (m, 2H), 1.68-1.76 (m, 2H), 2.27-2.31 (dd, J=7.5 and 8.0 Hz, 2H), 2.74-2.88 (m, 4H), 3.44-3.52 (m, 3H), 3.60-3.62 (m, 2H), 3.66 (m, 4H), 3.75 (s, 3H), 3.87 (s, 3H), 5.64 (d, J=11.0 Hz, 1H), 6.79 (d, J=8.0 Hz, 2H), 6.89-6.91 (dd, J=2.5 and 8.0 Hz, 1H), 6.97 (d, J=8.0 Hz, 2H), 7.06 (d, J=8.0 Hz, 1H), 7.54 (d, J=2.5 Hz, 1H). HFABMS m/z 562.3271 (calc for $C_{33}H_{44}N_3O_5$, $MH^+$, 562.3281).

General procedure for the preparation of N-thioureas or N-ureas of 3,3a-trans and 3,3a-cis-1-[3-(aryl)-3,3a,4,5-tetrahydro-benzo[g]indazoles], exemplified for (117): A suspension of 2-(4-methoxybenzylidene)-7-methoxy-1-tetralone (0.850 g, 0.0028 mol) and thiosemicarbazide (0.790 g, 0.0084 mol) in ethanol (30 mL) and concentrated HCl (2 mL) was refluxed for six hours.

The resulting solution was cooled to room temperature. The solid precipitate was filtered, washed with ethanol and recrystallized from ethanol to give (117) (0.985 g, 96%): mp 236-39° C., $^1$H NMR (500 MHz, $CDCl_3$): 1.04-1.13 (m, 1H), 1.76-1.81 (m, 1H), 2.75-2.87 (m, 2H), 3.60-3.66 (m, 1H), 3.76 (s, 3H), 3.85 (s, 3H), 6.07 (d, J=10.5 Hz, 1H), 6.83 (d, J=9.0 Hz, 2H), 6.93-6.95 (dd, 3.0 and 8.5 Hz, 1H), 6.99 (d, J=9.0 Hz, 2H), 7.08 (d, J=8.5 Hz, 1H), 7.49 (d, J=3.0 Hz, 1H). HFABMS m/z 368.1439 (calc for $C_{20}H_{21}N_3O_2S$, $MH^+$, 368.1433).

(118): yield 28%, mp 199-200° C., $^1$H NMR (500 MHz, $CDCl_3$): 1.02-1.11 (m, 1H), 1.76-1.81 (m, 1H), 2.75-2.86 (m, 2H), 3.21 (d, J=5.0 Hz, 3H), 3.56-3.62 (m, 1H), 3.75 (s, 3H), 3.87 (s, 3H), 6.10 (d, J=11.0 Hz, 1H), 6.80 (d, J=8.5 Hz, 2H), 6.91-6.94 (dd, J=3.0 and 8.5 Hz, 1H), 6.96 (d, J=8.5 Hz, 2H), 7.07 (d, J=8.5 Hz, 1H), 7.46 (m, 1H), 7.48 (d, J=3.0 Hz, 1H). HFABMS m/z 382.1579 (calc for $C_{21}H_{23}N_3O_2S$, $MH^+$, 382.1589).

(120): yield 75%, mp 217-20° C., $^1$H NMR (500 MHz, $CDCl_3$): 1.02-1.11 (m, 1H), 1.74-1.79 (m, 1H), 2.73-2.86 (m, 2H), 3.54-3.60 (m, 1H), 3.75 (s, 3H), 3.86 (S, 3H), 5.58 (d, J=10.5 Hz, 1H), 6.81 (d, J=8.5 Hz, 2H), 6.88-6.90 (dd, J=3.0 and 8.5 Hz, 1H), 7.01 (d, J=8.5 Hz, 2H), 7.05 (d, J=8.5 Hz, 1H), 7.47 (d, J=3.0 Hz, 1H). HFABMS m/z 352.1663 (calc for $C_{20}H_{21}N_3O_3$, $MH^+$, 352.1663).

Preparation of (119): A solution of (117) (0.5 g, 1.3 mmol) and methyl iodide (1.0 mL) in ethanol (10 mL) was refluxed for two hours. When the reaction mixture was concentrated to a fourth of its volume, a solid precipitate formed. The mixture was filtered and the solid washed with cold ethanol to give cis-8-methoxy-3-(4-methoxyphenyl)-3,3a,4,5-tetrahydrobenzo[g]indazole-2-carboximidothioic acid methyl ester hydroiodide (565 mg, 85%), which was used without further purification. A solution of cis-8-methoxy-3-(4-methoxyphenyl)-3,3a,4,5-tetrahydrobenzo[g]indazole-2-carboximidothioic acid methyl ester hydroiodide (175 mg, 0.34 mmol) and ammonia (2.0 N solution in ethanol, 15 mL) in ethanol (15 mL) was stirred at 60° C. for 16 hours. The reaction mixture was concentrated. The solid was recrystallized from methanol-diethyl ether to give (119) (105 mg, 88%): mp 170-75° C., $^1$H NMR (500 MHz, $CDCl_3$): 1.07-1.15 (m, 1H), 1.74-1.78 (m, 1H), 2.76-2.89 (m, 2H), 3.77 (s, 3H), 3.79-3.84 (m, 1H), 3.88 (s, 3H), 6.19 (d, J=10.5 Hz, 1H), 6.86 (d, J=8.5 Hz, 2H), 6.97-6.99 (dd, J=3.0 and 8.5 Hz, 1H), 7.10 (d, J=8.5 Hz, 2H), 7.50 (d, J=3.0 Hz, 1H). HFABMS m/z 351.1825 (calc for $C_{20}H_{22}N_4O_2$, $MH^+$, 351.1821).

Preparation of (135): To a solution of (19) (800 mg, 2.2 mmol) in acetonitrile (10 mL) under an argon atmosphere was added trimethylsilyl azide (1.517 mL, 5.0 eq.) followed by slow addition of [bis(trifluoroacetoxy)iodo]-benzene (2.948 g, 3.0 eq.). The reaction mixture was stirred at room temperature for 24 h. The reaction mixture was concentrated to give a dark brown residue that was purified by column chromatography on silica gel using ethyl acetate-hexane (1:3) as eluent to give (135) (252 mg, 29%), and recovered starting material, (19) (45 mg).

(135): thick oil, $^1$H NMR (500 MHz, $CDCl_3$): 1.82-1.88 (m, 1H), 3.74 (s, 3H), 3.86-3.89 (m, 2H), 3.91 (s, 3H), 4.66 (m, 1H), 5.70 (d, J=11.5 Hz, 1H), 6.80 (d, J=8.5 Hz, 2H), 6.96 (d, J=2H), 7.0-7.02 (dd, J=3.0 and 9.0 Hz, 1H), 7.19 (d, J=9.0 Hz, 1H), 7.60 (d, J=3.0 Hz, 1H). HFABMS m/z 392.1722 (calc for $C_{21}H_{22}N_5O_3$, $MH^+$, 392.1723).

Preparation of (136): A solution of (135) (0.240 g, 0.61 mmol) and 10% Pd—C (50 mg) in ethyl acetate (10 mL) was stirred under hydrogen (80 psi) for 24 h. The reaction mixture was filtered though a short column of celite. The filtrate was triturated with aqueous acetic acid (50%, 10 mL). The solid was recrystallized from ethyl acetate-water to give (136) (0.153 g, 59%): mp 116-19° C., $^1$H NMR (500 MHz, $CDCl_3$): 1.68-1.72 (m, 1H), 2.10-2.12 (m, 1H), 2.62 (s, 3H), 3.75 (s, 3H), 3.88 (s, 3H), 4.01-4.07 (m, 1H), 4.14-4.16 (m, 1H), 5.69 (d, J=11.0 Hz, 1H), 6.80 (d, J=8.5 Hz, 2H), 6.95-6.98 (m, 3H), 7.19 (d, J=9.0 Hz, 1H), 7.53 (d, J=3.0 Hz, 1H). HFABMS m/z 366.1818 (calc for $C_{21}H_{24}N_3O_3$, $MH^+$, 366.1818).

Preparation of (137): To a solution of (136) (210 mg, 0.57 mmol) in THF (10 mL) was added formic acid (0.150 mL) at 0° C., followed by slow addition of aqueous formaldehyde (37%). The reaction mixture was refluxed for 24 h. The solution was allowed to cool, basified with aqueous NaOH (25%), and the extracted with ethyl acetate. The organic layer was washed with water, dried over anhydrous $Na_2SO_4$, filtered and concentrated. The residue was purified by column chromatography on silica gel using ethyl acetate as eluent to give (137) (105 mg, 47%): mp 123-28° C., $^1$H NMR (500 MHz, $CDCl_3$): 0.9-1.02 (m, 1H), 2.21 (s, 6H), 2.43 (s, 3H), 3.23 (m, 1H), 3.73 (s, 3H), 3.89 (s, 3H), 4.03-4.09 (m, 1H), 5.66 (d, J=11.0 Hz, 1H), 6.78 (d, J=8.5 Hz, 2H), 6.90-6.92 (dd, J=2.5 and 8.5 Hz, 1H), 6.96 (d, J=8.5 Hz, 2H), 7.12 (d, J=8.5 Hz, 1H), 7.58 (d, J=2.5 Hz, 1H). Anal. Calcd for $C_{23}H_{27}N_3O_3$: C, 70.21; H, 6.92; N, 10.68. Found: C, 69.93; H, 7.14; N, 10.45.

Preparation of (122): To the solution of (19) (180 mg, 0.51 mmol) in THF (5 mL) was added $LiAlH_4$ (2.056 mL, 2.056 mmol; 1M in THF) at room temperature. The reaction mixture was stirred at room temperature for 1 h and then quenched with methanol followed by ice. The reaction mixture was extracted with ethyl acetate. Organic layer was washed with water, dried over anhydrous sodium sulfate and concentrated. The residue was purified by column chromatography on silica gel using 25% ethyl acetate-hexane as eluent to give (122) (30 mg, 17%): thick oil, $^1$H NMR (500 MHz, CDCl$_3$): 1.40 (t, J=7.0 Hz, 3H), 1.72-2.04 (m, 2H), 2.62-2.85 (m, 2H), 3.87 (s, 6H), 4.15 (q, J=7.0 Hz, 2H), 4.75 (d, J=10.5 Hz, 1H), 6.75-6.77 (dd, J=8.0 and 3.0 Hz, 1H), 7.01 (d, J=8.0 Hz, 2H), 7.12 (d, J=8.5 Hz, 1H), 7.29 (d, J=8.0 Hz, 2H), 7.44 (d, J=3.0 Hz, 1H). LRMS m/z 336.3 (calc for $C_{21}H_{24}N_2O_2$, M$^+$, 336.2).

Other compounds, e.g., (6), (7), (8), (9), (17), (18), (21), (27), (29), (30), (32), (33), (35), (37), (38), (40), (41), (42), (43), (44), (45), (46), (81), (83), (88), (96), (99), (106), (107), (108), (109), (110), (111), (112), (114), and (116) were prepared using analogous procedures to those described herein.

Example 22

The Role of Fas-Associated Death Domain Protein in zVAD-fmk/TNFα- or zVAD-fmk/DMSO-Induced Necrosis A cell expressing a dominant negative form of the protein Fas-associated death domain (FADD) can also prevent a cell from undergoing necrosis in response to treatment with zVAD-fmk/TNFα- or zVAD-fmk/DMSO. Jurkat cells were stably transfected with a FADD-FKBP fusion construct (Kawahara et al., J. Cell Biol. 143:1353-60, 1998). Normally, such cells undergo apoptosis when FADD is multimerized. However, these cells, in the presence of the caspase inhibitor zVAD-fmk, are protected from apoptosis, and instead undergo necrosis, thus establishing the dependence of apoptosis in this system on caspase activity and induction of necrosis in the absence of caspases.

The stably transfected Jurkat cells (500,000 cells/ml) were treated with 100 nM of FKBP dimerizer (Ariad Pharmaceuticals; used to stimulate FADD multimerization) in the presence of 100 μM of zVAD-fmk (pre-treated for one hour) and compounds from the library identified to decrease necrosis (dissolved in DMSO to give a final DMSO concentration of 0.5%; added 30 minutes after zVAD-fmk) for 48 hours. Cell viability was then assessed by measuring cellular ATP levels. The small molecules provided protection from necrosis induced in the presence of zVAD-fmk, but not from apoptosis induced by FADD dimerization in the absence of zVAD-fmk. These results indicate that FADD may be involved in mediating necrosis in response to zVAD-fmk/TNFα- or zVAD-fmK/DMSO. It is possible that the small molecules that decrease necrosis may function by interacting with FADD and disrupting FADD's normal function of promoting necrosis upon treatment of a cell with zVAD-fmk/TNFα or zVAD-fmk/DMSO.

Example 23

Identification of Intracellular Targets of Small Molecules that Decrease Necrosis Molecules within a cell that interact with the small molecule compounds that decrease necrosis can be identified using a number of different strategies. Each strategy involves detecting interactions between various proteins from a cell and a small molecule that decreases necrosis, identified according to the methods described above. To identify proteins that interact with a small molecule that decreases necrosis, the small molecule may be bound to a bead, using methods known to those skilled in the art. Each strategy should be carried out using proteins from cells which have been exposed to zVAD-fmk/TNFα or zVAD-fmk/DMSO.

In one strategy, the signaling complex containing FADD, among other proteins, may be immunoprecipitated, using standard techniques known to those skilled in the art. This complex may then be added to the beads containing the desired small molecule compound that decreases necrosis. Proteins that interact with the small molecule that decreases necrosis may be identified by Western blot detection of proteins contained in the complex, or other techniques known to those skilled in the field of molecular biology. Any detected binding interactions indicate that the target of the small molecule that decreases necrosis is present in the immunoprecipitated FADD complex.

In a second strategy for identifying targets of a small molecule that decreases necrosis, a cell may be fractionated, and the various fractionated pools may be assayed for interaction with the chemical compound using standard molecular biology techniques. A pool of proteins which interacts with the small molecule that decreases necrosis indicates that the pool contains a protein that is a target of the small molecule that decreases necrosis. The target of the small molecule that decreases necrosis may be isolated using techniques known to those skilled in the art.

A third strategy involves small pool expression screening systems. Targets of a small molecule that decreases necrosis can be identified from any cell in which the small molecule protects cells from necrosis triggered by zVAD-fmk/TNFα or zVAD-fmk/DMSO. This method for identifying targets of small molecules that decrease necrosis can be done, for example, according to the methods of Lustig et al. (Methods in Enzymology 283:83-99, 1997). In this method a cDNA library is made from a desired cell line, or any other desired source. The cDNA library is then divided into pools of 100 clones, and the cDNAs are transcribed and translated to form proteins pools for the detection of interactions between a protein and a small molecule that decreases necrosis. Interactions between the small molecules that decrease necrosis and pools of library proteins can be detected using standard molecular biology techniques, for example, SDS-PAGE.

Example 24

Structural Derivatives of Small Molecules that Decrease Necrosis

The following modifications of the small molecules that decrease necrosis may be made and evaluated for their efficacy in decreasing necrosis, for example, that induced by zVAD-fmk/TNF.alpha. or zVAD-fmk/DMSO.

The chemical compound 115807 may be modified, for example, by the introduction of a hydroxyl, methyl, carboxy, methoxyl, amino or nitro group into the benzyl ring (for example, at any or all of the $R_1$-$R_4$ positions of formula (VII)). Double bonds may be introduced in the linker between indol and hydantoin moieties (for example, in formula (VII), bonds (a), (b), or (c) may be double bonds, provided that not both of bonds (a) and (b) are double bonds). The thiourea moiety may be reduced or alkylated (for example, the moiety may be —SH or SR$_8$, wherein R$_8$ is an alkyl group). The indol amino group may be reduced, alkylated, or acylated (for example, in formula (VII), R$_5$ may be CH$_3$, CH$_3$(CH$_2$)$_n$, where n is between 1 and 4, and HOOC—(CH$_2$)$_n$, where n is between 1 and 4,

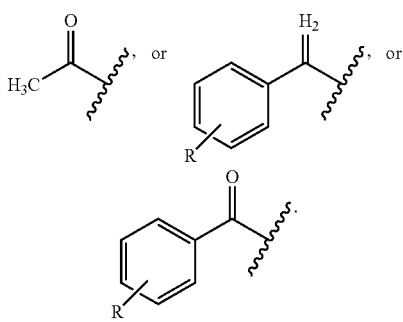

In addition, the hydantoin 3-methyl group may be substituted with linear or branching alkyl groups of varying length, and with hydroxyl, methyl, or acyl functionalities; for example, the following groups may be present at the $R_7$ position of formula (VII): $CH_3$, $CH_3(CH_2)_n$, where n is between 1 and 4, OH, or HOOC—$(CH_2)_n$—, where n is between 1 and 4. In addition, the linker $CH_2$ group between the indol and hydantoin moieties can be alkylated, acylated, halogenated, or hydroxylated; for example, in formula (VII), $R_7$ may be $CH_3$, $CH_3(CH_2)_n$, where n is between 1 and 4, and HOOC—$(CH_2)_n$, where n is between 1 and 4,

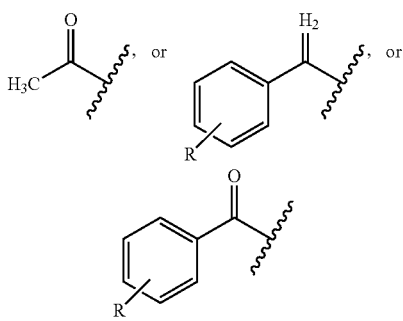

Lastly, the hydantoin ketone moiety may be reduced to a hydroxyl group or a hydrogen.

The chemical compound 210227 may be modified, for example, by the attachment of a halide, or hydroxyl or amino groups to either or both of the benzyl rings (for example, in any of the positions $R_1$-$R_2$ or $R_4$-$R_9$ of formula (XX)). The C=N double bond may be reduced, or the fluoride may be eliminated or substituted with a hydroxyl group or other halide.

The chemical compound 215686 may be modified, for example, by reducing the two central aliphatic double bonds, together, or each one individually. The ketone may also be reduced, or the methoxyl groups may be substituted with hydroxyl groups, each individually, or together.

The chemical compound 115681 may be modified, for example, in the following ways. The aliphatib double bond or the aliphatic ketone may be reduced. The nitro group may be substituted with a proton, halide, or sulfate. The C=O double bond in the flavone ring may be reduced. Either one or two of the oxygens attached to the flavone may also be eliminated.

Example 25

Synthetic Scheme for Nec-2 Compounds

Nec-2 compounds can be made by methods known in the art (see, e.g., Revue Roumaine de Chimie, 30:245-8, 1985; Indian Journal of Chemistry, Section B: Organic Chemistry Including Medicinal Chemistry, 42B:145-149, 2003; and Russian Journal of Organic Chemistry (Translation of Zhurnal Organicheskoi Khimii), 35:1516-1524, 1999). For example, Scheme 6 can be used:

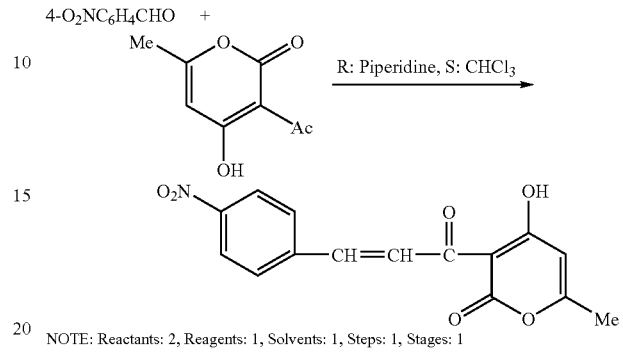

If 4-hydroxy-3-nitrobenzaldehyde (available from Matrix Scientific or Wako Pure Chemicals) is used as a starting material, Nec-2 can be produced with the above scheme:

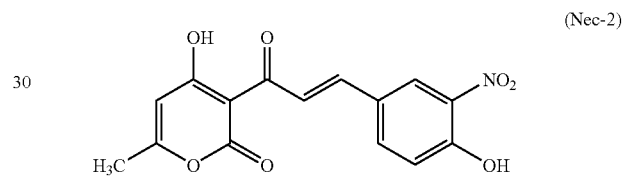

Three additional synthetic schemes that are useful for preparing Nec-2 compounds of the invention, in particular, compounds of formula (XVIII), are shown below in Scheme 7, 8, and 9:

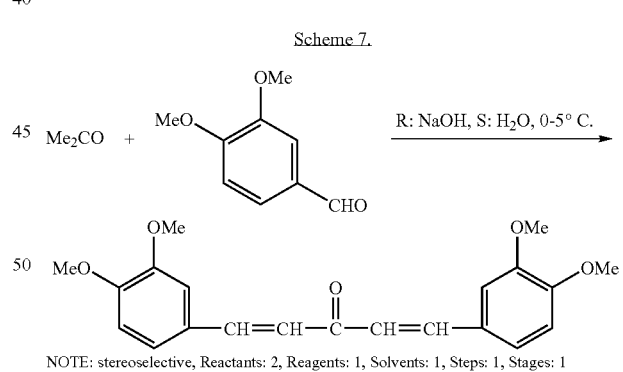

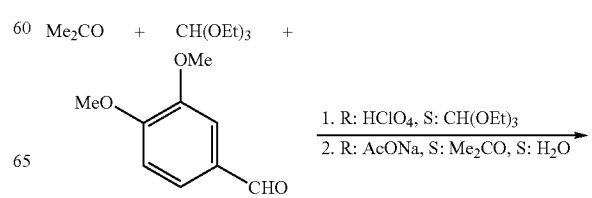

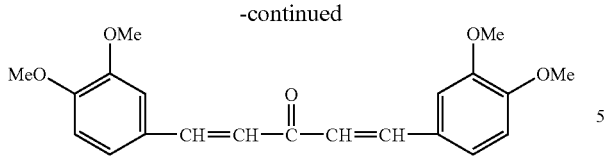

NOTE: Reactants: 3, Reagents: 2, Solvents: 3, Steps: 2, Stages: 2, Most stages in any one step: 1

Scheme 9.

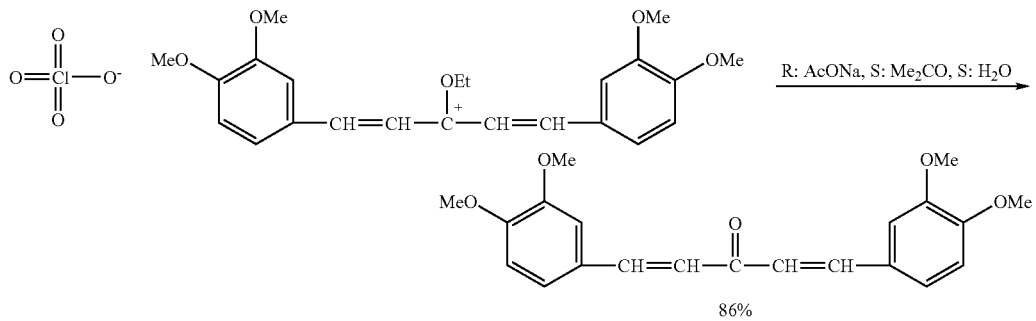

NOTE: Reactants: 1, Reagents: 1, Solvents: 2, Steps: 1, Stages: 1

Example 26

Structure-Activity Relationship for Nec-3 Compounds

A structure-activity relationship (SAR) study was carried out for a series of Nec-3 tricyclic compounds of formula (XXX) that inhibit tumor necrosis factor alpha (TNF-α) induced necroptosis.

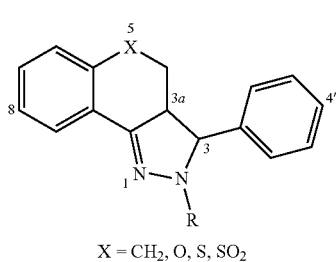

X = $CH_2$, O, S, $SO_2$

Chemistry

Compounds of formula (XXX), such as 3-phenyl-3,3a,4,5-tetrahydro-2H-benz[g]indazoles (X=$CH_2$), 3-phenyl-2,3,3a,4-tetrahydro[1]benzopyrano[4,3-c]pyrazoles (X=O) and 3-phenyl-2,3,3a,4-tetrahydro-[1]benzothiopyrano[4,3-c]pyrazoles (X=S), were prepared from 1-tetralones, 4-chromanones and 4-thiochromanones, respectively, according to the procedures outlined in Scheme 10. For example, compounds of formula (XXXI) (X=$CH_2$, O or S) were condensed with aromatic aldehydes in the presence of sodium hydroxide to give chalcone compounds of formula (XXXII). In the cases of 7-nitro-1-tetralone and 7-methoxy-4-chromanone condensations with 4-anisaldehyde were accomplished under acidic conditions. Treatment of compounds of formula (XXXII) with hydrazine hydrate in acetic acid gave a mixture of readily separable diastereomers of formula (XXXIII) [i.e. (3R,3aS)-rel-isomer] and formula (XXXIV) [i.e. (3R,3aR)-rel-isomer. 5,5-Dioxo-3-phenyl-2,3,3a,4-tetrahydro-[1]benzothiopyrano[4,3-c]pyrazoles (X=$SO_2$) compounds were prepared by oxidizing the corresponding 3-phenyl-2,3,3a,4-tetrahydro-[1]benzothiopyrano[4,3-c]pyrazoles of formula (XXXIII) and formula (XXXIV) with m-chloroperoxybenzoic acid (MCPBA).

Scheme 10.

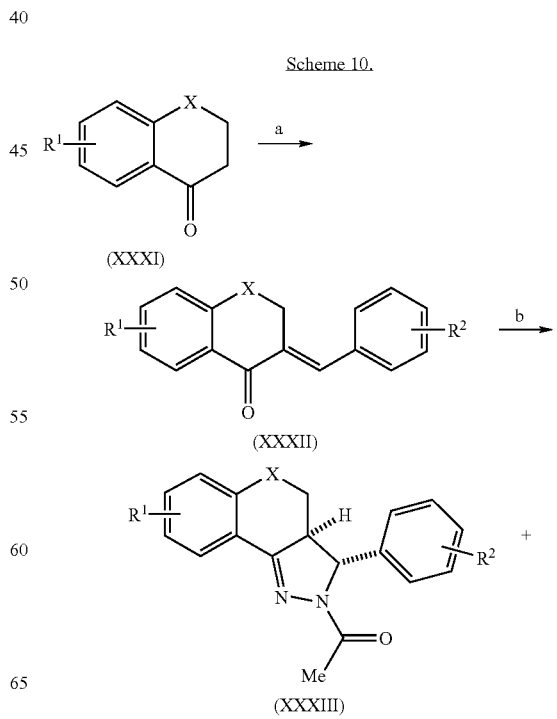

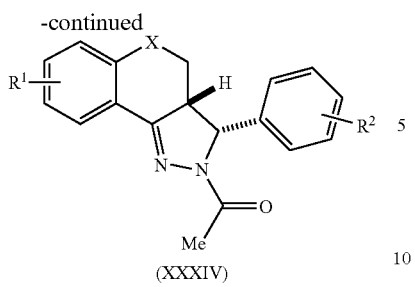

(XXXIV)

Reagents and conditions for Scheme 10: X = CH₂, O or S; (a) ArCHO, 8N NaOH, EtOH, room temperature, two hours; (b) CH₃CO₂H, NH₂NH·xH₂O, 120° C., 15 hours.

The stereochemical assignments were confirmed using $^1$H-NMR, 1-D nOe and HH—COSY experiments. For example, compound (141) was assigned as the (3R,3aR)-rel-isomer due to an intense nOe between protons at the 3a-position (δ 3.47-3.55) and the 3-position (δ 5.66), and a large coupling constant (J=11.2 Hz). The (3R,3aS)-rel-isomer (142) had a weak nOe between the protons at the 3a-position (δ 3.16-3.23) and at the 3-position (δ 4.91), a smaller coupling constant (J=9.2 Hz) and the proton at the 3a-position (δ 3.20) was shielded by the 4'-methoxyphenyl ring compared to the corresponding proton in the (3R,3aR)-rel-isomer.

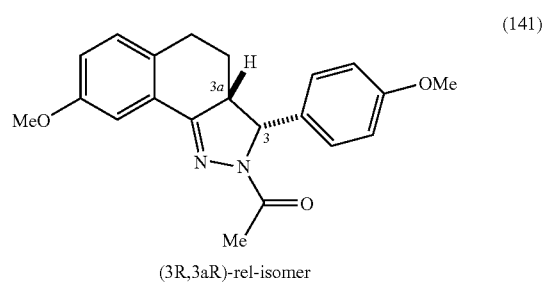

(141)

(3R,3aR)-rel-isomer

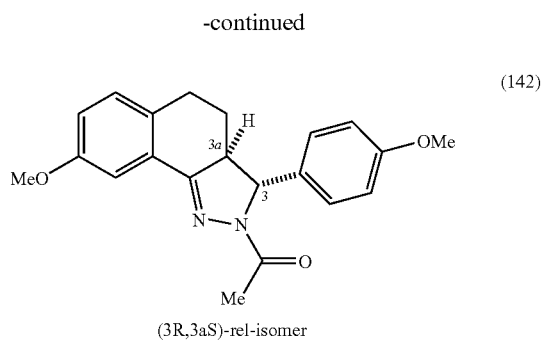

(142)

(3R,3aS)-rel-isomer

The 5-position of the 3,3a,4,5-tetrahydro-2H-benz[g]indazole ring system of (141) was modified as shown in Scheme 11. Introduction of an azide to this benzylic position utilizing Me₃SiN₃ in the presence of [bis(trifluoroacetoxy)iodo]-benzene was accomplished following the procedure of Kita et al. (Synlett 427-428, 1994) to give (143) in 29% yield. This reaction was also accompanied by an elimination reaction giving (144) in 31% yield. The azide (143) was subsequently reduced by hydrogenation to amine (145) and then converted to the tertiary amine (146) by reductive amination. The relative stereochemistry at the 5-position of (146) was established by $^1$H-NMR and HH—COSY experiments. The dimethylamine protons of (146) (δ 2.21) had an intense coupling interaction with the proton at the 3a-position (δ 4.03-4.09) indicative of a syn-relationship.

Scheme 11.

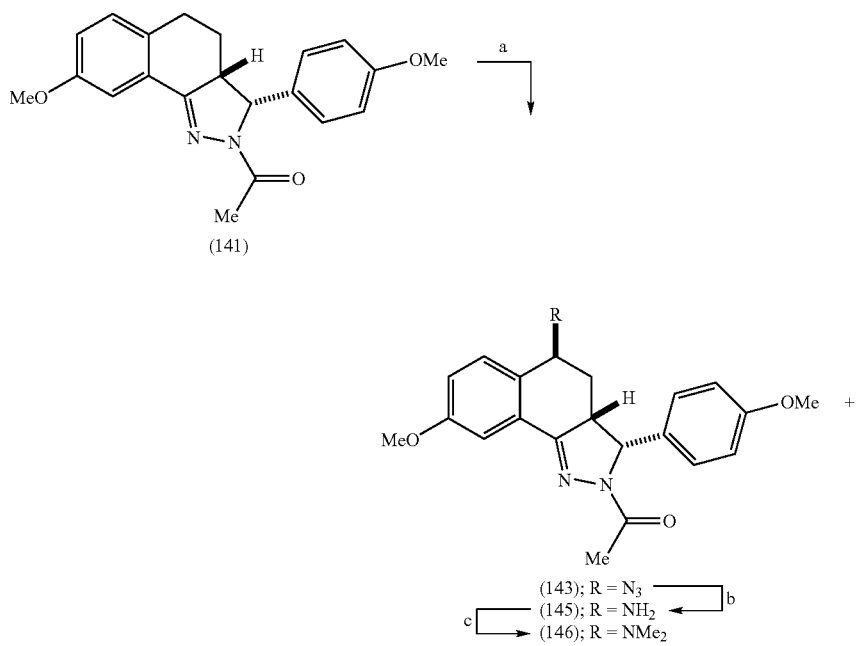

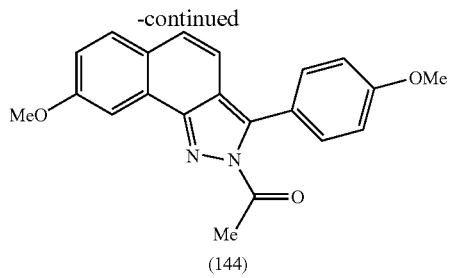

(144)

Reagents and conditions for Scheme 2: (a) Me₃SiN₃, [CF₃CO₂]₂PhI, room temperature, 24 hours (29% 9 and 31% 10); (b) H₂ (80 psi), 10% Pd—C, EtOAc, room temperature, 24 hours (59%); (c) aq. CH₂O, HCO₂H, THF, Δ 24 hours (47%).

Derivatives with various substituents on the 2-position of the tricyclic ring were also prepared. Compounds (147) and (148) were synthesized according to Scheme 10, except that formic acid and propionic acid, respectively, were used as solvent in place of acetic acid. When chalcone (I-15) was allowed to react with hydrazine hydrate in the presence of trimethylacetic acid, as shown in Scheme 12, amine (149) was isolated as a mixture of diastereomers (the material was subsequently used without purification). Unlike the case with acetic acid, utilizing a sterically demanding acid like trimethylacetic acid prevented direct amide formation and allowed for the isolation of the amine. Treatment of (149) with various acid chlorides yielded compounds of formula (XXXV) and formula (XXXVI). Amide (151) was subsequently generated from (150) upon treatment with NaOH in methanol. Cyclization of (I-15) with various semicarbazides and thiosemicarbazides, as depicted in Scheme 12, gave compounds of formula (XXXVII) and formula (XXXVIII). For example, (152), (153) and (154) are all compounds generated by this cyclization method. In all cyclization reactions reported herein the (3R,3aR)-rel- and (3R,3aS)-rel-isomers were isolated following separation by column chromatography on silica gel. Compound (152) was subsequently converted to (157) by a sequence of reactions involving alkylation with MeI to give intermediate (156) followed by treatment with ammonia in ethanol (Scheme 13). Finally, compound (213) was prepared from (141) by reduction with lithium aluminum hydride.

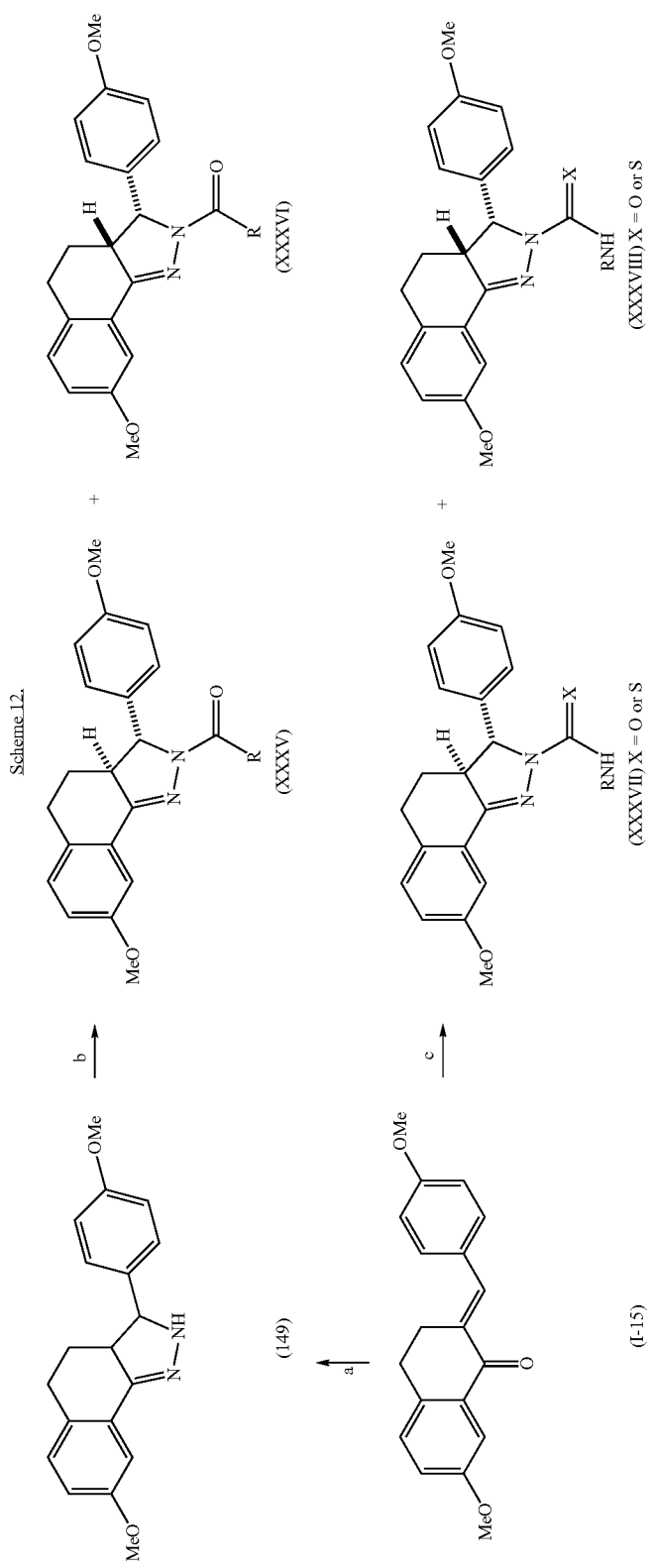

Scheme 13.

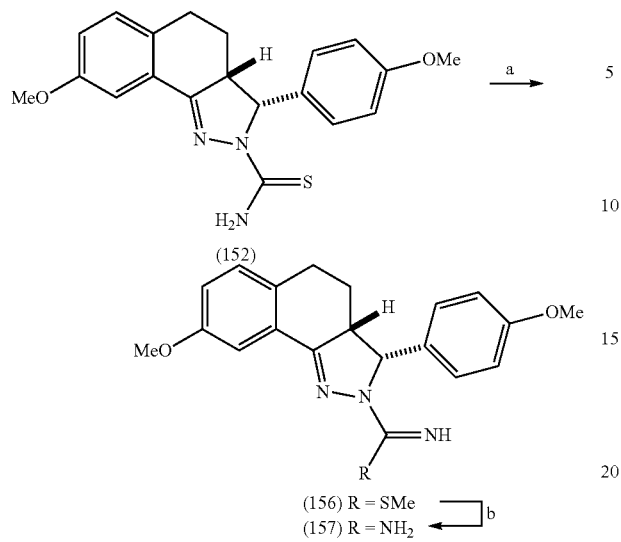

Reagents and conditions for Scheme 13: (a) MeI, EtOH, Δ, two hours (85%); (b) NH₃ (2.0 N in EtOH), 60° C., 16 hours (88%).

Evaluation of necroptosis inhibitory activity was performed using a FADD-deficient variant of human Jurkat T cells treated with TNF-α as described herein. Utilizing these conditions, the cells efficiently underwent necroptosis, which was completely and selectively inhibited by Nec-1 ($EC_{50}$=0.050 μM) as a positive control. For $EC_{50}$ value determinations, cells were treated with 10 ng/mL of human TNF-α in the presence of increasing concentration of test compounds for 24 hours followed by ATP-based viability assessment. For several key derivatives, $EC_{50}$ values were independently obtained in three separate experiments to verify accuracy and reproducibility. The $EC_{50}$ values±the standard deviations are shown.

TABLE 7

$EC_{50}$ determinations for inhibition of necroptosis in FADD-deficient Jurkat T cells treated with TNF-α

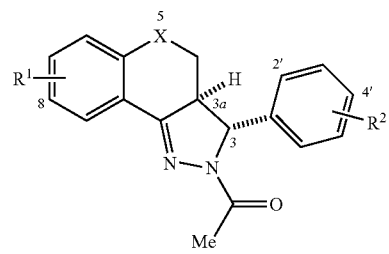

A = (3R, 3aS)-rel-isomer

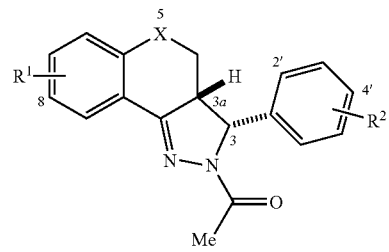

B = (3R, 3aR)-rel-isomer

| Cmpd | R¹ | R² | X | Rel-Isomer | $EC_{50}$ (μM)[a] |
|---|---|---|---|---|---|
| 160 | 8-OMe | 4'-F | CH₂ | A | 3.7 ± 0.75 |
| 161 | 8-OMe | 4'-F | CH₂ | B | 0.96 ± 0.085 |

TABLE 7-continued

EC$_{50}$ determinations for inhibition of necroptosis in FADD-deficient Jurkat T cells treated with TNF-α

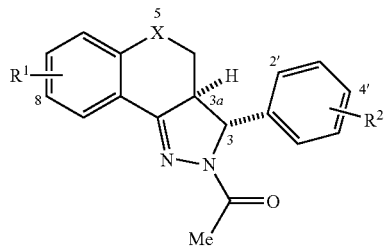

A = (3R, 3aS)-rel-isomer

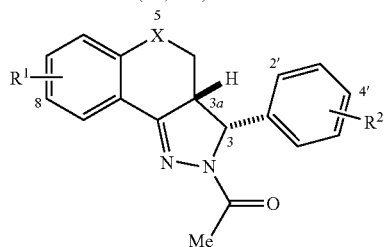

B = (3R, 3aR)-rel-isomer

| Cmpd | R$^1$ | R$^2$ | X | Rel-Isomer | EC$_{50}$ (μM)$^a$ |
|---|---|---|---|---|---|
| 162 | 7-OMe | 4'-F | CH$_2$ | A | >100 |
| 163 | 7-OMe | 4'-F | CH$_2$ | B | >100 |
| 164 | 7,8-di-OMe | 4'-F | CH$_2$ | B | >100 |
| 165 | H | 4'-F | CH$_2$ | B | 5.4 ± 1.1 |
| 166 | 8-OMe | 3'-F | CH$_2$ | B | 0.68 ± 0.0090 |
| 142 | 8-OMe | 4'-OMe | CH$_2$ | A | 6.4 ± 2.3 |
| 141 | 8-OMe | 4'-OMe | CH$_2$ | B | 0.29 ± 0.068 |
| 167 | H | 4'-OMe | CH$_2$ | B | 0.84 ± 0.32 |
| 168 | 8-NO$_2$ | 4'-OMe | CH$_2$ | A | >100 |
| 169 | 8-NO$_2$ | 4'-OMe | CH$_2$ | B | 3.5 ± 1.5 |
| 170 | 8-F | 4'-OMe | CH$_2$ | A | 2.7 ± 0.82 |
| 171 | 8-F | 4'-OMe | CH$_2$ | B | 0.28 ± 0.032 |
| 172 | 8-OMe | 4'-NO$_2$ | CH$_2$ | B | 1.8 ± 0.38 |
| 173 | 6-OMe | 4'-OMe | CH$_2$ | B | >100 |
| 174 | 8-OMe | 4'-OBn | CH$_2$ | B | >100 |
| 175 | 8-OMe | 4'-OH | CH$_2$ | B | 5.9 ± 1.4 |
| 176 | 8-OH | 4-OH | CH$_2$ | B | >100 |
| 177 | 8-OMe | 3', 4'-OCH$_2$O— | CH$_2$ | B | 2.6 ± 1.3 |
| 178 | 8-OMe | 3', 4'-O(CH$_2$)$_2$O— | CH$_2$ | B | 2.1 ± 0.65 |
| 179 | 8-OMe | 2'-OMe | CH$_2$ | B | >100 |
| 180 | 9-OMe | 4'-OMe | CH$_2$ | B | >50 |
| 181 | 8-OBn | 4'-OMe | CH$_2$ | B | 5.0 ± 0.70 |
| 182 | 8-OMe | 4'-SMe | CH$_2$ | B | 1.1 ± 0.69 |
| 183 | 8-O(CH$_2$)$_2$R$^b$ | 4'-OMe | CH$_2$ | B | >50 |
| 145$^c$ | 8-OMe | 4'-OMe | CHNH$_2$$^d$ | B | 1.2 ± 0.38 |
| 146 | 8-OMe | 4'-OMe | CHNMe$_2$$^d$ | B | 5.1 ± 2.2 |

$^a$EC$_{50}$ ± SD were determined from at least two independent experiments;
$^b$R = morpholine;
$^c$oxalate salt;
$^d$(5S)-rel- In five cases examined with the 3,3a,4,5-tetrahydro-2H-benz[g]indazole ring system, the (3R,3aR)-rel-isomers were more active than the corresponding (3R,3aS)-rel-isomers at inhibiting necroptosis (Table 7). For example, (141) was 28-times more potent than (142). In addition, introduction of the methoxy group at the 8-position of the tricyclic ring gave increased activity, e.g. (165) vs. (161) and (167) vs. (141).

Translocation of the methoxy group to the 6-, 7-, or 9-positions of the tricyclic ring, e.g. (173), (163) and (180), resulted in loss of activity. Increasing the size (181) or introduction of an amine onto the ether (183) at the 8-position of the tricyclic ring also resulted in diminished activity. An electron-withdrawing fluorine (171) was tolerated at the 8-position of the tricyclic ring. However, replacing the fluorine with a nitro group (169) diminished inhibitory activity. An electron-donating methoxy group on the 4'-position of the pendent phenyl ring resulted in increased activity compared to a fluorine or nitro substituent, e.g., (141) vs (161) and (172). However, increasing the size of the ether (174), transposition to the 2'-position (179), replacing it with a hydroxyl (175) or a thioether (182) was detrimental to activity to varying degrees. Introduction of a primary amine (145) or a tertiary amine (146) on the 5-position of the tricyclic ring also resulted in a significant (>10-fold) erosion of activity.

TABLE 8

EC$_{50}$ determinations for inhibition of necroptosis in FADD-deficient Jurkat T cells treated with TNF-α

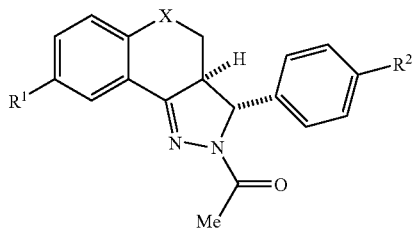

A = (3R, 3aS)-rel-isomer

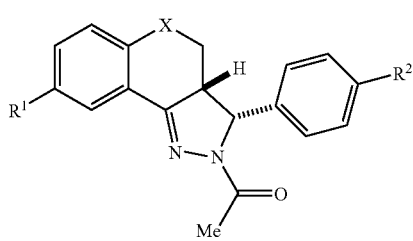

B = (3R, 3aR)-rel-isomer

| Cmpd | R$^1$ | R$^2$ | X | Rel-Isomer | EC$_{50}$ (μM)$^a$ |
|---|---|---|---|---|---|
| 184 | Me | F | O | A | >100 |
| 185 | Me | F | O | B | 11.6 ± 6.1 |
| 186 | OMe | F | O | B | 4.8 ± 1.3 |
| 187 | OMe | OMe | O | A | 9.9 ± 0.047 |
| 188 | OMe | OMe | O | B | 0.46 ± 0.0012 |
| 189 | F | OMe | O | A | >100 |
| 190 | F | OMe | O | B | 0.70 ± 0.13 |
| 191 | OMe | OMe | S | A | 5.1 ± 1.5 |
| 192 | OMe | OMe | S | B | 0.28 ± 0.070 |
| 193 | OMe | OMe | SO$_2$ | A | >100 |
| 194 | OMe | OMe | SO$_2$ | B | 0.75 ± 0.13 |

$^a$EC$_{50}$ ± SD were determined from at least two independent experiments.

Replacing the 3,3a,4,5-tetrahydro-2H-benz[g]indazole ring with a 2,3,3a,4-tetrahydro-[1]benzopyrano[4,3-c]pyrazole ring (Table 8) only resulted in a slight decrease in activity, e.g. (141) vs. (188) and (171) vs. (190). However, the difference in activities between the (3R,3aR)-rel- and (3R,3aS)-rel-isomers in some cases appeared to be more dramatic in the 2,3,3a,4-tetrahydro-[1]benzopyrano[4,3-c]pyrazole ring system, e.g. (189) vs. (190). The SAR of the pendent phenyl group appears to be comparable between the two ring systems. Replacing the 3,3a,4,5-tetrahydro-2H-benz[g]indazole ring with a 3-phenyl-2,3,3a,4-tetrahydro-[1]benzothiopyrano[4,3-c]pyrazole or a 5,5-dioxo-3-phenyl-2,3,3a,4-tetrahydro-[1]benzothiopyrano[4,3-c]pyrazole ring resulted in a more significant decrease in activity, e.g. (141) vs. (192) and (194).

Next, the SAR of various nitrogen substituents on the 2-position of the 3,3a,4,5-tetrahydro-2H-benz[g]indazole ring was examined (Table 9). In general, amides were best with the ethyl, hydroxymethyl and trifluoromethyl amides, i.e. (148), (191) and (159) being most comparable to (141). Introduction of ureas or thioureas to the 2-position of the tricyclic ring were detrimental to activity. Likewise, replacing the amide with an alkyl group (213) resulted in complete loss of necroptosis inhibitory activity.

TABLE 9

EC$_{50}$ determinations for inhibition of necroptosis in FADD-deficient Jurkat T cells treated with TNF-α

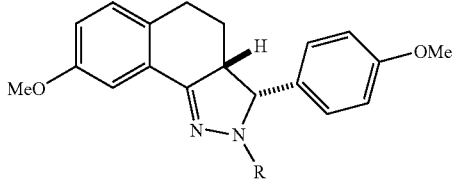

| Cmpd | R | EC$_{50}$ (μM)$^a$ |
|---|---|---|
| 147 | HC=O | 0.92 ± 0.091 |
| 148 | C(=O)Et | 0.15 ± 0.0035 |
| 150 | C(=O)CH$_2$OAc | 3.1 ± 0.17 |
| 151 | C(=O)CH$_2$OH | 0.16 ± 0.023 |
| 158 | C(=O)CH$_2$OMe | 0.44 ± 0.24 |
| 159 | C(=O)CF$_3$ | 0.39 ± 0.18 |
| 153 | C(=O)NH$_2$ | 4.3 ± 2.9$^b$ |
| 152 | C(=S)NH$_2$ | 8.8 ± 3.0 |
| 154 | C(=S)NHMe | 7.9 ± 2.0 |
| 157 | C(=NH)NH$_2$ | >100 |
| 213 | Et | >100 |

$^a$EC$_{50}$ ± SD were determined from at least two independent experiments.

The tricyclic compounds 3-phenyl-3,3a,4,5-tetrahydro-2H-benz[g]indazoles and 3-phenyl-2,3,3a,4-tetrahydro-[1]benzopyrano[4,3-c]pyrazoles were found to be potent necrostatins. A SAR study revealed that the (3R,3aR)-rel-diastereomers were more active then the corresponding (3R,3aS)-rel-diastereomers for both ring systems. Introduction of fluorine or methoxy to the 8-position of the tricyclic ring increased activity, while substitution at the 6, 7 and 9-positions were detrimental. Also, introduction of a methoxy group to the 4-position of the pendent phenyl ring increased activity, while placing the methoxy at the 2-position of the phenyl ring eliminated activity. Amides at the 2-position of the tricyclic ring systems were best. Furthermore, replacing the 3,3a,4,5-tetrahydro-2H-benz[g]indazole ring with a 3-phenyl-2,3,3a,4-tetrahydro-[1]benzothiopyrano[4,3-c]pyrazole or a 5,5-dioxo-3-phenyl-2,3,3a,4-tetrahydro-[1]benzothiopyrano[4,3-c]pyrazole ring resulted in a significant decrease in activity. Studies are currently underway to further evaluate these compounds in animal models of disease where necroptosis is likely to play a significant role (i.e., ischemic stroke). Moreover, these compounds can serve as molecular tools (i.e., infinity reagents) to further interrogate the mechanism(s) of necroptotic cell death.

Example 27

Methods

Chemistry Material and Methods

NMR spectra were obtained using a Bruker 400 MHz, Varian 400 MHz, or 500 MHz spectrometer. All $^1$H NMR spectra are reported in δ units ppm and are reference to tetramethylsilane (TMS) if conducted in CDCl$_3$, to the central line of the quintet at 3.30 ppm for samples in CD$_3$OD, to the central line of the quintet at 2.49 ppm for samples in d$_6$-DMSO. All $^{13}$C NMR spectra are reported in δ units ppm and are reference to the central line of the triplet at 77.23 ppm if conducted in CDCl$_3$, to the central line of the septet at 49.0 ppm for samples in CD$_3$OD, to the central line of the septet at 39.5 ppm for samples in d$_6$-DMSO. Coupling constants (J values) are reported in Hz. Column chromatography was performed on silica gel (Merck, grade 60, 230-400 mesh) or utilizing a CombiFlash Sg 100c separation system (ISCO) with RediSep disposable silica gel columns (ISCO). High-resolution mass spectra were obtained by using a SX-102A mass spectrometer (JEOL USA, Inc., Peabody, Mass.) or a LCT mass spectrometer (Micromass Inc., Beverly, Mass.). All melting points were taken in glass capillary tubes on a Mel-Temp® apparatus and are uncorrected. The elemental compositions of the compounds agreed to within±0.4% of the calculated values.

Preparation and Characterization of Compounds

General procedure for the synthesis of 2-arylidene-1-tetralones, 2-(arylidene)chroman-4-ones and 2-(arylidene)thiochroman-4-ones under basic conditions, exemplified for 2-(4-fluorobenzylidene)-7-methoxy-1-tetralone: To a solution of 7-methoxy-1-tetralone (1.760 g, 0.01 mol) and 4-fluorobenzaldehyde (1.240 g, 0.01 mol) in ethanol (20 mL) was slowly added an aqueous solution of NaOH (0.012 mol, 8 N) at room temperature. The mixture was stirred for two hours. The solid precipitate was collected by filtration and then washed sequentially with ethanol, water, and again with ethanol. The solid was dried in vacuo to give 2-(4-fluorobenzylidene)-7-methoxy-1-tetralone (2.485 g, 88%): mp 129-30° C., $^1$H NMR (500 MHz, CDCl$_3$): δ 2.88-2.91 (m, 2H), 3.06-3.10 (m, 2H), 3.87 (s, 3H), 7.06-7.13 (m, 3H), 7.17 (d, J=8.4 Hz, 1H), 7.42 (d, J=5.2 Hz, 1H), 7.44 (d, J=5.6 Hz, 1H), 7.61 (d, J=3.2 Hz, 1H), 7.81 (s, 1H). HFABMS m/z 283.1134 (calc for C$_{18}$H$_{16}$FO$_2$, MH$^+$, 283.1134).

General procedure for the synthesis of 2-arylidene-1-tetralones and 2-(arylidene)chroman-4-ones under acidic conditions, exemplified for 2-(4-methoxybenzylidene)-7-nitro-1-tetralone: A mixture of 7-nitro-1-tetralone (0.382 g, 2.0 mmol), 4-methoxybenzaldehyde (0.243 mL, 2.0 mmol) and concentrated HCl (10 mL) in methanol (5.4 mL) was heated at reflux for four hours. The mixture was allowed to cool to room temperature and then filtered. The residue was washed with a small amount of methanol and dried in vacuo to give 2-(4-methoxybenzylidene)-7-nitro-1-tetralone (2.485 g, 88%) as a pale yellow solid: $^1$H NMR (500 MHz, CDCl$_3$): δ 3.04-3.9 (m, 2H), 3.19-3.22 (m, 2H), 3.87 (s, 3H), 6.96-6.99 (m, 2H), 7.44-7.47 (m, 3H), 7.93 (s, 1H), 8.32 (dd, J$_1$=8.5 Hz, J$_2$=2.5 Hz, 1H), 8.94 (d, J=2.0 Hz, 1H). For characterization of other 2-arylidene-1-tetralones, 2-(arylidene)chroman-4-ones and 2-(arylidene)thiochroman-4-ones, see Example 2.

General procedure for the preparation of (3R,3aS)-rel- and (3R,3aR)-rel-2-acetyl-3,3a,4,5-tetrahydro-3-(aryl)-2H-benz[g]indazoles, 2-acetyl-2,3,3a,4-tetrahydro-[l]benzopyrano[4,3-c]pyrazoles and 2-acetyl-2,3,3a,4-tetrahydro-[l]benzothiopyrano[4,3-c]pyrazoles. Exemplified for (3R,3aS)-rel-2-acetyl-3,3a,4,5-tetrahydro-3-(4-fluorophenyl)-8-methoxy-2H-benz[g]indazole (160) and (3R,3aR)-rel-2-acetyl-3,3a,4,5-tetrahydro-3-(4-fluorophenyl)-8-methoxy-2H-benz[g]indazole (161): A solution of 2-(4-fluorobenzylidene)-7-methoxy-1-tetralone (0.300 g, 1.0 mmol), hydrazine hydrate (0.3 mL) in acetic acid (3 mL) was refluxed at 120° C. for 15 hours. The reaction mixture was concentrated and then dissolved in ethyl acetate. The organic layer was washed sequentially with water, saturated aqueous NaHCO$_3$, water and brine, dried over anhydrous Na$_2$SO$_4$, filtered and concentrated. The residue obtained was purified by silica gel column using ethyl acetate-hexane (3:7) to give (160) (0.051 g, 21%) and (161) (0.109 g, 45%). Yields were based on the recovery of starting material (95 mg).

(160): mp 165-67° C., $^1$H NMR (400 MHz, CDCl$_3$): δ 1.94-1.99 (m, 1H), 2.29-2.31 (m, 1H), 2.32 (s, 3H), 2.40-2.42 (m, 2H), 3.16-3.22 (m, 1H), 3.89 (s, 3H), 4.95 (d, J=9.6 Hz, 1H), 6.93-6.96 (dd, J=2.8 and 8.4 Hz, 1H), 7.04-7.08 (t, J=8.8 Hz, 2H), 7.12 (d, J=8.4 Hz, 1H), 7.28-7.32 (m, 2H), 7.46 (d, J=2.4 Hz, 1H). Anal. (C$_{20}$H$_{19}$FN$_2$O$_2$) C, H, N.

(161): mp 182-85° C., $^1$H NMR (400 MHz, CDCl$_3$): δ 1.02-1.06 (m, 1H), 1.75-1.78 (m, 1H), 2.48 (s, 3H), 2.81-2.87 (m, 2H), 3.54-3.57 (m, 1H), 3.90 (s, 3H), 5.72 (d, J=12.0 Hz, 1H), 6.93-7.11 (m, 6H), 7.56 (d, J=4.0 Hz, 1H). $^{13}$C NMR (400 MHz, CDCl$_3$): δ 22.13, 24.50, 28.30, 48.77, 55.73, 62.61, 107.83, 112.70, 115.62, 118.72; 127.99, 128.21, 130.26, 13225, 132.92, 155.79, 158.35, 161.13, 163.58, 168.72. Anal. (C$_{20}$H$_{19}$FN$_2$O$_2$) C, H, N.

(3R,3aS)-rel-2-acetyl-3,3a,4,5-tetrahydro-3-(4-fluorophenyl)-7-methoxy-2H-benz[g]indazole (162): yield 18%, mp 228-30° C., $^1$H NMR (400 MHz, CDCl$_3$): δ 1.89-2.00 (m, 1H), 2.24-2.30 (m, 1H), 2.38 (s, 3H), 2.88-2.94 (m, 2H), 3.12-3.19 (m, 1H), 3.83 (s, 3H), 4.89 (d, J=9.6 Hz, 1H), 6.68 (d, J=2.4 Hz, 1H), 6.83-6.85 (dd, J=2.4 and 8.4 Hz, 1H), 7.00-7.06 (m, 2H), 7.26-7.29 (m, 2H), 7.90 (d, J=8.8 Hz, 1H). Anal. (C$_{20}$H$_{19}$FN$_2$O$_2$) C, H, N.

(3R,3aR)-rel-2-acetyl-3,3a,4,5-tetrahydro-3-(4-fluorophenyl)-7-methoxy-2H-benz[g]indazole (163): yield 20%, $^1$H NMR (400 MHz, CDCl$_3$): δ 1.00-1.07 (m, 1H), 1.74-1.76 (m, 1H), 2.42 (s, 3H), 2.76-2.89 (m, 2H), 3.49-3.56 (m, 1H), 3.81 (s, 3H), 5.67 (d, J=10.8 Hz, 1H), 6.65 (s, 1H), 6.83-6.85 (dd, J=6.0 and 2.4 Hz, 1H), 6.94-7.06 (m, 4H), 7.99 (d, J=9.2 Hz, 1H). Anal. (C$_{20}$H$_{19}$FN$_2$O$_2$) C, H, N.

(3R,3aR)-rel-2-acetyl-3,3a,4,5-tetrahydro-3-(4-fluorophenyl)-7,8-dimethoxy-2H-benz[g]indazole (164): yield 33%, mp 189-93° C., $^1$H NMR (400 MHz, CDCl$_3$): δ 1.01-1.08 (m, 1H), 1.72-1.77 (m, 1H), 1.44 (s, 3H), 2.72-2.93 (m, 2H), 3.48-3.55 (m, 1H), 3.88 (s, 3H), 3.95 (s, 3H), 5.67 (d, J=10.8 Hz, 1H), 6.60 (s, 1H), 6.94-6.99 (dd, J=9.2 and 8.8 Hz, 2H), 7.04-7.07 (m, 2H), 7.47 (s, 1H). Anal. (C$_{21}$H$_{21}$FN$_2$O$_3$) C, H, N.

(3R,3aR)-rel-2-acetyl-3,3a,4,5-tetrahydro-3-(4-fluorophenyl)-2H-benz[g]indazole (165): yield 23%, mp 166-68° C., $^1$H NMR (400 MHz, CDCl$_3$): δ 1.06-1.11 (m, 1H), 1.77-1.81 (m, 1H), 2.47 (s, 3H), 2.87-2.95 (m, 2H), 3.56-3.63 (m, 1H), 5.72 (d, J=12.0 Hz, 1H), 7.00 (t, J=8.0 Hz, 2H), 7.06-7.10 (m, 2H), 7.19 (d, J=8.0 Hz, 1H), 7.28-7.36 (m, 2H), 8.09 (d, J=8.0 Hz, 1H). Anal. (C$_{19}$H$_{17}$FN$_2$O) C, H, N.

(3R,3aR)-rel-2-acetyl-3,3a,4,5-tetrahydro-3-(3-fluorophenyl)-8-methoxy-2H-benz[g]indazole (166): yield 39%, mp 176-77° C., $^1$H NMR (400 MHz, CDCl$_3$): δ 1.00-1.08 (m, 1H), 1.75-1.80 (m, 1H), 2.46 (s, 3H), 2.75-2.83 (m, 2H), 3.52-3.60 (m, 1H), 3.87 (s, 3H), 5.69 (d, J=11.2 Hz, 1H), 7.76-6.79 (dd, J=2.4 and 9.6 Hz, 1H), 6.86-6.95 (m, 3H), 7.06 (d, J=8.8 Hz, 1H), 7.23-7.28 (m, 1H), 7.53 (d, J=3.2 Hz, 1H). $^{13}$C NMR (400 MHz, CDCl$_3$): δ 22.18, 24.54, 28.97, 46.79, 55.75, 62.97, 107.18, 113.16, 114.65, 118.71, 121.92, 128.05, 130.27, 132.13, 139.57, 155.62, 156.22, 161.60, 164.24, 168.50. Anal. (C$_{20}$H$_{19}$FN$_2$O$_2$) C, H, N.

(3R,3a3)-rel-2-acetyl-3,3a,4,5-tetrahydro-3-(4-methoxyphenyl)-8-methoxy-2H-benz[g]indazole (142): yield 25%, mp 146-48° C., $^1$H NMR (400 MHz, CDCl$_3$): δ 1.89-1.95 (m, 1H), 2.25-2.29 (m, 1H), 2.39 (s, 3H), 2.85-2.87 (m, 2H), 3.16-3.23 (m, 1H), 3.79 (s, 3H), 3.86 (s, 3H), 4.91 (d, J=9.2 Hz, 1H), 6.87-6.93 (m, 3H), 7.09 (d, J=8.4 Hz, 1H), 7.22-7.25 (m, 2H), 7.44 (d, J=2.4 Hz, 1H). Anal. (C$_{21}$H$_{22}$N$_2$O$_3$) C, H, N.

(3R,3aR)-rel-2-acetyl-3,3a,4,5-tetrahydro-3-(4-methoxyphenyl)-8-methoxy-2H-benz[g]indazole (141): yield 30%, mp 151-53° C., $^1$H NMR (400 MHz, CDCl$_3$): δ 1.03-1.11 (m, 1H), 1.72-1.76 (m, 1H), 2.44 (s, 3H), 2.77-2.91 (m, 2H), 3.47-3.55 (m, 1H), 3.75 (s, 3H), 3.87 (s, 3H), 5.66 (d, J=11.2 Hz, 1H), 6.80 (d, J=8.8 Hz, 2H), 6.89-6.92 (dd, J=3.2 and 8.8 Hz, 1H), 6.99 (d, J=8.4 Hz, 2H), 7.06 (d, J=8.4 Hz, 1H), 7.54 (d, J=2.8 Hz, 1H). $^{13}$C NMR (400 MHz, CDCl$_3$): δ 22.15, 24.42, 28.93, 48.84, 55.42, 55.70, 63.03, 107.76, 112.66, 114.15, 118.56, 127.44, 127.88, 128.39, 129.26, 130.24, 132.32, 155.60, 158.28, 159.14, 168.56. Anal. ($C_{21}H_{22}N_2O_3$) C, H, N.

(3R,3aR)-rel-2-acetyl-3,3a,4,5-tetrahydro-3-(4-methoxyphenyl)-2H-benz[g]indazole (167): yield 30%, mp 257-60° C., $^1$H NMR (400 MHz, CDCl$_3$): δ 1.01-1.11 (m, 1H), 1.70-1.75 (m, 1H), 2.40 (s, 3H), 2.76-2.89 (m, 2H), 3.47-3.54 (m, 1H), 3.71 (s, 3H), 5.63 (d, J=11.2 Hz, 1H), 6.76 (d, J=8.4 Hz, 2H), 6.96 (d, J=8.8 Hz, 2H), 7.11 (d, J=6.8 Hz, 1H), 7.23-7.29 (m, 2H), 8.02-8.04 (dd, J=1.6 and 7.6 Hz, 1H). Anal. ($C_{20}H_{20}N_2O_2$) C, H, N.

(3R,3aS)-rel-2-acetyl-3,3a,4,5-tetrahydro-3-(4-methoxyphenyl)-8-nitro-2H-benz[g]indazole (168): yield 25%, $^1$H NMR (500 MHz, CDCl$_3$): δ 1.94-2.05 (m, 1H), 2.34-2.38 (m, 1H), 2.42 (s, 3H), 2.97-3.09 (m, 2H), 3.23-3.29 (m, 1H), 3.71 (s, 3H), 4.98 (d, J=9.5 Hz, 1H), 6.90 (d, J=9.0 Hz, 2H), 7.24 (d, J=7.0 Hz, 2H), 7.36 (d, J=8.5 Hz, 1H), 8.14 (dd, J=8.5 and 2.5 Hz, 1H), 8.79 (d, J=2.0 Hz, 1H). HFABMS m/z 366.1467 (calc for $C_{20}H_{20}N_3O_4$, MH$^+$, 366.1454).

(3R,3aR)-rel-2-acetyl-3,3a,4,5-tetrahydro-3-(4-methoxyphenyl)-8-nitro-2H-benz[g]indazole (169): yield 45%, $^1$H NMR (500 MHz, CDCl$_3$): δ 1.07-1.16 (m, 1H), 1.81-1.86 (m, 1H), 2.47 (s, 3H), 2.95-2.97 (m, 2H), 3.56-3.62 (m, 1H), 3.76 (s, 3H), 5.72 (d, J=11.5 Hz, 1H), 6.82 (d, J=9.0 Hz, 2H), 6.97 (d, J=8.5 Hz, 2H), 7.33 (d, J=8.5 Hz, 1H), 8.13 (dd, J=8.5 and 2.5 Hz, 1H), 8.89 (d, J=2.5 Hz, 1H). HFABMS m/z 366.1467 (calc for $C_{20}H_{20}N_3O_4$, MH$^+$, 366.1454).

(3R,3aS)-rel-2-acetyl-3,3a,4,5-tetrahydro-3-(4-methoxyphenyl)-8-fluoro-2H-benz[g]indazole (170): Required a second silica gel column chromatography purification using 2% MeOH in CH$_2$Cl$_2$; yield 26%, $^1$H NMR (500 MHz, CDCl$_3$): δ 1.89-1.99 (m, 1H), 2.27-2.32 (m, 1H), 2.38 (s, 3H), 2.85-2.95 (m, 2H), 3.18-3.24 (m, 1H), 3.70 (s, 3H), 4.92 (d, J=9.0 Hz, 1H), 6.88-6.91 (m, 2H), 7.01-7.05 (m, 1H), 7.14-7.16 (m, 1H), 7.23-7.25 (m, 2H), 7.63 (dd, J=9.5 and 2.5 Hz, 1H). HFABMS m/z 339.1523 (calc for $C_{20}H_{20}FN_2O_2$, MH$^+$, 339.1509).

(3R,3aR)-rel-2-acetyl-3,3a,4,5-tetrahydro-3-(4-methoxyphenyl)-8-fluoro-2H-benz[g]indazole (171): yield 29%, $^1$H NMR (500 MHz, CDCl$_3$): δ 1.03-1.12 (m, 1H), 1.74-1.79 (m, 1H), 2.44 (s, 3H), 2.78-2.89 (m, 2H), 3.49-3.55 (m, 1H), 3.76 (s, 3H), 5.67 (d, J=11.0 Hz, 1H), 6.81 (d, J=9.0 Hz, 2H), 6.97-7.04 (m, 3H), 7.11-7.13 (m, 1H), 7.72 (dd, J=9.5 and 3.0 Hz, 1H). HFABMS m/z 339.1493 (calc for $C_{20}H_{20}FN_2O_2$, MH$^+$, 339.1509).

(3R,3aR)-rel-2-acetyl-3,3a,4,5-tetrahydro-3-(4-nitroxyphenyl)-8-methoxy-2H-benz[g]indazole (172): yield 29%, mp 219-21° C., $^1$H NMR (400 MHz, CDCl$_3$): δ 0.91-1.01 (m, 1H), 1.71-1.75 (m, 1H), 2.43 (s, 3H), 2.75-2.82 (m, 2H), 3.57-3.64 (m, 1H), 3.84 (s, 3H), 5.74 (d, J=11.6 Hz, 1H), 6.88-6.91 (dd, J=3.2 and 8.4 Hz, 1H), 7.22 (d, J=9.6 Hz, 2H), 7.48 (d, J=3.2 Hz, 1H), 8.13 (d, J=9.6 Hz, 2H). Anal. ($C_{20}H_{19}N_3O_4$) C, H, N.

(3R,3aR)-rel-2-acetyl-3,3a,4,5-tetrahydro-3-(4-methoxyphenyl)-6-methoxy-2H-benz[g]indazole (173): yield 43%, mp 203-207° C., $^1$H NMR (500 MHz, CDCl$_3$): δ 0.98-1.07 (m, 1H), 1.74-1.79 (m, 1H), 2.43 (s, 3H), 2.45-2.52 (m, 1H), 3.04-3.09 (m, 1H), 3.48-3.54 (m, 1H), 3.76 (s, 3H), 3.82 (s, 3H), 5.68 (d, J=11.0 Hz, 1H), 6.80 (d, J=8.5 Hz, 2H), 6.86 (d, J=8.0 Hz, 1H), 7.00 (d, J=8.5 Hz, 2H), 7.24 (t, J=8.0 Hz, 1H), 7.68 (d, J=8.0 Hz, 1H). Anal. ($C_{21}H_{22}N_2O_3$) C, H, N.

(3R,3aR)-rel-2-acetyl-3,3a,4,5-tetrahydro-3-(4-benzyloxyphenyl)-8-methoxy-2H-benz[g]indazole (174): yield 41%, mp 156-61° C., $^1$H NMR (400 MHz, CDCl$_3$): δ 1.01-1.14 (m, 1H), 1.72-1.79 (m, 1H), 2.45 (s, 3H), 2.75-2.83 (m, 2H), 3.87 (s, 3H), 4.99 (s, 2H), 5.67 (d, J=10.8 Hz, 1H), 6.87-6.92 (m, 2H), 6.99 (d, J=8.4 Hz, 1H), 7.06 (d, J=8.8 Hz, 1H), 7.30-7.40 (m, 7H), 7.54 (d, J=3.2 Hz, 1H). Anal. ($C_{27}H_{26}N_2O_3$) C, H, N.

(3R,3aR)-rel-2-acetyl-3,3a,4,5-tetrahydro-3-(3,4-methylenedioxyphenyl)-8-methoxy-2H-benz[g]indazole (177): yield 41%, mp 206-209° C., $^1$H NMR (500 MHz, CDCl$_3$): δ 1.08-1.17 (m, 1H), 1.75-1.80 (m, 1H), 2.42 (s, 3H), 2.76-2.84 (m, 2H), 3.47-3.53 (m, 1H), 3.87 (s, 3H), 5.62 (d, J=11.4 Hz, 1H), 5.90 (s, 2H), 6.52 (d, J=1.5 Hz, 1H), 6.57-6.59 (dd, J=1.5 and 8.0 Hz, 1H), 6.72 (d, J=7.5 Hz, 1H), 6.90-6.92 (dd, J=3.0 and 8.5 Hz, 1H), 7.07 (d, J=8.2 Hz, 1H), 7.52 (d, J=2.5 Hz, 1H). Anal. ($C_{21}H_{20}N_2O_4$) C, H, N.

(3R,3aR)-rel-2-acetyl-3,3a,4,5-tetrahydro-3-(3,4-ethylenedioxyphenyl)-8-methoxy-2H-benz[g]indazole (178): yield 17%, mp 189-93° C., $^1$H NMR (500 MHz, CDCl$_3$): δ 1.06-1.15 (m, 1H), 1.78-1.80 (m, 1H), 2.41 (s, 3H), 2.75-2.86 (m, 2H), 3.46-3.52 (m, 1H), 3.87 (s, 3H), 4.22 (s, 4H), 5.60 (d, J=11.5 Hz, 1H), 6.55-6.58 (m, 2H), 6.76 (d, J=8.5 Hz, 1H), 6.89-6.91 (dd, J=3.0 and 9.0 Hz, 1H), 7.06 (d, J=8.0 Hz, 1H), 7.52 (d, J=3.0 Hz, 1H). Anal. ($C_{22}H_{22}N_2O_4$) C, H, N.

(3R,3aR)-rel-2-acetyl-3,3a,4,5-tetrahydro-3-(4-methoxyphenyl)-9-methoxy-2H-benz[g]indazole (180): yield 27%, mp 157-60° C., $^1$H NMR (500 MHz, CDCl$_3$): δ 1.09-1.18 (m, 1H), 1.67-1.72 (m, 1H), 2.49 (s, 3H), 2.83-2.95 (m, 2H), 3.53-3.59 (m, 1H), 3.78 (s, 3H), 3.98 (s, 3H), 5.57 (d, J=11.0 Hz, 1H), 6.77 (d, J=7.0 Hz, 1H), 6.80 (d, J=9.0 Hz, 2H), 6.84 (d, J=9.0 Hz, 1H), 7.04 (d, J=9.0 Hz, 2H), 7.25 (t, J=9.0 Hz, 1H). Anal. ($C_{21}H_{22}N_2O_3$) C, H, N.

(3R,3aR)-rel-2-acetyl-3,3a,4,5-tetrahydro-3-(4-methoxyphenyl)-8-benzyloxy-2H-benz[g]indazole (181): yield 36%, mp 155-57° C., $^1$H NMR (500 MHz, CDCl$_3$): δ 1.03-1.12 (m, 1H), 1.72-1.77 (m, 1H), 2.44 (s, 3H), 2.74-2.86 (m, 2H), 3.48-3.54 (m, 1H), 3.75 (s, 3H), 5.12 (s, 2H), 5.66 (d, J=10.5 Hz, 1H), 6.80 (d, J=8.5 Hz, 2H), 6.96 (d, J=3.0 Hz, 1H), 6.99 (d, J=8.5 Hz, 2H), 7.07 (d, J=8.0 Hz, 2H), 7.33-7.47 (m, 4H), 7.64 (d, J=3.0 Hz, 1H). Anal. ($C_{27}H_{26}N_2O_3$) C, H, N.

(3R,3aR)-rel-2-acetyl-3,3a,4,5-tetrahydro-3-(4-thiomethoxyphenyl)-8-methoxy-2H-benz[g]indazole (182): yield 22%, mp 144-47° C., $^1$H NMR (500 MHz, CDCl$_3$): δ 1.02-1.09 (m, 1H), 1.73-1.76 (m, 1H), 2.43 (s, 3H), 2.45 (s, 3H), 2.74-2.86 (m, 2H), 3.50-3.56 (m, 1H), 3.87 (s, 3H), 5.66 (d, J=10.5 Hz, 1H), 6.90-6.92 (dd, J=3.0 and 8.5 Hz, 1H), 6.99 (d, J=8.5 Hz, 2H), 7.06 (d, J=8.5 Hz, 1H), 7.16 (d, J=8.5 Hz, 2H), 7.53 (d, J=3.0 Hz, 1H). Anal. ($C_{21}H_{22}N_2O_2S$) C, H, N.

(3R,3aS)-rel-2-acetyl-2,3,3a,4-tetrahydro-3-(4-fluorophenyl)-8-methyl-[l]benzopyrano[4,3-c]pyrazole (184): yield 15%, mp 218-20° C., $^1$H NMR (400 MHz, CDCl$_3$): δ 2.36 (s, 3H), 2.42 (s, 3H), 3.53-3.57 (m, 1H), 4.13-4.19 (m, 1H), 4.60-4.64 (m, 1H), 4.99 (d, J=8 Hz, 1H), 6.85 (d, J=8 Hz, 1H), 7.05-7.09 (m, 2H), 7.16-7.31 (m, 3H), 7.63 (s, 1H). HFABMS m/z 325.1354 (calc for $C_{19}H_{17}FN_2O_2$, MH$^+$, 325.1352).

(3R,3aR)-rel-2-acetyl-3,3a,4,5-tetrahydro-3-(4-methoxyphenyl)-8-(4-morpholino)ethoxy-2H-benz[g]indazole (183): yield 33%, mp 122-26° C., $^1$H NMR (500 MHz, CDCl$_3$): δ 1.02-1.11 (m, 1H), 1.72 (m, 1H), 2.44 (s, 3H), 2.60 (t, J=4.5 Hz, 4H), 2.76-2.84 (m, 4H), 3.48-3.54 (m, 1H), 3.74-3.79 (m, 7H), 4.16-4.19 (m, 2H), 5.66 (d, J=10.5 Hz, 1H), 6.80 (d, J=8.5 Hz, 2H), 6.90-6.93 (dd, J=3.0 and 9.0 Hz, 1H), 6.99 (d, H=8.5 Hz, 2H), 7.06 (d, J=9.0 Hz, 1H), 7.55 (d, J=3.0 Hz, 1H). HFABMS m/z 450.2391 (calc for $C_{26}H_{31}N_3O_4$, MH$^+$, 450.2393).

(3R,3aR)-rel-2-acetyl-2,3,3a,4-tetrahydro-3-(4-fluorophenyl)-8-methyl-[l]benzopyrano[4,3-c]pyrazole (185): Required a second silica gel column chromatography purification using hexane/EtOAc/MeCN (65:25:10); yield 42%, mp 243-46° C., $^1$H NMR (400 MHz, CDCl$_3$): δ 2.36 (s, 3H), 2.48 (s, 3H), 3.29 (t, J=12 Hz, 1H), 3.72-3.83 (m, 1H), 4.14-

4.18 (m, 1H), 5.77 (d, J=12 Hz, 1H), 6.82 (d, J=8 Hz, 1H), 7.0-7.15 (m, 5H), 7.78 (s, 1H). HFABMS m/z 325.1359 (calc for $C_{19}H_{17}FN_2O_2$, MH$^+$, 325.1352).

(3R,3aR)-rel-2-acetyl-2,3,3a,4-tetrahydro-3-(4-fluorophenyl)-8-methoxy-[l]benzopyrano[4,3-c]pyrazole (186): yield 32%, mp 245° C. $^1$H NMR (500 MHz, CDCl$_3$): δ 2.45 (s, 3H), 3.21-3.27 (m, 1H), 3.84 (s, 3H), 3.82-3.87 (m, 1H), 4.10-4.14 (dd, J=10.5 and 12.5 Hz, 1H), 4.55-4.59 (dd, J=6.0 and 10.5 Hz, 1H), 5.75 (d, J=10.5 Hz, 1H), 6.82 (d, J=9.0 Hz, 1H), 6.91-6.94 (dd, J=3.5 and 9.5 Hz, 1H), 6.98-7.01 (dd, J=8.5 and 8.5 Hz, 2H), 7.06-7.08 (m, 2H), 7.33 (d, J=3.5 Hz, 1H). HFABMS m/z 341.1304 (calc for $C_{19}H_{17}FN_2O_3$, MH$^+$, 341.1301).

(3R,3aS)-rel-2-acetyl-2,3,3a,4-tetrahydro-3-(4-methoxyphenyl)-8-methoxy-[l]benzopyrano[4,3-c]pyrazole (187): yield 39%, $^1$H NMR (500 MHz, CDCl$_3$): δ 2.39 (s, 3H), 3.53-3:59 (m, 1H), 3.80 (s, 3H), 3.84 (s, 3H), 4.11 (dd, 1H, J=10.3, 12.8 Hz), 4.57 (dd, 1H, J=6.0, 10.5 Hz), 4.95 (d, 1H, J=10.0 Hz), 6.86 (d, 1H, J=9.0 Hz), 6.88-6.91 (m, 2H), 6.93 (dd, 1H, J=2.8, 9.3 Hz), 7.21-7.24 (m, 2H), 7.26-7.27 (m, 1H). HFABMS m/z 353.1485 (calc for $C_{20}H_{21}N_2O_4$, MH$^+$, 353.1501).

(3R,3aR)-rel-2-acetyl-2,3,3a,4-tetrahydro-3-(4-methoxyphenyl)-8-methoxy-[l]benzopyrano[4,3-c]pyrazole (188): yield 50%, $^1$H NMR (500 MHz, CDCl$_3$): δ 2.45 (s, 3H), 3.30 (dd, 1H, J=11.0, 13.0 Hz), 3.76 (s, 3H), 3.78-3.83 (m, 1H), 3.85 (s, 3H), 4.13 (dd, 1H, J=5.8, 10.8 Hz), 5.72 (d, 1H, J=11.0 Hz), 6.81-6.84 (m, 2H), 6.91 (dd, 1H, J=3.0, 9.5 Hz), 7.00-7.02 (m, 2H), 7.34 (d, 1H, J=3.5 Hz). HFABMS m/z 353.1492 (calc for $C_{20}H_{21}N_2O_4$, MH$^+$, 353.1501).

(3R,3aS)-rel-2-acetyl-2,3,3a,4-tetrahydro-3-(4-methoxyphenyl)-8-fluoro-[l]benzopyrano[4,3-c]pyrazole (189): yield 33%, $^1$H NMR (500 MHz, CDCl$_3$): δ 2.38 (s, 3H), 3.53-3.59 (m, 1H), 3.80 (s, 3H), 4.13 (dd, 1H, J=10.3, 12.8 Hz), 4.60 (dd, 1H, J=5.8, 10.3 Hz), 4.97 (d, 1H, J=9.5 Hz), 6.87-6.91 (m, 3H), 7.02-7.06 (m, 1H), 7.21-7.24 (m, 2H), 7.49 (dd, 1H, J=3.0, 8.0 Hz). HFABMS m/z 341.1312 (calc for $C_{19}H_{18}FN_2O_3$, MH$^+$, 341.1301).

(3R,3aR)-rel-2-acetyl-2,3,3a,4-tetrahydro-3-(4-methoxyphenyl)-8-fluoro[l]benzopyrano[4,3-c]pyrazole (190): yield 53%, $^1$H NMR (500 MHz, CDCl$_3$): δ 2.44 (s, 3H), 3.31 (dd, 1H, J=11.0, 13.0 Hz), 3.76 (s, 3H), 3.78-3.84 (m, 1H), 4.16 (dd, 1H, J=5.8, 11.3 Hz), 5.73 (d, 1H, J=11.0 Hz), 6.82-6.86 (m, 3H), 6.98-7.05 (m, 3H), 7.57 (dd, 1H, J=3.0, 8.5 Hz). HFABMS m/z 341.1310 (calc for $C_{19}H_{18}FN_2O_3$, MH$^+$, 341.1301).

(3R,3aS)-rel-2-acetyl-2,3,3a,4-tetrahydro-3-(4-methoxyphenyl)-8-methoxy-[l]benzothiopyrano[4,3-c]pyrazole (191): yield 36%, $^1$H NMR (500 MHz, CDCl$_3$): δ 2.39 (s, 3H), 3.07 (dd, 1H, J=4.5, 12.3 Hz), 3.33 (dd, 1H, J=12.3 Hz), 3.57-3.62 (m, 1H), 3.79 (s, 3H), 3.86 (s, 3H), 5.02 (d, 1H, J=8.5 Hz), 6.87-6.90 (m, 2H), 7.09 (d, 1H, J=9.0 Hz), 7.20-7.23 (m, 2H), 7.52 (d, 1H, J=3.0 Hz). HFABMS m/z 369.1273 (calc for $C_{20}H_{21}N_2O_3S$, MH$^+$, 369.1273).

(3R,3aR)-rel-2-acetyl-2,3,3a,4-tetrahydro-3-(4-methoxyphenyl)-8-methoxy-[l]benzothiopyrano[4,3-c]pyrazole (192): yield 52%, $^1$H NMR (500 MHz, CDCl$_3$): δ 2.41-2.51 (m, 2H), 2.45 (s, 3H), 3.77 (s, 3H), 3.86 (s, 3H), 3.89-3.95 (m, 1H), 5.67 (d, 1H, J=11.0 Hz), 6.83-6.85 (m, 2H), 6.88 (dd, 1H, J=3.0, 8.8 Hz), 7.00-7.03 (m, 2H), 7.09 (d, 1H, J=9.0 Hz), 7.65 (d, 1H, J=3.0 Hz). HFABMS m/z 369.1267 (calc for $C_{20}H_{21}N_2O_3S$, MH$^+$, 369.1273).

Preparation of (3R,3aR)-rel-2-acetyl-3,3a,4,5-tetrahydro-3-(4-hydroxyphenyl)-8-methoxy-2H-benz[g]indazole (175): A mixture of (174) (0.370 mg, 0.86 mmol) and 5% Pd—C (10 mg) in ethyl acetate (20 mL) was stirred under a hydrogen atmosphere for 20 h and then filtered though the pad of celite. The celite was then washed sequentially with ethyl acetate and acetic acid. The combined filtrates were concentrated. The solid obtained was recrystallized from ethyl acetate to give (175) (0.185 g, 63%): mp 240-41° C., $^1$H NMR (400 MHz, d$_6$-DMSO-CDCl$_3$): δ 0.99-1.11 (m, 1H), 1.72-1.76 (m, 1H), 2.43 (s, 3H), 2.67-2.83 (m, 2H), 3.46-3.53 (m, 1H), 3.87 (s, 3H), 5.61 (d, J=10.8 Hz, 1H), 6.74 (d, J=8.4 Hz, 2H), 6.87 (d, J=8.8 Hz, 2H), 6.61 (m, 1H), 7.07 (d, J=8.4 Hz, 1H), 7.43-7.46 (m, 1H), 7.52 (d, J=3.2 Hz, 1H). Anal. ($C_{20}H_{20}N_2O_3$) C, H, N.

Preparation of (3R,3aR)-rel-2-acetyl-3,3a,4,5-tetrahydro-3-(4-hydroxyphenyl)-8-hydroxy-2H-benz[g]indazole (176): To a solution of (175) (0.100 g, 0.28 mmol) under an argon atmosphere in dichloromethane (5 mL) was added BBr$_3$ (1.0 mL, 1.0 M solution in dichloromethane) at −78° C. The reaction mixture was stirred at room temperature for 1 h and then poured into an ice cold solution of HCl (1.0 N). The mixture was extracted in ethyl acetate. The organic layer was washed with water, dried over anhydrous Na$_2$SO$_4$, filtered and concentrated. The solid obtained was recrystallized from ethyl acetate to give (176): (62 mg, 67%): mp 164-67° C., $^1$H NMR (400 MHz, DMSO-CDCl$_3$): δ 0.70-0.90 (m, 1H), 1.41-1.46 (m, 1H), 2.41-2.57 (m, 5H), 3.15-3.22 (m, 1H), 5.29 (d, J=11.2 Hz, 1H), 6.43 (d, J=6.8 Hz, 2H), 6.53-6.57 (m, 3H), 6.68 (d, J=8.4 Hz, 1H), 7.19 (s, 1H). HFABMS m/z 323.1399 (calc for $C_{19}H_{18}N_2O_3$, MH$^+$, 323.1396).

Preparation of (3R,3aS)-rel-2-acetyl-2,3,3a,4-tetrahydro-3-(4-methoxyphenyl)-5,5-dioxo-8-methoxy-[l]benzothiopyrano[4,3-c]pyrazole (193) and (3R,3aR)-rel-2-acetyl-2,3,3a, 4-tetrahydro-3-(4-methoxyphenyl)-5,5-dioxo-8-methoxy-[l] benzothiopyrano[4,3-c]pyrazole (194): A solution of (191) (21 mg, 0.057 mmol) in dichloromethane (5 mL) at 0° C. was treated with MCPBA (60 mg). The reaction mixture was stirred at room temperature for 16 h and then diluted with ethyl acetate (50 mL), washed sequentially with saturated NaHCO$_3$ and brine, and dried over anhydrous sodium sulfate, filtered and concentrated. The residue was purified by column chromatography on silica gel using ethyl acetate-hexane (2:3) as eluent to give (193) (96%) as a white solid. (194) (92%) was prepared in a similar manner from (192).

(193): $^1$H NMR (500 MHz, CDCl$_3$): δ 2.41 (s, 3H), 3.54-3.62 (m, 2H), 3.81 (s, 3H), 3.95 (s, 3H), 4.09-4.15 (m, 1H), 5.03 (d, 1H, J=10.5 Hz), 6.89-6.92 (m, 2H), 7.14 (dd, 1H, J=2.3, 8.8), 7.21-7.24 (m, 2H), 7.56 (d, 1H, J=2.5 Hz), 7.88 (d, 1H, J=9.0 Hz). HFABMS m/z 401.1159 (calc for $C_{20}H_{21}N_2O_5S$, MH$^+$, 401.1171).

(194): $^1$H NMR (500 MHz, CDCl$_3$): δ 2.48 (s, 3H), 2.68 (dd, 1H, J=13.8 Hz), 3.11 (dd, 1H, J=4.3, 13.8 Hz), 3.77 (s, 3H), 3.95 (s, 3H), 4.40-4.46 (m, 1H), 5.80 (d, 1H, J=11.5 Hz), 6.84-6.86 (m, 2H), 6.96-6.98 (m, 2H), 7.14 (dd, 1H, J=3.0, 9.0 Hz), 7.64 (d, 1H, J=2.5 Hz), 7.86 (d, 1H, J=9.5 Hz). HFABMS m/z 401.1160 (calc for $C_{20}H_{21}N_2O_5S$, MH$^+$, 401.1171).

Preparation of (3R,3aS)-rel-2-formyl-3,3a,4,5-tetrahydro-3-(4-methoxyphenyl)-8-methoxy-2H-benz[g]indazole (195) and (3R,3aR)-rel-2-formyl-3,3a,4,5-tetrahydro-3-(4-methoxyphenyl)-8-methoxy-2H-benz[g]indazole (147): A solution of 2-(4-methoxybenzylidene)-7-methoxy-1-tetralone (2.0 g, 0.0068 mol), hydrazine hydrate (2.0 mL) in formic acid (20 mL) was heated at 120° C. for 2 days. The reaction mixture was concentrated and then extracted with ethyl acetate. The organic layer was washed sequentially with water, saturated aqueous NaHCO$_3$, water and brine, dried over anhydrous Na$_2$SO$_4$, filtered and then concentrated. The residue was purified by column chromatography on silica gel using ethyl acetate-hexane (3:7) as eluent to give compounds (195) (0.740 g, 32%) and (147) (0.905 g, 40%).

(195): mp 166-68° C., ¹H NMR (400 MHz, CDCl₃): δ 1.90-1.99 (m, 1H), 2.27-2.31 (m, 1H), 2.86-2.90 (m, 2H), 3.21-3.28 (m, 1H), 3.80 (s, 3H), 3.86 (s, 3H), 4.89 (d, J=9.6 Hz, 1H), 6.90-6.98 (m, 3H), 7.10 (d, J=8.8 Hz, 1H), 7.25-7.27 (m, 2H), 7.43 (d, J=2.4 Hz, 1H), 8.97 (s, 1H). Anal. (C₂₀H₂₀N₂O₃) C, H, N.

(147): mp 155-59° C., ¹H NMR (400 MHz, CDCl₃): δ 1.01-1.12 (m, 1H), 1.69-1.74 (m, 1H), 2.68-2.85 (m, 2H), 3.49-3.76 (m, 1H), 3.76 (s, 3H), 3.81 (s, 3H), 5.58 (d, J=11.2 Hz, 1H), 6.78-7.04 (m, 6H), 7.48 (d, J=3.2 Hz, 1H), 8.94 (s, 1H). Anal. (C₂₀H₂₀N₂O₃) C, H, N.

Preparation of (3R,3a8)-rel-2-propionyl-3,3a,4,5-tetrahydro-3-(4-methoxyphenyl)-8-methoxy-2H-benz[g]indazole (196) and (3R,3aR)-rel-2-propionyl-3,3a,4,5-tetrahydro-3-(4-methoxyphenyl)-8-methoxy-2H-benz[g]indazole (148): A solution of 2-(4-methoxybenzylidene)-7-methoxy-1-tetralone (0.500 g, 1.7 mmol) and hydrazine hydrate (0.5 mL) in propionic acid (5 mL) was refluxed at 140° C. for 2 days. The reaction mixture was concentrated and the residue dissolved in ethyl acetate (25 mL). The mixture was washed sequentially with water, saturated aqueous NaHCO₃ and water, dried over anhydrous Na₂SO₄, filtered and concentrated. The residue was purified by column chromatography on silica gel using ethyl acetate-hexane (3:7) as eluent to give (196) (0.217 g, 35%) and (148) (0.252 g, 41%).

(196): mp 133-36° C., ¹H NMR (400 MHz, CDCl₃): δ 1.15 (t, J=7.6 Hz, 3H), 1.85-1.96 (m, 1H), 2.23-2.29 (m, 1H), 2.74-2.87 (m, 4H), 3.15-3.22 (m, 1H), 3.78 (s, 3H), 3.86 (s, 3H), 4.89 (d, J=9.6 Hz, 1H), 6.87-6.92 (m, 3H), 7.08 (d, J=8.4 Hz, 1H), 7.23 (d, J=8.8 Hz, 2H), 7.44 (d, J=2.4 Hz, 1H). Anal. (C₂₂H₂₄N₂O₃) C, H, N.

(148): mp 150-52° C., ¹H NMR (400 MHz, CDCl₃): δ 1.05-1.10 (m, 1H), 1.21 (t, J=8.0 Hz, 3H), 1.70-1.78 (m, 1H), 2.74-2.88 (m, 4H), 3.47-3.52 (m, 1H), 3.75 (s, 3H), 3.87 (s, 3H), 5.65 (d, J=11.2 Hz, 1H), 6.80 (d, J=8.4 Hz, 2H), 6.89-6.92 (dd, J=3.2 and 8.4 Hz, 1H), 6.98 (d, J=8.8 Hz, 2H), 7.06 (d, J=8.4 Hz, 1H), 7.54 (d, J=3.2 Hz, 1H). Anal. (C₂₂H₂₄N₂O₃) C, H, N.

General procedure for the preparation of 2-substituted (3R,3aS)-rel- and (3R,3aR)-rel-3,3a,4,5-tetrahydro-3-(4-methoxyphenyl)-8-methoxy-2H-benz[g]indazoles. Exemplified for (3R,3aS)-rel-2-acetoxyacetyl-3,3a,4,5-tetrahydro-3-(4-methoxyphenyl)-8-methoxy-2H-benz[g]indazole (197) and (3R,3aR)-rel-2-acetoxyacetyl-3,3a,4,5-tetrahydro-3-(4-methoxyphenyl)-8-methoxy-2H-benz[g]indazole (150): A solution of 2-(4-methoxybenzylidene)-1-tetralone (1.0 g, 3.4 mmol), trimethylacetic acid (5.0 g), hydrazine hydrate (1.0 mL) in ethanol (5 mL) was refluxed for 6 h and then concentrated. The residue obtained was dissolved in ethyl acetate (10 mL) and then washed with water. The organic layer was slowly poured into a saturated NaHCO₃ solution (10 mL). The resulting solution was slowly treated with acetoxyacetyl chloride (1.83 mL, 17 mmol). The mixture was stirred at room temperature for 30 min. The ethyl acetate layer was separated, washed sequentially with water and brine, dried over anhydrous Na₂SO₄, filtered and concentrated. The residue was purified by column chromatography on silica gel column using ethyl acetate-hexane (2:3) as eluent to give compounds (197) (11%) and (150) (68%).

(197): mp 159-61° C., ¹H NMR (400 MHz, CDCl₃): δ 1.87-1.98 (m, 1H), 2.13 (s, 3H), 2.26-2.31 (m, 1H), 2.86-2.89 (m, 2H), 3.17-3.24 (m, 1H), 3.78 (s, 3H), 3.86 (s, 3H), 4.90 (d, J=9.2 Hz, 1H), 5.09 (d, J=15.6 Hz, 1H), 5.22 (d, J=15.6 Hz, 1H), 6.87-6.95 (m, 3H), 7.10 (d, J=8.8 Hz, 1H), 7.24 (d, J=8.8 Hz, 2H), 7.41 (d, J=3.2 Hz, 1H). Anal. (C₂₃H₂₄N₂O₅) C, H, N.

(150): mp 201-204° C., ¹H NMR (400 MHz, CDCl₃): δ 1.05-1.16 (m, 1H), 1.73-1.77 (m, 1H), 2.16 (s, 3H), 2.72-2.89 (m, 2H), 3.48-3.55 (m, 1H), 3.75 (s, 3H), 3.87 (s, 3H), 5.16-5.25 (m, 2H), 5.64 (d, J=11.2 Hz, 1H), 6.80 (d, J=8.8 Hz, 2H), 6.91-6.94 (dd, J=2.0 and 8.4 Hz, 1H), 6.99 (d, J=8.8 Hz, 2H), 7.07 (d, J=7.49 (d, J=3.2 Hz, 1H). Anal. (C₂₃H₂₄N₂O₅) C, H, N.

(3R,3aR)-rel-2-methoxyacetyl-3,3a,4,5-tetrahydro-3-(4-methoxyphenyl)-8-methoxy-2H-benz[g]indazole (158): yield 16%, mp 157-59° C., ¹H NMR (500 MHz, CDCl₃): δ 1.06-1.12 (m, 1H), 1.75-1.77 (m, 1H), 2.76-2.88 (m, 2H), 3.46-3.50 (m, 1H), 3.51 (s, 3H), 3.75 (s, 3H), 3.87 (s, 3H), 4.54 (d, J=16.0 Hz, 1H), 4.66 (d, J=16.0 Hi, 1H), 5.68 (d, J=11.0 Hz, 1H), 6.80 (d, J=9.5 Hz, 2H), 6.91-6.93 (dd, J=3.0 and 9.0 Hz, 1H), 6.98 (d, J=9.5 Hz, 2H), 7.07 (d, J=8.0 Hz, 1H), 7.50 (d, J=3.0 Hz, 1H). HFABMS m/z 381.1810 (calc for C₂₂H₂₄N₂O₄, MH⁺, 381.1814).

(3R,3aR)-rel-2-trifluoroacetyl-3,3a,4,5-tetrahydro-3-(4-methoxyphenyl)-8-methoxy-2H-benz[g]indazole (159): yield 22%, mp 220-22° C., ¹H NMR (500 MHz, CDCl₃): δ 1.09-1.18 (m, 1H), 1.75-1.80 (m, 1H), 2.77-2.89 (m, 2H), 3.53-3.59 (m, 1H), 3.76 (s, 3H), 3.87 (s, 3H), 5.68 (d, J=10 Hz, 1H), 6.84 (d, J=8.5 Hz, 2H), 6.94-6.97 (dd, J=3.0 and 8.5 Hz, 1H), 7.01 (d, J=8.5 Hz, 2H), 7.07 (d, J=8.5 Hz, 1H), 7.56 (d, J=3.0 Hz, 1H). HFABMS m/z 405.1432 (calc for C₂₁H₁₉F₃N₂O₃, MH⁺, 405.1426).

Preparation of (3R,3aR)-rel-2-hydroxyacetyl-3,3a,4,5-tetrahydro-3-(4-methoxyphenyl)-8-methoxy-2H-benz[g]indazole (151): To a solution 150 (0.150 g, 0.36 mmol) in methanol (10 mL) was added NaOH (50%, 2 mL) at room temperature. The reaction mixture was stirred at room temperature for 24 h before being diluted with ethyl acetate. The organic layer was washed with water, dried over anhydrous Na₂SO₄, filtered and concentrated. The residue obtained was purified by column chromatography on silica gel column using ethyl acetate-hexane (2:3) as eluent to furnish (151) (0.105 g, 78%): mp 163-64° C., ¹H NMR (400 MHz, CDCl₃): δ 1.06-1.17 (m, 1H), 1.72-1.78 (m, 1H), 2.76-2.89 (m, 2H), 3.76 (s, 3H), 3.87 (s, 3H), 4.55-7.70 (m, 2H), 5.66 (d, J=10.0 Hz, 1H), 6.82 (d, J=9.2 Hz, 2H), 6.92-6.95 (dd, J=2.4 and 8.8 Hz, 1H), 6.99 (d, J=9.2 Hz, 2H), 7.07 (d, J=8.4 Hz, 1H), 7.50 (d, J=2.4 Hz, 1H). ¹³C NMR (400 MHz, CDCl₃): δ 24.38, 28.90, 48.57, 55.46, 55.76, 61.40, 69.61, 108.02, 114.34, 119.12, 127.53, 127.84, 128.47, 130.32, 132.61, 157.67, 158.36, 159.42, 168.66. Anal. (C₂₁H₂₂N₂O₄) C, H, N.

General procedure for the preparation of 2-carbothioamides and 2-carboxamides of (3R,3aR)-rel-3,3a,4,5-tetrahydro-3-(4-methoxyphenyl)-8-methoxy-2H-benz[g]indazoles. Exemplified for (3R,3aR)-rel-2-carbothioamide-3,3a,4,5-tetrahydro-3-(4-methoxyphenyl)-8-methoxy-2H-benz[g]indazole (152): A suspension of 2-(4-methoxybenzylidene)-7-methoxy-1-tetralone (0.850 g, 0.0028 mol) and thiosemicarbazide (0.790 g, 0.0084 mol) in ethanol (30 mL) and concentrated HCl (2 mL) was refluxed for 6 h. The resulting solution was cooled to room temperature. The solid precipitate was isolated by filtration, washed with ethanol and then recrystallized from ethanol to give (152) (0.985 g, 96%): mp 236-39° C., ¹H NMR (500 MHz, CDCl₃): δ 1.04-1.13 (m, 1H), 1.76-1.81 (m, 1H), 2.75-2.87 (m, 2H), 3.60-3.66 (m, 1H), 3.76 (s, 3H), 3.85 (s, 3H), 6.07 (d, J=10.5 Hz, 1H), 6.83 (d, J=9.0 Hz, 2H), 6.93-6.95 (dd, J=3.0 and 8.5 Hz, 1H), 6.99 (d, J=9.0 Hz, 2H), 7.08 (d, J=8.5 Hz, 1H), 7.49 (d, J=3.0 Hz, 1H). HFABMS m/z 368.1439 (calc for C₂₀H₂₁N₃O₂S, MH⁺, 368.1433).

(3R,3aR)-rel-2-carboxamide-3,3a,4,5-tetrahydro-3-(4-methoxyphenyl)-8-methoxy-2H-benz[g]indazole (153): yield 75%, mp 217-20° C., ¹H NMR (500 MHz, CDCl₃): δ 1.02-1.11 (m, 1H), 1.74-1.79 (m, 1H), 2.73-2.86 (m, 2H), 3.54-3.60 (m, 1H), 3.75 (s, 3H), 3.86 (s, 3H), 5.58 (d, J=10.5

Hz, 1H), 6.81 (d, J=8.5 Hz, 2H), 6.88-6.90 (dd, J=3.0 and 8.5 Hz, 1H), 7.01 (d, J=8.5 Hz, 2H), 7.05 (d, J=8.5 Hz, 1H), 7.47 (d, J=3.0 Hz, 1H). HFABMS m/z 352.1663 (calc for $C_{20}H_{21}N_3O_3$, MH$^+$, 352.1663).

(3R,3aR)-rel-2-carbothioamide-3,3a,4,5-tetrahydro-3-(4-methoxyphenyl)-8-methoxy-N-methyl-2H-benz[g]indazole (154): yield 28%, mp 199-200° C., $^1$H NMR (500 MHz, CDCl$_3$): δ 1.02-1.11 (m, 1H), 1.76-1.81 (m, 1H), 2.75-2.86 (m, 2H), 3.21 (d, J=5.0 Hz, 3H), 3.56-3.62 (m, 1H), 3.75 (s, 3H), 3.87 (s, 3H), 6.10 (d, J=11.0 Hz, 1H), 6.80 (d, J=8.5 Hz, 2H), 6.91-6.94 (dd, J=3.0 and 8.5 Hz, 1H), 6.96 (d, J=8.5 Hz, 2H), 7.07 (d, J=8.5 Hz, 1H), 7.46 (m, 1H), 7.48 (d, J=3.0 Hz, 1H). HFABMS m/z 382.1579 (calc for $C_{21}H_{23}N_3O_2S$, MH$^+$, 382.1589).

Preparation of (3R,3aR)-rel-2-carboxamidine-3,3a,4,5-tetrahydro-3-(4-methoxyphenyl)-8-methoxy-2H-benz[g]indazole (156): A solution of (152) (0.5 g, 1.3 mmol) and methyl iodide (1.0 mL) in ethanol (10 mL) was refluxed for 2 h. When the reaction mixture was concentrated to a fourth of its volume a solid precipitate formed. The mixture was filtered and the solid was washed with cold ethanol to give (156) (565 mg, 85%) which was used without further purification. A solution of (156) (175 mg, 0.34 mmol) and ammonia (2.0 N solution in ethanol, 15 mL) in ethanol (15 mL) was stirred at 60° C. for 16 h. The reaction mixture was concentrated. The solid was recrystallized from methanol-diethyl ether to give (157) (105 mg, 88%): mp 170-75° C., $^1$H NMR (500 MHz, CDCl$_3$): δ 1.07-1.15 (m, 1H), 1.74-1.78 (m, 1H), 2.76-2.89 (m, 2H), 3.77 (s, 3H), 3.79-3.84 (m, 1H), 3.88 (s, 3H), 6.19 (d, J=10.5 Hz, 1H), 6.86 (d, J=8.5 Hz, 2H), 6.97-6.99 (dd, J=3.0 and 8.5 Hz, 1H), 7.10 (d, J=8.5 Hz, 2H), 7.50 (d, J=3.0 Hz, 1H). HFABMS m/z 351.1825 (calc for $C_{20}H_{22}N_4O_2$, MH$^+$, 351.1821).

Preparation of (3R,3aR,5S)-rel-2-acetyl-5-azido-3,3a,4,5-tetrahydro-3-(4-methoxyphenyl)-8-methoxy-2H-benz[g]indazole (143) and 2-acetyl-3-(4-methoxyphenyl)-8-methoxy-2H-benz[g]indazole (144): To a solution of (141) (800 mg, 2.2 mmol) in acetonitrile (10 mL) under an argon atmosphere was added trimethylsilyl azide (1.517 mL, 5.0 eq.) followed by slow addition of [bis(trifluoroacetoxy)iodo]benzene (2.948 g, 3.0 eq.). The reaction mixture was stirred at room temperature for 24 h. The reaction mixture was concentrated to give a dark brown residue that was purified by column chromatography on silica gel using ethyl acetate-hexane (1:3) as eluent to give (143) (252 mg, 29%), (144) (239 mg, 31%) and recovered starting material (141) (45 mg).

(143): thick oil, $^1$H NMR (500 MHz, CDCl$_3$): δ 1.24-1.28 (m, 1H), 1.82-1.88 (m, 1H), 2.46 (s, 3H), 3.74 (s, 3H), 3.86-3.89 (m, 1H), 3.91 (s, 3H), 4.66 (m, 1H), 5.70 (d, J=11.5 Hz, 1H), 6.80 (d, J=8.5 Hz, 2H), 6.96 (d, J=8.5 Hz, 2H), 7.0-7.02 (dd, J=3.0 and 9.0 Hz, 1H), 7.19 (d, J=9.0 Hz, 1H), 7.60 (d, J=3.0 Hz, 1H). HFABMS m/z 392.1722 (calc for $C_{21}H_{22}N_5O_3$, MH$^+$, 392.1723).

(144): mp 169-73° C., $^1$H NMR (500 MHz, CDCl$_3$): δ 3.02 (s, 3H), 3.91 (s, 3H), 4.04 (s, 3H), 7.10 (d, J=8.5 Hz, 2H), 7.27-7.29 (dd, J=3.0 and 8.5 Hz, 1H), 7.74 (d, J=2.5 Hz, 2H), 7.87 (d, J=8.5 Hz, 2H), 7.92 (d, J=8.5 Hz, 2H), 8.96 (d, J=2.5 Hz, 1H). HFABMS m/z 347.1365 (calc for $C_{21}H_{19}N_2O_3$, MH$^+$, 347.1396).

Preparation of (3R,3aR,5S)-rel-2-acetyl-5-amino-3,3a,4,5-tetrahydro-3-(4-methoxyphenyl)-8-methoxy-2H-benz[g]indazole (145): A solution of (143) (0.240 g, 0.61 mmol) and 10% Pd—C (50 mg) in ethyl acetate (10 mL) was stirred under hydrogen (80 psi) for 24 h. The reaction mixture was filtered though a short column of celite. The filtrate was triturated with aqueous acetic acid (50%, 10 mL). The solid was then recrystallized from ethyl acetate-water to give (145) (0.153 g, 59%): mp 116-19° C., $^1$H NMR (500 MHz, CDCl$_3$): δ 1.68-1.72 (m, 1H), 2.10-2.12 (m, 1H), 2.62 (s, 3H), 3.75 (s, 3H), 3.88 (s, 3H), 4.01-4.07 (m, 1H), 4.14-4.16 (m, 1H), 5.69 (d, J=11.0 Hz, 1H), 6.80 (d, J=8.5 Hz, 2H), 6.95-6.98 (m, 3H), 7.19 (d, J=9.0 Hz, 1H), 7.53 (d, J=3.0 Hz, 1H). HFABMS m/z 366.1818 (calc for $C_{21}H_{24}N_3O_3$, MH$^+$, 366.1818).

Preparation of (3R,3aR,5S)-rel-2-acetyl-5-(N,N-dimethylamino)-3,3a,4,5-tetrahydro-3-(4-methoxyphenyl)-8-methoxy-2H-benz[g]indazole (146): To a solution of (145) (210 mg, 0.57 mmol) in THF (10 mL) was added formic acid (0.150 mL) at 0° C., followed by slow addition of aqueous formaldehyde (37 wt %). The reaction mixture was refluxed for 24 h. The solution was allowed to cool, made basic with aqueous NaOH (25 wt %) and the extracted with ethyl acetate. The organic layer was washed with water, dried over anhydrous Na$_2$SO$_4$, filtered and concentrated. The residue was purified by column chromatography on silica gel using ethyl acetate as eluent to give (146) (105 mg, 47%): mp 123-28° C., $^1$H NMR (500 MHz, CDCl$_3$): δ 0.9-1.02 (m, 1H), 2.21 (s, 6H), 2.43 (s, 3H), 3.23 (m, 1H), 3.73 (s, 3H), 3.89 (s, 3H), 4.03-4.09 (m, 1H), 5.66 (d, J=11.0 Hz, 1H), 6.78 (d, J=8.5 Hz, 2H), 6.90-6.92 (dd, J=2.5 and 8.5 Hz, 1H), 6.96 (d, J=8.5 Hz, 2H), 7.12 (d, J=8.5 Hz, 1H), 7.58 (d, J=2.5 Hz, 1H). Anal. ($C_{23}H_{27}N_3O_3$) C, H, N.

Preparation of (3R,3aR)-rel-2-ethyl-3,3a,4,5-tetrahydro-3-(4-methoxyphenyl)-8-methoxy-2H-benz[g]indazole (157): To the solution of (141) (180 mg, 0.51 mmol) in THF (5 mL) was added LiAlH$_4$ (2.056 mL, 2.056 mmol; 1M in THF) at room temperature. The reaction mixture was stirred at room temperature for 1 h and then quenched with methanol followed by ice. The reaction mixture was extracted with ethyl acetate. Organic layer was washed with water, dried over anhydrous sodium sulfate and concentrated. The residue was purified by column chromatography on silica gel using 25% ethyl acetate-hexane as eluent to give (157) (30 mg, 17%): thick oil, $^1$H NMR (500 MHz, CDCl$_3$): δ 1.40 (t, J=7.0 Hz, 3H), 1.72-2.04 (m, 2H), 2.62-2.85 (m, 2H), 3.87 (s, 6H), 4.15 (q, J=7.0 Hz, 2H), 4.75 (d, J=10.5 Hz, 1H), 6.75-6.77 (dd, J=8.0 and 3.0 Hz, 1H), 7.01 (d, J=8.0 Hz, 2H), 7.12 (d, J=8.5 Hz, 1H), 7.29 (d, J=8.0 Hz, 2H), 7.44 (d, J=3.0 Hz, 1H). LRMS m/z 336.3 (calc for $C_{21}H_{24}N_2O_2$, M$^+$, 336.2).

Characterization of Compounds 198-212

(3R,3aS)-rel-2-acetyl-3,3a,4,5-tetrahydro-3-(4-fluorophenyl)-7,8-dimethoxy-2H-benz[g]indazole (198): yield 28%, mp 231-33° C., $^1$H NMR (400 MHz, CDCl$_3$): δ 1.92-1.97 (m, 1H), 2.24-2.27 (m, 1H), 2.40 (s, 3H), 2.86-2.90 (m, 2H), 3.11-3.18 (m, 1H), 3.89 (s, 3H), 3.96 (s, 3H), 4.89 (d, J=9.6 Hz, 1H), 6.63 (s, 1H), 7.01-7.06 (dd, J=2.4 and 8.8 Hz, 2H), 7.26-7.29 (m, 2H), 7.38 (s, 1H). HFABMS m/z 369.5 (calc for $C_{21}H_{22}FN_2O_3$, MH$^+$, 369.4095).

(3R,3aS)-rel-2-acetyl-3,3a,4,5-tetrahydro-3-(4-fluorophenyl)-2H-benz[g]indazole (199): yield 15%, mp 168-71° C., $^1$H NMR (400 MHz, CDCl$_3$): δ 2.00-2.04 (m, 1H), 2.31-2.35 (m, 1H), 2.42 (s, 3H), 2.96-2.99 (m, 2H), 3.19-3.25 (m, 1H), 4.97 (d, J=12.0 Hz, 1H), 7.07 (t, J=8.0 Hz, 2H), 7.22 (d, J=8.0 Hz, 1H), 7.28-7.35 (m, 4H), 7.99 (d, J=8.0 Hz, 1H). Anal. Calcd for $C_{19}H_{17}FN_2O$: C, 74.01; H, 5.56; N, 9.08. Found: C, 73.88; H, 5.48; N, 9.12.

(3R,3aS)-rel-2-acetyl-3,3a,4,5-tetrahydro-3-(3-fluorophenyl)-8-methoxy-2H-benz[g]indazole (200): yield 30%, mp 196-99° C., $^1$H NMR (400 MHz, CDCl$_3$): δ 1.92-1.99 (m, 1H), 2.27-2.32 (m, 1H), 2.42 (s, 3H), 2.86-2.89 (m, 2H), 3.14-3.20 (m, 1H), 3.87 (s, 3H), 4.93 (d, J=7.2 Hz, 1H), 6.91-7.01 (m, 3H), 7.08-7.10 (m, 2H), 7.29-7.34 (m, 1H), 7.43 (d, J=2.0 Hz, 1H). HFABMS m/z 339.1419 (calc for $C_{20}H_{19}FN_2O_2$, MH$^+$, 339.1509).

(3R,3aS)-rel-2-acetyl-3,3a,4,5-tetrahydro-3-(4-methoxyphenyl)-2H-benz[g]indazole (201): yield 20%, mp 260-62° C., $^1$H NMR (500 MHz, CDCl$_3$): δ 1.91-2.00 (m, 1H), 2.27-2.32 (m, 1H), 2.38 (s, 3H), 2.99-2.95 (m, 2H), 3.20-3.25 (m, 1H), 3.78 (s, 3H), 4.91 (d, J=9.5 Hz, 1H), 6.88 (d, J=9.0 Hz, 2H), 7.17 (d, J=2.5 Hz, 1H), 7.23-7.34 (m, 4H), 7.86 (d, J=7.0 Hz, 1H). Anal. Calcd for C$_{20}$H$_{20}$N$_2$O$_2$: C, 74.98; H, 6.29; N, 8.74. Found: C, 74.15; H, 6.18; N, 8.58.

(3R,3aS)-rel-2-acetyl-3,3a,4,5-tetrahydro-3-(4-nitroxyphenyl)-8-methoxy-2H-benz[g]indazole (202): yield 20%, mp 170-75° C., $^1$H NMR (400 MHz, CDCl$_3$): δ 1.90-2.01 (m, 1H), 2.23-2.28 (m, 1H), 2.38 (s, 3H), 2.83-2.87 (m, 2H), 3.10-3.17 (m, 1H), 3.83 (s, 3H), 4.98 (d, J=9.2 Hz, 1H), 6.89-6.91 (dd, J=2.4 and 7.6 Hz, 1H), 7.07 (d, J=8.4 Hz, 1H), 7.40 (d, J=2.4 Hz, 1H), 7.43 (d, J=8.4 Hz, 2H), 8.19 (d, J=8.4 Hz, 2H). HFABMS m/z 366.1462 (calc for C$_{20}$H$_{19}$N$_3$O$_4$, MH$^+$, 366.1454).

(3R,3aS)-rel-2-acetyl-3,3a,4,5-tetrahydro-3-(4-methoxyphenyl)-6-methoxy-2H-benz[g]indazole (203): yield 27%, mp 175-78° C., $^1$H NMR (500 MHz, CDCl$_3$): δ 1.85-1.89 (m, 1H), 2.32-2.35 (m, 1H), 2.38 (s, 3H), 2.53-2.60 (m, 1H), 3.09-3.18 (m, 2H), 3.79 (s, 3H), 3.84 (s, 3H), 4.91 (d, J=9.5 Hz, 1H), 6.86-6.89 (m, 3H), 7.23-7.27 (m, 3H), 7.57 (d, J=7.5 Hz, 1H). Anal. Calcd for C$_{21}$H$_{22}$N$_2$O$_3$: C, 71.98; H, 6.33; N, 7.99. Found: C, 71.72; H, 6.35; N, 8.02.

(3R,3aS)-rel-2-acetyl-3,3a,4,5-tetrahydro-3-(4-benzyloxyphenyl)-8-methoxy-2H-benz[g]indazole (204): yield 11%, mp 149-51° C., $^1$H NMR (500 MHz, CDCl$_3$): δ 1.88-1.97 (m, 1H), 2.25-2.29 (m, 1H), 2.39 (s, 3H), 2.86-2.88 (m, 2H), 3.17-3.22 (m, 1H), 3.87 (s, 3H), 4.95 (d, J=9.2 Hz, 1H), 5.07 (s, 2H), 6.90-6.92 (dd, J=3.0 and 9.0 Hz, 1H), 6.96 (d, J=9.0 Hz, 2H), 7.09 (d, J=8.5 Hz, 1H), 7.23 (d, J=8.5 Hz, 2H), 7.25 (s, 1H), 7.30-7.43 (m, 4H). Anal. Calcd for C$_{27}$H$_{26}$N$_2$O$_3$: C, 76.03; H, 6.14; N, 6.57. Found: C, 76.07; H, 5.95; N, 6.60.

(3R,3aS)-rel-2-acetyl-3,3a,4,5-tetrahydro-3-(3,4-methylenedioxyphenyl)-8-methoxy-2H-benz[g]indazole (205): yield 21%, mp 165-69° C., $^1$H NMR (500 MHz, CDCl$_3$): δ 1.87-1.94 (m, 1H), 2.25-2.29 (m, 1H), 2.41 (s, 3H), 2.86-2.88 (m, 2H), 3.14-3.19 (m, 1H), 3.84 (s, 3H), 4.87 (d, J=9.4 Hz, 1H), 5.94 (s, 2H), 6.76-6.78 (m, 3H), 6.90-6.93 (dd, J=3.0 and 8.5 Hz, 1H), 7.09 (d, J=9.0 Hz, 1H), 7.42 (d, J=2.5 Hz, 1H). Anal. Calcd for C$_{21}$H$_{20}$N$_2$O$_4$: C, 69.22; H, 5.53; N, 7.69. Found: C, 68.94; H, 5.65; N, 7.60.

(3R,3aS)-rel-2-acetyl-3,3a,4,5-tetrahydro-3-(3,4-ethylenedioxyphenyl)-8-methoxy-2H-benz[g]indazole (206): yield 28%, mp 194-97° C., $^1$H NMR (500 MHz, CDCl$_3$): δ 1.82-1.94 (m, 1H), 2.25-2.30 (m, 1H), 2.40 (s, 3H), 2.82-2.84 (m, 2H), 3.16-3.20 (M, 1H), 3.86 (s, 3H), 4.27 (s, 4H), 4.82 (d, J=9.0 Hz, 1H), 6.77-6.81 (m, 2H), 6.84 (d, J=8.0 Hz, 1H), 6.90-6.92 (dd, J=3.0 and 9.0 Hz, 1H), 7.08 (d, J=8.5 Hz, 1H), 7.42 (d, J=2.5 Hz, 1H). Anal. Calcd for C$_{22}$H$_{22}$N$_2$O$_4$: C, 69.83; H, 5.86; N, 7.40. Found: C, 68.58; H, 5.75; N, 7.25.

(3R,3aS)-rel-2-acetyl-3,3a,4,5-tetrahydro-3-(4-methoxyphenyl)-9-methoxy-2H-benz[g]indazole (207): yield 14%, mp 158-62° C., $^1$H NMR (500 MHz, CDCl$_3$): δ 1.91-1.99 (m, 1H), 2.23-2.28 (m, 1H), 2.42 (s, 3H), 2.95-2.97 (m, 2H), 3.19-3.24 (m, 1H), 3.79 (s, 3H), 3.98 (s, 3H), 4.84 (d, J=9.0 Hz, 1H), 6.79-6.80 (dd, J=1.0 and 8.5 Hz, 1H), 6.84 (d, J=8.5 Hz, 1H), 6.88 (d, J=9.0 Hz, 2H), 7.25-7.28 (m, 3H). Anal. Calcd for C$_{21}$H$_{22}$N$_2$O$_3$: C, 71.98; H, 6.33; N, 7.99. Found: C, 71.91; H, 6.38; N, 7.96.

(3R,3aS)-rel-2-acetyl-3,3a,4,5-tetrahydro-3-(4-methoxyphenyl)-8-benzyloxy-2H-benz[g]indazole (208): yield 19%, mp 144-46° C., $^1$H NMR (500 MHz, CDCl$_3$): δ 1.88-1.97 (m, 1H), 2.25-2.29 (m, 1H), 2.38 (s, 3H), 2.86-2.88 (m, 2H), 3.17-3.22 (m, 1H), 3.79 (s, 3H), 4.90 (d, J=9.5 Hz, 1H), 7.09 (s, 2H), 6.89 (d, J=9.0 Hz, 2H), 6.97-6.99 (dd, 2.0 and 8.5 Hz, 1H), 7.09 (d, J=8.5 Hz, 1H), 7.24 (d, J=9.0 Hz, 2H), 7.33-7.36 (m, 1H), 7.39-7.4 (m, 2H), 7.46-7.47 (m, 2H), 7.53 (d, J=2.0 Hz, 1H). HFABMS m/z 427.2029 (calc for C$_{27}$H$_{26}$N$_2$O$_3$, MH$^+$, 427.2022).

(3R,3aS)-rel-2-acetyl-3,3a,4,5-tetrahydro-3-(4-thiomethoxyphenyl)-8-methoxy-2H-benz[g]indazole (209): yield 19%, mp 144-45° C., $^1$H NMR (500 MHz, CDCl$_3$): δ 1.89-1.98 (m, 1H), 2.25-2.30 (m, 1H), 2.40 (s, 3H), 2.46 (s, 3H), 2.85-2.88 (m, 2H), 3.15-3.21 (m, 1H), 3.86 (s, 3H), 4.90 (d, J=9.5 Hz, 1H), 6.90-6.93 (dd, J=3.0 and 8.5 Hz, 1H), 7.09 (d, J=9.0 Hz, 1H), 7.22-7.25 (m, 4H), 7.43 (d, J=3.0 Hz, 1H). HFABMS m/z 367.1471 (calc for C$_{21}$H$_{22}$N$_2$O$_2$S, MH$^+$, 367.1480).

(3R,3aS)-rel-2-acetyl-3,3a,4,5-tetrahydro-3-(4-methoxyphenyl)-8-(4-morpholino)ethoxy-2H-benz[g]indazole (210): yield 30%, mp 97-99° C., $^1$H NMR (500 MHz, CDCl$_3$): δ 1.88-1.96 (m, 1H), 2.25-2.29 (m, 1H), 2.38 (s, 3H), 2.60 (t, J=3.6 Hz, 4H), 2.82-2.87 (m, 4H), 3.17-3.22 (m, 1H), 3.75 (t, J=4.5 Hz, 4H), 3.79 (s, 3H), 4.17 (d, J=5.5 Hz, 2H), 4.90 (d, J=9.5 Hz, 1H), 6.88 (d, J=9.5 Hz, 2H), 6.91-6.93 (dd, J=3.0 and 9.0 Hz, 1H), 7.08 (d, J=8.5 Hz, 1H), 7.24 (d, J=9.0 Hz, 2H), 7.45 (d, J=3.0 Hz, 1H). HFABMS m/z 450.2393 (calc for C$_{26}$H$_{31}$N$_3$O$_4$, MH$^+$, 450.2393).

(3R,3aS)-rel-2-acetyl-2,3,3a,4-tetrahydro-3-(4-fluorophenyl)-8-methoxy-[1]benzopyrano[4,3-c]pyrazole (211): yield 34%, mp 174-76° C. $^1$H NMR (500 MHz, CDCl$_3$): δ 2.40 (s, 3H), 3.50-3.56 (m, 1H), 3.84 (s, 3H), 4.10-4.14 (dd, J=10.5 and 12.5 Hz, 1H), 4.55-4.59 (dd, J=6.0 and 10.5 Hz, 1H), 4.97 (d, J=9.5 Hz, 1H), 6.86 (d, J=8.5 Hz, 1H), 6.92-6.94 (dd, J=3.0 and 8.5 Hz, 1H), 7.05 (dd, J=8.5 and 9 Hz, 2H), 7.25-7.28 (m, 3H). HFABMS m/z 341.1306 (calc for C$_{19}$H$_{17}$FN$_2$O$_3$, MH$^+$, 341.1301).

(3R,3aS)-rel-2-methoxyacetyl-3,3a,4,5-tetrahydro-3-(4-methoxyphenyl)-8-methoxy-2H-benz[g]indazole (212): yield 49%, mp 124-27° C., $^1$H NMR (500 MHz, CDCl$_3$): δ 1.87-1.96 (m, 1H), 2.26-2.30 (m, 1H), 2.86-2.88 (m, 2H), 3.15-3.21 (m, 1H), 3.48 (s, 3H), 3.78 (s, 3H), 3.87 (s, 3H), 4.50 (d, J=16.0 Hz, 1H), 4.56 (d, J=16.0 Hz, 1H), 4.93 (d, J=9.5 Hz, 1H), 6.88 (d, J=9.0 Hz, 2H), 6.91-6.94 (dd, J=3.0 and 8.5 Hz, 1H), 7.10 (d, J=8.5 Hz, 1H), 7.22 (d, J=9.0 Hz, 2H), 7.40 (d, J=3.0 Hz, 1H).

Evaluation of Necroptosis Inhibitory Activity

Necroptosis activity was performed using a FADD-deficient variant of human Jurkat T cells treated with TNF-α as described herein. For EC$_{50}$ value determinations, cells (500,000 cells/mL, 100 μL per well in a 96-well plate) were treated with 10 ng/mL of human TNF-α in the presence of increasing concentration of test compounds for 24 hours followed by ATP-based viability assessment. Compound test concentrations were 0.03-100 μM. Cell viability assessments were performed using a commercial luminescent ATP-based assay kit (CellTiter-Glo, Promega, Madison, Wis.). Cell viability values were adjusted to account for nonspecific toxicity, which in most cases were <10%. EC$_{50}$ values were calculated using nonlinear regression analysis of sigmoid dose-response (variable slope) curves from plots of log [I] verses viability values.

Example 28

Synthesis of Tetralones

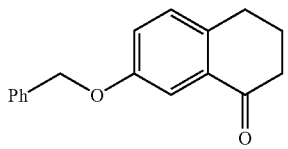

Preparation of 7-benzyloxy-1-tetralone: To a suspension of 7-hydroxy-1-tetralone (1.0 g, 0.0061 mol) and K$_2$CO$_3$ (5.5 g) in DMF (20 mL) under an argon atmosphere was added benzyl bromide (0.725 mL, 0.0061 mol) at room temperature. The reaction mixture was then stirred at room temperature for 18 h before being poured onto ice. The aqueous solution was extracted with ethyl acetate, washed with water, dried over anhydrous Na$_2$SO$_4$, filtered and concentrated. The residue was purified by column chromatography on silica gel using ethyl acetate-hexane (15%) as eluent to give compound 7-benzyloxy-1-tetralone (1.395 g, 90%): thick oil, $^1$H NMR (500 MHz, CDCl$_3$): δ 2.09-2.14 (m, 2H), 2.63 (d, J=6.5 Hz, 2H), 2.90 (d, J=6.0 Hz, 2H), 5.75 (s, 2H), 7.11-7.13 (dd, J=3.0 and 8.5 Hz, 1H), 7.17 (d, J=8.5 Hz, 1H), 7.31-7.45 (m, 5H), 7.62 (d, J=3.0 Hz, 1H). HFABMS m/z 253.1231 (calc for C$_{17}$H$_{16}$O$_2$, MH$^+$, 253.1229).

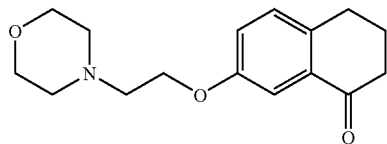

Preparation of 7-(2-morpholino-4-yl-ethoxy)-1-tetralone: To a suspension of 7-hydroxy-1-tetralone (0.900 g, 5.5 mmol) and K$_2$CO$_3$ (5 g) in DMF (20 mL) was added 4-(2-chloroethyl)morpholine hydrochloride (1.035 g, 5.5 mmol) at room temperature and under an argon atmosphere. The reaction mixture was stirred at room temperature for ~16 hours before being poured on ice. The aqueous solution was extracted in ethyl acetate, washed with water, and dried over anhydrous Na$_2$SO$_4$, filtered and concentrated. The residue was purified by column chromatography on silica gel using ethyl acetate-hexane (2:8) as eluent to give 7-(2-morpholino-4-ylethoxy)-1-tetralone (1.260 g, 83%): thick oil, $^1$H NMR (500 MHz, CDCl$_3$): δ 2.08-2.14 (m, 2H), 2.56-2.58 (m, 4H), 2.63 (t, J=7.0 Hz, 2H), 2.80 (t, J=5.0 Hz, 2H), 2.88 (t, J=6.5 Hz, 2H), 3.73 (t, J=5.0 Hz, 2H), 4.14 (t, J=6.0 Hz, 2H), 7.06-7.08 (dd, J=3.0 and 8.5 Hz, 1H), 7.17 (d, J=8.5 Hz, 1H), 7.51 (d, J=3.0 Hz, 1H). HFABMS m/z 276.1599 (calc for C$_{16}$H$_2$NO$_3$, MH$^+$, 276.1600).

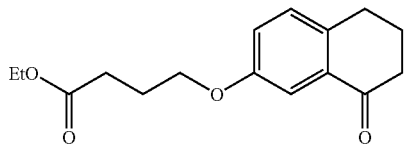

Preparation of 7-(3-etboxycarbonylpropoxy)-1-tetralone: To a suspension of 7-hydroxy-tetralone (0.870 g, 5.3 mmol) and K$_2$CO$_3$ (5 g, excess) in DMF (20 mL) was added ethyl-4-bromobutyrate (0.770 mL, 5.3 mmol) at room temperature and under argon atmosphere. The reaction mixture was stirred at room temperature for ~16 hours before being poured on ice. The aqueous solution was extracted in ethyl acetate, washed with water, and dried over anhydrous Na$_2$SO$_4$, filtered and concentrated. The residue was purified by column chromatography on silica gel using ethyl acetate-hexane (2:8) as eluent to give 7-(3-ethoxycarbonylpropoxy)-1-tetralone (1.180 g, 80%): mp 62-63° C., $^1$H NMR (500 MHz, CDCl$_3$): δ 1.26 (t, J=7.0 Hz, 3H), 2.08-2.14 (m, 4H), 2.48-2.51 (dd, J=7.00 and 7.5 Hz, 2H), 2.62-2.64 (dd, J=6.0 and 6.5 Hz, 2H), 2.88-2.90 (dd, J=6.0 and 6.5 Hz, 2H), 4.02-4.05 (dd, J=6.0 and 6.5 Hz, 2H), 4.15 (q, J=7.0 Hz, 2H), 7.03-7.05 (dd, J=3.0 and 8.0 Hz, 1H), 7.16 (d, J=8.0 Hz, 1H), 7.49 (d, J=3.0 Hz, 1H). HFABMS m/z 277.1436 (calc for C$_{16}$H$_{20}$O$_4$, MH$^+$, 277.1440).

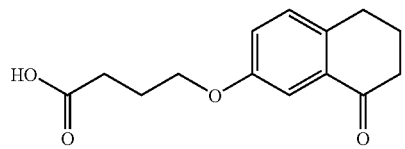

Preparation of 4-(8-oxo-5,6,7-tetrahydro-naphathalen-2-yloxy)butyric acid: The 7-(3-ethoxycarbonylpropoxy)-1-tetralone (1.100 g, 3.9 mmol) was dissolved in methanol (20 mL), and treated with NaOH (2 mL, 10N) and stirred at room temperature for 30 minutes, and acidified with dilute HCl (1.0 N). Then the reaction mixture was extracted in ethyl acetate, washed with water, and dried on Na$_2$SO$_4$. The residue obtained after concentration of ethyl acetate was recrystallized from ethyl acetate-hexane give acid 4-(8-oxo-5,6,7-tetrahydro-naphathalen-2-yloxy)butyric acid (0.970 g, 99%): mp 119-20° C., $^1$H NMR (500 MHz, CDCl$_3$): δ 2.10-2.15 (m, 4H), 2.56-2.59 (m, 2H), 2.63 (t, J=6.5 Hz, 2H), 2.89 (t, J=6.5 Hz, 2H), 4.06 (t, J=6.5 Hz, 2H), 7.03-7.05 (dd, J=3.0 and 8.5 Hz, 1H), 7.15 (d, J=8.5 Hz, 1H), 7.49 (d, J=3.0 Hz, 1H). HFABMS m/z 249.1132 (calc for C$_{14}$H$_{16}$O$_4$, MH$^+$, 249.1127).

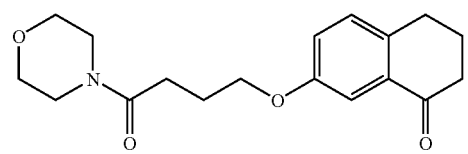

Preparation of 7-(4-morpholin-4-yl-4-oxo-butoxy)-1-tetralone: To a suspension of 7-(3-ethoxycarbonylpropoxy)-1-tetralone (0.925 g, 3.7 mmol), HUBT (1.415 g, 3.7 mmol), N,N-diisopropylethyl amine (1.3 mL) in CH$_2$Cl$_2$ (20 mL) was added morpholine (0.330 mL, 3.7 mmol) at room temperature and under argon atmosphere. The reaction mixture was then stirred at room temperature for 24 h and then concentrated. The residue dissolved in ethyl acetate (50 mL) and the organic layer was washed with dil. HCl, water, brine, and dried over anhydrous $Na_2SO_4$, filtered and concentrated. The residue was purified on the column of silica gel using ethyl acetate-hexane (8:2) as an eluent to give 7-(4-morpholin-4-yl-4-oxo-butoxy)-1-tetralone (1.010 g, 86%): mp 88-90° C., $^1$H NMR (500 MHz, $CDCl_3$): δ 2.07-2.15 (m, 4H), 2.50 (t, J=7.5 Hz, 2H), 2.61 (T, J=7.5 Hz, 2H), 2.88 (t, J=6.0 Hz, 2H), 3.46 (t, J=5.0 Hz, 2H), 3.59-3.66 (m, 6H), 4.04 (t, J=6.0 Hz, 2H), 7.01-7.03 (dd, J=3.0 and 8.5 Hz, 1H), 7.15 (d, J=8.5 Hz, 1H), 7.48 (d, J=3.0 Hz, 1H). HFABMS m/z 318.1706 (calc for $C_{18}H_{23}NO_4$, $MH^+$, 318.1705).

All 2-arylidene-1-tetralones, 2-(arylidene)chroman-4-ones and 2-(arylidene)thiochroman-4-ones were prepared using the basic conditions, except where noted.

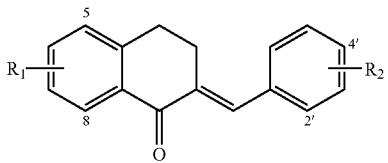

$R_1$=H; $R_2$=4'-F: yield 70%, mp 114-17° C., $^1$H NMR (500 MHz, $CDCl_3$): δ 2.95 (t, J=6.5 Hz, 2H), 3.09-3.12 (m, 2H), 7.09-7.13 (dd, J=9.0 and 8.5 Hz, 2H), 7.24-7.26 (m, 1H), 7.31-7.52 (m, 4H), 7.81 (s, 1H), 8.18 (d, J=9.00 Hz, 1H), HFABMS m/z 253.1026 (calc for $C_{17}H_{14}FO$, $MH^+$, 253.1029).

$R_1$=6-OMe; $R_2$=4'-F: yield 75%, mp 104-8° C., $^1$H NMR (500 MHz, $CDCl_3$): δ 2.90-2.93 (dd, J=6.0 and 6.5 Hz, 2H), 3.06-3.10 (m, 2H), 3.87 (s, 3H), 6.71 (d, J=3.0 Hz, 1H), 6.87 (dd, J=2.5 and 9.0 Hz, 1H), 7.08-7.11 (dd, J=9.0 and 8.5 Hz, 2H), 7.39-7.42 (dd, J=8.5 Hz each, 2H), 7.76 (s, 1H), 8.11 (d, J=9.0 Hz, 1H). HFABMS m/z 283.1132 (calc for $C_{18}H_{16}FO_2$, $MH^+$, 283.1134).

$R_1$=6,7-di-OMe; $R_2$=4'-F: yield 89%, mp 151-53° C., $^1$H NMR (500 MHz, $CDCl_3$): δ 2.88-2.91 (dd, J=6.5 and 7.0 Hz, 2H), 3.07-3.10 (m, 2H), 3.95 (s, 6H), 6.67 (s, 1H), 7.08-7.12 (dd, J=9.0 and 8.5 Hz, 2H), 7.39-7.42 (m, 2H), 7.62 (s, 1H), 7.77 (s, 1H). HFABMS m/z 313.1237 (calc for $C_{19}H_{18}FO_3$, $MH^+$, 313.1240).

$R_1$=7-OMe; $R_2$=3'-F: yield 57%, mp 95-97° C., $^1$H NMR (500 MHz, $CDCl_3$): δ 2.89-2.91 (m, 2H), 3.07-3.10 (m, 2H), 3.87 (s, 3H), 7.03-7.21 (m, 4H), 7.39-7.40 (m, 1H), 7.61 (d, J=2.4 Hz, 1H), 7.78 (s, 1H). HFABMS m/z 283.1230 (calc for $C_{18}H_{16}FO_2$, $MH^+$, 283.1134).

$R_1$=5-OMe; $R_2$=4'-OMe: yield 69%, mp 97-101° C., $^1$H NMR (500 MHz, $CDCl_3$): δ 2.91-2.98 (m, 2H), 3.09-3.12 (m, 2H), 3.85 (s, 3H), 3.87 (s, 3H), 6.95 (d, J=9.0 Hz, 2H), 7.04 (d, J=7.5 Hz, 1H), 7.31 (t, J=7.5 Hz, 1H), 7.43 (d, J=9.0 Hz, 2H), 7.74-7.76 (dd, J=1.0 and 7.5 Hz, 1H), 7.80 (s, 1H). HFABMS m/z 295.1335 (calc for $C_{19}H_{18}O_3$, $MH^+$, 295.1334).

$R_1$=7-OMe; $R_2$=4'-OMe: yield 78%, mp 133-37° C., $^1$H NMR (500 MHz, $CDCl_3$): δ 2.87-2.90 (dd, J=6.0 and 7.0 Hz, 2H), 3.10-3.13 (m, 2H), 3.85 (s, 3H), 3.87 (s, 3H), 6.94-6.96 (dd, J=2.5 and 7.00 Hz, 2H), 7.05-7.07 (dd, J=2.5 and 8.00 Hz, 1H), 7.16 (d, J=8.0 Hz, 1H), 7.42-7.44 (dd, J=2.0 and 7.0 Hz, 2H), 7.61 (d, J=2.5 Hz, 1H), 7.83 (s, 1H). HFABMS m/z 295.1339 (calc for $C_{19}H_{19}O_3$, $MH^+$, 295.1339).

$R_1$=8-OMe; $R_2$=4'-OMe: yield 70%, mp 117-20° C., $^1$H NMR (500 MHz, $CDCl_3$): δ 2.83-2.86 (m, 2H), 3.01-3.04 (m, 2H), 3.87 (s, 3H), 3.92 (s, 3H), 6.81-6.82 (d, J=7.0 Hz, 1H), 6.88 (d, J=8.5 Hz, 1H), 6.92 (d, J=9.0 Hz, 2H), 7.37-7.40 (dd, J=8.0 and 8.5 Hz, 1H), 7.42 (d, J=9.0 Hz, 2H), 7.82 (s, 1H). HFABMS m/z 295.1335 (calc for $C_{19}H_{19}O_3$, $MH^+$, 295.1334).

$R_1$=7-OMe; $R_2$=4'-$NO_2$: yield 86%, mp 158-62° C., $^1$H NMR (500 MHz, $CDCl_3$): δ 2.91-2.94 (dd, J=6.5 and 6.0 Hz, 2H), 3.06-3.09 (m, 2H), 3.87 (s, 3H), 7.09-7.12 (dd, J=2.5 and 8.0 Hz, 1H), 7.19 (d, J=8.0 Hz, 1H), 7.57 (d, J=9.0 Hz, 2H), 7.62 (d, J=2.5 Hz, 1H), 7.83 (s, 1H), 8.27 (d, J=9.0 Hz, 2H). HFABMS m/z 310.1081 (calc for $C_{18}H_{16}NO_4$, $MH^+$, 310.1079).

$R_1$=H; $R_2$=4'-OMe: yield 64%, mp 110-13° C., $^1$H NMR (500 MHz, $CDCl_3$): δ 2.94-2.96 (t, J=6.5 Hz, 2H), 3.13-3.16 (m, 2H), 3.87 (s, 3H), 6.94-6.97 (m, 2H), 7.25 (d, J=9.0 Hz, 1H), 7.34-7.37 (dd, J=7.5 and 7.0 Hz, 1H), 7.43 (d, J=9.0 Hz, 2H), 7.46-7.50 (m, 1H), 7.85 (s, 1H), 8.21 (d, J=8.0 Hz, 1H). HFABMS m/z 265.1223 (calc for $C_{18}H_{17}O_2$, $MH^+$, 265.1229).

$R_1$=7-OMe; $R_2$=4'-OBn: yield 53%, mp 119-24° C., $^1$H NMR (500 MHz, $CDCl_3$): δ 2.87-2.89 (dd, J=6.0 and 7.0 Hz, 2H), 3.10-3.13 (m, 2H), 3.87 (s, 3H), 5.11 (s, 2H), 7.01-7.05 (m, 2H), 7.06 (d, J=3.0 Hz, 1H), 7.07 (d, J=3.0 Hz, 1H), 7.16 (d, J=8.5 Hz, 1H), 7.33-7.45 (m, 6H), 7.61 (d, J=3.0 Hz, 1H), 7.83 (s, 1H). HFABMS m/z 371.1651 (calc for $C_{25}H_{23}O_3$, $MH^+$, 371.1647).

$R_1$=7-OMe; $R_2$=3',4'-$OCH_2O$: yield 57%, mp 134-35° C., $^1$H NMR (500 MHz, $CDCl_3$): δ 2.87-2.90 (dd, J=6.0 and 7.0 Hz, 2H), 3.09-3.12 (m, 2H), 3.87 (s, 3H), 6.01 (s, 2H), 6.86 (d, J=8.5 Hz, 1H), 6.95-6.99 (m, 2H), 7.06 (d, J=2.5 Hz, 1H), 7.07 (d, J=2.5 Hz, 1H), 7.16 (d, J=8.0 Hz, 1H), 7.60 (d, J=3.0 Hz, 1H), 7.78 (s, 1H). HFABMS m/z 309.1120 (calc for $C_{19}H_{16}O_4$, $MH^+$, 309.1127)

$R_1$=7-OMe; $R_2$=3',4'-$OCH_2CH_2O$: yield 61%, mp 128-34° C., $^1$H NMR (500 MHz, $CDCl_3$): δ 2.87-2.89 (dd, J=6.0 and 6.5 Hz, 2H), 3.10-3.13 (m, 2H), 3.87 (s, 3H), 4.28-4.31 (m, 4H), 6.90 (d, J=8.0 Hz, 1H), 6.97-7.01 (m, 2H), 7.05-7.07 (dd, J=3.0 and 8.8 Hz, 1H), 7.16 (d, J=8.0 Hz, 1H), 7.60 (d, J=3.0 Hz, 1H), 7.76 (s, 1H). HFABMS m/z 323.1279 (calc for $C_{20}H_{19}O_4$, $MH^+$, 323.1283).

$R_1$=7-OMe; $R_2$=4'-OMe: yield 60%, mp 100-104° C., $^1$H NMR (500 MHz, $CDCl_3$): δ 2.87-2.90 (m, 2H), 3.11-3.14 (m, 2H), 3.85 (s, 3H), 5.13 (s, 3H), 6.95 (d, J=9.0 Hz, 2H), 7.11-7.18 (m, 3H), 7.33-7.47 (m, 6H), 7.71 (d, J=2.5 Hz, 1H), 7.83 (s, 1H). HFABMS m/z 371.1642 (calc for $C_{25}H_{22}O_3$, $MH^+$, 371.1647).

$R_1$=7-$OCH_2CH_2$morpholine; $R_2$=4'-OMe: yield 79%, mp 62-65° C., $^1$H NMR (500 MHz, $CDCl_3$): δ 2.59 (t, J=4.5 Hz, 4H), 2.82 (t, J=5.5 Hz, 2H), 2.88 (t, J=5.5 Hz, 2H), 3.10-3.13 (m, 2H), 3.74 (t, J=4.5 Hz, 4H), 3.85 (s, 3H), 4.18 (t, J=6.0 Hz, 2H), 6.95 (d, J=9.0 Hz, 2H), 7.07-7.09 (dd, J=2.5 and 8.0 Hz, 1H), 7.16 (d, J=8.0 Hz, 1H), 7.43 (d, J=9.0 Hz, 2H), 7.62 (d, J=3.0 Hz, 1H), 7.83 (s, 1H). HFABMS m/z 394.2012 (calc for $C_{24}H_{27}NO_4$, $MH^+$, 394.2018).

$R_1$=7-$OCH_2CH_2CH_2C(O)$morpholine; $R_2$=4'-OMe: yield 92%, mp 128-31° C., $^1$H NMR (500 MHz, $CDCl_3$): δ 2.14-2.19 (m, 2H), 2.53 (t, J=6.5 Hz, 2H), 2.88 (t, J=6.5 Hz, 2H), 3.10-3.13 (m, 2H), 3.49 (t, J=5.0 Hz, 2H), 3.62-3.68 (m, 6H), 3.85 (s, 3H), 4.10 (t, J=6.5 Hz, 2H), 6.93-6.96 (m, 2H), 7.03-7.06 (dd, J=3.0 and 8.5 Hz, 1H), 7.16 (d, J=8.0 Hz, 1H), 7.43 (d, J=8.5 Hz, 2H), 7.60 (d, J=3.0 Hz, 1H), 7.83 (s, 1H). HFABMS m/z 436.2119 (calc for $C_{26}H_{29}NO_5$, $MH^+$, 436.2124).

$R_1$=7-OMe; $R_2$=4'-SMe: yield 68%, mp 104-6° C., $^1$H NMR (500 MHz, $CDCl_3$): δ 2.52 (s, 3H), 2.87-2.90 (m, 2H), 3.09-3.12 (m, 2H), 3.87 (s, 3H), 7.06-7.08 (dd, J=3.0 and 8.0 Hz, 1H), 7.16 (d, J=9.0 Hz, 1H), 7.27 (d, J=8.5 Hz, 1H), 7.38

(d, J=8.5 Hz, 1H), 7.62 (d, J=3.0 Hz, 1H), 7.81 (s, 1H). HFABMS m/z 311.1115 (calc for $C_{19}H_{18}O_2S$, $MH^+$, 311.1106).

$R_1$=7-F; $R_2$=4'-OMe: yield 63%, $^1H$ NMR (500 MHz, $CDCl_3$): δ 2.91-2.93 (m, 2H), 3.13-3.16 (m, 2H), 3.88 (s, 3H), 6.96 (d, J=9.0 Hz, 2H), 7.16-7.24 (m, 2H), 7.44 (d, J=9.0 Hz, 2H), 7.78 (dd, $J_1$=9.0 Hz, $J_2$=2.5 Hz, 1H), 7.86 (s, 1H).

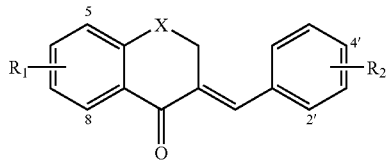

$R_1$=7-OMe; $R_2$=4'-F; X=O: yield 60%, mp 120-25° C., $^1H$ NMR (500 MHz, $CDCl_3$): δ 3.84 (s, 3H), 5.28 (s, 2H), 6.91 (d, J=9.0 Hz, 2H), 7.10-7.16 (m, 3H), 7.29-7.32 (m, 2H), 7.44 (d, J=3.5 Hz, 1H), 7.83 (s, 1H).

$R_1$=7-Me; $R_2$=4'-F; X=O: yield 53%, mp 145-49° C., $^1H$ NMR (500 MHz, $CDCl_3$): δ 2.34 (s, 3H), 5.90 (s, 2H), 6.87 (d, J=8.0 Hz, 1H), 7.11-7.16 (m, 2H), 7.28-7.31 (m, 3H), 7.80-7.81 (m, 1H).

$R_1$=7-OMe; $R_2$=4'-OMe; X=O: Prepared utilizing the acidic conditions. yield 62%, $^1H$ NMR (500 MHz, DMSO-$d_6$): δ 3.79 (s, 3H), 3.83 (s, 3H), 5.38 (d, 2H, J=2.0 Hz), 7.02 (d, 1H, J=8.5 Hz), 7.05-7.08 (m, 2H), 7.21 (dd, 1H, J=3.3, 9.3 Hz), 7.30 (d, 1H, J=3.5 Hz), 7.43-7.46 (m, 2H), 7.72 (1H, br s).

$R_1$=7-F; $R_2$=4'-OMe; X=O: $^1H$ NMR (500 MHz, DMSO-$d_6$): δ 3.83 (s, 3H), 5.43 (d, 2H, J=2.0 Hz), 7.05-7.08 (m, 2H), 7.13 (dd, 1H, J=4.5, 9.0 Hz), 7.44-7.47 (m, 2H), 7.49 (dd, 1H, J=3.5, 9.0 Hz), 7.55 (dd, 1H, J=3.3, 8.3 Hz), 7.74 (1H, br s).

$R_1$=7-OMe; $R_2$=4'-OMe; X=S: $^1H$ NMR (500 MHz, DMSO-$d_6$): δ 3.85 (s, 3H), 3.86 (s, 3H), 4.13 (d, 2H, J=1.0 Hz), 6.95-6.98 (m, 2H), 7.01 (dd, 1H, J=2.8, 8.8 Hz), 7.22 (d, 1H, J=9.0 Hz), 7.37-7.40 (m, 2H), 7.69 (d, 1H, J=3.0 Hz), 7.76 (s, 1H).

Combustion Analyses

TABLE 10

| Compound | Calculated | | | Observed | | |
|---|---|---|---|---|---|---|
| | C | H | N | C | H | N |
| 141 | 71.98 | 6.33 | 7.99 | 72.14 | 6.42 | 7.78 |
| 142 | 71.98 | 6.33 | 7.99 | 71.68 | 6.20 | 7.92 |
| 146 | 70.21 | 6.92 | 10.68 | 69.93 | 7.14 | 10.45 |
| 160 | 70.99 | 5.66 | 8.28 | 70.75 | 5.63 | 8.17 |
| 161 | 70.99 | 5.66 | 8.28 | 70.72 | 5.69 | 8.15 |
| 162 | 70.99 | 5.66 | 8.28 | 70.76 | 5.66 | 8.24 |
| 163 | 70.99 | 5.66 | 8.28 | 70.92 | 5.66 | 8.28 |
| 164 | 68.46 | 5.75 | 7.60 | 68.54 | 5.61 | 7.74 |
| 165 | 74.01 | 5.56 | 9.08 | 73.79 | 5.52 | 9.11 |
| 166 | 70.99 | 5.66 | 8.28 | 71.03 | 5.29 | 8.31 |
| 167 | 74.98 | 6.29 | 8.74 | 74.73 | 6.32 | 8.75 |
| 172 | 65.74 | 5.24 | 11.50 | 65.48 | 5.09 | 11.38 |
| 173 | 71.98 | 6.33 | 7.99 | 71.98 | 6.05 | 8.06 |
| 174 | 76.03 | 6.14 | 6.57 | 76.01 | 5.87 | 6.60 |
| 175 | 71.41 | 5.99 | 8.33 | 71.12 | 5.94 | 8.32 |

TABLE 10-continued

| Compound | Calculated | | | Observed | | |
|---|---|---|---|---|---|---|
| | C | H | N | C | H | N |
| 177 | 69.22 | 5.53 | 7.69 | 69.00 | 5.23 | 7.55 |
| 178 | 69.83 | 5.86 | 7.40 | 69.53 | 5.70 | 7.27 |
| 180 | 71.98 | 6.33 | 7.99 | 71.25 | 6.44 | 7.94 |
| 181 | 76.03 | 6.14 | 6.57 | 76.01 | 5.87 | 6.60 |
| 182 | 68.82 | 6.05 | 7.64 | 68.76 | 6.00 | 7.66 |
| 195 | 71.41 | 5.99 | 8.33 | 71.16 | 6.03 | 8.26 |
| 147 | 71.41 | 5.99 | 8.33 | 71.08 | 5.66 | 8.28 |
| 196 | 72.50 | 6.64 | 7.69 | 72.33 | 6.50 | 7.61 |
| 148 | 72.50 | 6.64 | 7.69 | 72.29 | 6.57 | 7.77 |
| 197 | 67.64 | 5.90 | 6.86 | 67.32 | 5.88 | 6.97 |
| 150 | 67.64 | 5.90 | 6.86 | 67.38 | 5.87 | 6.91 |
| 151 | 68.84 | 6.05 | 7.65 | 68.98 | 6.04 | 7.57 |

HPLC Methods and Purity Assessment

General HPLC information: Instrument Agilent 1100. Column: Discovery® C18, 25 cm×4.6 mm, 5-10 μL. Inection volume: 5-10 μL. Sample concentration: 1-2 mg/mL in 100% acetonitrile. λ: 254 nm HPLC method A: Elution solvent: 66% methanol; 34% water. Elution rate: 0.75 mL/min.

HPLC method B: Elution solvent: 50% acetonitrile; 50% water. Elution rate: 1.00 mL/min.

TABLE 11

| Compound | Method | Elution time (min) | Purity (%) |
|---|---|---|---|
| 169 | A | 18.2 | 100 |
| | B | 12.6 | 100 |
| 170 | A | 31.9 | 100 |
| | B | 19.3 | 100 |
| 171 | A | 24.9 | 99.1 |
| | B | 16.2 | 98.0 |
| 184 | A | 36.5 | 100 |
| | B | 21.3 | 100 |
| 185 | A | 32.9 | 99.5 |
| | B | 18.1 | 99.3 |
| 187 | A | 22.7 | 100 |
| | B | 12.4 | 100 |
| 188 | A | 18.7 | 100 |
| | B | 10.9 | 100 |
| 189 | A | 26.7 | 100 |
| | B | 11.3 | 100 |
| 190 | A | 22.7 | 96.0 |
| | B | 13.4 | 100 |
| 191 | A | 36.0 | 100 |
| | B | 18.9 | 100 |
| 192 | A | 30.7 | 100 |
| | B | 16.7 | 100 |
| 193 | A | 8.4 | 99.6 |
| | B | 7.7 | 99.2 |
| 194 | A | 8.4 | 98.9 |
| | B | 7.2 | 98.7 |
| 158 | A | 20.2 | 98.7 |
| | B | 12.4 | 97.4 |

Example 29

Compounds Related to Nec-3

The following Nec-3-like compounds were synthesized:

TABLE 12

| No. | cis or trans* | R |
|---|---|---|
| 214 | trans | $CH_2OH$ |
| 215 | cis | $CH_2OH$ |
| 216 | trans | $CH_3$ |
| 217 | cis | $CH_3$ |

*refers to the relative stereochemistry of the C3-aryl group and the C3a-methyl group.

The following synthetic scheme was used to generate compounds (216) and (217):

In general, any Nec-3 compound can be modified by the addition of a methyl group, or other alkyl or heteroalkyl group, to position C3a.

Other Embodiments

All publications, patents, and patent applications mentioned in the above specification are hereby incorporated by reference. Various modifications and variations of the described method and system of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention. Other embodiments are in the claims.

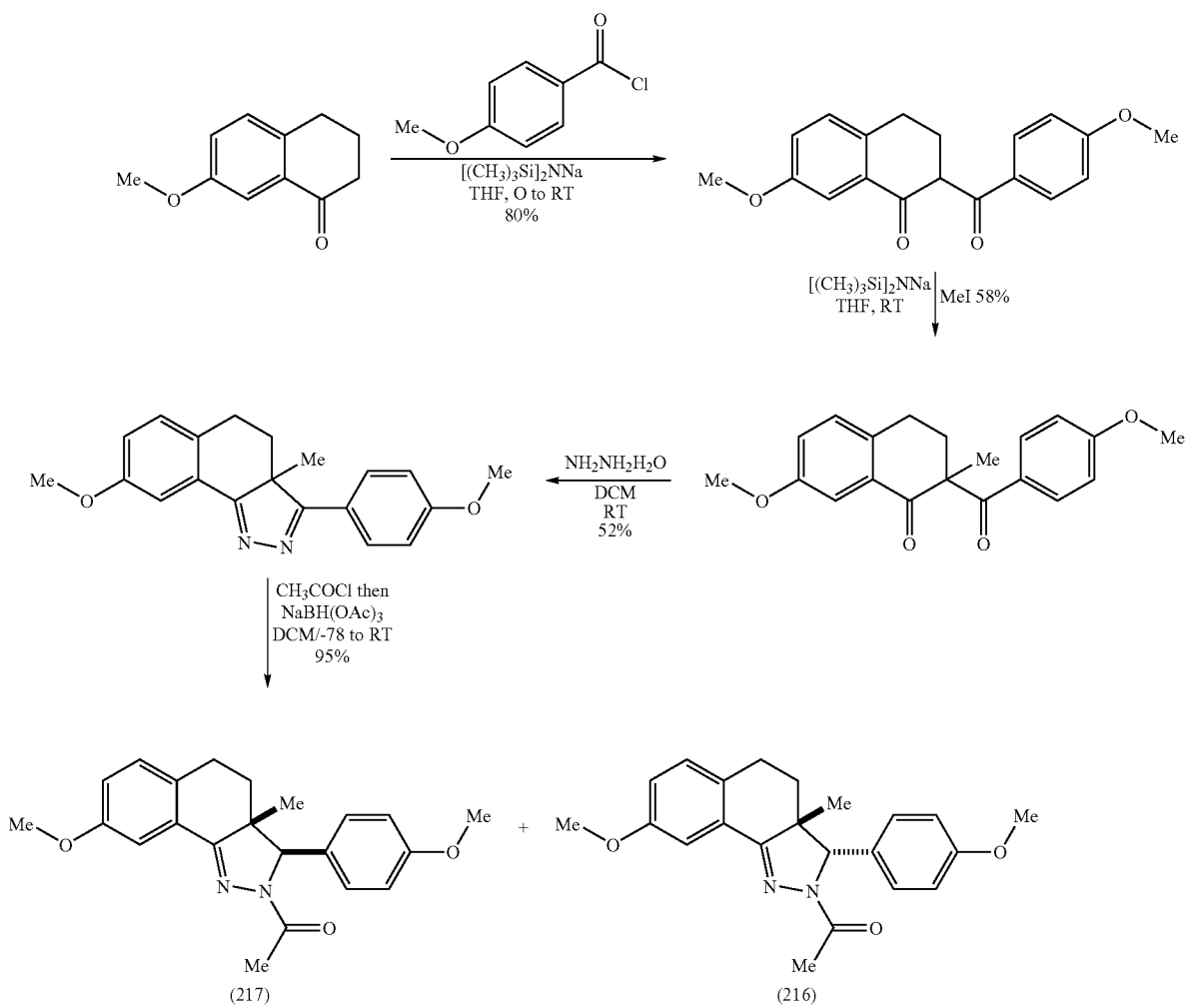

Scheme 14.

What is claimed is:

1. A Nec-3 compound of formula (VI),

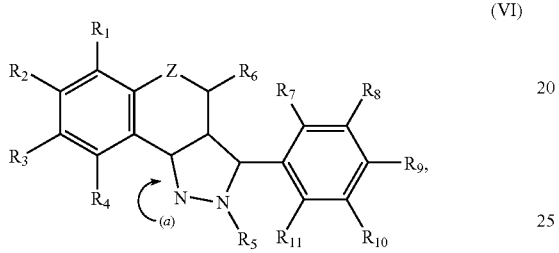

wherein
the bond indicated by (a) is a double bond; Z is $CH_2$; and each of $R_1$, $R_2$, $R_4$, $R_6$, $R_7$, $R_{10}$, and $R_{11}$, independently, represents hydrogen, $R_3$ is alkyl of one to six carbon atoms; alkoxy of one to six carbon atoms; halo; or amino;

$R_5$ is $C(O)R_{13}$, $C(S)R_{13}$, $C(O)OR_{13}$, $C(O)NR_{13}R_{14}$, $C(S)NR_{13}R_{14}$, $C(NH)R_{13}$, or $S(O_2)R_{13}$, wherein each of $R_{13}$ and $R_{14}$, independently, represents hydrogen, an optionally substituted $C_{1-12}$ alkyl, an optionally substituted $C_{1-7}$ heteroalkyl, an optionally substituted $C_6$ or $C_{10}$ aryl, an optionally substituted $C_{2-9}$ heteroaryl, an optionally substituted $C_{7-16}$ aralkyl, or an optionally substituted $C_{2-15}$ heteroaralkyl;

$R_8$ represents hydrogen, alkanoyl of one to six carbon atoms; alkyl of one to six carbon atoms; alkoxy of one to six carbon atoms; alkoxyalkyl, wherein the alkyl and alkylene groups are independently of one to six carbon atoms; alkylsulfinyl of one to six carbon atoms; alkylsulfinylalkyl, wherein the alkyl and alkylene groups are independently of from one to six carbon atoms; alkylsulfonyl of one to six carbon atoms; alkylsulfonylalkyl, wherein the alkyl and alkylene groups are independently of one to six carbon atoms; $C_{7-16}$ aralkyl; amino; aminoalkyl of one to six carbon atoms; $C_6$ or $C_{10}$ aryl; $C_7$ or $C_{11}$ aryloyl; azido; azidoalkyl of one to six carbon atoms; carboxaldehyde; (carboxaldehyde)alkyl, wherein the alkylene group is of one to six carbon atoms; cycloalkyl of three to eight carbon atoms; cycloalkylalkyl, wherein the cycloalkyl group is of three to eight carbon atoms and the alkylene group is of one to ten carbon atoms; halo; haloalkyl of one to six carbon atoms; $C_{2-9}$ heterocyclyl; $C_{2-9}$ (heterocyclyl)oxy; $C_{3-10}$ (heterocyclyl)oyl; hydroxyl; hydroxyalkyl of one to six carbon atoms; nitro; nitroalkyl of one to six carbon atoms; N-protected amino; N-protected aminoalkyl, wherein the alkylene group is of one to six carbon atoms; thioalkoxy of one to six carbon atoms; thioalkoxyalkyl, wherein the alkyl and alkylene groups are independently of from one to six carbon atoms; $-(CH_2)_qCO_2R_A$, wherein q is zero to four and $R_A$ is selected from the group consisting of (a) $C_{1-6}$ alkyl, (b) $C_6$ or $C_{10}$ aryl and (c) arylalkyl, wherein the alkylene group is of one to six carbon atoms; $-(CH_2)_qCONR_BR_C$, wherein $R_B$ and $R_C$ are independently selected from the group consisting of (a) hydrogen, (b) $C_{1-6}$ alkyl, (c) $C_6$ or $C_{10}$ aryl and (d) arylalkyl, wherein the alkylene group is of one to six carbon atoms; $-(CH_2)_qSO_2R_D$, wherein $R_D$ is selected from the group consisting of (a) $C_{1-6}$ alkyl, (b) $C_6$ or $C_{10}$ aryl and (c) arylalkyl, wherein the alkylene group is of one to six carbon atoms; $-(CH_2)_qSO_2NR_ER_F$, wherein $R_E$ and $R_F$ are independently selected from the group consisting of (a) hydrogen, (b) alkyl, (c) $C_6$ or $C_{10}$ aryl and (d) arylalkyl, wherein the alkylene group is of one to six carbon atoms; $-(CH_2)_qNR_GR_H$, wherein $R_G$ and $R_H$ are independently selected from the group consisting of (a) hydrogen; (b) an N-protecting group; (c) alkyl of one to six carbon atoms; (d) alkenyl of two to six carbon atoms; (e) alkynyl of two to six carbon atoms; (f) $C_6$ or $C_{10}$ aryl; (g) arylalkyl, wherein the alkylene group is of one to six carbon atoms; (h) cycloalkyl of three to eight carbon atoms and (i) cycloalkylalkyl, wherein the cycloalkyl group is of three to eight carbon atoms, and the alkylene group is of one to ten carbon atoms, with the proviso that no two groups are bound to the nitrogen atom through a carbonyl group or a sulfonyl group; $C_{1-6}$ perfluoroalkyl; $C_{1-6}$ perfluoroalkoxy; $C_6$ or $C_{10}$ aryloxy; $C_{3-8}$ cycloalkoxy; $C_{9-14}$ cycloalkylalkoxy; or $C_{7-16}$ arylalkoxy;

$R_9$ is alkyl of one to six carbon atoms or alkoxy of one to six carbon atoms; and wherein $R_5$ is not $C(O)CH_3$;

or a stereoisomer thereof, or a pharmaceutically acceptable salt thereof.

2. The Nec-3 compound of claim 1, wherein $R_3$ represents methoxyl; $R_5$ represents $C(O)CH_2OH$; and $R_9$ represents alkoxy of one to six carbon atoms, or a stereoisomer thereof, or a pharmaceutically acceptable salt thereof.

3. A Nec-3 compound selected from the group consisting of:

(a) a Nec-3 compound wherein $R_1$, $R_2$, $R_4$, $R_6$, $R_{10}$, and $R_{11}$ are H, $R_5$ is $-C(O)R_{13}$, the bond indicated by (a) is a double bond, and Z, $R_3$, $R_7$, $R_8$, $R_9$, and $R_{13}$ are as follows:

| Cmpd No. | Z | $R_3$ | $R_7$ | $R_8$ | $R_9$ | $R_{13}$ | C3/C3a* |
|---|---|---|---|---|---|---|---|
| 25 | $CH_2$ | $OCH_3$ | H | H | $OCH_3$ | H | cis |
| 26 | $CH_2$ | $OCH_3$ | H | H | $OCH_3$ | H | trans |
| 39 | $CH_2$ | $OCH_3$ | H | H | $OCH_3$ | $CH_2CH_3$ | cis |

-continued

| Cmpd No. | Z | $R_3$ | $R_7$ | $R_8$ | $R_9$ | $R_{13}$ | C3/C3a* |
|---|---|---|---|---|---|---|---|
| 42 | $CH_2$ | $OCH_3$ | H | H | $OCH_3$ | $CH_2Cl$ | cis |
| 46 | $CH_2$ | $OCH_3$ | H | H | $OCH_3$ | $CH_2N(CH_3)_2$ | cis |
| 47 | $CH_2$ | $OCH_3$ | H | H | $OCH_3$ | $CH_2OAc$ | cis |
| 71 | $CH_2$ | $OCH_3$ | H | H | $OCH_3$ | $CF_3$ | cis |
| 79 | $CH_2$ | $OCH_3$ | H | H | $OCH_3$ | $CH_2CH_3$ | trans |
| 80 | $CH_2$ | $OCH_3$ | H | H | $OCH_3$ | $CH_2OAc$ | trans |
| 85 | $CH_2$ | $OCH_3$ | H | H | $OCH_3$ | $(CH_2)_3CO_2CH_3$ | cis |
| 86 | $CH_2$ | $OCH_3$ | H | H | $OCH_3$ | $(CH_2)_3CO_2H$ | cis |
| 87 | $CH_2$ | $OCH_3$ | H | H | $OCH_3$ | $(CH_2)_3C(O)$-morpholine | cis |
| 88 | $CH_2$ | $OCH_3$ | H | H | $OCH_3$ | $CH_2NHCH_3$ | cis |
| 92 | $CH_2$ | $OCH_3$ | H | H | $OCH_3$ | $CH_2OCH_3$ | cis |

-continued

| Cmpd No. | Z | $R_3$ | $R_7$ | $R_8$ | $R_9$ | $R_{13}$ | C3/C3a* |
|---|---|---|---|---|---|---|---|
| 93 | $CH_2$ | $OCH_3$ | H | H | $OCH_3$ | OH | cis |
| 94 | $CH_2$ | $OCH_3$ | H | H | $OCH_3$ | $(CH_2)_8C(O)$-morpholine | cis |
| 97 | $CH_2$ | $OCH_3$ | H | H | $OCH_3$ | $CF_3$ | cis |
| 98 | $CH_2$ | $OCH_3$ | H | H | $OCH_3$ | $C(O)CH_3$ | cis |
| 99 | $CH_2$ | $OCH_3$ | H | H | $OCH_3$ | $(CH_2)_3C(O)$-$NH(CH_2)_3CO_2Et$ | cis |
| 138 | $CH_2$ | $OCH_3$ | H | H | $OCH_3$ | $(CH_2)_3CO_2CH_3$ | trans |

(b) a Nec-3 compound selected from the group consisting of

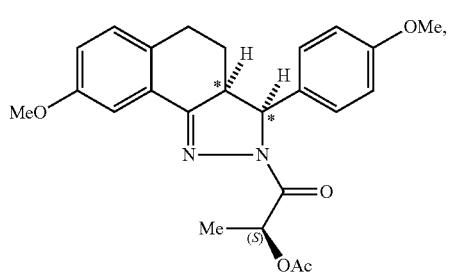
(100)

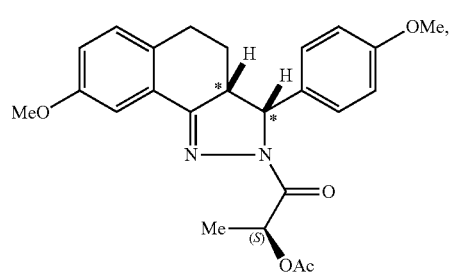
(101)

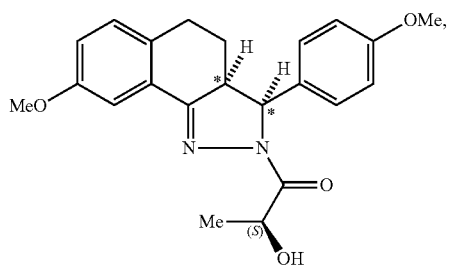
(102)

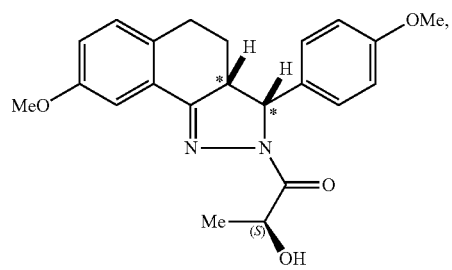
(103)

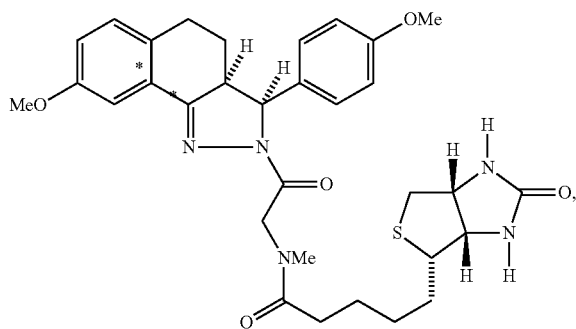
(114)

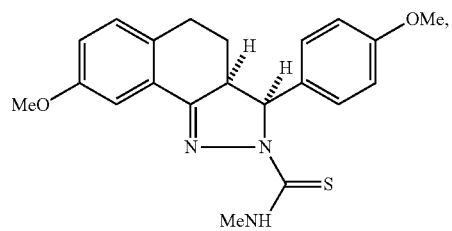
(116)

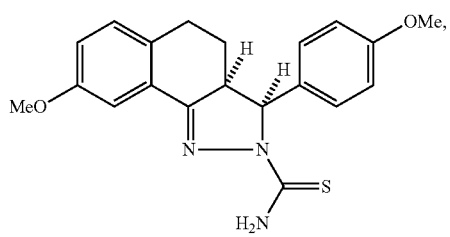
(117)

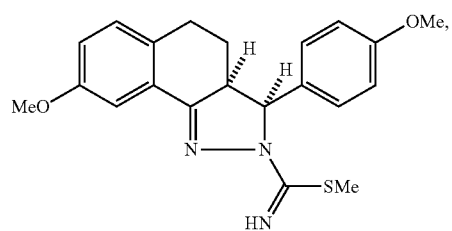
(118)

-continued
(119)
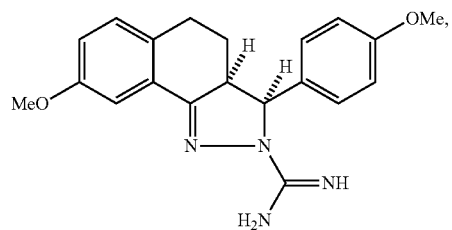
(120)
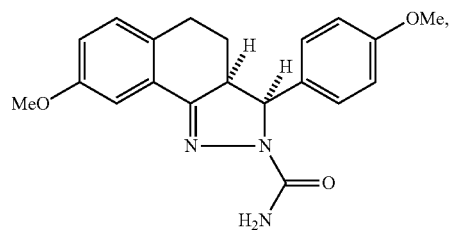
(122)
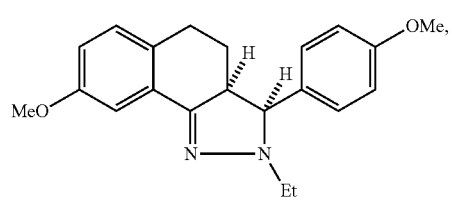
(125)
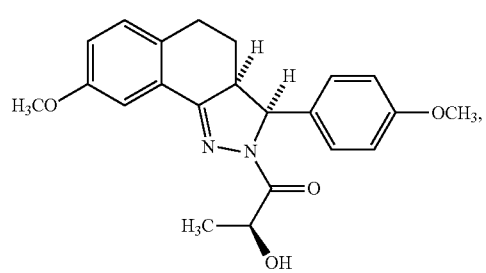
(126)
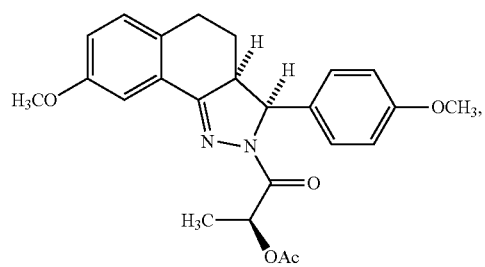
(127)
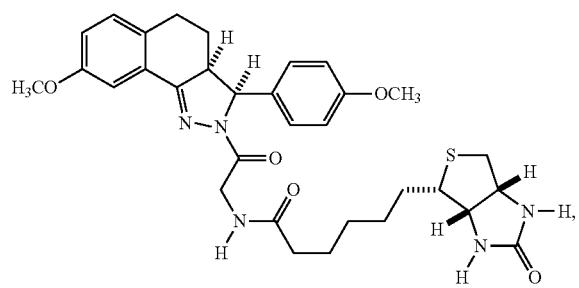
(130)
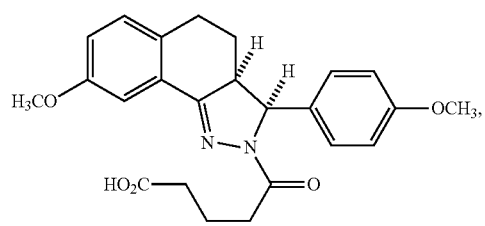
(131)
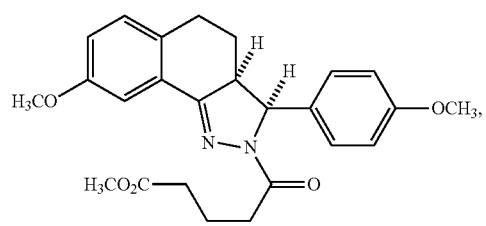
(133)
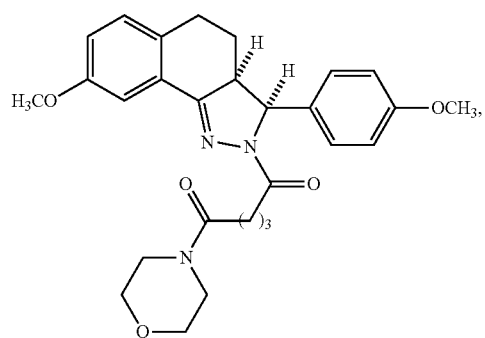
(134)
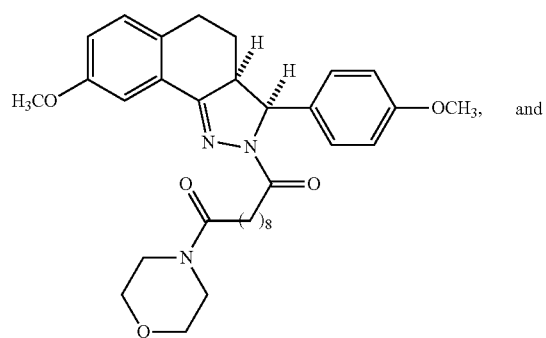
and

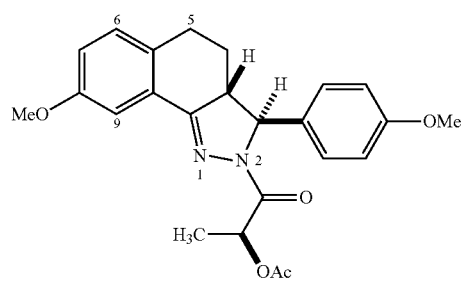
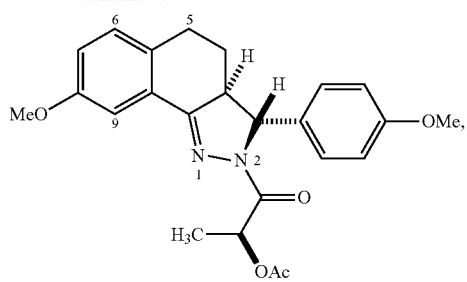

(139)

A=(3R,3aS)-rel-isomer  B=(3R,3aR)-rel-isomer
(d) a Nec-3 compound having the following structure,

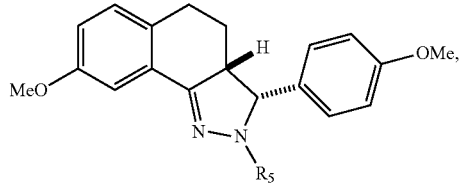

wherein $R_5$ is as follows

| Cmpd | R |
|---|---|
| 147 | HC=O |
| 148 | C(=O)Et |
| 150 | C(=O)CH$_2$OAc |
| 151 | C(=O)CH$_2$OH |
| 158 | C(=O)CH$_2$OMe |
| 159 | C(=O)CF$_3$ |
| 153 | C(=O)NH$_2$ |
| 152 | C(=S)NH$_2$ |
| 154 | C(=S)NHMe | and
(e) a Nec-3 compound having the following structure,

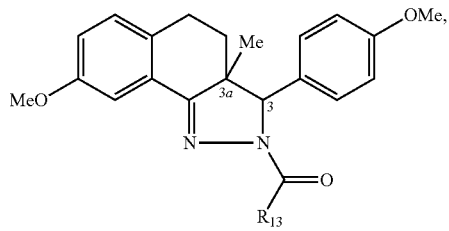

wherein $R_{13}$ and the relative C3/C3a stereochemistry are as follows

| No. | C3/C3a stereochemistry | $R_{13}$ |
|---|---|---|
| 214 | trans | CH$_2$OH |
| 215 | Cis | CH$_2$OH | or a stereoisomer thereof, or a pharmaceutically acceptable salt thereof.

4. The Nec-3 compound of claim 3, wherein said compound is selected from compounds (147), (148), (150), (151), (154), (158), and (159),
or a stereoisomer thereof, or a pharmaceutically acceptable salt thereof.

5. A Nec-3 compound of formula (VI):

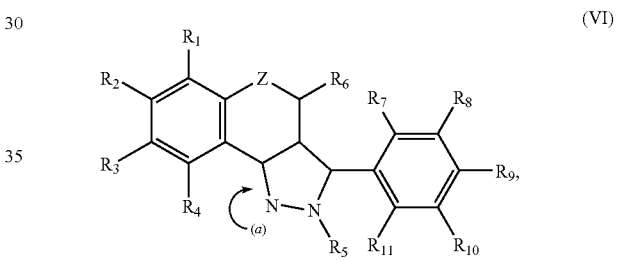

(VI)

or a stereoisomer thereof, or a pharmaceutically acceptable salt thereof wherein
Z is CH$_2$CH$_2$;
the bond indicated by (a) can be a single or double bond;
each of $R_1$, $R_2$, $R_4$, $R_7$, $R_8$, $R_{10}$, and $R_{11}$, independently, represents hydrogen, alkanoyl of one to six carbon atoms; alkyl of one to six carbon atoms; alkoxy of one to six carbon atoms; alkoxyalkyl, wherein the alkyl and alkylene groups are independently of one to six carbon atoms; alkylsulfinyl of one to six carbon atoms; alkylsulfinylalkyl, wherein the alkyl and alkylene groups are independently of from one to six carbon atoms; alkylsulfonyl of one to six carbon atoms; alkylsulfonylalkyl, wherein the alkyl and alkylene groups are independently of one to six carbon atoms; C$_{7-16}$ aralkyl; amino; aminoalkyl of one to six carbon atoms; C$_6$ or C$_{10}$ aryl; C$_7$ or C$_{11}$ aryloyl; azido; azidoalkyl of one to six carbon atoms; carboxaldehyde; (carboxaldehyde)alkyl, wherein the alkylene group is of one to six carbon atoms; cycloalkyl of three to eight carbon atoms; cycloalkylalkyl, wherein the cycloalkyl group is of three to eight carbon atoms and the alkylene group is of one to ten carbon atoms; halo; haloalkyl of one to six carbon atoms; C$_{2-9}$ heterocyclyl; C$_{2-9}$ (heterocyclyl)oxy; C$_{3-10}$ (heterocyclyl)oyl; hydroxyl; hydroxyalkyl of one to six carbon atoms; nitro; nitroalkyl of one to six carbon atoms; N-protected amino; N-protected aminoalkyl, wherein the alkylene group is of one to six carbon atoms; thioalkoxy of one to six carbon atoms; thioalkoxyalkyl, wherein the alkyl and alkylene groups are independently of from one to six carbon atoms; —$(CH_2)_qCO_2R_A$, wherein q is zero to four and $R_A$ is selected from the group consisting of (a) $C_{1-6}$ alkyl, (b) $C_6$ or $C_{10}$ aryl and (c) arylalkyl, wherein the alkylene group is of one to six carbon atoms; —$(CH_2)_qCONR_BR_C$, wherein $R_B$ and $R_C$ are independently selected from the group consisting of (a) hydrogen, (b) $C_{1-6}$ alkyl, (c) $C_6$ or $C_{10}$ aryl and (d) arylalkyl, wherein the alkylene group is of one to six carbon atoms; —$(CH_2)_qSO_2R_D$, wherein $R_D$ is selected from the group consisting of (a) $C_{1-6}$ alkyl, (b) $C_6$ or $C_{10}$ aryl and (c) arylalkyl, wherein the alkylene group is of one to six carbon atoms; —$(CH_2)_qSO_2NR_ER_F$, wherein $R_E$ and $R_F$ are independently selected from the group consisting of (a) hydrogen, (b) alkyl, (c) $C_6$ or $C_{10}$ aryl and (d) arylalkyl, wherein the alkylene group is of one to six carbon atoms; —$(CH_2)_qNR_GR_H$, wherein $R_G$ and $R_H$ are independently selected from the group consisting of (a) hydrogen; (b) an N-protecting group; (c) alkyl of one to six carbon atoms; (d) alkenyl of two to six carbon atoms; (e) alkynyl of two to six carbon atoms; (f) $C_6$ or $C_{10}$ aryl; (g) arylalkyl, wherein the alkylene group is of one to six carbon atoms; (h) cycloalkyl of three to eight carbon atoms and (i) cycloalkylalkyl, wherein the cycloalkyl group is of three to eight carbon atoms, and the alkylene group is of one to ten carbon atoms, with the proviso that no two groups are bound to the nitrogen atom through a carbonyl group or a sulfonyl group; $C_{1-6}$ perfluoroalkyl; $C_{1-6}$ perfluoroalkoxy; $C_6$ or $C_{10}$ aryloxy; $C_{3-8}$ cycloalkoxy; $C_{9-14}$ cycloalkylalkoxy; or $C_{7-16}$ arylalkoxy;

$R_3$ is alkoxy of one to six carbon atoms; halo; or amino;

$R_9$ is alkyl of one to six carbon atoms; alkoxy of one to six carbon atoms; or halo;

$R_5$ is $C(O)R_{13}$, $C(S)R_{13}$, $C(O)OR_{13}$, $C(O)NR_{13}R_{14}$, $C(S)NR_{13}R_{14}$, $C(NH)R_{13}$, or $S(O_2)R_{13}$, wherein each of $R_{13}$ and $R_{14}$, independently, represents hydrogen, an optionally substituted $C_{1-12}$ alkyl, an optionally substituted $C_{1-7}$ heteroalkyl, an optionally substituted $C_6$ or $C_{10}$ aryl, an optionally substituted $C_{2-9}$ heteroaryl, an optionally substituted $C_{7-16}$ aralkyl, or an optionally substituted $C_{2-15}$ heteroaralkyl; and $R_6$ is hydrogen, $C_{1-6}$ alkyl, an optionally substituted $C_6$ or $C_{10}$ aryl, an optionally substituted $C_{7-16}$ aralkyl, an optionally substituted $C_{2-9}$ heteroaryl, or an optionally substituted $C_{2-15}$ heteroaralkyl, wherein when each of $R_1$, $R_2$, $R_4$, and $R_6$ through $R_{11}$ is selected from the group consisting of hydrogen, amino, halide, and hydroxyl and Z is $CH_2$, $R_3$ is not hydroxyl or methoxyl; and wherein $R_5$ is not $C(O)CH_3$.

6. The Nec-3 compound of claim 1, wherein $R_8$ is H, or a stereoisomer thereof, or a pharmaceutically acceptable salt thereof.

* * * * *

SEQUENCE LISTING

```
<160> NUMBER OF SEQ ID NOS: 4

<210> SEQ ID NO 1
<211> LENGTH: 4
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: N-Acetylation
<220> FEATURE:
<221> NAME/KEY: MOD_RES
<222> LOCATION: (4)..(4)
<223> OTHER INFORMATION: Aldehyde makes up the C-terminus

<400> SEQUENCE: 1

Ile Glu Thr Asp
1

<210> SEQ ID NO 2
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: N-carbobenzyloxy residue
<220> FEATURE:
<221> NAME/KEY: MOD_RES
<222> LOCATION: (4)..(4)
<223> OTHER INFORMATION: Methyl ester on the side chain, fluoromethyl
      Ketone makes up the C-terminus

<400> SEQUENCE: 2

Tyr Val Ala Asp
1

<210> SEQ ID NO 3
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = N-[2-(6-hydroxy-3-oxo-3H-xanthen-9-
      yl)benzoyl]-L-a-aspartic acid
<220> FEATURE:
<221> NAME/KEY: MISC_FEATURE
<222> LOCATION: (3)..(3)
<223> OTHER INFORMATION: Xaa = N-[(1S)-1-(carboxymethyl)-3-fluoro-2-
      oxopropyl]-L-Valinamide (a modified form of valine)

<400> SEQUENCE: 3

Xaa Glu Xaa Asp
1

<210> SEQ ID NO 4
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
```

```
<223> OTHER INFORMATION: N-Acetylation
<220> FEATURE:
<221> NAME/KEY: MOD_RES
<222> LOCATION: (4)..(4)
<223> OTHER INFORMATION: Aldehyde makes up the C-terminus

<400> SEQUENCE: 4

Leu Glu His Asp
 1
```